United States Patent [19]
Chang et al.

[11] Patent Number: 5,849,564
[45] Date of Patent: Dec. 15, 1998

[54] POLYPEPTIDES FROM KAPOSI'S SARCOMA-ASSOCIATED HERPESVIRUS, DNA ENCODING SAME AND USES THEREOF

[75] Inventors: Yuan Chang, New York, N.Y.; Roy A. Bohenzky, Mountian View, Calif.; James J. Russo, New York, N.Y.; Isidore S. Edelman, New York, N.Y.; Patrick S. Moore, New York, N.Y.

[73] Assignee: The Trustees of Columbia University in the City of New York, New York, N.Y.

[21] Appl. No.: 770,379

[22] Filed: Nov. 29, 1996

[51] Int. Cl.$^6$ .......................... C07H 21/04; C12N 15/63; C12N 1/20

[52] U.S. Cl. .................. 435/252.3; 435/325; 435/320.1; 435/172.3; 536/24.32; 536/23.72; 935/9; 935/11; 935/22; 935/29; 935/32

[58] Field of Search .............................. 536/23.72, 24.32; 435/320.1, 252.3, 325, 172.3; 935/9, 11, 22, 29, 32

[56] References Cited

PUBLICATIONS

Albrecht et al (1992) Primary structure of the herpesvirus saimiri genome, J Virol 66, 5047–5058 (Exhibit 2).
Baggott et al. (1993) Antifolates in rheumatoid arthritis: a hypothetical mechanism of action, Clin & Exp'l Rheumatol 11 (Supp 8), S101–S105 (Exhibit 3).
Chang et al (1994) Identification of herpesvirus–like DNA sequences in AIDS–associated Kaposi's sarcoma, Science 266, 1865–1869 (Exhibit 4).
Fleming and Schilsky (1992) Antifolates: the next generation, Semin Oncol 19, 707–729 (Exhibit 5).
Jackson (1995) Toxicity prediciton from metabolic pathway modelling, Toxicology 102, 197–205 (Exhibit 7).
Moore et al (Jan. 1996) Primary characterization of a herpesvirus agent associated with Kaposi's sarcoma, J. Virol 70, 549–558 (Exhibit 8).
Schultz (1995) Newer antifolates in cancer therapy, Prog Drug Res 44, 129–157 (Exhibit 9).
Tur and Brenner (Mar. 1996) Treatment of Kaposi's sarcoma, Arch Dermatol 132, 327–331 (Exhibit 10).
Unger (1996) Current concepts of treatment anticancer durgs, J Can Res & Clin Oncol 122, 189–198 (Exhibit 11).
Weiss (Mar. 1996) Human herpesvirus 8 in lymphoma and Kaposi's sarcoma: now the virus can be propagated, Nature Medicine 2, 277–278 (Exhibit 12)
Zalla (1996) Kaposi's sarcoma: An update, Dermatol Surg 22, 274–287 (Exhibit 13).

*Primary Examiner*—Carla J. Myers
*Attorney, Agent, or Firm*—John P. White; Cooper & Dunham LLP

[57] ABSTRACT

This invention provides an isolated nucleic acid molecule which encodes Kaposi's Sarcoma-Associated Herpesvirus (KSHV) polypeptides. This invention provides an isolated polypeptide molecule of KSHV. This invention provides an antibody specific to the polypeptide. Antisense and triplex oligonucleotide molecules are also provided. This invention provides a vaccine for Kaposi's Sarcoma (KS). This invention provides methods of vaccination, prophylaxis, diagnosis and treatment of a subject with KS and of detecting expression of a DNA virus associated with Kaposi's sarcoma in a cell.

12 Claims, 16 Drawing Sheets

FIG. 2A

```
  1  CGTGAACACC CCGCGCCCCG CGCCCCCCAC ACCGGCGCCGC CCCTCCCCCT CCCCCGCTC
 61  GCCTCCCGGC GCTGCCGCCA GGCCCCGGCC GGAGCCGGCC GCCCGCGGGG GGCAGGGCGC
121  GCCCGGCGGC TCCCTCGCGG GGCGGGGGAC GGGGGAGGgg ggcgccggC CCCCGCGCGC
181  CGCGGCAGCG GAGCGCGAGc gccccgccg gccgccaGCG GCGGGCAGG CCCCGGGGCC
241  CCGAGCCCCG AGCCCCGCCG GGGTACGGGG CTAGgccacg cctactttt tttcgggcg
301  gccccccgac cctctctcgg ccccccGGTC CCCGGGCCC GCGCGCCC CCCCGGGGGG
361  GTAAACAGG GGGGGGGA TGCGGCCGCG GCGCGCCCCG CGGCGCGGC GGCGCTTGCt
421  ttcgttttct cccgcggccc cccggcgcg agccgcgcgg cggcgcggg cgccccctcc
481  cccggggggc tcggcggggg gccCCCTGTC CCcgcgcggg cccgcgaccc cGGCGCCGC
541  CGCGCCCCGA TCCCGGGGC GCCCCGCGGG CCTGCCGGGG ACGCCGCCGG GCCTGCGGCG
601  CCTCCCGCCC GGGCATGGGg ccgcgcgccg cctcagggcc cggcgcggcc ggcgcctggt
661  ccccgccccc gcccgcgggg gaccccgGGC AGCCGAGGGAA GGGGGCGCCC TCTCTCTACT
721  GTGCGAGGAG TCTGGGCTGC TGTGTGTGAG CCTGTTTGGG GGAGCCTCCT CAGTGCTTGC
781  TACGTGGAGC CCTGGACACT A
```

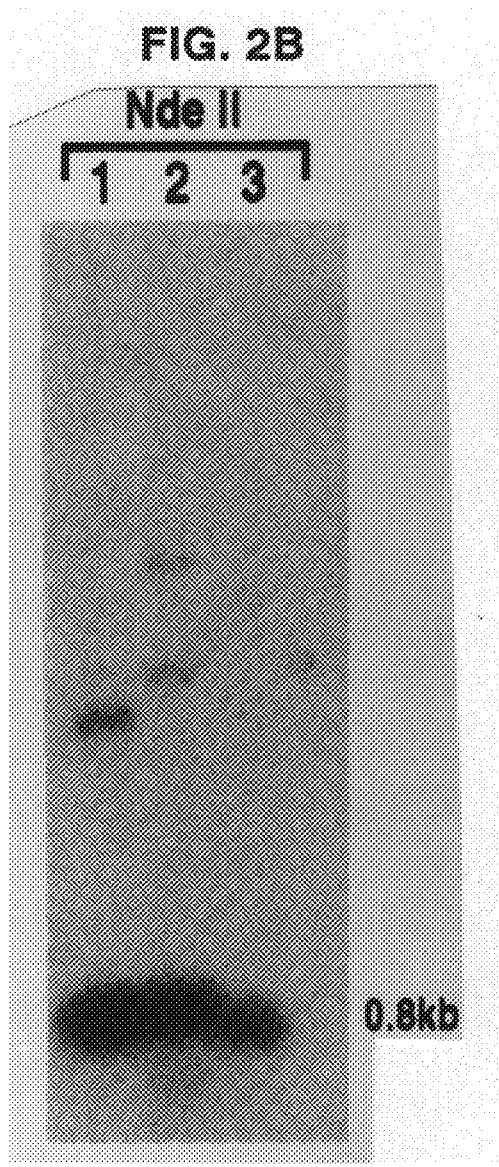

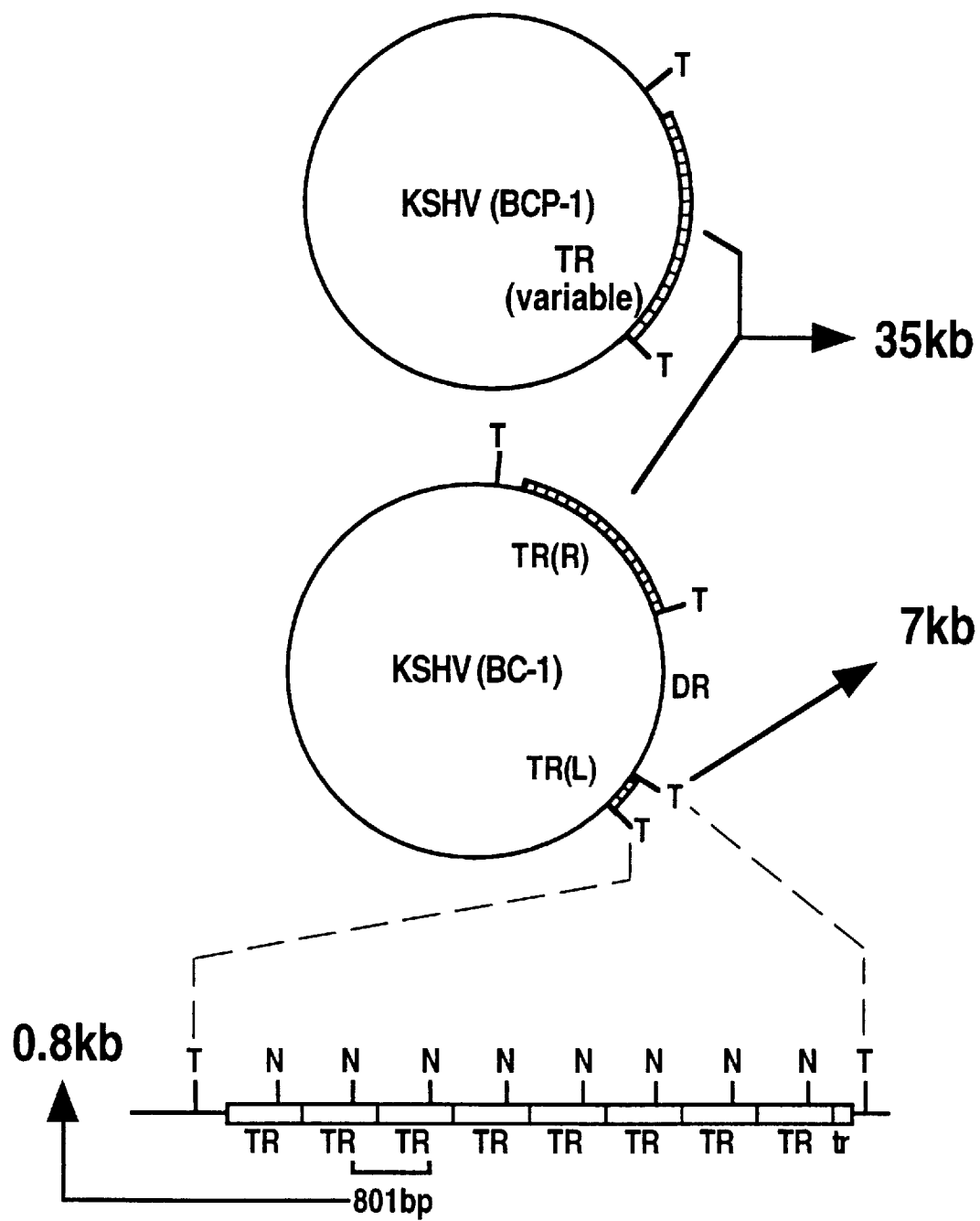

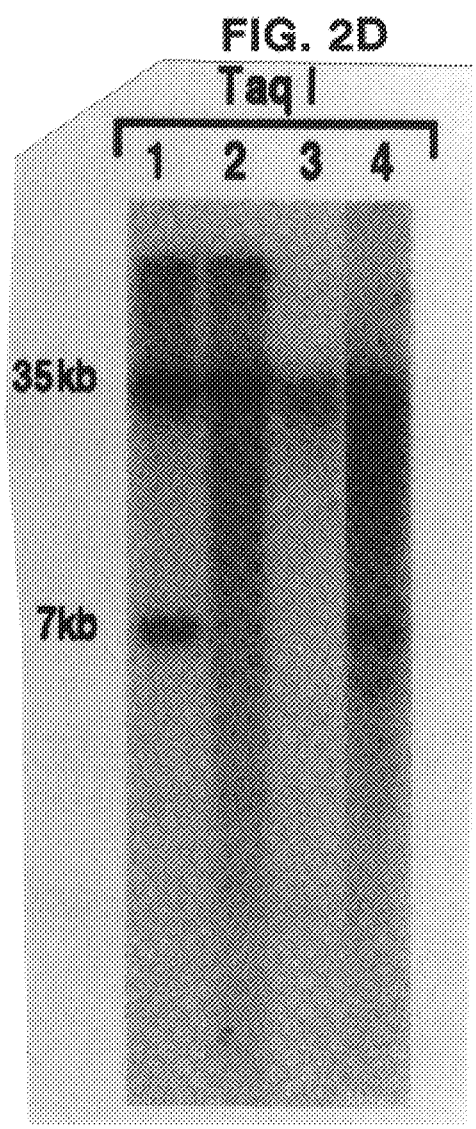

```
              10         20         30         40         50
vIRF     MDPGQRPNPF GAPGAIPKKP CLSQGSPGTS GSGAPCDEPS RSESPGEGPS
huISGF3γ
huICSBP 60         70         80         90        100
vIRF     GTGGSAAAGD ITRQAVVAAI TEWSRTRQLR
huISGF3γ                                  ISTGASEGKA SIKDWIVQQV
huICSBP                                   MASGRARCTR KLRNWVEQV
                                          MCDRNGGGR -LRQWLIEQI 110        120        130        140        150
vIRF     NSGKFPGVEW EDEERTRFRI PVTPLADPCF EWRRDGELGV VYIRERGNMP
huISGF3γ ESGQFPGVCW DDTAKTMFRI PWKHAGKQDF REDQDAAFFK AWAIFKGKYK
huICSBP  DSSMYPGLIW ENEEKSMFRI PWKHAGKQDY NQEVDASIFK AWAVFKGKFK 160        170        180        190        200
vIRF     VDASFKGTRG RRRMLAALRR TRGLQEEIG-K GISQDGHHFL VFRVRKPEEE
huISGF3γ EGDTGGPAVW KTRLRCALNK SSEFKEVPER GRMDVAEPYK VYQLLPPGIV
huICSBP  EGDKAEPATW KTRLRCALNK SPDFEEVTDR SQLDISEPYK VYRIVPEEDQ 210        220        230        240        250
vIRF     QCVECGVVAG -RLLQEGFFS -----PGQCL PGEIVTPVPS
huISGF3γ SGQPGTQKVP ERKEEEDAMQ NCTLSP---- DSLNNEEGA
huICSBP  KCKLGVATAG CVNEVTEMEC GRSEIDELIK EPPSVDD YMGMIKRSPS 260        270        280        290        300
vIRF     CTTAEGQEAV IDWG------ ---------- ---------- --RL
huISGF3γ SGGAVHSDIG SSSSSSPEP QEVTDTTEAP FQGDQRSLEF LLPPEPDYSL
huICSBP  PPDACRSQLL PDWAHEPST GRRLVTGYTT YDAHHSAFS- ------- QM
```

FIG. 3C-2

```
                                                                                          350
vIRF       FIRMYYNGEQ VHELLTTSQS GCRISALRR- DPAVHYCAVG SPGQWLP-N
huISGF3γ   LLTFIYNGRV VGEAQVQSLD -CRLVAE--- -P--SGS-ES SMEQVLFPKP
huICSBP    VISFYYGGKL VGQATTTCPE GCRLSLQPG LPGTKLYGPE GLELVRFP-P 400
vIRF       VPNLACEIAK RELCDTLDAC AKGILLTSSC NGIFCVCYHN GPVHFIGNTV
huISGF3γ   GPLEPT--QR I--LLSQLFG ERGILVASNP RGLFVQRLCP IPISWNAPQA
huICSBP    ADTIPSERQR QVTRKLFGHL ERGVLHSSR- QGVFVKRLCQ GRVFCVVVVV 450
vIRF       PPDSGPLLLP QGKPTRIFNP NTFLVGLAN- -S--PLPAP SHVTCPLVKL
huISGF3γ   PPGPGPHLLP SNECVELFRT AYFCRDLVRY FQGLGPPPP QVTLNFWEES
huICSBP    VCKGRPNKLE RDEVVQVFDT SQFFRELQQF YNSQGRLPDG RVVLCFGEEF 500
vIRF       WLGKPVAVGK LEPHAPSP-A RDFAARCSNF SDACVVLEIM PKPLWDAMQ-
huISGF3γ   HGSSHTPQNL HTVKMEQAFA RYLLEQTPEQ QAAILSLV-- --------
huICSBP    PDMAPLRSKL ILVQIEQLYV RQLAEEAGKS CGAGSVMQAP EEPPPDQVFR vIRF       ----------  ----------  ----------  ----------
huISGF3γ   ----------  ----------  ----------  ----------
huICSBP    MFPDICASHQ RSFFRENQQI TV
```

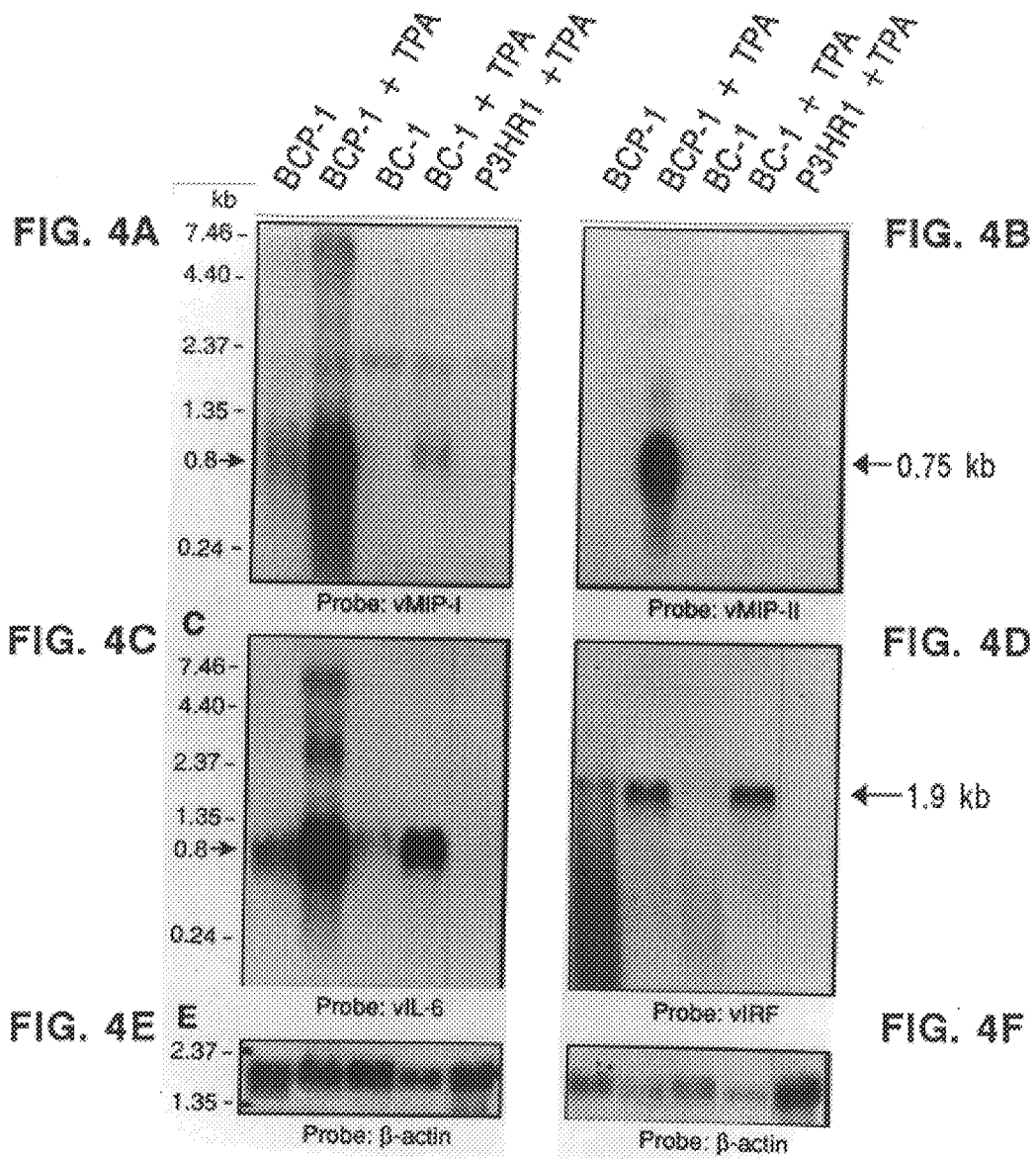

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
    ( A ) LENGTH: 210 amino acids
    ( B ) TYPE: amino acid
    ( D ) TOPOLOGY: linear ( i i ) MOLECULE TYPE: protein ( x i ) SEQUENCE DESCRIPTION: SEQ ID NO:1:

```
Met Asp Pro Thr Leu Tyr Cys Val Val Ala Val Asp Thr Lys Leu Gly
  1               5                  10                  15

Ile Gly Lys Asn Arg Cys Leu Pro Trp Pro Ala Leu Arg Gly Asp Met
                 20                  25                  30

Arg Arg Phe Arg Gln Leu Thr Thr Asp Cys Ala Pro Gly Lys Gln Asn
             35                  40                  45

Met Val Val Met Gly Arg Arg Thr Trp Leu Ser Ile Pro Ala Gly Cys
         50                  55                  60

Arg Pro Leu Ala Gly Arg Ile Asn Val Val Leu Ser Arg Thr Leu Glu
 65                  70                  75                  80

Thr Pro Pro Pro Gly Ala His Phe Leu Ala Ser Ser Leu Asp Ala Ala
                 85                  90                  95

Leu Gly Leu Ala Arg Ser Pro Glu Leu Ala Gln Gln Ile Asp Lys Val
             100                 105                 110
```

```
Trp  Val  Ile  Gly  Gly  Gly  Asp  Leu  Tyr  Arg  Glu  Ala  Leu  Thr  Gly  Pro
          115                      120                     125

Trp  Pro  Val  Arg  Leu  Phe  Leu  Thr  Arg  Val  Leu  His  Asp  Phe  Ala  Cys
     130                      135                     140

Asp  Val  Phe  Leu  Ser  His  Asp  Ser  Leu  Ala  Ala  Tyr  Ala  Arg  Val  Asn
145                           150                     155                     160

Pro  Lys  Pro  Gly  Glu  Gln  Glu  Arg  Val  Phe  Gln  Glu  Arg  Gly  Ile  Phe
                    165                      170                          175

Tyr  Met  Phe  Glu  Thr  Tyr  Ile  Lys  Val  Thr  Gln  Ser  Ser  Asp  Thr  Ala
               180                 185                          190

Leu  Pro  Asp  Leu  Glu  Arg  Pro  Arg  Pro  Ala  Thr  Pro  Pro  Phe  Ser  Glu
               195                 200                     205

Thr  Ser
     210
```

(2) INFORMATION FOR SEQ ID NO:2:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:2:

```
Thr  His  Tyr  Ser  Pro  Pro  Lys  Phe  Asp  Arg
1                   5                        10
```

(2) INFORMATION FOR SEQ ID NO:3:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO:3:

```
Pro  Asp  Val  Thr  Pro  Asp  Val  His  Asp  Arg
1                   5                        10
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:4:

AGCATATAAG GAACTCGGCG TTAC        24

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

( i i i ) HYPOTHETICAL: N ( i v ) ANTI-SENSE: N ( x i ) SEQUENCE DESCRIPTION: SEQ ID NO:5:

GGTAGATAAA TCCCCCCCCT TTG 23

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:6:

TGCATCAGCT TCTTCACCCA G 21

( 2 ) INFORMATION FOR SEQ ID NO:7:

( i ) SEQUENCE CHARACTERISTICS:
        ( A ) LENGTH:23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO: 7:

TGCTGTCTCG GTTACCAGAA AAG 23

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:8:

TCACGTCGCT CTTTACTTAT CGTG 24

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:9:

CGCCCTTCAG TGAGACTTCG TAAC 24

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:10:

CTTGCGATGA ACCATCCAGG 20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:11:

ACAACACCCA ATTCCCCGTC 20

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:12:

TCACGTCGCT CTTTACTTAT CGTG 24

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:13:

CGCCCTTCAG TGAGACTTCG TAAC 24

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:14:

```
AGCATATAAG GAACTCGGCG TTAC                                               24
```

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:15:

```
GGTAGATAAA CTCCCCCCCT TTG                                                23
```

( 2 ) INFORMATION FOR SEQ ID NO:16:

( i ) SEQUENCE CHARACTERISTICS:
        ( A ) LENGTH: 801 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( x i ) SEQUENCE DESCRIPTION: SEQ ID NO:16:

```
CGTGAACACC CCGCGCCCCG CGCCCCCCAC ACCGCGCCGC CCCTCCCCCT CCCCCCGCTC        60
GCCTCCCGGC GCTGCCGCCA GGCCCCGGCC GGAGCCGGCC GCCCGCGGGG GGCAGGGCGC       120
GCCCGGCGGC TCCCTCGCGG GGCGGGGGAC GGGGGAGGGG GGCGCCGGGC CCCCGCGCGC       180
CGCGGCAGCG GAGCGCGAGG GCCCCCGCCG GCCGCCAGCG GCGGCGCAGG CCCCGGGGGC       240
CCGAGCCCCG AGCGGGGCCG GGGTACGGGG CTAGGCCACG AATAATTTTT TTTTCGGGCG       300
GCCCCCCGAA CCTCTCTCGG CCCCCCGGTC CCCGCGGCCC GCGCGCGCCC CCCCGGGGGG       360
GTAAAACAGG GGGGGGGGA TGCGGCCGCG GCGGCGCCCG CGGCGGCGGC GGCGCTTGCT        420
TTCGTTTTCT CCCGCGGCCC CCCGGGCGCG AGCCGCGCGG CGGCGGCGGG CGCCCCCTCC       480
CCCGGGGGGC TCGGCGGGGG GCCCCCTGTC CCCGCGCGGG CCCGCGACCC CCGGCGCCGC       540
CGCGCCCCGA TCCCGCGGGC GCCCCGCCCC CCTGCCGGGG ACGCCGCCGG GCCTGCGGCG       600
CCTCCCGCCC GGGCATGGGG CCGCGCGCCG CCTCAGGGCC CGGCGCGGCC GGCGCCTGGT       660
CCCCGCCCCC GCCCGCGGGG GAACCCGGGC AGCGAGGGAA GGGGGCGCCC TCTCTCTACT       720
```

| | | | | | |
|---|---|---|---|---|---|
| GTGCGAGGAG | TCTGGGCTGC | TGTGTGTGAG | CCTGTTTGGG | GGAGCCTCCT | CAGTGCTTGC | 780 |
| TACGTGGAGC | CCTGGACACT | A | | | | 801 |

( 2 ) INFORMATION FOR SEQ ID NO:17:

( i ) SEQUENCE CHARACTERISTICS:
        ( A ) LENGTH: 35100 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

| | | | | | |
|---|---|---|---|---|---|
| TACTAATTTT | CAAAGGCGGG | GTTCTGCCAG | GCATAGTCTT | TTTTTCTGGC | GGCCCTTGTG | 60 |
| TAAACCTGTC | TTTCAGACCT | TGTTGGACAT | CCTGTACAAT | CAAGATGTTC | CTGTATGTTG | 120 |
| TCTGCAGTCT | GGCGGTTTGC | TTTCGAGGAC | TATTAAGCCT | TTCTCTGCTA | TCGTCTCCAA | 180 |
| ATTTGTGCCC | TGGAGTGATT | TCAACGCCTT | ACACGTTGAC | CTGTCTGTCT | AATGCATCCT | 240 |
| TGCCAATATC | CTGGTATTGC | AACAATACTC | GGCTTTTGCG | ACTGACGGAG | AGAAGAGTCA | 300 |
| TTCTTGACAC | CATTGCCTGC | AATTTTACTT | GTGTGGAACA | ATCTGGGCAT | CGACAGAGCA | 360 |
| TTTGGATTAC | ATGGCGTGCA | CAACCTGTCT | TACAAACCTT | GTGTGCACAG | CCATCAAACA | 420 |
| CAGTCACTTG | TGGTCAGCAT | GTTACTTTGT | ATTGTTCTAC | CTCTGGAAAT | AATGTTACCG | 480 |
| TTTGGCATCT | ACCAAACGGA | CGAAATGAAA | CCGTGTCACA | AACTAAATAC | TATAATTTTA | 540 |
| CGCTGATGAG | CCAAACTGAG | GGGTGTTATA | CTTGTTCTAA | CGGGCTGTCG | TCTCGCCTGT | 600 |
| CAAATCGTAT | ATGTTTTGG | GCGCGTTGTG | CCAATATAAC | TCCAGAAACT | CATACTGTAT | 660 |
| CTGTCAGCAG | TACTACAGGC | TTTAGAACAT | TGAGTACTAA | TAGCTTAGTG | AAGATAATCC | 720 |
| ATGCAACCAC | ACGTGATGTA | GTTGTAGTGA | AAGAAGCAAA | ATCTACACAT | TTTCATATTG | 780 |
| AAGTGCATTT | TCTTGTATTT | ATGACACTCG | TAGCTCTGAT | AGGAACCATG | TGTGGTATCT | 840 |
| TAGGAACTAT | TATCTTTGCC | CATTGTCAAA | ACAACGTGA | CTCAAACAAA | ACAGTGCCAC | 900 |
| AACAATTGCA | GGATTATTAT | TCCCTACACG | ATTTGTGCAC | GGAAGACTAT | ACGCAACCAG | 960 |
| TGGATTGGTA | CTGACATTCA | GGTAAGATAA | TCTAAATATT | CTCTATAACA | TAATTGTAAT | 1020 |
| GTGTTTTATG | TTTATAGCTA | CAAATGTTTT | ATGCAAAATA | CATTTTATGA | GGTCGGATAC | 1080 |
| TTATTAAAAG | CATTGTCTTA | AGTACATTAA | AAGGACATTG | TATAACCGTG | CTACTTACAG | 1140 |
| CATGGCCTTT | TTAAGACAAA | CACTGTGGAT | TTTATGGACA | TTTACCATGG | TTATTGGCCA | 1200 |
| GGACAATGAA | AAGTGTTCCC | AAAAAACCTT | AATTGGATAT | AGACTTAAAA | TGTCTCGTGA | 1260 |
| CGGTGACATT | GCAGTTGGAG | AAACAGTGGA | ATTACGTTGT | AGATCTGGAT | ACACTACTTA | 1320 |
| TGCCCGCAAT | ATAACAGCAA | CATGTTTACA | AGGTGGGACG | TGGTCTGAAC | CAACGGCAAC | 1380 |
| ATGTAACAAA | AAGTCCTGTC | CAAACCCAGG | TGAAATACAA | AATGGAAAGG | TTATATTTCA | 1440 |
| TGGTGGACAA | GATGCCTTAA | AATATGGGGC | AAACATTTCA | TATGTTTGTA | ATGAAGGATA | 1500 |
| TTTTTTGGTT | GGTCAGAAT | ACGTGCGATA | TTGTATGATT | GGAGCATCTG | GCCAAATGGC | 1560 |
| GTGGTCATCT | TCTCCTCCTT | TTTGTGAAAA | AGAAAAGTGT | CACAGACCGA | AAATCAAAAA | 1620 |
| TGGAGATTTT | AAGCCTGATA | AAGATTATTA | TGAGTATAAT | GATGCAGTTC | ATTTTGAATG | 1680 |
| TAATGAAGGA | TATACTCTAG | TTGGACCACA | TTCCATTGCA | TGTGCAGTTA | ATAACACGTG | 1740 |
| GACATCTAAC | ATGCCAACCT | GTGAACTCGC | AGGCTGTAAA | TTTCCATCGG | TGACTCATGG | 1800 |
| TTATCCAATC | CAAGGTTTTT | CTCTTACTTA | TAAACATAAG | CAAAGTGTTA | CTTTTGCATG | 1860 |
| CAATGATGGA | TTTGTTCTCA | GAGGATCCCC | CACAATTACG | TGTAACGTTA | CTGAATGGGA | 1920 |

```
CCCACCACTT  CCTAAGTGTG  TTTTGGAAGA  TATAGATGAT  CCAAACAATT  CAAATCCTGG   1980
ACGTTTGCAT  CCAACACCCA  ATGAAAAACC  AAATGGTAAT  GTCTTTCAAC  GCTCAAACTA   2040
TACAGAACCT  CCAACAAAGC  CTGAAGACAC  CCATACAGCA  GCTACTTGTG  ATACCAACTG   2100
TGAACAGCCA  CCTAAAATCC  TGCCAACATC  CGAAGGTTTT  AATGAGACTA  CCACATCTAA   2160
TACAATTACA  AAACAATTAG  AGGATGAGAA  AACTATATCC  CAGCCAAATA  CACATATTAC   2220
ATCTGCCTTA  ACATCCATGA  AAGCGAAAGG  TAACTTTACC  AACAAGACCA  ATAACTCTAC   2280
TGATCTACAT  ATAGCGTCTA  CACCCACTTC  CAAGATGAT   GCTACGCCTT  CAATACCTAG   2340
TGTACAGACA  CCCAATTATA  ATACTAACGC  ACCGACACGT  ACACTAACGT  CTCTCCATAT   2400
TGAAGAAGGC  CCATCCAATT  CTACTACTTC  AGAAAAGGCC  ACTTCCTCTA  CTCTCTCACA   2460
CAACTCACAC  AAAAATGACA  CCGGAGGCAT  ATACACAACA  TTAAACAAAA  CAACACAGTT   2520
GCCATCCACT  AATAAACCTA  CAAACAGTCA  AGCCAAGAGT  TCCACTAAGC  CACGCGTTGA   2580
GACACACAAT  AAAACAACCA  GTAATCCTGC  CATTTCTTTA  ACAGATTCTG  CAGATGTGCC   2640
TCAGAGACCG  CGAGAACCAA  CACTCCCTCC  CATTTTCAGG  CCACCGGCGT  CTAAAAATCG   2700
CTATCTGGAA  AAGCAACTAG  TTATTGGACT  ACTAACCGCT  GTCGCCCTAA  CGTGTGGACT   2760
GATTACCTTA  TTTCACTATC  TGTTCTTTCG  TTAGCCTAGA  ACTTGCTCCA  GTGTTAGACA   2820
GGGCTATGAT  TGCTTCTCCA  CGCTGTCCAC  CTTAACACTT  CCCAATAACA  AATCCGGTAT   2880
GCAGCAGCGT  GACACTACTA  ATGTAACCTA  AAAAATGTGC  ATGTGGTATG  TATTGTACTA   2940
AAGATACCGA  CCAATACAAG  ACAACTAATA  TTAACCATAG  TGTGCGTTTC  TTTGTATAAA   3000
ATACGCGTGT  GGGAAAGCGA  CAGAAGGGGG  CGGCGTTTCC  ATATGAGGCC  AAGTGCATTG   3060
GCTATTTTAG  GGGCGGTGAC  CACGCACTAT  AGTGCGCGGT  GTGGCAGAAA  ATTCACACCG   3120
TATATAAACA  AGGAAAGGGG  ACTCTGCGCG  CTTAAGCGCC  AAGCCATTAT  ACACACGGGT   3180
TTTTTGTTGT  CTTGGCCAAT  CGTGTCTCCA  TGGCGCTAAA  GGGACCACAA  ACCCTCGAGG   3240
AAAATATTGG  GTCTGCGGCC  CCCACTGGTC  CCTGCGGGTA  CCTCTATGCC  TATCTGACAC   3300
ACAACTTCCC  CATAGGGGAA  GCCTCCCTGC  TGGGCAATGG  CTACCCGGAG  GCAAAAGTAT   3360
TTTCACTACC  TCTTTTGCAC  GGGCTCACAG  TGGAATCCGA  TTTCCCCTTA  AACGTAAAGG   3420
CGGTGCACAA  GAAAATCGAT  GCAACCACAG  CTTCTGTGAA  ATTAACTTCA  TACCACAGGG   3480
AGGCCATCGT  CTTTCATAAT  ACTCACTTAT  TTCAGCCAAT  CTTTCAAGGA  AAGGGACTGG   3540
AAAAGTTATG  TCGAGAGAGC  CGAGAGCTGT  TTGGATTTTC  AACGTTTGTT  GAGCAACAAC   3600
ACAAAGGGAC  GCTCTGGAGC  CCAGAGGCAT  GCCCTCAGCT  ACCCTGCGCG  AATGAGATTT   3660
TTATGGCGGT  CATAGTTACA  GAGGGATTCA  AGGAGAGACT  GTACGGCGGC  AAACTGGTGC   3720
CCGTGCCCTC  TCAGACAACG  CCCGTACACA  TTGGGGAACA  CCAGGCGTTC  AAGATACCCT   3780
TGTATGACGA  GGATCTGTTT  GGTCCAAGTC  GCGCCCAAGA  ACTATGTAGG  TTTTACAACC   3840
CCGATATCAG  TAGATACCTA  CATGACTCCA  TATTCACTGG  AATAGCACAG  GCTCTAAGGG   3900
TAAAGGACGT  TAGCACGGTC  ATCCAAGCCT  CAGAAAGGCA  ATTTGTGCAC  GACCAATACA   3960
AGATACCAAA  GCTGGTCCAA  GCCAAGGACT  TCCCCCAGTG  TGCTTCCAGG  GGAACCGACG   4020
GGTCTACCCT  AATGGTGATA  GACAGTCTGG  TGGCTGAACT  TGGTATGAGT  TATGGTCTGT   4080
CCTTTATTGA  GGGACCCCAG  GATAGCTGCG  AGGTTCTAAA  TTATGACACG  TGGCCCATCT   4140
TTGAAAACTG  CGAGACGCCA  GATGCCCGCC  TTCGTGCACT  AGAAGTTTGG  CACGCAGAGC   4200
AGGCCTTGCA  TATTGGCGCC  CAGCTGTTTG  CGGCCAACTC  TGTGCTCTAC  CTGACCAGAG   4260
TGGCAAAGCT  GCCTCAGAAG  AATCAGAGAG  GAGACGCCAA  CATGTACAAC  TCATTCTACC   4320
```

```
TACAGCATGG  CCTGGGATAC  CTCTCAGAGG  CAACAGTAAA  GGAAAATGGA  GCCTCTGCCT  4380
TCAAGGGCGT  GCCAGTGTCT  GCACTGGATG  GGTCATCTTA  CACCCTCCAG  CACCTGGCCT  4440
ACGCGTCCTC  TTTCTCCCCA  CATCTCCTGG  CAAGGATGTG  TTACTATCTG  CAGTTCTTGC  4500
CCCACCATAA  AAACACCAAC  AGTCAGTCAT  ACAATGTGGT  GGACTACGTG  GGCACCGCGG  4560
CACCTAGTCA  AATGTGTGAC  CTGTGTCAGG  GGCAATGTCC  AGCTGTATGC  ATCAACACGC  4620
TGTTTTACAG  GATGAAGGAC  AGGTTCCCAC  CTGTTCTGTC  AAACGTTAAG  AGAGACCCAT  4680
ATGTGATCAC  GGGCACAGCG  GGAACGTACA  ATGACCTAGA  GATTCTCGGA  AACTTTGCCA  4740
CCTTCAGGGA  GAGAGAGGAG  GAGGGGAATC  CTGTGGAAGA  TGCTCCAAAG  TATACATATT  4800
GGCAACTATG  CCAGAATATA  ACCGAGAAGC  TAGCGTCCAT  GGGCATCTCG  GAGGGCGGCG  4860
ATGCCCTAAG  AACCCTCATT  GTGGACATCC  CCAGCTTCGT  CAAAGTGTTC  AAGGGGATAG  4920
ACAGCACGGT  AGAGGCAGAG  CTCCTAAAGT  TTATTAACTG  CATGATCAAA  AACAATTACA  4980
ACTTCAGAGA  GAACATCAAA  TCCGTCCATC  ACATCCTTCA  GTTTGCATGC  AACGTATACT  5040
GGCAGGCGCC  GTGCCCGGTT  TTTCTGACCC  TTTACTACAA  GTCACTGCTG  ACGGTCATAC  5100
AGGACATATG  TCTGACGTCA  TGTATGATGT  ACGAGCAGGA  CAACCCGGCC  GTGGGAATTG  5160
TACCATCCGA  GTGGCTTAAA  ATGCACTTTC  AGACAATGTG  GACCAACTTC  AAGGGTGCCT  5220
GCTTCGACAA  AGGAGCAATC  ACGGGCGGGG  AACTAAAAAT  AGTCCACCAG  TCCATGTTCT  5280
GTGACCTCTT  TGACACCGAC  GCTGCCATAG  GAGGGATGTT  TGCACCCGCT  CGGATGCAGG  5340
TCAGGATAGC  CAGAGCAATG  CTCATGGTTC  CAAAAACCAT  AAAAATAAAA  AACAGGATCA  5400
TCTTTTCCAA  CTCCACCGGA  GCAGAGTCGA  TCCAGGCAGG  TTTTATGAAG  CCGGCCAGCC  5460
AAAGGGATTC  ATACATCGTC  GGAGGACCCT  ACATGAAATT  CCTAAACGCC  CTGCACAAAA  5520
CACTTTTTCC  TTCCACAAAA  ACTTCTGCCC  TGTACTTGTG  GCATAAGATT  GGCCAGACCA  5580
CAAAAAATCC  CATACTACCA  GGTGTCTCGG  GGGAACACCT  AACGGAGTTA  TGTAATTATG  5640
TAAAGGCAAG  TAGCCAGGCT  TTCGAAGAGA  TAAATGTTTT  GGACCTTGTG  CCAGACACCC  5700
TGACATCATA  TGCGAAAATA  AAACTAAACA  GTTCCATTCT  CCGGGCTTGC  GGACAGACAC  5760
AGTTTTATGC  AACTACTCTC  TCTTGCCTTT  CGCCAGTGAC  TCAGCTGGTT  CCGGCCGAGG  5820
AGTACCCCCA  CGTACTGGGG  CCAGTGGGGT  TGTCATCTCC  AGATGAATAC  AGGGCAAAAG  5880
TCGCCGGCAG  GTCTGTAACC  ATTGTACAGT  CAACACTGAA  GCAAGCTGTT  TCCACCAACG  5940
GACGACTCCG  GCCTATCATT  ACCGTGCCAC  TGGTGGTCAA  CAAATATACA  GGGAGCAACG  6000
GGAACACAAA  CGTCTTTCAC  TGTGCAAACC  TGGGATACTT  CTCGGGGAGA  GGGGTGGACA  6060
GAAATCTCAG  GCCAGAAAGC  GTCCCCTTTA  AAAAGAATAA  TGTCAGCTCT  ATGCTAAGAA  6120
AACGCCACGT  GATTATGACC  CCCCTGGTAG  ACAGGCTGGT  AAAGAGAATA  GTTGGCATCA  6180
ACTCTGGGGA  ATTCGAGGCA  GAAGCGGTTA  AGAGAAGTGT  GCAGAATGTC  CTGGAAGACA  6240
GAGATAACCC  AAACCTGCCG  AAGACAGTTG  TATTAGAGTT  GGTTAAGCCA  CCTCGGTGGA  6300
GCTCCTGTGC  AAGTCTCACA  GAGGAGGACG  TGATTTACTA  CCTGGGCCCT  TATGCCGTAC  6360
TTGGGGACGA  GGTCCTGTCA  TTACTGAGCA  CAGTGGGCCA  GGCGGGGTG  CCATGGACGG  6420
CCGAGGGTGT  GGCCTCGGTC  ATCCAGGACA  TAATAGATGA  TTGCGAGTTA  CAGTTTGTGG  6480
GCCCAGAAGA  GCCTTGCCTT  ATCCAAGGAC  AGTCGGTAGT  GGAGGAGCTT  TTTCCGTCCC  6540
CGGGCGTCCC  AAGCCTGACA  GTGGGTAAAA  AACGAAAAAT  CGCATCCCTG  CTCTCTGACC  6600
TGGATTTGTA  GTTGTGTACC  CGTAACGATG  GCAAAGGAAC  TGGCGGCGGT  CTATGCCGAT  6660
GTGTCAGCCC  TAGCCATGGA  CCTCTGTCTT  CTTAGTTACG  CAGACCCGGC  AACACTGGAC  6720
```

```
ACTAAAAGTC  TGGCCCTCAC  TACAGGGAAG  TTTCAGAGCC  TTCACGGCAC  ACTACTCCCC    6780
CTCCTCAGAC  GACAAAACGC  ACACGAATGC  TCAGGTCTGT  CACTAGAATT  GGAGCACTTT    6840
TGGAAAACGT  GGCTGATGCT  CTGGCCACGT  TGGGAGTGTG  CACTAGCAGA  AAACTGTCTC    6900
CAGAAGAGCA  TTTTTCCCTC  CTGCATTTGG  ACACAACATG  CAACAAGCAA  CCGGAGCGTT    6960
AGGTTTAATT  TTTACGGAAA  TTGGGCCTTG  GAGTTAAAGC  TGTCACTAAT  AAACGACGTT    7020
GAAATTTTCT  TTAAACGTCT  TAGTAGCGTT  TTTTATTGTA  TAGGATCGGG  CAGTGCTCTG    7080
GAGGGTTTAG  GGGAGGTATT  GCGTTTCGTT  GGGAAGCTGA  GGGGTATCTC  ACCCGTACCT    7140
GGGCCGGACC  TATATGTCTC  AAATCTGCCC  TGCCTAGAAT  GCCTTCAGGA  AGTGTGTCTG    7200
ACTCCCAACC  AGGGCACCAG  TCTGCAGGCC  ATGCTCCCAG  ACACGGCCTG  CAGTCACATA    7260
TGTACCCCCG  CATGCGGTGA  GCCTGTCCGG  GGCCTCTTTG  AGAACGAGCT  AAAACAGCTC    7320
GGGCTTCAAA  CCCCTGAGTC  CATACCTACT  ACCCCTGTC   AGTCCCGGGT  AAGGCAAGAT    7380
GATGAAATCA  GACAGAGCTC  TCTAATGGCG  GTAGGAGATC  ACCACATTTT  CGGAGAGGTG    7440
ACCAGATCTG  TCCTGGAAAT  CTCAAACCTG  ATCTATTGGA  GCTCTGGCCA  CTCGGATGCC    7500
ACCTGCGACG  GAGACAGAGA  CTGCTCTCAC  CTGGCCTCGC  TGTTTACTCA  CGAGGCTGAC    7560
ATGCATAAAA  GGCGCGTCGA  CCTGGCCGGA  TGCTTGGGCG  AACGCGGCAC  GCCCAAACAC    7620
TTTTTTGACT  GCTTTCGCCC  AGACTCCCTA  GAAACCCTTT  TCTGTGGTGG  TCTTTTTAGC    7680
TCCGTGGAGG  ACACCATAGA  AAGTCTCCAA  AAGGACTGCT  CTTCTGCCTT  CTACCAACAG    7740
GTAAACTACA  CTACTGCACT  GCAAAAACAG  AACGAGTTTT  ACGTCCGACT  CAGCAAACTG    7800
CTGGCAGCTG  GTCAGCTAAA  TTTGGGCAAA  TGTTCCACTG  AAAGTTGCCA  ATCCGAGGCC    7860
CGTAGGCAGC  TGGTAGGTGG  GGGCAAACCA  GAGGAAGTGC  TGAGGGATGC  AAAACACCGG    7920
CAAGAACTAT  ACCTTCAGAA  AGTGGCACGC  GACGGTTTTA  AAAAACTCTC  TGATTGTATA    7980
AGACACCAGG  GCCACATCCT  GTCTCAGACC  CTGGGTCTAA  GACTGTGGGG  GTCTGTCATC    8040
TACAACGAGG  CATCTGCCCT  ACAAAACCAC  TTTTTACACA  GAGCACAGTT  CATATCCCTC    8100
CCCTGGCAGG  ACCTGACGGT  CGACTGTCCA  ACGCGGTTTG  AAAATTCTAA  ATATATCAAA    8160
AATTCTCTGT  ACTGCCAGCG  TCTGGGGCGG  GAACACGTAG  AGATCCTGAC  ACTGGAGTTC    8220
TACAAACTTA  TCACGGGCCC  GCTGTCAAAG  CGACATACTT  TATTTCCCAG  TCCTCCAAAT    8280
GTGACGCTGG  CTCAGTGCTT  CGAGGCTGCG  GGCATGCTTC  CCCATCAAAA  GATGATGGTA    8340
TCAGAGATGA  TCTGGCCCAG  CATAGAGCCG  AAGGACTGGA  TAGAGCCCAA  CTTCAACCAG    8400
TTCTATAGCT  TTGAGAATCA  AGACATAAAC  CATCTGCAAA  AGAGAGCTTG  GGAATATATC    8460
AGAGAGCTGG  TATTATCGGT  TTCTCTGTAC  AACAGAACTT  GGGAGAGGGA  GCTAAAAATA    8520
CTTCTCACGC  CTCAGGGCTC  ACCGGGGTTT  GAGGAACCGA  AACCCGCAGG  ACTCACAACG    8580
GGGCTGTACC  TAACATTTGA  GACATCTGCG  CCCTTGGTGT  TGGTGGATAA  AAAATATGGC    8640
TGGATATTTA  AAGACCTGTA  CGCCCTTCTG  TACCACCACC  TGCAACTGAG  CAACCACAAT    8700
GACTCCCAGG  TCTAGATTGG  CCACCCTGGG  GACTGTCATC  CTGTTGGTCT  GCTTTTGCGC    8760
AGGCGCGGCG  CACTCGAGGG  GTGACACCTT  TCAGACGTCC  AGTTCCCCCA  CACCCCCAGG    8820
ATCTTCCTCT  AAGGCCCCCA  CCAAACCTGG  TGAGGAAGCA  TCTGGTCCTA  AGAGTGTGGA    8880
CTTTTACCAG  TTCAGAGTGT  GTAGTGCATC  GATCACCGGG  GAGCTTTTC   GGTTCAACCT    8940
GGAGCAGACG  TGCCCAGACA  CCAAAGACAA  GTACCACCAA  GAAGGAATTT  TACTGGTGTA    9000
CAAAAAAAAC  ATAGTGCCTC  ATATCTTTAA  GGTGCGGCGC  TATAGGAAAA  TTGCCACCTC    9060
TGTCACGGTC  TACAGGGGCT  TGACAGAGTC  CGCCATCACC  AACAAGTATG  AACTCCCGAG    9120
```

| | | | | | | |
|---|---|---|---|---|---|---|
| ACCCGTGCCA | CTCTATGAGA | TAAGCCACAT | GGACAGCACC | TATCAGTGCT | TTAGTTCCAT | 9180 |
| GAAGGTAAAT | GTCAACGGGG | TAGAAAACAC | ATTTACTGAC | AGAGACGATG | TTAACACCAC | 9240 |
| AGTATTCCTC | CAACCAGTAG | AGGGGCTTAC | GGATAACATT | CAAAGGTACT | TTAGCCAGCC | 9300 |
| GGTCATCTAC | GCGGAACCCG | GCTGGTTTCC | CGGCATATAC | AGAGTTAGGA | CCACTGTCAA | 9360 |
| TTGCGAGATA | GTGGACATGA | TAGCCAGGTC | TGCTGAACCA | TACAATTACT | TTGTCACGTC | 9420 |
| ACTGGGTGAC | ACGGTGGAAG | TCTCCCCTTT | TTGCTATAAC | GAATCCTCAT | GCAGCACAAC | 9480 |
| CCCCAGCAAC | AAAAATGGCC | TTAGCGTCCA | AGTAGTTCTC | AACCACACTG | TGGTCACGTA | 9540 |
| CTCTGACAGA | GGAACCAGTC | CCACTCCCCA | AAACAGGATC | TTTGTGGAAA | CGGGAGCGTA | 9600 |
| CACGCTTTCG | TGGGCCTCCG | AGAGCAAGAC | CACGGCCGTG | TGTCCGCTGG | CACTGTGGAA | 9660 |
| AACCTTCCCG | CGCTCCATCC | AGACTACCCA | CGAGGACAGC | TTCCACTTTG | TGGCCAACGA | 9720 |
| GATCACGGCC | ACCTTCACGG | CTCCTCTAAC | GCCAGTGGCC | AACTTTACCG | ACACGTACTC | 9780 |
| TTGTCTGACC | TCGGATATCA | ACACCACGCT | AAACGCCAGC | AAGGCCAAAC | TGGCGAGCAC | 9840 |
| TCACGTCCCT | AACGGGACGG | TCCAGTACTT | CCACACAACA | GGCGGACTCT | ATTTGGTCTG | 9900 |
| GCAGCCCATG | TCCGCGATTA | ACCTGACTCA | CGCTCAGGGC | GACAGCGGGA | ACCCCACGTC | 9960 |
| ATCGCCGCCC | CCCTCCGCAT | CCCCCATGAC | CACCTCTGCC | AGCCGCAGAA | AGAGACGGTC | 10020 |
| AGCCAGTACC | GCTGCTGCCG | GCGGCGGGGG | GTCCACGGAC | AACCTGTCTT | ACACGCAGCT | 10080 |
| GCAGTTTGCC | TACGACAAAC | TGCGGGATGG | CATTAATCAG | GTGTTAGAAG | AACTCTCCAG | 10140 |
| GGCATGGTGT | CGCGAGCAGG | TCAGGGACAA | CCTAATGTGG | TACGAGCTCA | GTAAAATCAA | 10200 |
| CCCCACCAGC | GTTATGACAG | CCATCTACGG | TCGACCTGTA | TCCGCCAAGT | TCGTAGGAGA | 10260 |
| CGCCATTTCC | GTGACCGAGT | GCATTAACGT | GGACCAGAGC | TCCGTAAACA | TCCACAAGAG | 10320 |
| CCTCAGAACC | AATAGTAAGG | ACGTGTGTTA | CGCGCGCCCC | CTGGTGACGT | TTAAGTTTTT | 10380 |
| GAACAGTTCC | AACCTATTCA | CCGGCCAGCT | GGGCGCGCGC | AATGAGATAA | TACTGACCAA | 10440 |
| CAACCAGGTG | GAAACCTGCA | AAGACACCTG | CGAACACTAC | TTCATCACCC | GCAACGAGAC | 10500 |
| TCTGGTGTAT | AAGGACTACG | CGTACCTGCG | CACTATAAAC | ACCACTGACA | TATCCACCCT | 10560 |
| GAACACTTTT | ATCGCCCTGA | ATCTATCCTT | TATTCAAAAC | ATAGACTTCA | AGGCCATCGA | 10620 |
| GCTGTACAGC | AGTGCAGAGA | AACGACTCGC | GAGTAGCGTG | TTTGACCTGG | AGACGATGTT | 10680 |
| CAGGGAGTAC | AACTACTACA | CACATCGTCT | CGCGGGTTTG | CGCGAGGATC | TGGACAACAC | 10740 |
| CATAGATATG | AACAAGGAGC | GCTTCGTAAG | GGACTTGTCG | GAGATAGTGG | CGGACCTGGG | 10800 |
| TGGCATCGGA | AAAACGGTGG | TGAACGTGGC | CAGCAGCGTG | GTCACTCTAT | GTGGCTCATT | 10860 |
| GGTTACCGGA | TTCATAAATT | TTATTAAACA | CCCCCTAGGT | GGCATGCTGA | TGATCATTAT | 10920 |
| CGTTATAGCA | ATCATCCTGA | TCATTTTTAT | GCTCAGTCGC | CGCACCAATA | CCATAGCCCA | 10980 |
| GGCGCCGGTG | AAGATGATCT | ACCCCGACGT | AGATCGCAGG | GCACCTCCTA | GCGGCGGAGC | 11040 |
| CCCAACACGG | GAGGAAATCA | AAAACATCCT | GCTGGGAATG | CACCAGCTAC | AACAAGAGGA | 11100 |
| GAGGCAGAAG | GCGGATGATC | TGAAAAAAAG | TACACCCTCG | GTGTTTCAGC | GTACCGCAAA | 11160 |
| CGGCCTTCGT | CAGCGTCTGA | GAGGATATAA | ACCTCTGACT | CAATCGCTAG | ACATCAGTCC | 11220 |
| GGAAACGGGG | GAGTGACAGT | GGATTCGAGG | TTATTGTTTG | ATGTAAATTT | AGGAAACACG | 11280 |
| GCCCGCCTCT | GAAGCACCAC | ATACAGACTG | CAGTTATCAA | CCCTACTCGT | TGCACACAGA | 11340 |
| CACAAATTAC | CGTCCGCAGA | TCATGGATTT | TTTCAATCCA | TTTATCGACC | CAACTCGCGG | 11400 |
| AGGCCCGAGA | AACACTGTGA | GGCAACCCAC | GCCGTCACAG | TCGCCAACTG | TCCCCTCGGA | 11460 |
| GACAAGAGTA | TGCAGGCTTA | TACCGGCCTG | TTTCCAAACC | CCGGGGCGAC | CCGGCGTGGT | 11520 |

```
TGCCGTGGAC  ACCACATTTC  CACCCACCTA  CTTCCAGGGC  CCCAAGCGGG  GAGAAGTATT  11580
CGCGGGAGAG  ACTGGGTCTA  TCTGGAAAAC  AAGGCGCGGA  CAGGCACGCA  ATGCTCCTAT  11640
GTCGCACCTC  ATATTCCACG  TATACGACAT  CGTGGAGACC  ACCTACACGG  CCGACCGCTG  11700
CGAGGACGTG  CCATTTAGCT  TCCAGACTGA  TATCATTCCC  AGCGGCACCG  TCCTCAAGCT  11760
GCTCGGCAGA  ACACTAGATG  GCGCCAGTGT  CTGCGTGAAC  GTTTTCAGGC  AGCGCTGCTA  11820
CTTCTACACA  CTAGCACCCC  AGGGGGTAAA  CCTGACCCAC  GTCCTCCAGC  AGGCCCTCCA  11880
GGCTGGCTTC  GGTCGCGCAT  CCTGCGGCTT  CTCCACCGAG  CCGGTCAGAA  AAAAAATCTT  11940
GCGCGCGTAC  GACACACAAC  AATATGCTGT  GCAAAAAATA  ACCCTGTCAT  CCAGTCCGAT  12000
GATGCGAACG  CTTAGCGACC  GCCTAACAAC  CTGTGGGTGC  GAGGTGTTTG  AGTCCAATGT  12060
GGACGCCATT  AGGCGCTTCG  TGCTGGACCA  CGGGTTCTCG  ACATTCGGGT  GGTACGAGTG  12120
CAGCAATCCG  GCCCCCCGCA  CCCAGGCCAG  AGACTCTTGG  ACGGAACTGG  AGTTTGACTG  12180
CAGCTGGGAG  GACCTAAAGT  TTATCCCGGA  GAGGACGGAG  TGGCCCCCAT  ACTCAATCCT  12240
ATCCTTTGAT  ATAGAATGTA  TGGGCGAGAA  GGGTTTTCCC  AACGCGACTC  AAGACGAGGA  12300
CATGATTATA  CAAATCTCGT  GTGTTTTACA  CACAGTCGGC  AACGATAAAC  CGTACACCCG  12360
CATGCTACTG  GGCCTGGGGA  CATGCGACCC  CCTTCCTGGG  GTGGAGGTCT  TTGAGTTTCC  12420
TTCGGAGTAC  GACATGCTGG  CCGCCTTCCT  CAGCATGCTC  CGCGATTACA  ATGTGGAGTT  12480
TATAACGGGG  TACAACATAG  CAAACTTTGA  CCTTCCATAC  ATCATAGCCC  GGGCAACTCA  12540
GGTGTACGAC  TTCAAGCTGC  AGGACTTCAC  CAAAATAAAA  ACTGGGTCCG  TGTTTGAGGT  12600
CCACCAACCC  AGAGGCGGTT  CCGATGGGGG  CAACTTCATG  AGGTCCCAGT  CAAAGGTCAA  12660
AATATCGGGG  ATCGTCCCCA  TAGACATGTA  CCAGGTTTGC  AGGGAAAAGC  TGAGTCTGTC  12720
AGACTACAAG  CTGGACACAG  TGGCTAAGCA  ATGCCTCGGT  CGACAAAAAG  ATGACATCTC  12780
ATACAAGGAC  ATACCCCCGC  TTTTTAAATC  TGGGCCTGAT  GGTCGCGCAA  AGGTGGGAAA  12840
CTACTGTGTT  ATTGACTCGG  TCCTGGTTAT  GGATCTTCTG  CTACGGTTTC  AGACCCATGT  12900
TGAGATCTCG  GAAATAGCCA  AGCTGGCCAA  GATCCCCACC  CGTAGGGTAC  TGACGGACGG  12960
CCAACAGATC  AGGGTATTTT  CCTGCCTCTT  GGAGGCTGCT  GCCACGGAAG  GTTACATTCT  13020
CCCCGTCCCA  AAAGGAGACG  CGGTTAGCGG  GTATCAGGGG  GCCACTGTAA  TAAGCCCCTC  13080
TCCGGGATTC  TATGACGACC  CCGTACTCGT  GGTGGATTTT  GCCAGCTTGT  ACCCCAGTAT  13140
CATCCAAGCG  CACAACTTGT  GCTACTCCAC  ACTGATACCC  GGCGATTCGC  TCCACCTGCA  13200
CCCACACCTC  TCCCCGGACG  ACTACGAAAC  CTTTGTCCTC  AGCGGAGGTC  CGGTCCACTT  13260
TGTAAAAAAA  CACAAAAGGG  AGTCCCTTCT  TGCCAAGCTT  CTGACGGTAT  GGCTCGCGAA  13320
GAGAAAAGAA  ATAAGAAAGA  CCCTGGCATC  ATGCACGGAC  CCCGCACTGA  AAACTATTCT  13380
AGACAAACAA  CAACTGGCCA  TCAAGGTTAC  CTGCAACGCC  GTTTACGGCT  TCACGGGCGT  13440
TGCCTCTGGC  ATACTGCCTT  GCCTAAACAT  AGCGGAGACC  GTGACACTAC  AAGGGCGAAA  13500
GATGCTGGAG  AGATCTCAGG  CCTTTGTAGA  GGCCATCTCG  CCGGAACGCC  TAGCGGGTCT  13560
CCTGCGGAGG  CCAATAGACG  TCTCACCCGA  CGCCCGATTC  AAGGTCATAT  ACGGCGACAC  13620
TGACTCTCTT  TTCATATGCT  GCATGGGTTT  CAACATGGAC  AGCGTGTCAG  ACTTCGCGGA  13680
GGAGCTAGCG  TCAATCACCA  CCAACACGCT  GTTTCGTAGC  CCCATCAAGC  TGGAGGCTGA  13740
AAAGATCTTC  AAGTGCCTTC  TGCTCCTGAC  TAAAAGAGA   TACGTGGGGG  TACTCAGTGA  13800
CGACAAGGTT  CTGATGAAGG  GCGTAGACCT  CATTAGGAAA  ACAGCCTGTC  GTTTTGTCCA  13860
GGAAAAGAGC  AGTCAGGTCC  TGGACCTCAT  ACTGCGGGAG  CCGAGCGTCA  AGGCCGCGGC  13920
```

| | | | | | | |
|---|---|---|---|---|---|---|
| CAAGCTTATT | TCGGGGCAGG | CGACAGACTG | GGTGTACAGG | GAAGGGCTCC | CAGAGGGGTT | 13980 |
| CGTCAAGATA | ATTCAAGTGC | TCAACGCGAG | CCACCGGGAA | CTGTGCGAAC | GCAGCGTACC | 14040 |
| AGTAGACAAA | CTGACGTTTA | CCACCGAGCT | AAGCCGCCCG | CTGGCGGACT | ACAAGACGCA | 14100 |
| AAACCTCCCG | CACCTGACCG | TGTACCAAAA | GCTACAAGCT | AGACAGGAGG | AGCTTCCACA | 14160 |
| GATACACGAC | AGAATCCCCT | ACGTGTTCGT | CGACGCCCCA | GGTAGCCTGC | GCTCCGAGCT | 14220 |
| GGCAGAGCAC | CCCGAGTACG | TTAAGCAGCA | CGGACTGCGC | GTGGCGGTGG | ACCTGTACTT | 14280 |
| CGACAAGCTG | GTACACGCGG | TAGCCAACAT | CATCCAATGC | CTCTTCCAGA | ACAACACGTC | 14340 |
| GGCAACCGTA | GCTATGTTGT | ATAACTTTTT | AGACATTCCC | GTGACTTTTC | CCACGCCCTA | 14400 |
| GTGACTCAGA | CGCGGAAACA | GCGCCTAGAA | AGTTTCCTCT | TGCGCTATGT | GGGACAACTA | 14460 |
| GAGTCCAACC | TGGCAAGCAG | TGGAGCAAGA | CGCCAGACAG | CCGATCTCGA | AAAAAATAAT | 14520 |
| GCAGACAGAG | GCAACGTTCA | TCCTAGGTGA | CTGGGAGATA | ACGGTGTCTA | ACTGCCGGTT | 14580 |
| TACTTGCAGC | AGCCTAACAT | GTGGCCCCCT | TTACAGATCT | AGCGGCGACT | ACACGCGGCT | 14640 |
| AAGAATCCCC | TTCTCTCTGG | ATCGACTAAT | ACGTGACCAT | GCCATCTTTG | GGCTAGTGCC | 14700 |
| AAATATTGAG | GATCTGTTAA | CCCATGGGTC | ATGCGTCGCC | GTAGTGGCCG | ACGCAAACGC | 14760 |
| CACAGGCGGC | AACGCGCGAC | GCATCGTCGC | GCCTGGCGTG | ATAAACAATT | TTTCAGAACC | 14820 |
| CATCGGCATT | TGGGTACGCG | GCCCTCCGCC | GCAAACGCGC | AAGGAAGCTA | TTAAGTTCTG | 14880 |
| CATATTTTTT | GTCAGTCCCC | TGCCCCCGCG | GGAGATGACC | ACATATGTGT | TCAAGGGCGG | 14940 |
| CGATTTGCCT | CCCGGAGCAG | AGGAACCCGA | AACACTACAC | TCCGCCGAGG | CACCCCTACC | 15000 |
| GTCGCGCGAG | ACGCTGGTAA | CTGGACAGCT | GCGATCCACC | TCGCCGCGAA | CGTATACGGG | 15060 |
| ATACTTTCAC | AGTCCTGTCC | CGCTCTCTTT | TTTGGACCTC | CTGACATTCG | AGTCCATTGG | 15120 |
| GTGTGACAAC | GTGGAAGGTG | ACCCCGAGCA | ATTGACACCC | AAGTACTTGA | CGTTCACGCA | 15180 |
| GACGGGAGAA | AGACTTTGCA | AAGTAACCGT | TTACAACACC | CATTCGACAG | CATGCAAGAA | 15240 |
| GGCCCGTGTT | CGTTTCGTCT | ACAGACCGAC | GCCGTCCGCC | CGTCAGCTTG | TCATGGGTCA | 15300 |
| GGCTTCACCC | CTCATAACAA | CCCCTCTGGG | AGCCAGGGTA | TTCGCAGTCT | ATCCAGACTG | 15360 |
| TGAGAAAACT | ATCCCACCTC | AGGAAACCAC | CACCCTGAGG | ATTCAATTGC | TGTTCGAGCA | 15420 |
| GCATGGTGCC | AACGCCGGAG | ACTGCGCCTT | TGTCATCATG | GGGCTCGCCC | GTGAAACAAA | 15480 |
| GTTTGTCTCA | TTTCCCGCAG | TACTCCTTCC | GGGCAAGCAC | GAACACCTTA | TTGTATTCAA | 15540 |
| CCCACAGACA | CATCCTCTGA | CCATTCAACG | GGACACAATA | GTGGGCGTGG | CAATGGCTTG | 15600 |
| CTATATCCAC | CCCGGTAAGG | CAGCCAGCCA | GGCACCATAC | AGCTTCTACG | ACTGCAAGGA | 15660 |
| AGAGAGCTGG | CACGTGGGGC | TCTTCCAGAT | CAAACGCGGA | CCGGGAGGGG | TCTGTACACC | 15720 |
| ACCTTGCCAC | GTAGCGATTA | GGGCCGACCG | CCACGAGGAA | CCCATGCAAT | CGTGACTGTC | 15780 |
| CGAGCACATA | TGGCGCAGGA | GTCAGAGCAG | TGCTCCCGTG | CGTTTGCAGT | GTGCAGTAGT | 15840 |
| AAACGACAGC | TCGGGCGCGG | CGAGCCCGTG | TGGGATTCCG | TCATTCACCC | GAGCCACATC | 15900 |
| GTCATCTCTA | ATCGAGTACC | CCTCTTACTA | AGAGAACAGC | ACATATGTCT | CCCTTCGTGC | 15960 |
| CCCAGCGTCG | GCCAGATCCT | CCACAGAGCC | TACCCCAACT | TTACATTTGA | CAACACGCAC | 16020 |
| CGCAAGCAGC | AAACGGAGAC | CTACACTGCA | TTCTACGCTT | TTGGGGACCA | AAATAACAAG | 16080 |
| GTTAGGATCT | TGCCCACTGT | TGTGGAAAGC | TCCTCGAGCG | TGCTGATTTT | TAGACTGCGT | 16140 |
| GCATCGGTCT | CTGCGAACAT | CGCCGTGGGA | GGGCTCAAAA | TAATAATACT | TGCTCTCACC | 16200 |
| CTGGTGCATG | CCCAAGGAGT | GTACCTGCGT | TGCGGTAAGG | ACCTTTCTAC | ACCACACTGC | 16260 |
| GCACCGGCTA | TTGTTCAGCG | TGAGGTGCTG | AGCAGCGGGT | TTGAGCCGCA | GTTTACCGTA | 16320 |

| | | | | | | |
|---|---|---|---|---|---|---|
| ACTGGCATTC | CAGTGACATC | CTCGAACTTA | AACCAATGCT | ACTTTCTGGT | AAGAAAGCCA | 16380 |
| AAAAGCCGGC | TGGCAAAGCC | GTTTGCACGC | CTGTCCGCGG | AGACGACTGA | GGAGTGTCGC | 16440 |
| GTCAGGTCTA | TCCGCCTTGG | GAAGACACAC | CTGCGGATAT | CGGTGACTGC | GCCTGCGCAG | 16500 |
| GAAACGCCCG | TCTGGGGGCT | CGTGACCACG | AGCTTCAGCC | TTACCCCCAC | CGCACCGCTG | 16560 |
| GCCTTTGATC | GTAACCCGTA | CAATCACGAG | ACATTTGCCT | GTAATGCCAA | GCACTACATC | 16620 |
| CCAGTCATCT | ACAGCGGACC | AAAAATTACG | CTGGCCCCGC | GCGGCCGCCA | GGTAGTCTGG | 16680 |
| CACAACAACA | GCTACACGTC | CTCCCTGCCA | TGCAAAGTCA | CAGCCATCGT | GTCAAACCAC | 16740 |
| TGCTGTAACT | GTGACATATT | TTTAGAGGAC | TCGGAATGGC | GCCCAAACAA | GCCAGCACCC | 16800 |
| CTGAAACTGG | TGAACACGAG | TGATCATCCC | GTCATATTGG | AGCCGGACAC | ACACATTGGA | 16860 |
| AACGCCCTCT | TCATCATCGC | ACCCAAGGCC | CGAGGTTTAC | GCAGACTGAC | TCGCTTAACC | 16920 |
| ACAAAACCA | TTGAACTTCC | TGGCGGGGTA | AAGATAGACA | GCAGGAAATT | ACAAACATTC | 16980 |
| AGAAAAATGT | ATGTTGCCAC | CGGACGCAGT | TAGGTGTCCG | GTTCCACCC | ACACATTTGT | 17040 |
| CTTTATTGCT | TTCAAATAAA | ACGGTGTTCT | GTCAACCTCC | TCCGGGCTCA | CTAGTATTGT | 17100 |
| GTTCCCATAC | GCGCCTGTCG | CCCCAGGATC | AACACTTCGT | CCCCTATCCA | CCCTAATACA | 17160 |
| TAACACACAC | AAAGACATAG | TGACTGTAGA | CAGTTAATCT | TTATTGTCTA | GACACGCAAA | 17220 |
| GTATATTAGT | GTTATAAGAA | ATTTTATGTC | ACGTCGCTCT | TTACTTATCG | TGGACGTCAG | 17280 |
| GAGTCACGTC | TGGGATAGAG | TCCAAAACAC | GCACCGCTTG | ACCTGCAAAC | TTTTCCATTG | 17340 |
| CACTCAGAAC | ATAAAACGAA | GCAAAGTGTC | TCACCCAATA | CTTAAGTCCC | TGAAGCCTCC | 17400 |
| CTAATAGACC | GCGGTCAAAT | TTGGGTGGAC | TGTAGTGCGT | CTTAGTCAGC | TTATTGAGCT | 17460 |
| CTTCCTGTAT | GTCCCATCCT | AAGGTCTTCG | TCAGAAGCTC | CATGACGTCC | ACGTTTATCA | 17520 |
| CTGATTTTCC | AAACTCCGTC | GTTAAAAACT | TAAACAACAC | CTCGAATTCA | AAAAAGCCAT | 17580 |
| CGGCGAGCTT | TTTAAGGCAG | CTAGTCTCAT | TAAATCCTAT | TAACCCGCAG | TGATCAGTAT | 17640 |
| CGTTGATGGC | TGGTAGTTTC | AGATGAAAAA | TAGCAGCGGG | CTCTAGAATA | CCCTTGCAGA | 17700 |
| TGCCGGTACG | GTAACAGAGG | TCGCGGAAGC | ATTCATCGAT | CACCCATAGC | ATCCAATTGA | 17760 |
| GTCTCTGAAT | GAGAAGATCC | TTTTCAAACT | CGGGGGCGTC | CGGCAACTTG | CCCCGCGTTC | 17820 |
| CAGATACCAG | CAGTGAACCG | ACCAGCAAGA | GAGACCACAA | CTTGAACCAG | CACATGGCTG | 17880 |
| CTAACGCGGC | ATACACTAGC | CGGTGGTGCC | CGAGCGGGAG | TTACGAAGTC | TCACTGAAGG | 17940 |
| GCGGGGTCGC | GGGTCGGGGC | CGCTCCAAAT | CAGGCAACGC | CGTATCCGAA | CTCTGAGTCA | 18000 |
| CTTTTATGTA | GGTCTCAAAC | ATGTAAAAGA | TACCACGTTC | TTGAAAAACC | CTCTCTTGCT | 18060 |
| CGCCAGGCTT | GGGGTTCACG | CGGGCATACG | CAGCCAAGCT | ATCATGCGAG | AGAAACACGT | 18120 |
| CACACGCAAA | GTCATGTAAA | ACCCGGGTTA | AAAATAGCCT | AACTGGCCAG | GGGCCAGTGA | 18180 |
| GCGCCTCCG | GTACAAGTCC | CCACCCCCGA | TGACCCAAAC | CTTGTCAATT | TGCTGTGCTA | 18240 |
| GCTCTGGGCT | TCTCGCCAAC | CCAAGCGCGG | CATCGAGCGA | ACTCGCCAAA | AAGTGAGCAC | 18300 |
| CAGGGGCGG | GGTTTCTAAC | GTGCGACTTA | GAACCACATT | GATTCTACCC | GCCAATGGTC | 18360 |
| GACAGCCCGC | GGGAATCGAA | AGCCATGTGC | GCCGCCCCAT | AACAACCATG | TTTTGTTTTC | 18420 |
| CAGGGGCACA | GTCGGTAGTC | AGCTGTCGAA | AACGCCTCAT | GTCTCCCCGC | AATGCAGGCC | 18480 |
| ACGGAGACA | TCTGTTTTTT | CCGATCCCGA | GTTTGGTATC | AACCGCAACT | ACACAGTAAA | 18540 |
| GTGTAGGATC | CATGCCGCGA | GGGTATAGGT | AAACACCACC | AACCACACAG | TGTGCTCTTA | 18600 |
| TATACTTTTA | ATGAAACATA | AGGGCAGACG | AAACAGCCGA | ACGTTCCTA | ATCACGCCCA | 18660 |
| TGGAACCATA | GCCACCCCCA | GGCAAACCCT | GTGGAAGGAT | ATCAACTAGA | GAGGAGGGTC | 18720 |

```
CAGCCTTATT ATGGCAGGAG ACACTATAAG CCCCATCGCC CGACTGGGCA CCAACATAAC    18780
CGCCACAGTA AGTGGCCCTA TACCGCTCAG CGCCCAAGTT GTTACAGTCA CACCCAACCG    18840
CGGTTGGCTC TACATTGTCA TCACGTCCAT CATTATGTGT TGGTTCTCCC GCTTCCTTGT    18900
ACCCTGCAGC TTCATCCACG GATTCTTCTG AGTCGCGATG CACAGGAGCG CCATCCGCGG    18960
GGCCATCTTG GTCGCCTGGA GCTGCCCCCG CGGGGCCATT TTGGTCGCCT GGAGCTGCCC    19020
CCGCGGGCCC CTCCTCGTCC TGGTTATCCC CACGGGGAAG AATTTCCTGA AGCTCGATCT    19080
CCTCTACTGC ACACTCTGGT GATGTCGGCC GAGGTCTATA TGGAAACACT TCAACCCGCG    19140
TGTTTACAGC AGCGTATGCC CGCCCCACGT GGCGCATCAT GTGGAAAAAC GCACCCAACC    19200
CAAAAACGAC AAACAATTGG TAAAACACGA AAAAAACGTA GTACGCGGCT GCAGCGACGT    19260
GATCTATCTC TGGGTCATGA CCGCCCACTA TATATAGCCA AACCCACGTC GCAGCGGCAA    19320
GGCCAGCGGC CCCCAATGTC ATAATGAAAA TAAAAACAAT CAGTTCCAGA CCCTCCTGGT    19380
AAGTCAGCCG AGGCAATAGC GTCATTTCGC GCAAGGGTCG CCAGACCACG CGCGTGTTGT    19440
ATACGACGCC ACATATCTGA CAGGCCGTGT TTCTAGAGAT AGTGAGCCAG GTGCTTAAAC    19500
AACTTCTATG GACGTTCTCG AGCTCTCCTG TGCATCCACA GGCTCTAAAT CTCTCATTTC    19560
CGAGCTCCTC GTTGCAAATC CAGCAGACAG GAACATCCTC ATCTTCCATA TCCTGAGAGA    19620
GAACCCACAA TAAAACATGG CATTAACCCC TGCAACAAGT GACCGTACCA GGGCACGCGT    19680
CCAGGCAACC GGGGTCCCCC TCGTTGGTCT ATACAATTCC ATGACTACCT ACTGGTAATG    19740
CTACAGCCAC TCACTGTACA AGCCGGTTAA CTGGGAGGCG ACGCTGGCGT GGTATCGGCC    19800
AACTGAAACA CACCACTCCA CTCCAAACAC TTATGTACTT TGTGGCTCGG CTTTATTGTA    19860
ACAGCCAAGA GGGGCGTTTG TGGCTCAGCT TTATTGTAAC AGCCAAGAGG GACGTATGTG    19920
GCTATCTCAC AAAAAGTCAC CGATTCATGT AGACAACCCG CTCCCACGAA TTCGGTTTTT    19980
AAAAAGCCCT CACGTATACA GACGGGCCAC TAAATACGCA CATGAGCGGG CATCCTGTTT    20040
CCGCCTTGAC GCCCACCACT CTGACCGCAC GCTAAACATC GCCCTACCTG CTATACTGCC    20100
ATTTCCATAC GAATGGTAGG ATGCGGGCAG TAGTCCACCA GTCTAAAATC ATCAGGTGTA    20160
AACTCTTCCA TGGAAGAAAC AGACCGGAGT ATCTCCAGGC GCGGAAAGGG ACGTGGAGTG    20220
CGCGTCAGCT GCAGCCGTAG TGGCTCTATA TGCGTTTTGT AGATGTGGGC ATCTCCCAAC    20280
GTGTGAATAA ACTCCCCGGG TCTAAGACCA GTAACATGAG CAAGCATATA AGTTAAGAGG    20340
GAATAGCTGG CAATGTTAAA AGGAACTCCC AAACCCATGT CTCCCGACCT CTGATACAGC    20400
TGACAGGAAA GCTCACCGTC AGCTACATAA AATTGACATA ACAAGTGACA GGGCGGAAGC    20460
GCCATCAACG ACAAGTCCGC CGGGTTCCAC GCACACATAA TGATTCTTCT ATCGTGCGGA    20520
TTATTTTTTA TTAAATCCAC AATGTACGAC AATTGGTCAA ACCCCTGGCC TGTATAGTCA    20580
GCATCCGCGT CCACGTACGC CGCCCCAAAG TGCCTCCACT GGAAACCGTA ACAGGTCCC    20640
AAATCCCCCT CCCTTCTGTG CGCCAGGCCG CGCCCGGCCA GGAACTCCCT GGAGCCATTT    20700
TTGTCCCATA TCTTGACTCC TGTTCTTGAA AGCTCCCTGG AGTCAGTACT CCCCTTCAGA    20760
AACCAAAGCA GCTCTTGCAC TACGCCTCGC CAAAACACCC GCTTTGTGGT TAGTAAGGGA    20820
AAGTGGTCCC GCAGACTATA CCTGGCCTGC ATGCCAAATA GAGAGAGGGT GCCTATGCCG    20880
GTGCGGTCGA GTCGATCGCT GCCACGGCAC AAAATTTCCC TCAACTGCCT GAGATACTGA    20940
AGTTCCTCGT GGGGCGTCTC AGCCCCAGTT ACCTCATGCT GAATCGAACA AGGGTCAACC    21000
TCGGGGGCCA AAGCCAAGAC GCCAGGCTTT TGACAGAAGC GAAACCCCCT GGCACGGAAT    21060
AACTTTTTGG CGACATACAA GCTTAAAGGT ACAAACGGAA ACATGATAGA TCCTGGAAGT    21120
```

```
TTGTGAAGCC  CTGTGCCCGG  AGAGACACCC  CTCAACTCGC  AGTGCTCGGA  GACCTACATG   21180
TATACTCAGG  CTCTTCTATA  AACCCTCCCC  AAAAGTTTAT  AAAACACCGT  ACGTAATACA   21240
CATTACTCAC  AGTTCCCACG  GTGACGCCCA  AACCCATGCA  CACGGGCGTG  ATCGATACCA   21300
GAAAACATCA  CAAGAACAAA  AAGTGTGTGT  CTGACATTCA  CATTTATTTT  TACAAGACAA   21360
TTTTGTGCAG  TAGAGTTGTG  CCTTCCGACA  CCCCGCGCCG  TTCGCTGTTC  TCCTGTAATT   21420
GGGAGATCCC  ACTCCTTGGC  AGGCACGTTT  CACGAAACGC  TCTTGTCTCG  CTGGCCTTAG   21480
ACTTGTGGAC  CCAACATGGG  TATCGTTAGA  GATCCGTCGC  GTAAATGCGC  AGCTGGCAAA   21540
GCATTCTTCA  GCGAGCAGTG  ACTGGTAATT  GCTGCATCAG  CTTCTTCACC  CAGTCTTTCG   21600
ATTTGTCGGC  ACACACCTGG  CGACCACGCT  TTGTCAAAAA  TATCACACCC  GGCTTGCTGC   21660
ACAGTTGGGA  GGTGGGGTAC  CAGCTGGACA  GAAGCACCTG  TGGTAATGGT  CTTTTCTGGT   21720
AACCGAGACA  GCACTTGTCC  GGTCTATGCC  AGGACGCTCC  CAGCGTGTCC  CCAGATTGCA   21780
AACAAAGCAA  GGCAGTCAGC  ACAGCGACGA  GCAGGATGCC  CTTGGTGTCC  ATAACTCCCC   21840
TCGTGTGTCC  TCGTGTAAAT  GCGAAACGGC  GATGTTAGGT  CAGGCGCGGT  AAACAGCTCA   21900
ACTCGGTTCA  AAACACGTAC  GTGATGTAGT  GCTGGTTCTA  CGACGCCTAC  CTGTAAACTC   21960
CAGGATCCTG  GGCTTTTATT  ACGAAGGCCA  ACACCCCAAA  AAATCCACGC  CCCCGTGACC   22020
GCAGGGGCGG  TTACTAACGA  CGGTTACAGG  TCCCTCCCGA  GCCACGCACC  TGCCATGTAA   22080
CCTGCAAGGT  AACCAGACAA  ACATCTAGGA  AGCGTAAATA  TCCCCAGGTA  GGAGAAGTAT   22140
TGCATATGTC  ACAGACTCAA  CACACACGGG  CCGTTACGCA  ACGGCTAGGG  GCATAACCCT   22200
TTACCGGCGC  GAAGCGCTAC  GCGCTTCGCG  AGAGGTATCT  CCGTGTGCTT  CTCCATCAGA   22260
AGACGCGTGC  GCCGCTTCGC  AGGCGACCCG  CATACTTTCC  GCCCCGAGTG  CGTTACAAAA   22320
ATGACTGCCT  TCTGGCGACA  ATACACGGTG  GACGTCCAGT  ACCACCCGCA  TATCAGCTTA   22380
TCCGGTGGCA  ATCTGGCACT  GGACAGGGAA  TTCTCGCAAC  AATCCGAGGC  CATGATGGTG   22440
GCAGGACCGC  TGGCCGCACA  TAGCTCAATC  ACGGCCACCC  AGAAGAGCAG  CCCCAAATGT   22500
GCGCGCAACA  CCCAGCACAT  GCTCCACATA  CAGTTCTGGC  GCCACAACGA  TGATGCGCAA   22560
AGGGGTGCAT  TACCCTAAAT  CCCAGCCTAG  TTATAAATTA  TTGAAGCCCA  GGCGACCAGG   22620
GGTCGCCGCG  CTTTTCCTCC  CCAAACGCGA  CGATAAAGAC  CAGCGTTGCC  AAATGTAACT   22680
TATGTATAAC  CCAAAATATT  GCGCATCGAT  AAGGTTTGCC  AAAACACCCG  AAAGTACACA   22740
CACAAAAAAA  CAGCAACAAG  ACGCTCACTA  GACATTCACC  CCTTCCCCCA  CCCCGAAAA    22800
CAAAACAACT  TGACACAGGG  GAAACACCAG  GGGCGGCGGA  GGTTGTCAAT  AGTGTCCAGT   22860
ATTTCGTTAG  ACGCGGGTTC  TTGGACCCGA  TGTCCCAGGT  CATTAAAGTC  TCAAATGGGA   22920
TTAAGGATC   ATAGTTCCCA  GGTTTAATAC  TCCAAGCTAT  CCCAGAACAG  GACCCCGGCA   22980
GAACCCCGCT  TAACAGCACC  AAATCCACTT  GCGGTCCCAG  AAAAGGTCGC  CGAGGTGGCA   23040
AGGTGACTGA  AAAGGTCATA  GAGAGGACAC  CGGTCCCATT  TCCCACGGTC  CAAAAATCCA   23100
GCGCGCCCCA  CCGGCTTTCC  GAGAACTTCG  GCAAAGCTAA  TTTGCATGCG  CTAATCCTTT   23160
TATGTGCATA  AATTATGTAG  ATGAGGAGTC  GCGCATGCGC  AGAAAAATTC  AGAGCGCCCG   23220
GGTGCACGGG  GTCACCTCCA  GGTCACGCCG  CTAGGTGGGA  CCGTGAGCGA  CTCGAAAAAT   23280
TATAATTTTT  GGCCATTTCA  TGGGCGCCGC  CATCTTGAAT  TTGCTAATCC  CCCATAATCC   23340
TCTGCCCCGC  TCCCATTGGT  CCGCCGGCCC  GTCAATCAAA  GTTTTCGGAG  CCGCCATTGG   23400
CCCATCCGGC  CGACCAATCC  CGTTCGAGCT  AGGCGACCGC  GCCATTCCAT  TGGACGCCCC   23460
AGCCGTCAAT  CAAATTCGGA  GGCCTCCCAT  TGGCCCCTAT  CCCTAGAACT  CCCAAGCTGA   23520
```

```
TTGGCCCAGA  GCGGGAACCA  ATCAGCGATT  AGAGTTTTGT  TTTGATTTTT  CCTATATATA   23580
TATATATAAT  CCTTTAATCC  TAGCGCAGCT  GAGTCATCGC  AGCCCCTATT  CCAGTAGGTA   23640
TACCCAGCTG  GGTAATCCAG  TAGGTATACC  CAGGTGGGTG  AACCCAGCTG  GGTATACCCA   23700
GCTGCAATTC  TATAATTAAA  CAAGGTAGAA  ACCAACGGGG  TCCTCAGGTG  GTATTTCCGG   23760
AAGCATTACC  AAATAAGGCA  ACCTCAGCTG  GGAATACCAG  CGGACTACCC  CCAACTGTAT   23820
TCAACCCTCC  TTTGTTTTCC  GGAAGTATAT  CCATTTATGG  AAATCAGCTG  GTCACTCTA    23880
CTGGGTTATT  CTTTATAATA  GGGCCCGATG  AGTCATGGGG  TTGGGATTTT  TCTACTAGGT   23940
CGTTTCGGTG  GATGGGTGCC  AGGATTATAG  GGGCCCTGTC  CACGGGGTTG  TTCGGTGGCG   24000
GGGGGGGGGC  TAGTGAGTCA  CGGGCCTGGA  ATCTCGCCTC  TGGGTGGTTT  CGGTAGATGG   24060
GGGCCGGGAG  GATGGGGCCC  CGCCCACCGC  TGGCGCGCCC  CAGAACATGG  GTGGCTAACG   24120
CCTACATGGG  CAGCTTGTCC  TACGGTTACG  CCCATTTGAG  ACGGGTAAC   CAACTGTTAC   24180
ACCCCTTCGC  CGGGAACGCT  ATAAAAACGA  GGGACAGCAG  CCCCCCCTCG  CGCACTGCGC   24240
GCGCGGCGGC  ACGTGGGACG  GATCTCTTGG  ATTACCCGT   AACGAGGAGC  CCCGGCAGCA   24300
CCCCAGGAGC  CCCGGCAGCA  CCCCAGGAGC  CCCGGCAGCA  CCCCAGGAGC  CCCGGCAGCA   24360
CCCCAGGAGC  CCCGGCAGCA  CCCCAGGAGC  CCCGGCAGCA  CCCCAGGAGC  CCCGGCAGCA   24420
CCCCAGGAGC  CCCGGCAGCA  CCCCAGGAGC  CCCGGCAGCA  CCCCAGGAGC  CCCGGCAGCA   24480
CCCCAGGAGC  CCCGGCAGCA  CCCCAGGAGC  CCCGGCAGCA  CCCCAGGAGC  CCCGGCAGCA   24540
CCCCAGGAGC  CCCGGCAGCA  CCCCAGGAGC  CCCGGCAGCA  CCCCAGGAGC  CCCGGCAGCA   24600
CCCCAGGAGC  CCCGGCGCGC  CACCCTCCCC  GGAGGGGGAT  CCCGGCGCGC  CACCCTCCCC   24660
GGAGGGGGAT  CCCGGCGCGC  CACCCTCCCC  GGAGGGGGAT  CCCGGCGCGC  CACCCTCCCC   24720
GGAGGGGGAT  CCCGGCGCGC  CACCCTCCCC  GGAGGGGGAT  CCCGGCGCGC  CACCCTCCCC   24780
GGAGGGGGAT  CCCGGCGCGC  CACCCTCCCC  GGAGGGGGAT  CCCGGCGCGC  CACCCTCCCC   24840
GGAGGGGGAT  CCCGGCGCGC  CACCCTCCCC  GGAGGGGGAT  CCCGGCGCGC  CACCCTCCCC   24900
GGCAACAACC  TGTTGCCATG  TATGGCGATT  TGTATCAGTC  ACAAGCACAC  AACCCCTGCT   24960
AGTATTAATG  GTGTTTAAAA  CGTTCTACAC  GTACGGCGGA  CCGCATCCGT  CGCAAGCACG   25020
CGCATATAAC  CCCCAAATGC  ACCATGATGA  GAAGCACAGC  CACGCGTCAA  AAAACTTTAA   25080
AAACATCGTT  ATCCAATATC  ATTAAAAACC  ACACCGAAAT  TTACACAGGT  AGCACGTCAC   25140
CGTGTTAGTG  TCACCCACTG  TACACAAGGC  GTGTCGTATA  TGTAGTATAG  GTATTTGATG   25200
AGGCGGAAGC  ATATCCCGCT  TCCAGCGAAC  GGAAATAAGA  ATCATCCGTT  CCAGCATTTA   25260
TTCAAAGAGG  GCACAGAGGA  TTCACATTGT  TTAGAGAGAG  TTTTCTTAG   TCACCATTCC   25320
ATACTTGGGC  AGTATTGGCC  TACGATTTGG  GCGACGTTTC  AGGCTGGTCT  ATTCTCCGTC   25380
CACTTTTCCC  CGGCTATTCT  GTCCCAGCAT  AGGCTCTTGA  AATAAACAAT  GTTTACCGAG   25440
TAAAAGGTTC  CACTCACCCT  CATTTGTCGT  TGCACCCATC  CCCCCTTTGC  TTAATCACCC   25500
GAAAACTAGA  GGACACGGAT  GGAAAACATA  TCGCACGCGG  GTTGTTGAA   AGTCAACAGC   25560
TACTTGTTTT  TAATGAGGAC  AGATTTGGGC  ACAGGCCAGA  GGGTAAAGCC  CTACGTGTGC   25620
GCGGGGGGG   GGGTGTATAC  GCTGCGAAAA  CCTGCACGGT  GCATAACACC  CAGGGCGTCA   25680
CGTCACATAT  CTCTGTGCAC  CCAAGTGGTT  GTTCAACCGT  TGTTTTTGG   ATGATTTTC    25740
CGCACCGGCT  TTTTTGTGGG  CGCGCATAGG  TCGGTACGCG  CTGTCCCCCT  AAGTCCCGCA   25800
CGGTCGTTCG  GGCCCCCGTC  CGGCTCGTCT  CCGGATGAAC  CGTCACGTTC  TTTGTCTCCA   25860
GAGGCGACGT  CTCCTTCAGA  TGACTCGTCC  GTGGGCTCCT  CGTCCGTCCC  GCCCGCGGGT   25920
```

```
CCGACAAGGA  CCGTCAATTC  GATGTTATCT  TCGTTCGCGG  TTGGCCGGCG  CGGCCGTCGG    25980
TATGGCAGTA  CGGTCACCCG  GGTGTTATTT  GCCGCGTATA  ATGCCCTCAC  AGTGCCACTT    26040
ACGCGGCATA  TGCCGCCAAA  TGCAAACACA  ATAAATATTT  GGTAAAACCC  AAAGAAGCAG    26100
AGAAAACCGA  GCACGGCCCC  GGGGGAGAAT  GTTCCCGCAG  GAGCAGTTAG  GATGACCAGG    26160
AGCGTCCAGG  TGCACAACGC  CACGCCGACA  AGCCCAGCCA  CCACCACAGA  CATCAGCAGA    26220
AACAGTTCAA  AAATTTCTTG  GCGCTCCATC  TCCGGCCACA  GGTTAAGGCG  ACTACGCCAC    26280
TGCGTGCGCG  TGCGGTATAT  AACGCGACAC  ATTTGACAGG  CCGTGTTTCG  AGACACTGTT    26340
AGCCAAGTGC  TTAAACACTG  CGGGTGGACG  ACATCCAGCT  CTCCGGTACA  GGCGCAGGGG    26400
TGTATGCCCT  CGTTCCCCAC  CTCTTCCCTA  CATATCCAGC  AGATGGGTCC  CTCTACACCC    26460
TCTTCTACGT  CCTTAGACGC  CATCTCTGCA  GCTGGGGTGG  AAGTCTGAAA  AAGGGAAAGG    26520
GGAGGTGAGC  AGAGTGCCCA  GTTAGTCTCC  GACCCGCCGT  CCGCCCTACT  GTCGCTATCC    26580
CGCCTTGACA  GATGTCTAAC  GTATTCACGG  ACGCCACATG  TGTGTCTATT  TTCCTACATC    26640
CAGGCTTTCC  CTGGAAAACT  GTCACAACCC  ACCCTGCTTT  AGCTCTACAT  CTGTATTTTT    26700
GTTTACGCAC  AGGATCAACG  CTTCGTGCCC  GTCCACCCCC  GCGCTCTCCG  CCTGTGTTTG    26760
GAGGTTTTAT  GAGTGGTTAG  TTCTAGGCAG  CTCCGGACAA  GTTGTCCAAA  ACACGGCGCG    26820
CCCCGCCCTT  CCTTCCCTCC  GGATCCGCCC  ACACCGGACC  TATGAAATAA  GGGACACGCG    26880
TCATCACTAG  TTATGAGAGA  AAAACCACAA  CAGCTTTATT  GGAAAACACC  TGAGTGGATC    26940
CCCCACCCCC  CGCGTACGAC  AGGCGTTTCT  GTGGTGCGCT  TCTGGGAAAA  ACGTTTTCC    27000
CCCATTTCTT  CCTCGACAGG  TCTTCTAAGG  TAGATAAATC  CCCCCCCTTT  GCGCGTCTCC    27060
TAGAATGGCC  TAGGCGCACG  ATGGCGTTGT  CGCCTCGAGC  AGTTGGGCCG  CAGTGATATC    27120
TTCAACTTTC  GACCGTCTAA  GCTATGGCAG  GCAGCCGCTG  CATCAGCTGC  CTAACCCAGT    27180
TTTTGGAAGG  GTCTGCGCAG  ATCTGACGCC  CTCGCTTGGT  CAGCAAAATA  ACTCCGGGTT    27240
TTGGGCACGC  TGGGGACGTG  GGATACCACT  CTTTTAGAAT  TTGGACGGGC  GGTGGGTGCT    27300
GCTGGAACCC  GTAGCAGCAG  CTATTAGGCG  TGTACGACAC  GAGTGACCCC  GCGCTTTCTG    27360
TGGGCGTCAG  GTAAAACGTG  GCAAGCAGTA  CGCTAACGCA  GCATAAAACG  TGGACGGGGG    27420
CCATCTGGAG  GTGCCAAGTT  CGCAACAGTC  TAAAGAAAAC  CGTAAAGGCT  ATTTGGGGTT    27480
TCTGTTCTGT  CAGATGTAAC  GCCGAGTTCC  TTATATGCTT  ACCTGATTCT  GGTCTCACCT    27540
GTTTATTTAT  AGTGGCGTAT  GCTAACCGCC  AGCTTACATG  CGGGATAAGT  TGGCCTAACT    27600
CACCAAAAAC  GGGTTGCAGA  CAAAAGTGAT  TGTTGGGGCG  CTTACTTAGA  AGGTGTGAGG    27660
GTTTCTAAGA  AACCCCGCCA  ACGCCCGGAA  ACCGCATGCG  TTCCAGTCGG  TGCGGCCTGC    27720
GCCGGCGTCG  CTGTGGCGCC  TTTGTGGGCT  TTGAGTTCTG  TCATTAAGCC  AGGTTTCCAT    27780
TGCCACCCGG  GCGAAAACAA  GCCGGGTAGT  TTCAGGGGTC  ATCTGGCGAT  CAGTGTACCA    27840
TATTCCCACG  ACCCATCAAC  ACCGCTGCTT  GAGGCGTGTC  TCTGTATGTG  TCACCGGAGA    27900
CTGCATGTAT  CGTGCATATC  TGTATTGTGC  GCTTGCGCGG  AGACAACATA  CCGACGACCA    27960
AGTCAGGGGT  CACCTCCAGT  GCACGCCGCT  AGGTGGGACC  GTGGGCGAGC  CGAAATAATT    28020
ATATATTTTT  TTGGCACGGT  TGTGAGCAAC  GCCATCGTGA  GTTGGTTAAT  ACCCTCTAAA    28080
CGCATAGTCT  TTTTTTATTT  GTCAACCAAC  CAGTCAATCA  CCTGTCATCG  CCGCTCAGAA    28140
GCACACGTCT  TCGGCCAATG  CCGTGTTGGC  GGGTTTGACC  ACGGTTACTG  ATAGGTAGAC    28200
GAGTCCGACA  ATCACACACG  TCCGCCAGCG  ATTTGCAGCG  CAGCTAAAAT  CGCGTGGCCG    28260
GGTTGGTAGA  AGCAAATTAT  CCAATGGTCG  TGTTTGGGTT  TGTTTTGGGG  TTATCTACAT    28320
```

```
ATTATATTCC TTATCCCGAC TGGTTGCGGA AGTATTCGCA GCTTGGCTAC TCTGCTCGAT     28380
TACCCCGTGA ATAACTGGGC GGGGGGTGAC CCAACATAGT GATTCGGTAG ATTTGGGGGA     28440
CTGGATGAAC ATTAATGAAA GTTTATTAAT GTTCATCCGT ATTGTGTATA TGTAATTTGG     28500
TTTCCATATT TGGTAGGAGT ATGGAGTTTT CTTATGGATT ATTAAGGGTC AGCTTGAAGG     28560
ATGATGTTAA TGACATAAAG GGGCGTGGCT TCCAAAAATG GGTGGCTAAC CTGTCCAAAA     28620
TATGGGAACA CTGGAGATAA AAGGGGCCAG CTTGAGTCAG TTTAGCACTG GGACTGCCCA     28680
GTCACCTTGG CTGCCGCTTC ACCTATGGAT TTTGTGCTCG CTGCTTGCCT TCTTGCCGCT     28740
TCTGGTTTTC ATTGGTGCCG CCGATTGTGG GTTGATTGCG TCGCTTTTGG CAATATACCC     28800
ATCCTGGCTT TCGGCTAGGT TTTCCGTCCT ACTTTTCCCA CATTGGCCTG AGAGCTGTAG     28860
TACAAAAAAC ACCGCGCGGT CTGGAGCTCT CCATAAGCCC GCAGAACAAA AGCTGCGATT     28920
TGCCCAAAAA CCTTGCCATG GCAACTATAC AGTCACCCCT TGCGGGTTAT TGCATTGGAT     28980
TCAATCTCCA GGCCAGTTGT AGCCCCCTTT TATGATATGC GAGGATACTT AACGTGTCTG     29040
AATGTGGAAT ATAATGTGAA AGGAAAGCAG CGCCCACTGG TGTATCAGAA CAGTGGTGCA     29100
CTACCTATCT GCTCATTCGT TGTTTCGGTT CTGTGTTTGT CTGATTCTTA GATAGTGTTG     29160
AGGTAATTCT AGAAAGCGGA TTGAGTGTAA ATCGGGCCAC TTTGCCCTAA ATGTGACAAT     29220
CTGGATGTGT ATCTTATTGG TGCGTTGTGA AGCATTTTAA AATGCGTTTT AGATTGTATC     29280
AGGCTAGTGC TGTAATGGTG TGTTTATTTT TCCAGTGTAA GCAAGTCGAT TTGAATGACA     29340
TAGGCGACAA AGTGAGGTGG CATTTGTCAG AAGTTTCAAA GTCGTGTAAG AACATTGGAC     29400
TAAAGTGGTG TGCGGCAGCT GGGAGCGCTC TTTCAATGTT AATGTTTTAA TGTGTATGTT     29460
GTGTTGGAAG TTCCAGGCTA ATATTTGATG TTTTGCTAGG TTGACTAACG ATGTTTTCTT     29520
GTAGGTGAAA GCGTTGTGTA ACAATGATAA CGGTGTTTTG GCTGGGTTTT TCCTTGTTCG     29580
CACCGGACAC CTCCAGTGAC CAGACGGCAA GGTTTTTATC CCAGTGTATA TTGGAAAAAC     29640
ATGTTATACT TTTGACAATT TAACGTGCCT AGAGCTCAAA TTAAACTAAT ACCATAACGT     29700
AATGCAACTT ACAACATAAA TAAAGGTCAA TGTTTAATCC ATATTTCCTG ACTTGTGTCT     29760
TGACTTGCGT CGATTGGGAT GGGGGTGTGG GATGGGGGTG TGGGATGGGG GTGTGGGATG     29820
GGGGTGTGGG ATGGGGTGT GGGATGGGGG TGTGGGATGG GGTGTGGGA TGGGGGTGTG     29880
GGATGGGGGT GTGGGATGGG GGTGTGGGAT GGGGGTGTGG GATGGGGGTG TGGGATGGGG     29940
GTAAATGACA ATGGGGGTAA ATGACAATGG GGCGCTTGGT GACACATTTG CCCCACCGTC     30000
GCCTGCCCGG AACCAGCTTG GTGATGTGCT GTCTGGCTCT CAGGTGCACT TTATGCAAAG     30060
CAGTTGAGGC GCATTAGATA TATAAACTT GGGTACACAC CCTTGGTGCT GTGCGCGTGC     30120
TATGTGCCCT GGTGACCGTC CACAATGGAC GAGGACGTTT TGCCTGGAGA GGTGTTGGCC     30180
ATTGAAGGGA TATTCATGGC CTGTGGATTA AACGAACCTG AGTACCTGTA CCATCCTTTG     30240
CTCAGCCCTA TTAAGCTATA CATCACAGGC TTAATGCGAG ACAAGGAGTC TTTATTCGAG     30300
GCCATGTTGG CTAATGTGAG ATTTCACAGC ACCACCGGTA TAAACCAGCT TGGGTTGAGC     30360
ATGCTGCAGG TTAGCGGCGA TGGAAACATG AACTGGGGGC GAGCCCTGGC TATACTGACC     30420
TTTGGCAGTT TTGTGGCCCA GAAGTTATCC AACGAACCTC ACCTGCGAGA CTTTGCTTTG     30480
GCCGTTTTAC CTGTATATGC GTATGAAGCA ATCGGACCCC AGTGGTTTCG CGCTCGCGGA     30540
GGCTGGCGAG GCCTGAAGGC GTATTGTACA CAGGTGCTTA CCAGAAGAAG GGGACGGAGA     30600
ATGACAGCGC TATTGGGAAG CATTGCATTA TTGGCCACTA TATTGGCAGC GGTCGCGATG     30660
AGCAGGAGAT AACGCGTAAT TCGAGGTCCC CGGAAGAGTA GAGGGTTGCA TGTTATACAA     30720
```

| | | | | | | |
|---|---|---|---|---|---|---|
| ACAACATAAA | CATTAAATGA | ACATTGTTCA | AAACGTATGT | TTATTTTTTT | TCAAACAGGG | 30780 |
| GAGTAGGGTA | GGAAGGGTAC | GTCTAATACG | TAACTGTTCG | CTACTGCTTG | TTCAGGAGCT | 30840 |
| CCTCGCAGAA | CATCTTGCGA | ATTTTAGATT | TTGGACTAGA | GCGACTGCTG | GCTTCAACGC | 30900 |
| GGTTCGATGT | AGGGTTCGGC | GTAGGAGCGT | CTTTCTCCAC | CGCCGCGCAT | GGTGTATGCG | 30960 |
| TGGTCTCCGG | TGCCTGTTGT | TGGATGCTCT | GCGTGCTGGA | GGCGGGGGTG | GGTTCAGCGG | 31020 |
| GTGGTGCGCC | AACTACCGCG | AGTCCTGTAG | AGACTGGCGG | GTGGCTCACA | TGTGGCTGAG | 31080 |
| CAAAAAGGAT | GGGCGCCGCT | TGCTGGAACT | GACCGTGTGG | CGCCTGCACG | TAAATGGGTG | 31140 |
| GGTGTACGTA | GGTTCCTCCG | TGCTCCTTCA | TTGTCGGGAA | TTGACACGGG | ACCGCTGAAT | 31200 |
| TGGCGTGGGG | CCTGTAGTGT | GGATCTACTG | CGGCTGCTGC | TGCAGAGGAG | GACGGCGGTG | 31260 |
| GCCCTGCGTG | CCAACCGTTC | AGTTTCATCT | CTTTGAGTTC | AGACTGTATT | TCCGCTATGT | 31320 |
| TCTTTGACAT | GGACAAGATA | TCCTTGTGAT | ACGCCGGCTC | CTCTCCTGGA | AAGAGGTGTC | 31380 |
| CTTCGTCGTC | CTCTGCGCCG | CGCTTGCGCT | TCCCCGTCCT | ATATCCAGGC | AGCTGTGGCG | 31440 |
| AGTAATACCA | TGGATCGTAT | GGGTTCTTGT | AAGCGTAGCC | GTATGGTGGC | GCTGGGTTTG | 31500 |
| AAACATACGA | AGGTAGGTGA | TGGTCGGTGG | GGAACATCTG | GCCCCACAC | CCCATTAGGC | 31560 |
| CTGGCCCTGA | AAGTGTATGT | GACATTTTG | CCGCTGTGGT | CTTCATTCCA | TCGATGCTGC | 31620 |
| TTTGTAGCAT | GCTCAGGAAG | GCGGATTTGG | GGATGGATAT | GATATCCTCT | TGACCAGAGC | 31680 |
| TGTTCATGGC | TGGTCTGGGT | GGTGTGACGG | CTTGGATGCC | GACCGGGAAT | TGGCTGGCCT | 31740 |
| TTAAATACGC | CGGGCTCAAT | ATGCTGGCCA | CACCTCTGTC | AGTTTTCAAT | AGGTCGAGGC | 31800 |
| GGTCCCGTAT | GAAGCTGGCA | TCTATAGCTT | TTGCCATTAA | GGTCTCCAGG | GGACTGACGA | 31860 |
| AATTTGGTGT | GGAAAGGTCC | TCCAGCCTGC | AGCTACTTAC | GTGCTGGAGG | ATGTGGGCGC | 31920 |
| GCTCCGACTT | AGATACTGAT | GAGAATCTGG | AAACCACCCA | CTCGGCGTCG | TGTCCGTACA | 31980 |
| CGGCCACTGT | GCCGCGTCGG | CGCCCCAGGG | CGCATAGTGA | TACGTGTTGA | AACACGGGAC | 32040 |
| CGCTGGGAGT | CTGGGATAAC | TCGCGGGGAT | GTATAGACGA | TAAAGACAGC | CCCGGGAGCC | 32100 |
| ACGTGTGGAG | TATCTCCAAC | AGTGGTTCCT | TAGGGAGATT | TTTCACGGGG | GCTCTGGCCA | 32160 |
| CGTGGGAGGT | GTCCGCCAGC | CTGGATGCCA | GCTCTAGGAA | GGCTGGCGAC | GTGATGGCTC | 32220 |
| CGGTGCAGAA | AATACCGTGG | GACACTTGAA | ATAGACCCAG | TGTCCAGCCC | ACTTCTGTCT | 32280 |
| CTGGTAGGTG | TTCGATTGTT | ATTGGAAGGG | GTTCTGTGAC | TGGGAGATAA | TCCGTCACCT | 32340 |
| GATCCGGATC | GAGATAGAGC | TCTTGCTCCA | GCTTGGGGCA | GGACACAACA | TCTACAAACC | 32400 |
| CTCCGACGTA | CAGGCCCTGT | GCCATGCTCG | GAAAATACGT | GTGTGAGACC | GAGCCGCTGA | 32460 |
| GCCCGGGGCT | TAGGAGGCTC | ATGTGGCGCT | TTTTGCAAAA | TAAGAATTTA | AATACATTCC | 32520 |
| ACGCCCAAGA | GCTGCGTTTT | ATTCATTTGG | TTCTCTGCAG | GATGTACAAT | TTCGGTCTAA | 32580 |
| ATGTGTACCT | GTTAAGGGAG | GCTACTGCCA | ATGCCGGGAC | CTACGACGAG | GTGGTCCTGG | 32640 |
| GACGCAAGGT | TCCTGCGGAG | GTGTGGAAGC | TCGTGTACGA | TGGGCTCGAG | GAGATGGGCG | 32700 |
| TGTCAAGTGA | GATGCTGCTG | TGTGAGGCAT | ACCGGACAG | CCTCTGGATG | CACTTGAACG | 32760 |
| ATAAGGTGGG | GCTCTTGAGG | GGCCTGGCGA | ATTATCTGTT | TCACCGGCTA | GGGGTCACCC | 32820 |
| ACGACGTTCG | CATCGCCCCG | GAAAACCTGG | TGGACGGAAA | CTTTTTGTTT | AATCTGGGAA | 32880 |
| GTGTGCTCCC | CTGCAGGCTG | CTCCTTGCGG | CGGGCTACTG | CCTCGCCTTT | TGGGGCAGCG | 32940 |
| ATGAACACGA | ACGCTGGGTG | CGCTTCTTCG | CCCAGAAGCT | TTTCATTTGC | TACCTGATAG | 33000 |
| TCTCCGGGCG | TCTTATGCCA | CAGAGGTCTC | TGCTAGTTTG | GGCCAGCGAA | ACGGGCTATC | 33060 |
| CCGGTCCGGT | GGAGGCAGTC | TGTCGCGACA | TCCGCTCCAT | GTACGGCATA | CGAACGTATG | 33120 |

| | | | | | | |
|---|---|---|---|---|---|---|
|CGGTCTCGGG|TTATCTTCCG|GCTCCGTCCG|AAGCGCAGCT|GGCCTACCTT|GGTGCGTTTA|33180|
|ACAACAACGC|GGTTTAAACG|ACCGCGAGGA|CCACCGGCAG|GCAGCCAAGA|ACCATAAAGT|33240|
|ACGCTCTATC|GTAGTCATCG|CCGCCGCCAA|ACTGGGACTT|GATAATCTCC|TGGAGAAGGG|33300|
|TGGGTGGGGA|TGGGTGTGAA|AGCAGGACGT|CCAGGCCCTC|TTCTGTTGCC|AGGCGGAGGG|33360|
|CTGTTCTCGC|CTGGAGCAGC|GCCAGTGGAT|CTCGGAATGT|AAGCTGCTGG|TTCAGGATTT|33420|
|CGAATATCTC|ATTAAACCTA|CTGCCTGTCA|GATTTACAAA|TGGTCCGGGT|TGTTTGTGGG|33480|
|ACACGGTCGA|TCGCGCCTCG|AGGGCGGCCA|GTATTATGCC|AGGGAAGATG|AAGGACACGG|33540|
|GGGCGTTTGG|ATTAGCCTGC|AGTGTGGGGA|TTATGTAGTG|CTCCGATATG|AACGAAAATA|33600|
|GCTGGCCCCT|TTTCAGCATG|GGGGCGTTTG|GATCCGGTAG|GGCACCGGGC|TGAAATTTGG|33660|
|GTCCCAGCAG|GGATACCAGG|TTCAAGCGGC|GGTTTGGGTG|CCCTCGCGCG|ACTTGCCCAA|33720|
|ACTCCAGCAA|TCCATACGCG|AGGATAAACA|CCTCCAGCGC|AACAATCCCC|GCTCGCAGGT|33780|
|TCCACTGGTA|TGCGGAAAAT|GGTGGTATAT|CGGACCCAAA|CATGGCGCTC|GTAATGGCGA|33840|
|ATACCAAGTC|CATGGCGGGC|GCTGTCCCTG|GCGCGCCCGT|ACCCTTGTTG|TGGGGAAATA|33900|
|ATCCAGCCTT|AGCCATCATT|GCGTGAAGCT|TGTGGCGCTG|GAAGAAGGCT|GTCGGATAGC|33960|
|GGCTCTCCTT|ATTGAGAGGC|GCCAGCGAGG|CGCGCTCCTG|GGGGTTGAG|TATGTGAAGC|34020|
|TGAAGTCCCC|AGGACCGCTT|TCCTGTTTTA|GCTGAGTGAT|TAGCAGGTCT|AGCTTTTGAG|34080|
|GCAGGTCTGC|TAACAGGTCA|TCGGGAGTAG|CGGGCAGTTG|CCTGGATGTC|TTTTGACAAA|34140|
|AGTACGCGTT|GACGAGGCAA|AGCGCGGCCT|GGGTGTCCGT|GAGATGCCTG|GCGTCGGCGA|34200|
|AAAAGTCAGC|GGTGGTCGAG|GCGACCGTCG|TCAGGGTGTG|AGAGATGAGT|TTGAGCGATG|34260|
|TGGAATTCTG|AAAGTTAACA|GTCCCCTTTA|GTTCTTTAGG|GAAGACGCGC|CGCTGCATGG|34320|
|CGTTGTCCGT|GAGGCTGATG|AACCACGGCC|CAAAGGATGG|CAACCACTGA|TTCTGGTTCA|34380|
|TGTACAGGGT|GGGCATGAGC|TCGCCGCGCA|GGTCCCTGTC|AACGGAGAAG|TGAGGGTCCC|34440|
|CGGGGACGAT|CGCCACGGTG|AAGTTACGGT|GGCTGGCCTG|CGGGGGGGAT|GTCACTAAGG|34500|
|GAGGCTCATG|GGAACGGCTT|TGGGGCATGT|CTATGTTGTC|AGACCATGTC|ATGTTGCCTA|34560|
|TCATCTGTTT|CACCGCGTCG|ATATCTGCGT|TAATGACGCG|GACGCGTGAG|TCATGGACCT|34620|
|GAACAAGCCG|GTCCAGCTCT|AGGGAAAGCA|GGTGTGCCTT|TGTCTTTCGT|TCTCGATTTC|34680|
|GCACGAGTTG|GCTGCGCAGT|CCAAGGGCGA|CCCTTCTTGT|TTCTTCCATG|GTGGGCTTGT|34740|
|GAATAAACAG|CACGTTTTCC|GGGTGTGGGG|CCCAGAATCT|TCCCGCCTCT|GTCCATCTTC|34800|
|GGTTTTTTGG|GTACCTTAGA|TAGGACCTTT|CTGATGTCAG|CATTTTCTCT|AGCAGTGAGA|34860|
|AAGGCGCACA|ATTTTCCTTC|GGTGGTGTGC|ACCGGCGTGG|GAAACGCCCC|GGGTGATTCA|34920|
|GAGTATACTG|TCTTTAGTGT|TTTCTGATTC|TTAAATATCA|GCAGGGCGT|GATAGTCCAC|34980|
|GCCTCGGTAC|CCGGAGGGC|CGAGTGAGCG|ATGTAATGGA|TCGAGTCGGA|GAGTTGGCAC|35040|
|AGGCCTTGAG|CTCGCTGTGA|CGTTCTCACG|GTGTTGGTTG|GGATCAGCTG|GTGACTCAGA|35100|

( 2 ) INFORMATION FOR SEQ ID NO:18:

( i ) SEQUENCE CHARACTERISTICS:
        ( A ) LENGTH: 35100 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

| | | | | | | |
|---|---|---|---|---|---|---|
| CAAGTCTTGA | GCTCTACAAC | GTAACATACG | GGCTGATGCC | CACCCGATAC | CAGAATTACG | 60 |
| CAGTCGGCAA | TTCTGTGCCC | TAGAGTCACC | TCAAAGAATA | ATCTGTGGTG | TCCAAGGGGA | 120 |
| GGGTTCTGGG | GCCGGCTACT | TAGAAACCGC | CATAGATCGG | GCAGGGTGGA | GTACTTGAGG | 180 |
| AGCCGGCGGT | AGGTGGCCAG | GTGGGCCCGG | TTACCTGCTC | TTTTGCGTGC | TGCTGGAAGC | 240 |
| CTGCTCAGGG | ATTTCTTAAC | CTCGGCCTCG | GTTGGACGTA | CCATGGCAGA | AGGCGGTTTT | 300 |
| GGAGCGGACT | CGGTGGGGCG | CGGCGGAGAA | AAGGCCTCTG | TGACTAGGGG | AGGCAGGTGG | 360 |
| GACTTGGGGA | GCTCGGACGA | CGAATCAAGC | ACCTCCACAA | CCAGCACGGA | TATGGACGAC | 420 |
| CTCCCTGAGG | AGAGGAAACC | ACTAACGGGA | AAGTCTGTAA | AAACCTCGTA | CATATACGAC | 480 |
| GTGCCCACCG | TCCCGACTAG | CAAGCCGTGG | CATTTAATGC | ACGACAACTC | CCTCTACGCA | 540 |
| ACGCCTAGGT | TTCCGCCCAG | ACCTCTCATA | CGGCACCCTT | CCGAAAAAGG | CAGCATTTTT | 600 |
| GCCAGTCGGT | TGTCAGCGAC | TGACGACGAC | TCGGGAGACT | ACGCGCCAAT | GGATCGCTTC | 660 |
| GCCTTCCAGA | GCCCCAGGGT | GTGTGGTCGC | CCTCCCCTTC | CGCCTCCAAA | TCACCCACCT | 720 |
| CCGGCAACTA | GGCCGGCAGA | CGCGTCAATG | GGGGACGTGG | GCTGGGCGGA | TCTGCAGGGA | 780 |
| CTCAAGAGGA | CCCCAAAGGG | ATTTTAAAA | ACATCTACCA | AGGGGGGCAG | TCTCAAAGCC | 840 |
| CGTGGACGCG | ATGTAGGTGA | CCGTCTCAGG | GACGGCGGCT | TTGCCTTTAG | TCCTAGGGGC | 900 |
| GTGAAATCTG | CCATAGGGCA | AAACATTAAA | TCATGGTTGG | GGATCGGAGA | ATCATCGGCG | 960 |
| ACTGCTGTCC | CCGTCACCAC | GCAGCTTATG | GTACCGGTGC | ACCTCATTAG | AACGCCTGTG | 1020 |
| ACCGTGGACT | ACAGGAATGT | TTATTTGCTT | TACTTAGAGG | GGGTAATGGG | TGTGGGCAAA | 1080 |
| TCAACGCTGG | TCAACGCCGT | GTGCGGGATC | TTGCCCCAGG | AGAGAGTGAC | AAGTTTTCCC | 1140 |
| GAGCCCATGG | TGTACTGGAC | GAGGGCATTT | ACAGATTGTT | ACAAGGAAAT | TTCCCACCTG | 1200 |
| ATGAAGTCTG | GTAAGGCGGG | AGACCCGCTG | ACGTCTGCCA | AAATATACTC | ATGCCAAAAC | 1260 |
| AAGTTTTCGC | TCCCCTTCCG | GACGAACGCC | ACCGCTATCC | TGCGAATGAT | GCAGCCCTGG | 1320 |
| AACGTTGGGG | GTGGGTCTGG | GAGGGGCACT | CACTGGTGCG | TCTTTGATAG | GCATCTCCTC | 1380 |
| TCCCCAGCAG | TGGTGTTCCC | TCTCATGCAC | CTGAAGCACG | GCCGCCTATC | TTTTGATCAC | 1440 |
| TTCTTTCAAT | TACTTTCCAT | CTTTAGAGCC | ACAGAAGGCG | ACGTGGTCGC | CATTCTCACC | 1500 |
| CTCTCCAGCG | CCGAGTCGTT | GCGGCGGGTC | AGGGCGAGGG | GAAGAAAGAA | CGACGGGACG | 1560 |
| GTGGAGCAAA | ACTACATCAG | AGAATTGGCG | TGGGCTTATC | ACGCCGTGTA | CTGTTCATGG | 1620 |
| ATCATGTTGC | AGTACATCAC | TGTGGAGCAG | ATGGTACAAC | TATGCGTACA | AACCACAAAT | 1680 |
| ATTCCGGAAA | TCTGCTTCCG | CAGCGTGCGC | CTGGCACACA | AGGAGGAAAC | TTTGAAAAAC | 1740 |
| CTTCACGAGC | AGAGCATGCT | ACCTATGATC | ACCGGTGTAC | TGGATCCCGT | GAGACATCAT | 1800 |
| CCCGTCGTGA | TCGAGCTTTG | CTTTTGTTTC | TTCACAGAGC | TGAGAAAATT | ACAATTTATC | 1860 |
| GTAGCCGACG | CGGATAAGTT | CCACGACGAC | GTATGCGGCC | TGTGGACCGA | AATCTACAGG | 1920 |
| CAGATCCTGT | CCAATCCGGC | TATTAAACCC | AGGGCCATCA | ACTGGCCAGC | ATTAGAGAGC | 1980 |
| CAGTCTAAAG | CAGTTAATCA | CCTAGAGGAG | ACATGCAGGG | TCTAGCCTTC | TTGGCGGCCC | 2040 |
| TTGCATGCTG | GCGATGCATA | TCGTTGACAT | GTGGAGCCAC | TGGCGCGTTG | CCGACAACGG | 2100 |
| CGACGACAAT | AACCCGCTCC | GCCACGCAGC | TCATCAATGG | GAGAACCAAC | CTCTCCATAG | 2160 |
| AACTGGAATT | CAACGGCACT | AGTTTTTTTC | TAAATTGGCA | AAATCTGTTG | AATGTGATCA | 2220 |
| CGGAGCCGGC | CCTGACAGAG | TTGTGGACCT | CCGCCGAAGT | CGCCGAGGAC | CTCAGGGTAA | 2280 |
| CTCTGAAAAA | GAGGCAAAGT | CTTTTTTTCC | CCAACAAGAC | AGTTGTGATC | TCTGGAGACG | 2340 |
| GCCATCGCTA | TACGTGCGAG | GTGCCGACGT | CGTCGCAAAC | TTATAACATC | ACCAAGGGCT | 2400 |

| | | | | | | |
|---|---|---|---|---|---|---|
| TTAACTATAG | CGCTCTGCCC | GGGCACCTTG | GCGGATTTGG | GATCAACGCG | CGTCTGGTAC | 2460 |
| TGGGTGATAT | CTTCGCATCA | AAATGGTCGC | TATTCGCGAG | GGACACCCCA | GAGTATCGGG | 2520 |
| TGTTTTACCC | AATGATTGTC | ATGGCCGTCA | AGTTTTCCAT | ATCCATTGGC | AACAACGAGT | 2580 |
| CCGGCGTAGC | GCTCTATGGA | GTGGTGTCGG | AAGATTTCGT | GGTCGTCACG | CTCCACAACA | 2640 |
| GGTCCAAAGA | GGCTAACGAG | ACGGCGTCCC | ATCTTCTGTT | CGGTCTCCCG | GATTCACTGC | 2700 |
| CATCTCTGAA | GGGCCATGCC | ACCTATGATG | AACTCACGTT | CGCCCGAAAC | GCAAAATATG | 2760 |
| CGCTAGTGGC | GATCCTGCCT | AAAGATTCTT | ACCAGACACT | CCTTACAGAG | AATTACACTC | 2820 |
| GCATATTTCT | GAACATGACG | GAGTCGACGC | CCCTCGAGTT | CACGCGGACG | ATCCAGACTA | 2880 |
| GGATCGTATC | AATCGAGGCC | AGGCGCGCCT | GCGCAGCTCA | AGAGGCGGCG | CCGGACATAT | 2940 |
| TCTTGGTGTT | GTTTCAGATG | TTGGTGGCAC | ACTTTCTTGT | TGCGCGGGGC | ATTACCGAGC | 3000 |
| ACCGATTTGT | GGAGGTGGAC | TGCGTGTGTC | GGCAGTATGC | GGAACTGTAT | TTTCTCCGCC | 3060 |
| GCATCTCGCG | TCTGTGCATG | CCCACGTTCA | CCACTGTCGG | GTATAACCAC | ACCACCCTTG | 3120 |
| GCGCTGTGGC | CGCCACACAA | ATAGCTCGCG | TGTCCGCCAC | GAAGTTGGCC | AGTTTGCCCC | 3180 |
| GCTCTTCCCA | GGAAACAGTG | CTGGCCATGG | TCCAGCTTGG | CGCCCGTGAT | GGCGCCGTCC | 3240 |
| CTTCCTCCAT | TCTGGAGGGC | ATTGCTATGG | TCGTCGAACA | TATGTATACC | GCCTACACTT | 3300 |
| ATGTGTACAC | ACTCGGCGAT | ACTGAAAGAA | AATTAATGTT | GGACATACAC | ACGGTCCTCA | 3360 |
| CCGACAGCTG | CCCGCCCAAA | GACTCCGGAG | TATCAGAAAA | GCTACTGAGA | ACATATTTGA | 3420 |
| TGTTCACATC | AATGTGTACC | AACATAGAGC | TGGGCGAAAT | GATCGCCCGC | TTTTCCAAAC | 3480 |
| CGGACAGCCT | TAACATCTAT | AGGGCATTCT | CCCCCTGCTT | TCTAGGACTA | AGGTACGATT | 3540 |
| TGCATCCAGC | CAAGTTGCGC | GCCGAGGCGC | CGCAGTCGTC | CGCTCTGACG | CGGACTGCCG | 3600 |
| TTGCCAGAGG | AACATCGGGA | TTCGCAGAAT | TGCTCCACGC | GCTGCACCTC | GATAGCTTAA | 3660 |
| ATTTAATTCC | GGCGATTAAC | TGTTCAAAGA | TTACAGCCGA | CAAGATAATA | GCTACGGTAC | 3720 |
| CCTTGCCTCA | CGTCACGTAT | ATCATCAGTT | CCGAAGCACT | CTCGAACGCT | GTTGTCTACG | 3780 |
| AGGTGTCGGA | GATCTTCCTC | AAGAGTGCCA | TGTTTATATC | TGCTATCAAA | CCCGATTGCT | 3840 |
| CCGGCTTTAA | CTTTTCTCAG | ATTGATAGGC | ACATTCCCAT | AGTCTACAAC | ATCAGCACAC | 3900 |
| CAAGAAGAGG | TTGCCCCCTT | TGTGACTCTG | TAATCATGAG | CTACGATGAG | AGCGATGGCC | 3960 |
| TGCAGTCTCT | CATGTATGTC | ACTAATGAAA | GGGTGCAGAC | CAACCTCTTT | TTAGATAAGT | 4020 |
| CACCTTTCTT | TGATAATAAC | AACCTACACA | TTCATTATTT | GTGGCTGAGG | GACAACGGGA | 4080 |
| CCGTAGTGGA | GATAAGGGGC | ATGTATAGAA | GACGCGCAGC | CAGTGCTTTG | TTTCTAATTC | 4140 |
| TCTCTTTTAT | TGGGTTCTCG | GGGGTTATCT | ACTTTCTTTA | CAGACTGTTT | CCATCCTTT | 4200 |
| ATTAGACGGT | CAATAAAGCG | TAGATTTTTA | AAAGGTTTCC | TGTGCATTCT | TTTTGTATGG | 4260 |
| GCATATACTT | GGCAAGAAAT | CCGAGCACCT | CAGAAAGTGG | ATTGCCGTCA | CATATCAGTT | 4320 |
| CGACCACCCC | TGCACCTAGC | CATGCGGCGC | TTTGACGGTC | TTTGGGGCTA | CACATCATAA | 4380 |
| AGTACTTTTC | CATGGCTTCT | ATAAGCACCT | TGGAACAATC | TGGGGGTTGG | CGAATGGGTT | 4440 |
| CCCTAAACGG | GAAATCCTCT | ATGGTATTCA | GGCAGAAGAC | CGCGTCCTCC | ACCCGACGTT | 4500 |
| TGAGTCTTTC | TAGCAGAGCG | CCGAAGAACT | CCCGCTCGTG | TGTTTTCGCA | GGGGCAAGTT | 4560 |
| CTGCGCCGTA | CAGCGATGAG | AAACACGACA | CGATGTTTTC | CAGCCCATG | CTGCGCAGCA | 4620 |
| ACACGTGCTT | CAGGAACAGG | TGTTGTAGCC | GGTTCAGTTT | TAGCTTGGGT | AGAAAAGTTA | 4680 |
| TCGAGTTGTT | AGCACGCTCC | ATGATGGTAA | CGGTGTTGAA | GTCACAGACC | GGGCTTTCTC | 4740 |
| CGAGTCTCGG | CCGCCTGAGT | CCAATCATGT | AGAACATAGA | CGCGGCCTCG | TTGTCTGTGT | 4800 |

-continued

| | | | | | | |
|---|---|---|---|---|---|---|
| TAAGTGACAC | GATATCCCGT | TCGCAAACCT | GTGCGATGTT | GTGTTTCAGT | ATAGATCTGG | 4860 |
| TCTGACCGGC | ACGGGGTGTT | ATGGGGTGAC | GCGGTAAAGG | CGACTCTGGG | TCAAACACCT | 4920 |
| TTATGCGGTT | GGCGGCCTCG | TCGATGACGA | CACGCTTGTT | CGCGGCGTGT | ATGGGACGC | 4980 |
| GACGGCATCC | CGCTGGCAGA | TCTATAATCT | TAAAGTTGGT | ATAAGACTGG | TCGCTCGTTA | 5040 |
| TGGCCAGCCG | GCACTCCGGT | AGTATCTGCG | TGTCCTCGAA | TTCGTGGCCG | CGTACGACTG | 5100 |
| GCTTGGAGTG | CAGGTAAACG | CCAAGAGATG | CGGTCTCTTC | GCCTACGCAC | AAGTGGCTTC | 5160 |
| TTAACGCGTA | GGGGTGCGGT | GAGAGCATGA | TCCGTAGCAA | CGATAGTTCC | GGGTGCCTAG | 5220 |
| CCGCGTAGAG | TGGCAGGGTA | GACGAGTCCG | GAGTCCCAAA | CTTTTCGAAC | AACAGTGGCA | 5280 |
| TCGGGACTTC | AGGATTAGAG | ACTCCCACCA | TGGCCGCCAC | CGCCGGAGAG | GTCAAGACGT | 5340 |
| GAAACACGCG | CTCGCCTGTC | GACAGGCGCG | CCGCGCCCTC | TACTAGACTA | GCCTTCACGT | 5400 |
| CCGGAACTCG | TAACATAGCT | TAGACCAGCG | GACGGACGCA | ACGTACGTGG | GGATCGGCTG | 5460 |
| GCGGTGTCTG | CTCGTTGGAC | GCGGCCGTTC | GGTGGCGCCA | GTGCAGGCCT | AGTTTGCGAA | 5520 |
| TGGCGTGACG | GACAATTTGT | GGCTTTAGAG | CGGCGAACCG | ATGACCCGTG | GTGGCGACGA | 5580 |
| ACGAAATGAA | GTTTGCATTG | CGGCCCAACT | CGTCTAGCCT | GGTCTTCTTG | TTTCGGGCAT | 5640 |
| AGATTTTCGG | GATTAGGTTA | CACTTTTTAT | ATCCAGTAC | TGCGCACTCG | TGTTTGCTTT | 5700 |
| TAGTGTGACT | GATTATCTTC | TTTGAGAAGT | CAAACAGGCC | CCGGGCGGCG | GCTCGCCTAA | 5760 |
| TGCAAGCCAC | GTCAAGCCTG | AGAAACGAAC | AGCATTCCAC | CAGACACTCC | AGGAACCTTT | 5820 |
| TGTGTAGCGT | CTGTATTTGG | GAACGGTTTC | TGTGCTCAAG | TAGGGAGAAT | ATTCTATTTT | 5880 |
| TGTTTCCGTC | GATGCGCGCG | TGCTGGTCCG | TGAGAATGGG | CGCCAGCTCG | TGGCGAATCT | 5940 |
| GTTCCACAAG | AGGCTGCCCG | TACACTTTAG | AAATCGTGGC | TGTCGCGGCC | TTAAACCAGG | 6000 |
| ACACGTTTAG | CCCATCCTTG | CTGGAGACCA | CAGATGGAAA | GTTTGTGGTC | CAAAATACGT | 6060 |
| TTTTTCGCCC | CATTCTCACC | ATGTACTGGT | TTTCCAGTCC | GTGCAGGTCC | AACGTGGAGT | 6120 |
| TCCAATTTGC | TATCGATACA | GGAAATATGT | GCCTGATTGG | CAGAAAGCAT | TTCAGCGTAC | 6180 |
| CCATTGCGAA | GAGAAAGTGC | AGCATGTCCC | CACTGATGTT | GATGTTATT | GCGGTGCCTT | 6240 |
| GACACATGTT | GTCGGAAAAA | AACACGCTTA | TGGTAAAAGA | AGGTTCCTTT | ACGGAGTACT | 6300 |
| TTCGTATAAC | AAAATTGTTG | GTCAATCTGG | GGATGTTTAA | AATAGTCTTT | TGCAGGGTGT | 6360 |
| TAGGAACGTG | GCAGCTTATC | TTAGTGTTAA | TCACCATGTT | GGTGTTGAAT | ATGGTGATCT | 6420 |
| TGAAGTTTTC | CAAACTGACG | TGTTTTGTGG | GTTCCAGCAT | GTCTGACACT | GTAGAGCTGC | 6480 |
| CCAGAGTCCG | CGCGTCCGTG | GCCGCGTATC | GTTGGAAGCA | CGCCTGCAAA | TTTCCTTTCA | 6540 |
| TGGCTGCTCG | CCGGTCTTTC | GGCGCGTACC | GGATTCTTGA | AAGCGTCGCC | GCCAGGAGAC | 6600 |
| GCGGTGTCTC | GTGGGTGCCT | AAAAAGTTTG | CGCAGGGGTG | CAGTCCGCTG | CACGAGTGGC | 6660 |
| CGATGCAGTC | TGCCACTGCC | ATACACATGA | CGAGTCTGTA | GATGGCCGGT | GTGCCCGGAT | 6720 |
| ACACTAGATA | GTAGGTACAA | TCTGGGGTAC | TGACGACCAC | CCTGTATGGC | TTTGGTCCGG | 6780 |
| GGTCCTTGCG | TTGGATTTTT | ACGTGCAGAC | GGGACACGAG | CTGGTTTAGA | GCCAGCTGAA | 6840 |
| AGCCCACCAG | ATCCCGTCCG | TTAACCTTGA | CGTCCTGGTG | CTTACTCTGT | TTCGACAGGT | 6900 |
| TCTTCAGCAC | GGTGGGCAGT | CGCTCTACGT | TGTGAGCGAT | GGCACGGCGC | AGCGAGACCA | 6960 |
| GCTCTCCGTG | CCACCCCCAC | GTGGCCATGA | AGCTGCTGAT | GTTAAACTTT | AAAAAATGTA | 7020 |
| GCTGTGCGTC | TGGGATGCG | GGTGGCATTA | TTGAAAACGA | GAGATGCTTC | AGGCTCTCCA | 7080 |
| GGAGTGCAAA | ATAATTTTGA | TAGATTGTGG | GTTGTAGACT | ATGGGCAAC | ACCGCCAGAA | 7140 |
| ACGCATGAAA | ACACTGTTCG | AACTCCCAGA | ACTCCAGGTA | CCTGCACACT | ATCCTGAACA | 7200 |

| | | | | | | |
|---|---|---|---|---|---|---|
| TGGCTTTGTA | ACATATGGTG | CACGTTAGTA | GCGCGGGAAG | ATACAGCGAG | CGTAGCTCCC | 7260 |
| TGAATTCGCA | GGGTTTATCA | CAATCATCGG | TAAGTTCCCA | TGATCCCACC | GCAGGTAGGT | 7320 |
| AGTTGTCGGT | GTCTATCTGT | CCGCGCGTAA | ACACTCCACC | ACCGTCAATT | ATTAAACCTT | 7380 |
| CGCCGCTGTA | CCGTCGACCC | ACTTTTCCCA | AAAGAGTCCC | TTCTTGATGT | ATAAAAGGGT | 7440 |
| GGAGGCGTTC | CCCCAGGAGT | AGTCTGCGTA | TCGCTCTGCA | GGCGAAAAAG | GTGGGCTCGG | 7500 |
| GCTGCATCAT | CTTATCAAGA | CCTTCTAAGG | TCAGCTCTGC | CTGCAGGTGC | GAGTTGGTGG | 7560 |
| CCAGACAGCA | GAATATTTCC | AGCTGTGATT | CCCAAGTCGC | TTGATAACAC | GTGGTCTGCG | 7620 |
| GACTCGTCGT | CAGGGAGGCG | CTCGGTGGCA | GTAGTAGGGG | GCCCTCGAGC | GCTGCCATGG | 7680 |
| AGGCGACCTT | GGAGCAACGA | CCTTTCCGT | ACCTCGCCAC | GGAGGCCAAC | CTCCTAACGC | 7740 |
| AGATTAAGGA | GTCGGCTGCC | GACGGACTCT | TCAAGAGCTT | TCAGCTATTG | CTCGGCAAGG | 7800 |
| ACGCCAGAGA | AGGCAGTGTC | CGTTTCGAAG | CGCTACTGGG | CGTATATACC | AATGTGGTGG | 7860 |
| AGTTTGTTAA | GTTTCTGGAG | ACCGCCCTCG | CCGCCGCTTG | CGTCAATACC | GAGTTCAAGG | 7920 |
| ACCTGCGGAG | AATGATAGAT | GGAAAAATAC | AGTTTAAAAT | TTCAATGCCC | ACTATTGCCC | 7980 |
| ACGGAGACGG | GAGGAGGCCC | AACAAGCAGA | GACAGTATAT | CGTCATGAAG | GCTTGCAATA | 8040 |
| AGCACCACAT | CGGTGCGGAG | ATTGAGCTTG | CGGCCGCAGA | CATCGAGCTT | CTCTTCGCCG | 8100 |
| AGAAAGAGAC | GCCCTTGGAC | TTCACAGAGT | ACGCGGGTGC | CATCAAGACG | ATTACGTCGG | 8160 |
| CTTTGCAGTT | TGGTATGGAC | GCCCTAGAAC | GGGGGTTAGT | GGACACGGTT | CTCGCAGTTA | 8220 |
| AACTTCGGCA | CGCTCCACCC | GTCTTTATTT | TAAAGACGCT | GGGCGATCCC | GTCTACTCTG | 8280 |
| AGAGGGGCCT | CAAAAAGGCC | GTCAAGTCTG | ACATGGTATC | CATGTTCAAG | GCACACCTCA | 8340 |
| TAGAACATTC | ATTTTTCTA | GATAAGGCCG | AGCTCATGAC | AAGGGGAAG | CAGTATGTCC | 8400 |
| TAACCATGCT | CTCCGACATG | CTGGCCGCGG | TGTGCGAGGA | TACCGTCTTT | AAGGGTGTCA | 8460 |
| GCACGTACAC | CACGGCCTCT | GGGCAGCAGG | TGGCCGGCGT | CCTGGAGACG | ACGGACAGCG | 8520 |
| TCATGAGACG | GCTGATGAAC | CTGCTGGGGC | AAGTGGAAAG | TGCCATGTCC | GGGCCCGCGG | 8580 |
| CCTACGCCAG | CTACGTTGTC | AGGGGTGCCA | ACCTCGTCAC | CGCCGTTAGC | TACGGAAGGG | 8640 |
| CGATGAGAAA | CTTTGAACAG | TTTATGGCAC | GCATAGTGGA | CCATCCCAAC | GCTCTGCCGT | 8700 |
| CTGTGGAAGG | TGACAAGGCC | GCTCTGGCGG | ACGGACACGA | CGAGATTCAG | AGAACCCGCA | 8760 |
| TCGCCGCCTC | TCTCGTCAAG | ATAGGGGATA | AGTTTGTGGC | CATTGAAAGT | TTGCAGCGCA | 8820 |
| TGTACAACGA | GACTCAGTTT | CCCTGCCCAC | TGAACCGGCG | CATCCAGTAC | ACCTATTTCT | 8880 |
| TCCCTGTTGG | CCTTCACCTT | CCCGTGCCCC | GCTACTCGAC | ATCCGTCTCA | GTCAGGGGCG | 8940 |
| TAGAATCCCC | GGCCATCCAG | TCGACCGAGA | CGTGGGTGGT | TAATAAAAAC | AACGTGCCTC | 9000 |
| TTTGCTTCGG | TTACCAAAAC | GCCCTCAAAA | GCATATGCCA | CCCTCGAATG | CACAACCCCA | 9060 |
| CCCAGTCAGC | CCAGGCACTA | AACCAAGCTT | TTCCCGATCC | CGACGGGGA | CATGGGTACG | 9120 |
| GTCTCAGGTA | TGAGCAGACG | CCAAACATGA | ACCTATTCAG | AACGTTCCAC | CAGTATTACA | 9180 |
| TGGGGAAAAA | CGTGGCATTT | GTTCCGATG | TGGCCCAAAA | AGCGCTCGTA | CCACGGAGG | 9240 |
| ATCTACTGCA | CCCAACCTCT | CACCGTCTCC | TCAGATTGGA | GGTCCACCCC | TTCTTTGATT | 9300 |
| TTTTTGTGCA | CCCCTGTCCT | GGAGCGAGAG | GATCGTACCG | CGCCACCCAC | AGAACAATGG | 9360 |
| TTGGAAATAT | ACCACAACCG | CTCGCTCCAA | GGGAGTTTCA | GGAAAGTAGA | GGGGCGCAGT | 9420 |
| TCGACGCTGT | GACGAATATG | ACACACGTCA | TAGACCAGCT | AACTATTGAC | GTCATACAGG | 9480 |
| AGACGGCATT | TGACCCCGCG | TATCCCTGT | TCTGCTATGT | AATCGAAGCA | ATGATTCACG | 9540 |
| GACAGGAAGA | AAAATTCGTG | ATGAACATGC | CCCTCATTGC | CCTGGTCATT | CAAACCTACT | 9600 |

| | | | | | | |
|---|---|---|---|---|---|---|
| GGGTCAACTC | GGGAAAACTG | GCGTTTGTGA | ACAGTTATCA | CATGGTTAGA | TTCATCTGTA | 9660 |
| CGCATATGGG | GAATGGAAGC | ATCCCTAAGG | AGGCGCACGG | CCACTACCGG | AAAATCTTAG | 9720 |
| GCGAGCTCAT | CGCCCTTGAG | CAGGCGCTTC | TCAAGCTCGC | GGGACACGAG | ACGGTGGGTC | 9780 |
| GGACGCCGAT | CACACATCTG | GTTTCGGCTC | TCCTCGACCC | GCATCTGCTG | CCTCCCTTTG | 9840 |
| CCTACCACGA | TGTCTTTACG | GATCTTATGC | AGAAGTCATC | CAGACAACCC | ATAATCAAGA | 9900 |
| TCGGGGATCA | AAACTACGAC | AACCCTCAAA | ATAGGGCGAC | ATTCATCAAC | CTCAGGGGTC | 9960 |
| GCATGGAGGA | CCTAGTCAAT | AACCTTGTTA | ACATTTACCA | GACAAGGGTC | AATGAGGACC | 10020 |
| ATGACGAGAG | ACACGTCCTG | GACGTGGCGC | CCCTGGACGA | GAATGACTAC | AACCCGGTCC | 10080 |
| TCGAGAAGCT | ATTCTACTAT | GTTTTAATGC | CGGTGTGCAG | TAACGGCCAC | ATGTGCGGTA | 10140 |
| TGGGGGTCGA | CTATCAAAAC | GTGGCCCTGA | CGCTGACTTA | CAACGGCCCC | GTCTTTGCGG | 10200 |
| ACGTCGTGAA | CGCACAGGAT | GATATTCTAC | TGCACCTGGA | GAACGGAACC | TTGAAGGACA | 10260 |
| TTCTGCAGGC | AGGCGACATA | CGCCCGACGG | TGGACATGAT | CAGGGTGCTG | TGCACCTCGT | 10320 |
| TTCTGACGTG | CCCTTTCGTC | ACCCAGGCCG | CTCGCGTGAT | CACAAAGCGG | GACCCGGCCC | 10380 |
| AGAGTTTTGC | CACGCACGAA | TACGGGAAGG | ATGTGGCGCA | GACCGTGCTT | GTTAATGGCT | 10440 |
| TTGGTGCGTT | CGCGGTGGCG | GACCGCTCTC | GCGAGGCGGC | GGAGACTATG | TTTTATCCGG | 10500 |
| TACCCTTTAA | CAAGCTCTAC | GCTGACCCGT | TGGTGGCTGC | CACACTGCAT | CCGCTCCTGG | 10560 |
| CAAACTATGT | CACCAGGCTC | CCCAACCAGA | GAAACGCGGT | GGTCTTTAAC | GTGCCATCCA | 10620 |
| ATCTCATGGC | AGAATATGAG | GAATGGCACA | AGTCGCCCGT | CGCGGCGTAT | GCCGCGTCTT | 10680 |
| GTCAGGCCAC | CCCGGGCGCC | ATTAGCGCCA | TGGTGAGCAT | GCACCAAAAA | CTATCTGCCC | 10740 |
| CCAGTTTCAT | TTGCCAGGCA | AAACACCGCA | TGCACCCTGG | TTTTGCCATG | ACAGTCGTCA | 10800 |
| GGACGGACGA | GGTTCTAGCA | GAGCACATCC | TATACTGCTC | CAGGGCGTCG | ACATCCATGT | 10860 |
| TTGTGGGCTT | GCCTTCGGTG | GTACGGCGCG | AGGTACGTTC | GGACGCGGTG | ACTTTTGAAA | 10920 |
| TTACCCACGA | GATCGCTTCC | CTGCACACCG | CACTTGGCTA | CTCATCAGTC | ATCGCCCCGG | 10980 |
| CCCACGTGGC | CGCCATAACT | ACAGACATGG | GAGTACATTG | TCAGGACCTC | TTTATGATTT | 11040 |
| TCCCAGGGGA | CGCGTATCAG | GACCGCCAGC | TGCATGACTA | TATCAAAATG | AAAGCGGGCG | 11100 |
| TGCAAACCGG | CTCACCGGGA | AACAGAATGG | ATCACGTGGG | ATACACTGCT | GGGGTTCCTC | 11160 |
| GCTGCGAGAA | CCTGCCCGGT | TTGAGTCATG | GTCAGCTGGC | AACCTGCGAG | ATAATTCCCA | 11220 |
| CGCCGGTCAC | ATCTGACGTT | GCCTATTTCC | AGACCCCCAG | CAACCCCCGG | GGGCGTGCGG | 11280 |
| CGTGCGTGGT | GTCGTGTGAT | GCTTACAGTA | ACGAAAGCGC | AGAGCGTTTG | CTCTACGACC | 11340 |
| ATTCAATACC | AGACCCCGCG | TACGAATGCC | GGTCCACCAA | CAACCCGTGG | GCTTCGCAGC | 11400 |
| GTGGCTCCCT | CGGCGACGTG | CTATACAATA | TCACCTTTCG | CCAGACTGCG | CTGCCGGGCA | 11460 |
| TGTACAGTCC | TTGTCGGCAG | TTCTTCCACA | AGGAAGACAT | TATGCGGTAC | AATAGGGGGT | 11520 |
| TGTACACTTT | GGTTAATGAG | TATTCTGCCA | GGCTTGCTGG | GGCCCCGCC | ACCAGCACTA | 11580 |
| CAGACCTCCA | GTACGTCGTG | GTCAACGGTA | CAGACGTGTT | TTTGGACCAG | CCTTGCCATA | 11640 |
| TGCTGCAGGA | GGCCTATCCC | ACGCTCGCCG | CCAGCACAG | AGTTATGCTT | GACGAGTACA | 11700 |
| TGTCAAACAA | GCAGACACAC | GCCCCAGTAC | ACATGGGCCA | GTATCTCATT | GAAGAGGTGG | 11760 |
| CGCCGATGAA | GAGACTATTA | AAGCTCGGAA | ACAAGGTGGT | GTATTAGCTA | ACCCTTCTAG | 11820 |
| CGTTGGCTAG | TCATGGCACT | CGACAAGAGT | ATAGTGGTTA | ACTTCACCTC | CAGACTCTTC | 11880 |
| GCTGATGAAC | TGGCCGCCCT | TCAGTCAAAA | ATAGGGAGCG | TACTGCCGCT | CGGAGATTGC | 11940 |
| CACCGTTTAC | AAAATATACA | GGCATTGGGC | CTGGGGTGCG | TATGCTCACG | TGAGACATCT | 12000 |

| | | | | | | |
|---|---|---|---|---|---|---|
| CCGGACTACA | TCCAAATTAT | GCAGTATCTA | TCCAAGTGCA | CACTCGCTGT | CCTGGAGGAG | 12060 |
| GTTCGCCCGG | ACAGCCTGCG | CCTAACGCGG | ATGGATCCCT | CTGACAACCT | TCAGATAAAA | 12120 |
| AACGTATATG | CCCCCTTTTT | TCAGTGGGAC | AGCAACACCC | AGCTAGCAGT | GCTACCCCCA | 12180 |
| TTTTTTAGCC | GAAAGGATTC | CACCATTGTG | CTCGAATCCA | ACGGATTTGA | CCTCGTGTTC | 12240 |
| CCCATGGTCG | TGCCGCAGCA | ACTGGGGCAC | GCTATTCTGC | AGCAGCTGTT | GGTGTACCAC | 12300 |
| ATCTACTCCA | AAATATCGGC | CGGGGCCCCG | GATGATGTAA | ATATGGCGGA | ACTTGATCTA | 12360 |
| TATACCACCA | ATGTGTCATT | TATGGGGCGC | ACATATCGTC | TGGACGTAGA | CAACACGGAT | 12420 |
| CCACGTACTG | CCCTGCGAGT | GCTTGACGAT | CTGTCCATGT | ACCTTTGTAT | CCTATCAGCC | 12480 |
| TTGGTTCCCA | GGGGGTGTCT | CCGTCTGCTC | ACGGCGCTCG | TGCGGCACGA | CAGGCATCCT | 12540 |
| CTGACAGAGG | TGTTTGAGGG | GGTGGTGCCA | GATGAGGTGA | CCAGGATAGA | TCTCGACCAG | 12600 |
| TTGAGCGTCC | CAGATGACAT | CACCAGGATG | CGCGTCATGT | TCTCCTATCT | TCAGAGTCTC | 12660 |
| AGTTCTATAT | TTAATCTTGG | CCCCAGACTG | CACGTGTATG | CCTACTCGGC | AGAGACTTTG | 12720 |
| GCGGCCTCCT | GTTGGTATTC | CCCACGCTAA | CGATTTGAAG | CGGGGGGGGG | GTATGGCGTC | 12780 |
| ATCTGATATT | CTGTCGGTTG | CAAGGACGGA | TGACGGCTCC | GTCTGTGAAG | TCTCCCTGCG | 12840 |
| TGGAGGTAGG | AAAAAAACTA | CCGTCTACCT | GCCGGACACT | GAACCCTGGG | TGGTAGAGAC | 12900 |
| CGACGCCATC | AAAGACGCCT | TCCTCAGCGA | CGGGATCGTG | GATATGGCTC | GAAAGCTTCA | 12960 |
| TCGTGGTGCC | CTGCCCTCAA | ATTCTCACAA | CGGCTTGAGG | ATGGTGCTTT | TTTGTTATTG | 13020 |
| TTACTTGCAA | AATTGTGTGT | ACCTAGCCCT | GTTTCTGTGC | CCCCTTAATC | CTTACTTGGT | 13080 |
| AACTCCCTCA | AGCATTGAGT | TTGCCGAGCC | CGTTGTGGCA | CCTGAGGTGC | TCTTCCCACA | 13140 |
| CCCGGCTGAG | ATGTCTCGCG | GTTGCGATGA | CGCGATTTTC | TGTAAACTGC | CCTATACCGT | 13200 |
| GCCTATAATC | AACACCACGT | TTGGACGCAT | TTACCCGAAC | TCTACACGCG | AGCCGGACGG | 13260 |
| CAGGCCTACG | GATTACTCCA | TGGCCCTTAG | AAGGGCTTTT | GCAGTTATGG | TTAACACGTC | 13320 |
| ATGTGCAGGA | GTGACATTGT | GCCGCGGAGA | AACTCAGACC | GCATCCCGTA | ACCACACTGA | 13380 |
| GTGGGAAAAT | CTGCTGGCTA | TGTTTTCTGT | GATTATCTAT | GCCTTAGATC | ACAACTGTCA | 13440 |
| CCCGGAAGCA | CTGTCTATCG | CGAGCGGCAT | CTTTGACGAG | CGTGACTATG | GATTATTCAT | 13500 |
| CTCTCAGCCC | CGGAGCGTGC | CCTCGCCTAC | CCCTTGCGAC | GTGTCGTGGG | AAGATATCTA | 13560 |
| CAACGGGACT | TACCTAGCTC | GGCCTGGAAA | CTGTGACCCC | TGGCCCAATC | TATCCACCCC | 13620 |
| TCCCTTGATT | CTAAATTTTA | AATAAGGTG | TGTCACTGGT | TACACCACGA | TTAAAAACCA | 13680 |
| CTCACTGAGA | TGTCTTTTTA | ACCGCTAAGG | GATTATACCG | GGATTTAAAA | CCGCCCACTG | 13740 |
| ATTTTTTTAC | GCTAAGAGTT | GGGTGCTTGG | GGGGTTTTGC | ATTGCTCTGT | TGTAAACTAT | 13800 |
| ATATAAGTTA | AACCAAAATT | CGCAGGGAGA | CAAGGTGACG | GTGGTGAGAA | CTCAGTTGAG | 13860 |
| AGTCAGAGAA | TACAGTGCTA | ATCAGGGTAG | ATGAGCATGA | CTTCCCCGTC | TCCAGTCACC | 13920 |
| GGAGGAATGG | TGGACGGCTC | CGTCCTGGTG | CGAATGGCCA | CCAAGCCTCC | CGTGATTGGT | 13980 |
| CTTATAACAG | TGCTCTTCCT | CCTAGTCATA | GGCGCCTGCG | TCTACTGCTG | CATTCGCGTG | 14040 |
| TTCCTGGCGG | CTCGACTGTG | GCGCGCCACC | CCACTAGGCA | GGGCCACCGT | GGCGTATCAG | 14100 |
| GTCCTTCGCA | CCCTGGGACC | GCAGGCCGGG | TCACATGCAC | CGCCGACGGT | GGGCATAGCT | 14160 |
| ACCCAGGAGC | CCTACCGTAC | AATATACATG | CCAGATTAGA | ACGGGGTGTG | TGCTATAATG | 14220 |
| GATGGCTATG | GGGGGGCTGT | AGATAATTGA | GCGCTGTGCT | TTTATTGTGG | GGATATGGGC | 14280 |
| TTGTACATGT | GTCTATCATC | GGTAGCCATA | AAATGGGCCA | TGACAACTGC | CACAAGTAAG | 14340 |
| TCGTCCGACA | TGTGCTTTTG | CTTGGCGCTG | TATGACTGCC | CTCCATCCCT | AAGCGGGACG | 14400 |

| | | | | | | |
|---|---|---|---|---|---|---|
| CACTTGATCG | CGCGGACCTG | TTCTACCAGG | TAGGTCACCG | GGTCAAATGA | TATTTTGATG | 14460 |
| GTGTTGGACA | CCACCGTCTG | GCTGGCGCTC | AGGGTGCCGG | AGTTCAGAGC | GTAGATGAAT | 14520 |
| GTCTCAAACG | CGGAGGATTT | CTCGCCTCCC | AACATGTAAA | TTGGCCACTG | CAGGGCGCTG | 14580 |
| CTCTTGTCAG | TATAGTGTAG | AAAATGTATG | GGGAGCGGGC | ATATTTCGTT | AAGGACGGTT | 14640 |
| GCAATGGCCA | CCCCAGAATC | TTGGCTGCTG | TTGCCTTCGA | CCGCCGCGTT | CACGCGCTCA | 14700 |
| ATTGTGGGGT | GGAGCACAGC | GATCGCCTTA | ATCATCGTGC | ATGCGCAGGA | CGCTATCTCG | 14760 |
| TAAGCAGCTG | CGCCAGTGAG | GTCGCGCAGG | AAGAAATGCT | CCATGCCCAA | TATGAGGCTT | 14820 |
| CTGGTGGGAG | TCTGAGTACT | CGTGACAACG | GCGCCCACGC | CAGTACCGGA | CGCCTCCGTG | 14880 |
| TTGTTCGTAT | ACGCGGGGTC | GATGTAAACA | AACAGCTGTT | TTCCAAGGCA | CTTCTGAACC | 14940 |
| TGCTGGGCGG | TGGTGTCTAC | CCGACACATG | TCAAACTGTG | TCAGCGCTGC | GTCACCCACC | 15000 |
| ACGCGGTAAA | GCGTAGCATT | TGACGACGCT | GCTCCCTCGC | CCATTAGTTC | GGTGTCGAAT | 15060 |
| GCCCCCTCCA | TAAAGAGGTT | GGTGGTGGTT | TTGATGGATT | CGTCGATGGT | GATGTACGTC | 15120 |
| GGAATGTGCA | GTCTGTAACA | AGGACAGGAC | ACTAGTGCGT | CTTGCAGGTG | GAAATCTTCG | 15180 |
| CGGTGGTCCG | CACACACGTA | ACTGACCACA | TTCAGCATCT | TTTCCTGGGC | GTTCCTGAGG | 15240 |
| TTAAGCAGGA | AACTCGTGGA | GCGGTCTGAC | GAGTTCACGG | ATGATATAAA | TATAAGCTTG | 15300 |
| GCGTCTTTCT | GAAGCATGAA | ACCCAGAATA | GCCGGCAGTG | CATCCTTTTT | AATAAAATTC | 15360 |
| GCCTCGTCTA | CGTAGAGCAG | GTTAAAGGTC | TGTCCCCGAA | TGCTCTGCAG | ACACGGAAAG | 15420 |
| ACACAAAAGA | GGGGCTCATA | AGCGGCTAAC | AGTAAAGGAG | AGGAGGCGAA | CAGTGCGTGG | 15480 |
| CTCTTGTTCT | TGGGAATAAA | AGGGGGCGTG | TGTGCCGATC | GTATGGGTGA | GCCAGTGGAT | 15540 |
| CCTGGACATG | TGGTGAATGA | GAAAGATTTT | GAGGAGTGTG | AACAATTTTT | CAGTCAACCC | 15600 |
| CTTAGGGAGC | AAGTGGTCGC | GGGGGTCAGG | GCACTCGACG | GCCTCGGTCT | CGCTGACTCT | 15660 |
| CTATGTCACA | AAACAGAAAG | ACTCTGCCTG | CTGATGGACC | TGGTGGGCAC | GGAGTGCTTT | 15720 |
| GCGAGGGTGT | GCCGCCTAGA | CACCGGTGCG | AAATGAAGAG | TGTGGCGAGT | CCCTTATGTC | 15780 |
| AGTTCCACGG | CGTGTTTTGC | CTGTACCAGT | GTCGCCAGTG | CCTGGCATAC | CACGTGTGTG | 15840 |
| ATGGGGCGC | CGAATGCGTT | CTCCTGCATA | CGCCGGAGAG | CGTCATCTGC | GAACTAACGG | 15900 |
| GTAACTGCAT | GCTCGGCAAC | ATTCAAGAGG | GCCAGTTTTT | AGGGCCGGTA | CCGTATCGGA | 15960 |
| CTTTGGATAA | CCAGGTTGAC | AGGGACGCAT | ATCACGGGAT | GCTAGCGTGT | CTGAAACGGG | 16020 |
| ACATTGTGCG | GTATTTGCAG | ACATGGCCGG | ACACCACCGT | AATCGTGCAG | GAAATAGCCC | 16080 |
| TGGGGACGG | CGTCACCGAC | ACCATCTCGG | CCATTATAGA | TGAAACATTC | GGTGAGTGTC | 16140 |
| TTCCCGTACT | GGGGGAGGCC | CAAGGCGGGT | ACGCCATGGT | CTGTAGCATG | TATCTGCACG | 16200 |
| TTATCGTCTC | CATCTATTCG | ACAAAAACGG | TGTACAACAG | TATGCTATTT | AAATGCACAA | 16260 |
| AGAATAAAAA | GTACGACTGC | ATTGCCAAGC | GGGTGCGGAC | AAAATGGATG | CGCATGCTAT | 16320 |
| CAACGAAAGA | TACGTAGGTC | CTCGCTGCCA | CCGTTTGGCC | CACGTGGTGC | TGCCTAGGAC | 16380 |
| CTTTCTGCTG | CATCACGCCA | TACCCTGGA | GCCCGAGATC | ATCTTTTCCA | CCTACACCCG | 16440 |
| GTTCAGCCGG | TCGCCAGGGT | CATCCCGCCG | GTTGGTGGTG | TGTGGGAAAC | GTGTCCTGCC | 16500 |
| AGGGGAGGAA | AACCAACTTG | CGTCTTCACC | TTCTGGCTTG | GCGCTTAGCC | TGCCTCTGTT | 16560 |
| TTCCCACGAT | GGGAACTTTC | ATCCATTTGA | CATCTCGGTA | CTGCGCATTT | CCTGCCCTGG | 16620 |
| TTCTAATCTT | AGTCTTACTG | TCAGATTTCT | CTATCTATCT | CTGGTGGTGG | CTATGGGGC | 16680 |
| GGGACGGAAT | AATGCGCGGA | GTCCGACCGT | TGACGGGGTA | TCGCCGCCAG | AGGGCGCCGT | 16740 |
| AGCCCACCCT | TTGGAGGAAC | TGCAGAGGCT | GGCGCGTGCT | ACGCCGGACC | CGGCACTCAC | 16800 |

-continued

```
CCGTGGACCG TTGCAGGTCC TGACCGGCCT TCTCCGCGCA GGGTCAGACG GAGACCGCGC    16860
CACTCACCAC ATGGCGCTCG AGGCTCCGGG AACCGTGCGT GGAGAAAGCC TAGACCCGCC    16920
TGTTTCACAG AAGGGGCCAG CGCGCACACG CCACAGGCCA CCCCCGTGC GACTGAGCTT     16980
CAACCCCGTC AATGCCGATG TACCCGCTAC CTGGCGAGAC GCCACTAACG TGTACTCGGG    17040
TGCTCCCTAC TATGTGTGTG TTTACGAACG CGGTGGCCGT CAGGAAGACG ACTGGCTGCC    17100
GATACCACTG AGCTTCCCAG AAGAGCCCGT GCCCCCGCCA CCGGGCTTAG TGTTCATGGA    17160
CGACTTGTTC ATTAACACGA AGCAGTGCGA CTTTGTGGAC ACGCTAGAGG CCGCCTGTCG    17220
CACGCAAGGC TACACGTTGA GACAGCGCGT GCCTGTCGCC ATTCCTCGCG ACGCGGAAAT    17280
CGCAGACGCA GTTAAATCGC ACTTTTTAGA GGCGTGCCTA GTGTTACGGG GGCTGGCTTC    17340
GGAGGCTAGT GCCTGGATAA GAGCTGCCAC GTCCCCGCCC CTTGGCCGCC ACGCCTGCTG    17400
GATGGACGTG TTAGGATTAT GGGAAAGCCG CCCCCACACT CTAGGTTTGG AGTTACGCGG    17460
CGTAAACTGT GGCGGCACGG ACGGTGACTG GTTAGAGATT TTAAAACAGC CCGATGTGCA    17520
AAAGACAGTC AGCGGGAGTC TTGTGGCATG CGTGATCGTC ACACCCGCAT GGAAGCCTG    17580
GCTTGTGTTA CCTGGGGGTT TTGCTATTAA AGGCCGCTAT AGGGCGTCGA AGGAGGATCT    17640
GGTGTTCATT CGAGGCCGCT ATGGCTAGCC GGAGGCGCAA ACTTCGGAAT TTCCTAAACA    17700
AGGAATGCAT ATGGACTGTT AACCCAATGT CAGGGGACCA TATCAAGGTC TTTAACGCCT    17760
GCACCTCTAT CTCGCCGGTG TATGACCCTG AGCTGGTAAC CAGCTACGCA CTGAGCGTGC    17820
CTGCTTACAA TGTGTCTGTG GCTATCTTGC TGCATAAAGT CATGGGACCG TGTGTGGCTG    17880
TGGGAATTAA CGGAGAAATG ATCATGTACG TCGTAAGCCA GTGTGTTTCT GTGCGGCCCG    17940
TCCCGGGGCG CGATGGTATG GCGCTCATCT ACTTTGGACA GTTTCTGGAG GAAGCATCCG    18000
GACTGAGATT TCCCTACATT GCTCCGCCGC CGTCGCGCGA ACACGTACCT GACCTGACCA    18060
GACAAGAATT AGTTCATACC TCCCAGGTGG TGCGCCGCGG CGACCTGACC AATTGCACTA    18120
TGGGTCTCGA ATTCAGGAAT GTGAACCCTT TTGTTTGGCT CGGGGGCGGA TCGGTGTGGC    18180
TGCTGTTCTT GGGCGTGGAC TACATGGCGT TCTGTCCGGG TGTCGACGGA ATGCCGTCGT    18240
TGGCAAGAGT GGCCGCCCTG CTTACCAGGT GCGACCACCC AGACTGTGTC CACTGCCATG    18300
GACTCCGTGG ACACGTTAAT GTATTTCGTG GGTACTGTTC TGCGCAGTCG CCGGGTCTAT    18360
CTAACATCTG TCCCTGTATC AAATCATGTG GGACCGGGAA TGGAGTGACT AGGGTCACTG    18420
GAAACAGAAA TTTTCTGGGT CTTCTGTTCG ATCCCATTGT CCAGAGCAGG GTAACAGCTC    18480
TGAAGATAAC TAGCCACCCA ACCCCCACGC ACGTCGAGAA TGTGCTAACA GGAGTGCTCG    18540
ACGACGGCAC CTTGGTGCCG TCCGTCCAAG GCACCCTGGG TCCTCTTACG AATGTCTGAC    18600
TACTTCAGCC GCTTGCTGAT ATATGAGTGT AAAAAACTTA AGGCCCTGGG CTTACGTTCT    18660
TATTGAAGCA TGTTGCGCAC ATCAGCGAGC TGGACCGTCC TCCGGGTCGC GTGTAGATTA    18720
TGGTTCCGTT CTCCTTCTTG ATGTTTAAAT TTTTGGGGGG GAACCACCGA CAAAGCGTCT    18780
TTATGATTTC CGCGAACACG GAGTTGGCTA CGTGCTTTTG GTGGGCTACG TACCCAATGT    18840
TAATGTTCTC TACGGATGCC AGTAGCATGC TGATGATCGC CACCACTATC CATGTCTTTC    18900
CGTGTCTCCT TGGTATTAGG AATACGCTTG CCTTTTGCTT AAACGTCTGT AAAACACTGT    18960
TTGGAGTTTC AAATAAACCG AAGTACTGCT TAAACAATCC AAACAACTGG TGCGTCTTTT    19020
GTGGGGCCTT GATTGAAACC AAAAAGAAAA AAGTGTGCAT TACTAGCTGC TGTTGGAAGG    19080
GCTCCAGCCA GTGCACCCCG GGAACGTAAC AGCCGTTCAG AAAGGACGAA AGGTTAACCA    19140
GAAAAGCCTG AAGTTCGCGG TAGACAGAGC AGGCGTGCAG GGAGTCGTGT GTTTTTCTGG    19200
```

| | | | | | | |
|---|---|---|---|---|---|---|
| CCGCCTGGTA | CTCGACCAGT | TGATCGGCCG | TGGAGACGTG | CGCGTCCTCG | CGCACACACC | 19260 |
| GCATCTGCAA | GTATGTTGAT | AGGGACTCCA | ATAGGCGCGG | CTTTGCGGGG | ACGTTGTCCT | 19320 |
| CGGACGGTCT | GGGGGTTCCC | ACGTCGGGAT | TTGCTGACGT | GGGCGTGGCG | GGATGGTGCC | 19380 |
| GTGTGCAGTA | TGTTTCCAGG | ACCGAACTGT | ATGAGTTTAT | TCTGTGCACC | ACGCCAATAA | 19440 |
| AAGGGTGCGC | CATCCGTGCC | GTTTTGGGAC | AGTGTCGCGT | GAATGTCGGG | GCACTCAGTT | 19500 |
| CCCACCTCTC | TCCGGCGTCT | TTGGCGGTCT | CCTGCAGGTT | GGCGGCAAGG | CGCTCCCTGT | 19560 |
| GACGGCTGAG | CAGCATGTTT | GCTTTGAGCT | CGCTCGTGTC | CGAGGGTGAC | CCGGAGGTGA | 19620 |
| CCAGTAGGTA | CGTCAAGGGC | GTACAACTTG | CCCTGGACCT | TAGCGAGAAC | ACACCTGGAC | 19680 |
| AATTTAAGTT | GATAGAAACT | CCCCTGAACA | GCTTCCTCTT | GGTTTCCAAC | GTGATGCCCG | 19740 |
| AGGTCCAGCC | AATCTGCAGT | GGCCGGCCGG | CCTTGCGGCC | AGACTTTAGT | AATCTCCACT | 19800 |
| TGCCTAGACT | GGAGAAGCTC | CAGAGAGTCC | TCGGGCAGGG | TTTCGGGGCG | GCGGGTGAGG | 19860 |
| AAATCGCACT | GGACCCGTCT | CACGTAGAAA | CACACGAAAA | GGGCCAGGTG | TTCTACAACC | 19920 |
| ACTATGCTAC | CGAGGAGTGG | ACGTGGGCTT | TGACTCTGAA | TAAGGATGCG | CTCCTTCGGG | 19980 |
| AGGCTGTAGA | TGGCCTGTGT | GACCCCGGAA | CTTGGAAGGG | TCTTCTTCCT | GACGACCCCC | 20040 |
| TTCCGTTGCT | ATGGCTGCTG | TTCAACGGAC | CCGCCTCTTT | TTGTCGGGCC | GACTGTTGCC | 20100 |
| TGTACAAGCA | GCACTGCGGT | TACCCGGGCC | CGGTGCTACT | TCCAGGTCAC | ATGTACGCTC | 20160 |
| CCAAACGGGA | TCTTTTGTCG | TTCGTTAATC | ATGCCCTGAA | GTACACCAAG | TTTCTATACG | 20220 |
| GAGATTTTTC | CGGGACATGG | GCGGCGGCTT | GCCGCCCGCC | ATTCGCTACT | TCTCGGATAC | 20280 |
| AAAGGGTAGT | GAGTCAGATG | AAAATCATAG | ATGCTTCCGA | CACTTACATT | TCCCACACCT | 20340 |
| GCCTCTTGTG | TCACATATAT | CAGCAAAATA | GCATAATTGC | GGGTCAGGGG | ACCCACGTGG | 20400 |
| GTGGAATCCT | ACTGTTGAGT | GGAAAAGGGA | CCCAGTATAT | AACAGGCAAT | GTTCAGACCC | 20460 |
| AAAGGTGTCC | AACTACGGGC | GACTATCTAA | TCATCCCATC | GTATGACATA | CCGGCGATCA | 20520 |
| TCACCATGAT | CAAGGAGAAT | GGACTCAACC | AACTCTAAAA | GAGAGTTTAT | TAAGTCGGCT | 20580 |
| CTGGAGGCCA | ACATCAACAG | GAGGGCAGCT | GTATCGCTAT | TTGATCGTTT | TGGGGGTAGC | 20640 |
| AGCGCCGTGT | TTGAGAAGCA | GTTTCAGGAC | GCACAGCATG | CCGTCAGGGC | CCACGGTGCA | 20700 |
| CTGAAGCGCG | AAGCCGAGCT | CGGGACTCTG | GTACGCAAGG | CGGGCCAGAG | GTTTGAGGCG | 20760 |
| CTGAAAAGGG | AACGGTCAAT | TTTGCGCCAG | CCGCGCGACC | TCCCACGGGT | CGCCGACATT | 20820 |
| GACGCCCTGG | TCGACGCCGT | CGCGGACCTC | AAAGAAGAGG | TGGCCGTGCG | CCTAGATGCG | 20880 |
| CTGGAAGAGA | ATGGAGAGGA | GACCCCCACT | CACTCCTCTT | CGGAGATCAA | GGACACAATC | 20940 |
| GTCAGGTGGA | GGCTTGACGA | TTTGCCCCCG | GTGTGCCCTG | AAACTCCCTA | AGGCTACCCG | 21000 |
| GATTTCAGAG | AGACCCTGGG | CGTCCACATG | GCAGCTGAAT | CAGCATATAC | AGGTGTCCAA | 21060 |
| GACTAAAAAG | GCCACCGCGT | ATCTTAAAGC | GCCCCGTGAA | TGGGGGCAGT | GCACGCACCA | 21120 |
| GGATCCAGAC | TGGTCCAAGC | GTCTGGGTCG | TGGCGCCTTT | GGCATAATCG | TCCCTATCTC | 21180 |
| CGAGGATCTG | TGTGTGAAGC | AGTTTGATAG | CCGCCGGGAG | TTTTTCTACG | AGGCAATTGC | 21240 |
| CAACGACCTG | ATGCAGGCCA | CCCGAGAGAG | GTACCCCATG | CATTCTGGTG | GATCTAGACT | 21300 |
| GCTAGGATTC | GTGCAGCCTT | GCATACCCTG | TAGATCGATT | GTGTATCCTA | GAATGAAGTG | 21360 |
| CAACCTGCTG | CAGCTGGACT | GGAGTCAGGT | CAACCTGAGT | GTCATGGCGG | CGGAGTTCAC | 21420 |
| CGGCCTAATG | GCGGCGGTGT | CCTTTCTAAA | CAGATACTGT | GGCATGGTGC | ACTGCGACGT | 21480 |
| TAGTCCAGAC | AATATTTTGG | CCACAGGAGA | CCTAACGCCC | ATGAACCCCG | GGAGGCTGGT | 21540 |
| CCTTACCGAT | TTCGGTTCCG | TTGCGCTACA | CTCTGGGAGC | AAGTGGACTA | ACCTTGTGGT | 21600 |

| | | | | | | |
|---|---|---|---|---|---|---|
| GACCTCTAAC | CTGGGGTTTA | AGCAACACTG | CTACGACTTC | AGGGTGCCAC | CCAAACTCAT | 21660 |
| TTGTAAGCAT | CTCTATAAGC | CGTCTTGCGT | CCTCTTCCAG | TGTTACCTAT | CCAGTCTCGG | 21720 |
| TAAGATGCAC | GCGCAGGTAT | TGGACCAACC | GTACCCTATC | AGCCCTAACA | TGGGACTGAC | 21780 |
| CATCGACATG | TCCTCGTTGG | GCTACACTCT | GCTGACATGC | CTGGAACTCT | ATCTCGATCT | 21840 |
| GCCGCTAAAC | AACCCTCTGA | AGTTCTTGGG | TTCAGCCACC | AGAGACGGAC | GCCCCGAACC | 21900 |
| CATGTACTAC | TTGGGCTTCA | TGATTCCCAG | GGTGGTGATG | ACTCAGATCC | TGTCCGCTGT | 21960 |
| GTGGACCATG | ACGCTTGACC | TGGGACTAGA | TTGCACCGGC | AAAGCCCAGG | CGATTCCCAT | 22020 |
| GCGACAGGAG | CACCAGCTGG | CGTTTCAGAA | GCAGTGCTAT | TTATATAAAG | CCAACCAAAA | 22080 |
| GGCAGAGTCG | TTAGCGAACT | GCTCCGATAA | GCTAAACTGC | CCCATGTTAA | AGTCTCTCGT | 22140 |
| TAGAAAGCTA | CTAGAGCGAG | ACTTTTTCAA | CCATGGAGGC | CACCCCACA | CCCGCGGACT | 22200 |
| TGTTTTCTGA | AGACTATCTG | GTTGACACCC | TGGATGGGTT | AACAGTGGAT | GACCAACAGG | 22260 |
| CTGTCCTCGC | AAGCTTGAGC | TTTTCAAAGT | TTCTAAAGCA | CGCCAAGGTT | CGAGACTGGT | 22320 |
| GCGCACAGGC | CAAGATCCAA | CCCAGCATGC | CTGCGCTGCG | CATGGCTTAC | AACTATTTCC | 22380 |
| TTTTTTCAAA | AGTGGGCGAG | TTTATTGGTA | GTGAGGATGT | GTGTAACTTT | TCGTGGACC | 22440 |
| GTGTGTTTGG | TGGTGTCAGG | TTACTGGACG | TGGCCAGCGT | GTACGCCGCC | TGTTCGCAAA | 22500 |
| TGAACGCACA | TCAGCGGCAC | CACATCTGCT | GTCTAGTGGA | GAGGGCCACT | AGTAGTCAGA | 22560 |
| GTCTGAACCC | CGTGTGGGAC | GCCCTGCGAG | ACGGAATTAT | ATCTTCATCC | AAGTTTCACT | 22620 |
| GGGCAGTTAA | ACAACAGAAC | ACTTCAAAAA | AGATATTCAG | CCCATGGCCT | ATAACGAACA | 22680 |
| ACCACTTTGT | CGCGGGCCCG | CTTGCCTTTG | GGCTGCGGTG | CGAGGAGGTG | GTGAAAACGT | 22740 |
| TGCTGGCCAC | CCTTTTGCAC | CCGGACGAGA | CAAATTGTCT | CGATTATGGG | TTTATGCAGA | 22800 |
| GTCCGCAAAA | TGGAATATTT | GGCGTGTCGC | TGGATTTCGC | GGCGAACGTC | AAAACTGACA | 22860 |
| CCGAGGGTCG | TCTACAGTTT | GACCCTAACT | GTAAAGTGTA | TGAAATAAAA | TGCAGGTTCA | 22920 |
| AGTACACCTT | TGCGAAAATG | GAGTGTGACC | CCATATACGC | CGCGTATCAG | CGGCTGTACG | 22980 |
| AGGCACCCGG | AAAGCTGGCA | CTGAAGGACT | TCTTCTATAG | CATTTCCAAG | CCTGCGGTTG | 23040 |
| AGTACGTGGG | ACTTGGAAAA | CTGCCCAGTG | AATCTGATTA | CTTGGTGGCT | TATGATCAGG | 23100 |
| AATGGGAGGC | GTGTCCTCGC | AAAAAGAGGA | AATTAACGCC | CCTTCACAAT | CTTATTAGGG | 23160 |
| AGTGTATTTT | GCACAACTCG | ACCACGGAGT | CTGACGTCTA | CGTACTTACT | GATCCTCAAG | 23220 |
| ATACTCGGGG | TCAAATCAGT | ATTAAAGCCC | GCTTCAAAGC | CAACCTCTTC | GTGAACGTCC | 23280 |
| GTCACAGCTA | CTTTTATCAG | GTATTGCTGC | AGAGTTCGAT | CGTCGAGGAG | TACATTGGCC | 23340 |
| TAGATAGCGG | CATTCCTCGC | CTCGGATCAC | CGAAATACTA | CATCGCCACC | GGCTTCTTCA | 23400 |
| GAAAGCGGGG | CTATCAGGAT | CCTGTCAACT | GTACCATCGG | TGGCGATGCT | TTAGACCCGC | 23460 |
| ACGTGGAGAT | TCCTACGCTG | CTAATCGTAA | CCCCCGTCTA | CTTTCCCCGA | GGCGCAAAGC | 23520 |
| ATCGTCTGCT | TCACCAAGCT | GCCAACTTTT | GGTCAAGAAG | TGCGAAGGAC | ACCTTTCCAT | 23580 |
| ATATCAAATG | GGATTTCTCC | TATCTATCTG | CAAACGTCCC | TCACAGCCCG | TAGACGTGGA | 23640 |
| CGGGGAACCG | CTCGACGTAG | TCGTGGACTA | TGACCCCATT | CGCGTTTCAG | AAAAGGGCAT | 23700 |
| GTTGCTTGAG | CAATCGCAAT | CCCCATATCC | CGCATTAAAA | AGAAGAAAA | AAATAAAGA | 23760 |
| AGCAATTTAT | TAAGCAAACA | GTATGGTTTT | CTGTACGTAT | TTTATTCCGT | GGTGGGTGAA | 23820 |
| AAATAACGGG | GGATGGAGGA | AGAGGGATGG | GTTTATAATG | CCAATATATC | AGCTAAATGA | 23880 |
| ATATCATTTG | CGTTTCGTCG | ATTTCACTGT | CACTTTCATG | GTCGGACTGG | TATTGGGTCC | 23940 |
| TCGGGGCGGG | CGTCGATATG | TCCTTCACTT | TGGCGCGGGC | TCTGGTCTTT | GCTGGGAGGG | 24000 |

```
GCGGCGGTTT  CTGGTGAACA  GTCGGAGTTC  TATCGACCGT  CGGCGCCGAC  GTCGCCAGAG  24060
GCATGTATGC  CGCACTCGGC  GTACAGAGTC  CCCAGTCGCT  CCTTATAACG  CGTATAACGA  24120
TGGCTAGGAT  GCACAGTATA  GGGATACAGG  AGATATTGAT  AGCCACTATG  TAGTGGAGAT  24180
TAGCCTGCAC  GAACGCGTTT  TCATACCTGA  TGACAGGCAG  CAGTAGAATC  AGATAACCCA  24240
CCAATACTCC  CACGTAAAAG  CCTACCTGCC  GTCTCATAAA  CTTTACCAGG  AAAAATTCCG  24300
TGTTTATGTA  CCACACGACC  GTCAAGGCTA  GGAACATGTT  CACCGCACCA  AAAATGGCGT  24360
CTGACACGAG  CACGTAAAAG  CTGTTGCCAA  CGGCCATCAT  GGTGCTCAAT  GAAAACAGCA  24420
GCATTTCCAA  GGCGGTTGTT  GATAGGTACA  GGTTGACGCA  GACCGGTTTC  CACCGAGTCA  24480
GCAGTGACTC  CATCATGGTA  TTATCAGGTA  CGTGCTGTTC  CAGGAGAGGT  ATTTCCCACT  24540
GGGCGGAGTT  ACATGTTATC  AGTGACTGGA  TGTGGGCAAA  GGATATGCAA  AAATGAATGC  24600
AGTAGACAAA  GGCTGCCATA  AGTACGTGTT  TATATGACAG  AACATGGATA  AACAGTTGCA  24660
TGCTCCACAT  CCTTAAGATG  GCGACATAAA  GCACGCTATG  TGATCCAAGT  AGCGCTATCC  24720
AGGATTGCAT  GCTCATCATG  GTAGTGGCGT  GAACATGCTT  GGCCCGATAT  ACGGCCACCG  24780
CCGCGAGACA  GTAGTATACT  ATGGCAATGC  CGTCCACGAT  AAAAGTCCAA  AATATGTACA  24840
CCAGCATCTC  TGGTTTCTCT  AAAAACAGGG  TCGGGGTGAG  GTGCTTCGCT  GAGTTGCGCA  24900
CCGTGAGGTT  TAGCGCGCTG  TAGTTTACCA  GATTGTTGAA  GTAGCAGGGG  AAACCAAGGC  24960
CCTCGTACGT  GGCGGCCATG  GGCACGACTG  CAGAGCAAAT  GTACATAATT  ACAGCCACAA  25020
ACAACAGCTT  GACCCAGGAG  GACATGAGAA  AACGGTCGCT  CTTTGAAGCG  CGCATGTTTC  25080
TCGGTCTTTT  TAACTTTCGC  CAGGCGGCGC  TGCGGCGGGA  GAGCCAATCT  GATGCCACTG  25140
CCTATCGCGG  TTGACTTTTA  AATACGCGCC  CCGGGCAGAA  GCCAGAGGTA  GTCGACTCAT  25200
TGACTCAATG  GCAACGAGCG  AAGAAACGGC  GGCCGGTTAT  GTCATCGGTG  TCTACTTTCA  25260
CAGCGTTCAC  GTCCACTGCC  GCATTATTGT  CTGGCAGGTT  AATTTTCTAC  CCCTGGACCC  25320
AAACGACGGG  GAGACTGAAT  GCTACTTTGT  GGTGGACACG  CTGACGAAAG  AGGCGATGGA  25380
GCGCATGCCC  GAAATCCAGG  AATGCGTCCC  GTCTATTACT  GAACACGCCC  GTGACCTGGC  25440
GATCTGGGAG  TTGGCGCTGC  GACTGCAGAA  TCAGACGATC  GTCAAGGCCG  TCCGGACAGC  25500
GTCGCTTCCG  GTGGTTCTAA  TTATGACTGT  GGGTCGCATA  GTGAATGATG  TGATTCCCTG  25560
CCCCAACGTC  AGAACACCCA  GACCACTAGC  CTGTGCTTAC  CTACACTGTG  AGGCGACGGT  25620
GACCTTTGAG  GTCCCACTAA  CCGGGCCCGC  GGCGTCCACC  GGAACGTGGC  ACAGCTCTAT  25680
CTATAGGGAA  TGTGCGATCT  CGGCTATCGA  GATATGCTTG  AAGACCAGTC  GAGGCATATA  25740
CTCCTGCCAG  TCGAACGAGG  CCCCTGAGGC  CAAGAGGGAA  AAGCGAGGTT  TAGACATATC  25800
AGATGTGTTT  GTCTGTCTCA  CGTATGATAT  CCCTATCGCA  GGGCGGGTCC  TTTCTCTGCT  25860
GGTGCCCCAC  GCGCCCGCTT  TTCACGTCTT  ATGGATCAAT  GAGGACAGCA  AGTGGAACGG  25920
GGCAGCCGTC  GAATTTTTCA  GAGCCCTACA  CCATAAGCTG  TTCAGTGAAC  GCAATGGTAT  25980
ACCCCCTCTG  TGGTTGTACG  TGTTCCCGGG  AGCTGTGGAA  GAGGGCACAG  CCTTTGCGCC  26040
ATTACTTCCC  GCATTCCCTT  GCATACCTTT  GCGGTATGGG  TCGCCTACCT  CTCTGGACAG  26100
GGCGTCCGTG  CAGTGGGACC  TATTTGAACC  GCACATCCTG  ACCCACTTTG  ACGGGATAAA  26160
GCGAACTTCT  TTGGCAGATA  CAGTGTTTGG  GTACGACTCC  CTGGCCATTT  CAAGGGAATG  26220
TGAAGATCAG  TATGTGTGGC  CCACGCCTGT  CACTGACATT  AATATTAATT  TGTGCACGGA  26280
TAGTGACACT  ATGGCCATCG  TTAGAGAACC  ATCCGGTCTG  GTGGCCGTGA  ATCTAGAAGC  26340
CCTGTTGCGC  ACCGACTCCG  TATTATCGCG  GGTCTCGTCC  ATTGTCTCAC  TCGATACGCT  26400
```

-continued

| | | | | | |
|---|---|---|---|---|---|
| CTTGGACCTT | TCCACCCCGG | AGTGCCGTAG | GAGCGTGGAG | CTTAGATACA | ACTCACTTTT | 26460 |
| GTCGACTGTA | TTATCATGGT | CCACCTCTAG | GGGTCACAAA | TGGGCCGCAA | TCGTGAAGTG | 26520 |
| GAAGTTATTT | TTCCTCGTCC | AAGCTTTGGA | GCCTGAGGTG | AGACCTACTG | TCCCTGCTTG | 26580 |
| AAGCGGAGAG | GGGGTGGTGC | GAGTTGGCAG | TTGACGGGTT | TGTGATAGCT | GGAGTGCTGA | 26640 |
| CCACGGCACA | GGACCCATTA | ACTTTCCTAT | GTGTTTATTT | TTAGCAATGG | TCTCCAGAAT | 26700 |
| TCAAGGATCT | CAAAAGGGCC | TGCCAGATGG | CCGGGTTTAC | TCTGAAGGGG | GGGACTTCGG | 26760 |
| GGGATCTTGT | ATTCTCATCG | CATGCGAACT | TGCTCTTTTC | AACCTCGATG | GGATATTTCC | 26820 |
| TCCATGCAGG | CAGTCCAAGG | TCGACAGCGG | GGACGGGGGG | TGAGCCTAAC | CCACGTCACA | 26880 |
| TCACCGGACC | AGACACTGAG | GGAAATGGGG | AACACAGAAA | CTCCCCCAAC | CTCTGCGGCT | 26940 |
| TTGTTACCTG | GCTGCAAAGC | TTAACCACAT | GCATTGAACG | AGCCCTAAAC | ATGCCTCCCG | 27000 |
| ACACTTCCTG | GCTGCAGCTG | ATAGAGGAAG | TGATACCCCT | GTATTTTCAT | AGGCGAAGAC | 27060 |
| AAACATCATT | CTGGCTCATC | CCCCTATCGC | ACTGTGAAGG | GATCCCAGTA | TGCCCCCCTT | 27120 |
| TACCATTTGA | CTGCCTAGCA | CCAAGGCTGT | TTATAGTAAC | AAAGTCCGGA | CCCATGTGTT | 27180 |
| ACCGGGCAGG | CTTTTCGCTT | CCTGTGGATG | TTAATTACCT | GTTCTATTTA | GAGCAGACTC | 27240 |
| TGAAAGCTGT | CCGGCAAGTT | AGCCCACAGG | AACACAACCC | CAAGACGCA | AAGGAAATGA | 27300 |
| CTCTACAGCT | AGAGGCCTGG | ACCAGGCTTT | TATCTTTATT | TTGAAAAAG | GAAACAATG | 27360 |
| GGGGGTTTGA | AAAGGGTGCA | CATTTTCAGA | TATTTTAAAA | CTTCATTGTT | CTCCAGGTGC | 27420 |
| TTGGTAAAGA | TGGTATCACA | ATAAAAATG | TTTACTGGGT | CCGCGCAGGT | TTGTTTGTCA | 27480 |
| TCTTCATTCT | CTCCACTAGA | CTCCAGTTTA | AAAGACTCTA | GATAAATGGG | TTTCATTAGT | 27540 |
| CCCCCCATGG | GGGTTGAAGC | GTCGCCTATC | GCCTTATGAA | GCTTAAACAT | AACGAGTGGG | 27600 |
| GTGGCCCTGA | AATGATCGTC | CACGGACAGC | TCGTAAACAA | AGGCGGCCGT | GGCAGTCAAC | 27660 |
| GTCTCTATAC | CGTGCATGAC | GAAGGCCGCG | TCCATCCCCG | GCGTCCTCTC | ATGTGTCTTT | 27720 |
| CTGGCGCGAC | AAATAATAGA | TCTCAAAAAC | GTTGGTGACA | TGTCTCGACA | GTTCTCGAGC | 27780 |
| ATCGATAACA | GGCAGCAGAG | CTCGGTTATG | CCGGGAGATG | TAGGTCTAAG | GAGGCACACT | 27840 |
| CGCTCTTGGA | ACACGTGAGG | GTGTAGGTCT | ATGTGGGTCA | CCATGTCTTC | GTGCTCCACC | 27900 |
| AGGCACACCA | CCGTAAATCC | CACAAAGTTG | GGCGAGGACA | GGCGAGATTT | CACGTGCTCC | 27960 |
| CTGAGACACG | CTATATCTAA | GTGGCCCATC | ACGGACATTT | TGGGGGTATT | GCTTCCAACC | 28020 |
| AGTGCGTTGT | TTTTCCTATG | CACTTCCAGG | ACAAGGCGGG | GCACCACAGG | GTGGGGTAT | 28080 |
| ACGGGACAGG | CCTCTTCTGA | CTCGCGAGTC | TTCGGGGCAT | GAGTACTCAT | TGGCACTCCA | 28140 |
| GTCAGTCTCG | CCAGGGCCCT | TTCCAGGGAC | ATTCTCGAAG | GGTGGTGTAA | CTAGACAGTA | 28200 |
| TTTCTGTCCC | ACGTCGGTTA | TATACACAAA | GAGTCTGCTA | GTCTGATATA | AATAGGCCGC | 28260 |
| GATGTCCTGC | AAGCTGGAGG | ATACGAAGGA | GTGACTAATG | AGCTCCATCT | GAAGCAGGTC | 28320 |
| CGCGATCACA | TACGTGAATG | GACCAAGCAG | GATGGATATG | GTGTCCTGAG | AATAGGTGAC | 28380 |
| GCTGAGCCGC | TGCCCTTGGT | TGTCAACAAC | GGGAGCCAGC | TTGTAGGTTT | GAAACATCTC | 28440 |
| GCTTTCCCAC | AGGTTCGTGA | GATCTTTCAT | GCTTTCTCTC | ACTGGGGTA | TGTAAGAAGA | 28500 |
| GAAAAGCTA | TTTAGCACGG | CACTGCCCGA | TGGGATATGG | GAAGACGTTA | GCTGCAGAGA | 28560 |
| GGGGTCCTGT | AAACGTCCCA | GAGATTGAAA | TGTGTTGGCG | GTCAGCAGAT | TCACACTCCC | 28620 |
| GGGACCCTTT | GCGTCACCGG | GCTGTTGGTG | TGACAGCTGT | GTCTCAATAC | ATTTTAGCCT | 28680 |
| CTTCATGCAG | AGCTCCCTCT | CCTTTTCAAG | TTGAGTTATT | GTGTCAAATT | GTTCGTTTAT | 28740 |
| CTGGTTGGTG | AGACACTTGA | AAACGCTGTT | GGACACCTGG | CGCCTGAGCC | CCTGAGTGGT | 28800 |

```
CGTCTCTTGG CCTGTGCCGA ATAGTTTATT CTTGTCTACT ATGTTTGGG  ACACGTCGGT    28860
GACAAAGTCC TCCACGACGT CGGTGACACC GCTCACTGTC TTGTTTTCTG CCAGTTTCAT    28920
GAGCAGGTTG AGGAGCTCTC GCTTGGGGTC TGTTCTCTGA GAGGCCTGCT CCAGGTGGGT    28980
CATGATGTCT TTGTACACAT TGTTACAGGC GCTTCCAACG AGGGCCTTGG TGGGGGCTGT    29040
GTTCAGGAGC TGGCAAAGTT TTGCGTGCTC TGCCGTCCGG TGACAGCTCA TAATGCTGGT    29100
ATACATCCTC TGAATGGGGC TGTCAAAGAT CACCCGCCCA GCCAAGATGG CGGGCATAGT    29160
AATCACCTCC ACATGAACCC TTTTCTGCTT ATACAATCCC ACGAAAGTGT TTTTAACACA    29220
GTCATAGTCT ATGCTCACCT CTGAGTAGCC CGGAATATAG AGGGCGCTTA AACTAGACAC    29280
CAGGTTGCTA ATCTCCTGAG TCACGCTGGT GAGTATCCGG CCTATGGTTT TTTCACCAGA    29340
GGCCAGACGC TGGCAATCTT TCATCAGCTG TTCCTGGATA GAGTTAACCA GCTTGTGGTC    29400
GGGTGTGTGC TTGACGACTG GTACCATTCC TACCGTGACC ACCCAGTCTA CGTATCTCTC    29460
ATACGAGAGC TGTGTCTTGG CGTAGAGGAC CCGGTTGATG GCATTGAGAA GCAGGTGGTC    29520
TAATGTCATG CGCATAGTCT GGGCCCAGGA GTCGAAGGTT GACCTTCTGT AAGACCCCCA    29580
CTGTGCTTCC TTTTCTGGCC ACCTGGTTTT TGCTGAGGAC TCGTATGTCC TCCAGTCGGA    29640
CAAGACGTGG TCGTAGCTAC AGTTGGCCAA TGCATTCTTG TACAGGTGGA TAAATAGCTG    29700
TCTGAAAAAA ACACCCGGGT TTCGCAGGCT GCAGTGTAGA GTCTGACCTC TGACATAAGA    29760
ATACTTGCCT TGCAGGATCT CAAAGAGGGA GATGGACAGC TCGGAAGGGT GCACTGATAT    29820
GGACGAGCCC AGCCCCGGGT TCATCCTCAA CATGACATCG GATGCCAAAG TCAGGAGCGT    29880
AGTGGAACAG ATTGACAGGT TGTCAAATAT CACTACCTCG CCCCCGGAGA TGGGCTGGTA    29940
TGACCTAGAG TTCGATCCAC TGGAAGACGA AGGCCCCTTT CTGCCGTTTT CGGCATACGT    30000
AATAACGGGG ACTGCAGGAG CGGGGAAAAG CACCAGCGTA TCCGCCCTAC ATCAGAATCT    30060
CAACTGCCTA ATTACGGGGG CTACAGTGGT AGCGGCACAG AATCTTTCCA GGGCTTTAAA    30120
GTCCTACTGT CCCACTATAT ACCACGCCTT CGGATTCAAG AGCAGACACA TTAATATCTG    30180
CCAGAGGAAA GTGCCCAAGG TAACTCAGTC CTCCATCGAG CAACTCCAGA GATACGAGCT    30240
GGCTAGGTAC TGGCCAACTG TCACCGATAT TATTCGAGAA TTTATGCGCA AGAAACAAAA    30300
GGGGCAGTAT AGCTCCCTCT CTCAAAGCGC TTTCAGACTC CTTTGCCGTA TGGGTGGAGC    30360
CAATTTGTGG ACGAGTAACA TTATCGTGAT AGACGAAGCT GGAACCCTCT CGTCCCATAT    30420
TTTGACGGCC GTGGTGTTCT TCTATTGGTT TTACAACAGT TGGCTGGACA CCCCGCTATA    30480
CAGAAATGGT GCCGTGCCTT GCATAGTCTG CGTGGGGTCT CCCACCCAGA CGGACGCCTT    30540
TCAGTCGGTC TTCAACCACA CGCAGCAGAG AAACGAGATA TCTGCCTGTG ATAATGTGCT    30600
CACCTTCCTA TTGGGAAAAC GTGAGGTTGC AGATTATATT AGGCTGGACG AGAATTGGGC    30660
CCTATTTATA AACAATAAGC GCTGTACGGA TCCCCAGTTT GGTCACTTGC TGAAGACCTT    30720
AGAATATAAT CTAGACATAT CACCAGAGTT AATGGACTAT ATAGATAGGT TTGTGGTTCC    30780
GAAGAGTAAG ATTCTGGACC CGCTCGAGTA TGCAGGGTGG ACAAGACTCT TCATCTCACA    30840
CCAGGAGGTG AAGTCTTTTC TGGCAACGCT GCACACCTGC CTGTCGAGTA ATAAGGATGC    30900
TGTGTCCACA AAGCTTTTCA CCTGCCCAGT GGTCTGTGAG GTGTTTACAG AGCCATTTGA    30960
GGAGTACAAA CGGGCGGTAG GCCTCACACA CATGACTCCC ATAGAATGGG TAACAAAAAA    31020
TCTTTTCAGG CTAAGTAACT ACTCGCAGTT TGCTGATCAG GACATGGCTG TGGTTGGGAC    31080
CTATATCACA GACGCGTCCA CACAGATCAC CTTCGCCACT AAATTTGTCA AAAACAGCTA    31140
TGCTACCCTT ACTGGAAAGA CCAAAAAATG TATATGCGGG TTTCACGGGT CATACCAAAG    31200
```

| | | | | | | |
|---|---|---|---|---|---|---|
| ATTCAAGTCC | ATCCTAGACG | GGGAGCTATT | TATCGAAAGT | CATTCGCACG | ATAACCCCGC | 31260 |
| TTATGTGTAC | AGTTTCCTTA | GTACCCTGCT | ATATAATGCC | ATGTACTCAT | TTTACGCGCA | 31320 |
| CGGGGTGAAG | CAGGGGCATG | AAGAATTCCT | CAGGGACCTC | AGGGAACTGC | CGGTGTCTCA | 31380 |
| AGAGCTGATC | TCTGAGATGA | GCTCCGAGGA | CGTTCTGGGG | CAGGAGGGGG | ACACAGATGC | 31440 |
| CTTCTACCTC | ACCGCCAGCC | TCCCACCATC | CCCCACCCAC | GCGGCTCTTC | CAACACTGGT | 31500 |
| GGCCTATTAC | TCCGGGGCCA | AGGAACTATT | CTGCAACAGG | CTGGCCCTGG | CACGCCGACA | 31560 |
| CTTTGGTGAC | GAGTTCCTCC | ACTCCGATTT | TTCAACGTTT | ACGGTGAACA | TCGTGGTGCG | 31620 |
| AGATGGCGTG | GACTTTGTGT | CCACTTCCCC | CGGGCTCCAC | GGTCTAGTGG | CATACGCATC | 31680 |
| CACTATAGAC | ACCTATATAA | TCCAGGGATA | TACGTTCCTC | CCAGTGAGAT | TCGGCCGTCC | 31740 |
| AGGAGGACAG | CGCCTCAGCG | AGGACCTGCG | CAGAAAGATG | CCCTCCATAG | TTGTCCAGGA | 31800 |
| CTCATCGGGG | TTCATTGCCT | GCCTGGAAAA | TAACGTCACC | AAGATGACAG | AGACCCTCGA | 31860 |
| AGGTGGCGAC | GTGTTTAACA | TATGTTGTGC | AGGGGACTAC | GGTATCAGTT | CTAATCTGGC | 31920 |
| TATGACCATA | GTGAAGGCAC | AGGGGGTTTC | ACTAAGTAGG | GTGGCCATAT | CGTTCGGCAA | 31980 |
| CCACCGCAAT | ATCAGAGCCA | GTCTAGTGTA | TGTGGGTGTA | TCCAGGGCCA | TCGACGCTCG | 32040 |
| TTACCTGGTA | ATGGACAGTA | ATCCCCTTAA | GCTAATGGAC | CGCGGTGACG | CCCAGTCCCC | 32100 |
| ATCCTCAAAG | TACATCATCA | AAGCCCTATG | CAACCCCAAG | ACTACTCTGA | TCTACTGACC | 32160 |
| CGTACCCCTC | TCTTAGGACA | CTGATGTGTT | TGGAATAAA | GCATGAGACT | TGACACCTAT | 32220 |
| AATGGTCTGT | ATTGACACCA | TTCTTTTATT | TATCAGTCCA | GCCACGGCCA | GTTATATGCA | 32280 |
| CCGTTTCCAC | ACAGGGGTGG | CGTGGAGGCC | AGGATGCGGG | TTGGGTCGCT | GCACCTGGAC | 32340 |
| CCCGCGGTAG | TTGTGCTTCC | TGATGAAATC | GAGTGGGCGG | AAGTACTGGG | AGATTGGGTT | 32400 |
| GGGAGGTGAC | CCTTTGTGCT | CGACGGAGAC | ACGATCACGC | TCACGGCGGA | CGAGGGCTCC | 32460 |
| TCGTCTGTGT | CACTCCCCGA | GGATATAATT | ATCACGGACG | CCACTGCTTT | GCGGCTTAAG | 32520 |
| TTTGGTTGTC | TCTGGCAGCG | CACCACATCC | TCGCTACCAG | AGGAGGCGGT | AGACTGCCTT | 32580 |
| TTGCGCTTCT | GGCCCACGTC | CATGAGCCCG | ATTCTCTGAC | TCAATACTTC | CCCTTGGTCT | 32640 |
| TCTCCGTCCT | CCTCGGACGA | GGGTGGCTGG | TGGGAAAAAT | GGCGCGCGTC | GGTAAACGCG | 32700 |
| GCCTCATTGT | TCACGTCCGG | AGAGTTGGAA | CTGTCATCGC | TATCAGAGTC | CGATGTCAGG | 32760 |
| TCGACGATCG | CGGTGGGTGC | GGCGCGCAGG | GGGCGCCACG | AGGGCCCTTC | ATCAGGGTCG | 32820 |
| CTGTATGGTG | AACTTTGTGT | TCCAGGTACA | CTATTTCTGG | AAGCAGGTGA | AAGTCCGTAT | 32880 |
| GCCCCGGTCC | CAGTGTATGC | CGCCATCGGT | TCCAGGATAG | CAACCCCCTC | GTCGTCTGAA | 32940 |
| GGTGAGAGCC | CAGCAGGGGA | AAATCCGTCA | TCCTGACTAA | CCCATCCCAT | GGACGCCTCG | 33000 |
| GACTCCGCCG | TGTCCGTTGA | ACTGCGCACG | CGGCCCGCTA | CCACTGCTAC | CGGTTTGGGC | 33060 |
| GTATGGGCCC | GTCTGGCCAG | AGGCCTCGGG | CGCAAGTGAG | ATAAAGGTTG | AAAAAAGTCT | 33120 |
| GCAGGGTACC | CCTCTGGCTC | GTCTTCCTCC | TGAACATCGT | CATTTTCTTC | TTCATCTTCA | 33180 |
| TCTTCCTCAT | CCTCGTCATA | TTCAGATTCG | CCGCTCGACT | GATCCGGGGA | TATCTGTAGA | 33240 |
| TCCAGAGGGG | TTGCTGGCGG | CGATGGCGTG | TCCTCGGCGA | AGACGTCGTC | TGGGGCAGAC | 33300 |
| ATATCTATCA | CCGTGGGTCC | AGCATAGCCG | CGCGGCCTGC | CAAATCCTGG | AAGTGATGAA | 33360 |
| AGAGGTGGAG | GTGGGAATAT | GAACTTCACG | GGGGTCGTC | TGCGAGGCGC | TCCTTCAATT | 33420 |
| GGAAGCATTC | TCTCTTCATC | GTGTGTGCTA | GACGAGGTCC | TCACAAACAT | CGCCATGGCC | 33480 |
| TTGTACGGGG | TTGACCGCTA | GGGGCGGAAA | TTTACAAAGC | ACACGAGTTA | TTGCCTTTAC | 33540 |
| TGCTCCAACA | GGCCCCAGTC | CACAGTCTCA | CGCCGGTGGC | GAGTCAAATA | GTCGTTGGCT | 33600 |

| | | | | | | |
|---|---|---|---|---|---|---|
| AGGTTAAAGT | GATTACAGCC | CTGGAACCGA | GGCCATCGCG | AGTGTCGGCC | ACCAAGAGAG | 33660 |
| GCCAGCGGAG | ATGGATGCTG | GGCCGTAAGC | ACCAGGTGTT | TCTGTGCGTT | TATGAGCGGA | 33720 |
| GTTCTGTCAA | TGGCCTTGCG | CCCCCACAGG | AGAAAAACGC | AATGTTCTAA | CTTTGAGGAT | 33780 |
| ATGCTACTGA | TGATGAAACT | CGTGAACCAA | TCCCAGCCAA | GTCCCTCGTG | TGAGCCGGCC | 33840 |
| CTCCCCTTCT | CCACCGTCAA | AACTGTGTTT | AGTAGCAACA | CACCCTGGCG | AGCCCAGCTG | 33900 |
| TCGAGGCACC | CGTGGGAAGG | AGTACTGAAA | TTGGGACGG | AAGCCTCTAG | CTCTCTAAAG | 33960 |
| ATGCTTCTCA | AACTGGGTGG | AACCTGACAT | TGCGGATCCA | CACTAAACGC | CAGGCCAGTA | 34020 |
| GCTTGGCCCT | TGTGGTACGG | GTCCTGGCCT | AAGATCACCA | CTTTAATATC | CTCTGGATCG | 34080 |
| CAGCAGTGGG | ACCACCACAT | CAGCTTGTCC | TGTGGGGAT | ACACTGTGGT | GGTTAGCCTA | 34140 |
| AGTTCCCGAA | TCTGTCTGAG | CAGCGAGAGC | AGTTTCTGTT | TCAGAAATGA | TGAGAGGCTC | 34200 |
| AGAAAGGAAA | TCCACTTAGG | TGCCAGTAAC | AGATCCCGGT | CGTCCACCCC | CTGACTGATG | 34260 |
| GATAGGGTGC | CCCTAAAGAC | CGTCTGTTGC | AACCATGCGT | CCATGTTGAA | CTTATTTTCC | 34320 |
| CTTTTGACCT | GCGTGCGCTC | TCCGGCTGCT | GCTTTTAGCC | CGAGTCTGAC | TTCCGCTAAC | 34380 |
| AGAACCTGTC | CGGTTCATGG | CCTTTCCCAC | GCTTATTATA | ATTATGTTTA | CGTTGTGAAT | 34440 |
| AGAGCTATCT | GCAGTGGTCG | CGTTAAAACC | TACAGTATAG | GCCGTCAAAC | TTCGTTGTAA | 34500 |
| ATACCACAAC | AACCTCAGGT | TTTCCTGCGA | CGCCCAGGAC | CCCAATCTTC | GAACGACCGC | 34560 |
| GACTAAAAAT | GACCTCAGAT | TAAACCCATT | CACGCATGTT | TCCACGGTAA | TGTCGCCTGT | 34620 |
| TTTGCTTCGC | AGCTTGGCTA | TACAGACCCC | GTTGCAGTGA | TTCGGATCGG | CGAAGTGGAT | 34680 |
| AGAGTGGACC | GCAAAGAACA | ACGGCAGGGT | AGAGGCTGCC | GATGCCTGAA | TTGCGCAACA | 34740 |
| TGGTAAGGCG | ACGTATGCGT | GAGATGTGAC | CAATAGGGTG | GTCCACAGGA | CGGCAAATAG | 34800 |
| CGCAAAGATC | CCCATGGGGC | AAATCCGGGT | TTCACCCTTG | TGTTGCCTGG | TTCGGTGCTC | 34860 |
| CCCAGGGAGC | CCCCTTCCGT | AATATCTGTT | TTATATAGTG | AGGGTTCACG | CATGCGCGAG | 34920 |
| TCCCGACTAA | TGAGGACAAT | TACTGAAATT | GACCTTTTCG | CGACACGGGG | GTGAGGTCTA | 34980 |
| TTTCCCACGA | CATACTTCCG | CGGAAAAATA | CCCACGCTCC | TTAATTTCCG | TGGGAAGACG | 35040 |
| ATGGGGGAAA | TGTGGCATTA | CCTGACACGG | TTTCAATCAT | ACTCATCGTC | GGAGCTGTCA | 35100 |

( 2 ) INFORMATION FOR SEQ ID NO:19:

( i ) SEQUENCE CHARACTERISTICS:
        ( A ) LENGTH: 35100 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

| | | | | | | |
|---|---|---|---|---|---|---|
| CACGTCTGGC | TGAGATTTTC | TAAAAAGTCA | TCCAATGAAT | CATCGGAATC | ATCAGCACAC | 60 |
| TCTAGAACTA | CTCCATATGC | CGGGGTGCGC | GGGGGTCCCG | AGTAGTGCAC | GTCGCCATCG | 120 |
| GGAGACACAG | ATGATGGGTT | TGAAATGTCC | ATACGGGCCG | TGTGCACAAG | GGTCACGTCC | 180 |
| CCATCCCCAA | CACAAGGACC | TTTAGATACC | CTCTCCCGGC | ATGTGCGCGT | ATCCGGGCAA | 240 |
| GCAAGCTGGT | GTTCTGGATT | CCAAACGTGC | CCAGCGGTAC | CCAAAATCGC | CAGGGCGTGT | 300 |
| TTTATTATTT | CCACAGGAAC | CGGTTTCTCT | AATTGCATCA | CCAGGGTATC | CAAAAGCCGG | 360 |
| GCTTCCACGT | TGATCCGGCT | TACCGACAGT | TCTTTCCAGG | GTTCCTGGT | GGGGCGCGGC | 420 |
| AGCTGACTCA | AAAAGGTCAC | TGCCTCTGCC | CATGGGCGGG | TGGGTGACAG | TCCGCCATAC | 480 |
| TCTTCCAGGA | CACTGGCCAT | GCATGACTCC | AACCGTCTCA | CGTCCGAGGT | AATGTGCTCT | 540 |

-continued

| | | | | | | |
|---|---|---|---|---|---|---|
| ATGAAGATGT | GGTAGAGCCA | GCAGACGTTC | AAACACGATG | AAATCAAGCT | AAGCTCCCGC | 600 |
| CGGAACTCCA | CATCCACAAA | GGGGTATTGC | TCCGGTGTCT | GTATTAGGTC | TGGAATAGAA | 660 |
| AACTCAGAAA | AAGACACTGA | CCCACCAAGG | AGAACCTGGC | GTCTTGCAAA | GTTGATGAGC | 720 |
| CCCGCAGAAA | GAATGTGTCT | CCCGTGGGAC | AAAGAGCTTG | GGGGGGCAGA | GATGGCGCTA | 780 |
| CAGTGGGTGA | TTTCTTCTAC | CACGGTCATA | CATTGGTGGC | ACCCACAGGC | CTGTTCCAGT | 840 |
| ATCAGCATAA | ATCTATCTTT | GCAGTCATCC | CAGATCAAAG | TCATGTCAGA | TGCTGTTGCC | 900 |
| TGGCATTTTG | CCCGCATGTA | CATTTCCTGT | CCCACATATT | TTAACATCTG | TAATACTGGA | 960 |
| AGTAGATTCA | GTCTGGTGTT | GAGCCCCCCC | GGGGAAGCCA | GCGTATGCTT | CAGGACCACC | 1020 |
| AGGGACGCTA | AGAACCCCGG | GTGTCCGCGC | TCCGGAAACA | GACCTCTGAG | AATACGCTCG | 1080 |
| GTCTTGACGA | AACCCGATGT | GGTACCGAAT | GCCACAATCT | GTGCCCTCCA | GCTCTCACAA | 1140 |
| TTTTCATCTC | CAATACCCGG | AATTGGGATA | CACACCTCCA | TGTTCAGTCA | CATGTACGCT | 1200 |
| AGGGTCTCCC | CACCCAACCC | CCATAGGACC | CAGCTACAGC | TTATCCTCCA | CTAAATACCA | 1260 |
| GGCAGCTACC | GGCGACTCAT | TAAGCCCCGC | CCAGAAACCA | GTAGCTGGGT | GGCAATGACA | 1320 |
| CGTCCCCTTT | AAAAGTCAA | CCTTACTCCG | CAAGGGGTAG | TCTGTTGTGA | GAATACTGTC | 1380 |
| CAGGCAGCCA | CAAAAATGGC | GCAAGATGAC | AAGGTAAAGA | TCGACCTTTT | TATTGTATAC | 1440 |
| TGAACAATGC | GTGTTTACAA | TGGTGTAGGT | GGGAGCAGAG | TTCGCCAAGC | TCTACGTCCG | 1500 |
| AACAGTCGGG | TGTCAGGGCT | CTTATTAAGT | GTTCGGTGTA | CTTGACCAAA | GCCGCGGAAC | 1560 |
| CTAGGTTGGG | TCTGTACAGG | TCGTACCAGG | CAAAAAGGA | TCGGGCGGTG | CTTTTCAGGA | 1620 |
| GAGTTAGGGA | CGTGCTGATT | ATGTGGACAA | GCTTCTGCTC | GTAAATGCAC | CGCTGGTACA | 1680 |
| TCTGAACGAC | AGCTGTCCAA | AAAAACAAA | GGTTCAGCTG | CACGTTAAAA | TCTGTATCCT | 1740 |
| GAAAGTCCTC | GTAAATGACA | GTTTCTACCA | AGAAAAACTT | TTTTACCACG | CTGGCCATCC | 1800 |
| ACTGAAAGGA | GGGAGCACAC | GTCCCGTTGT | GCGTTGTTAG | GATATCCCTA | ACTTCGGAGC | 1860 |
| GGAGACGGCC | GGACGCTCCC | ACAAAATGGG | AGAGGCACCA | CTCTGTGCAG | TCCGCGGTCT | 1920 |
| GGGGTTCTGA | TTCCAGGGGC | GCCGTGTGGG | GGTATTGGAG | AGTCAAAACT | CTGGGCAGTC | 1980 |
| CCTTAATGAG | CTCTCTCTCA | AAACCTATGC | AGCCAGCGTC | CACTAGTGGC | AGCATGCCGT | 2040 |
| TAATAACACC | CCTTATCTTG | TCGTTGCCAA | GTTTGTACAA | CTGCTGCAGG | GAATAAGCCA | 2100 |
| AATTCGCCCT | AGCCGCGGGA | ACCAGGTACG | GCTCGCTTTG | TCGGTGCTGG | ACCAATATCT | 2160 |
| GAATGGTCTT | TGCAAGGTAT | AGGGTCTTCT | CAACGTTTAG | AGCGGGTACG | TGGCAGTCTG | 2220 |
| GATTGAGGGT | GGCGACGGAC | AGGGTATCTA | ACTCCTGAAG | TATCTGATCC | CAGGACGGGT | 2280 |
| AATGATACCT | AAACAGATGG | TTGAACAGGT | GATCTTTAAG | GGGCCTTCTC | GATGTCATTG | 2340 |
| TAAAAACTAT | GACACGCCAC | TCTCTCCTTA | GGGTAAGAAG | CTTCGGCGGT | CCTGTGTGGA | 2400 |
| AAGCTTCGTC | GGCCTCTCGG | ACGAACTGAA | GGCCCAACTC | TACCAGTGTG | TGCTCCTTAT | 2460 |
| AAATGACGCA | TACGAAACAA | TCTACGATCC | CAGTGACCTA | AATAGAGTGG | TGGAAGATGT | 2520 |
| GTGCATTCGG | ATTATGAAAG | AATGTTCCAA | GCTTGGTGCG | CTATGTGGTC | TGTTTACAGA | 2580 |
| CATTAACATG | TTTAACCTTT | TCTGCTTTTT | TCGTGCCTCT | CGAATGAGGA | CCAAAGGCGC | 2640 |
| GGCCGGGTAC | AACGTGCCAT | GCGCAGAGGC | ATCCCAAGGC | ATTATTCGGA | TCCTCACGGA | 2700 |
| GAGGATCTTA | TTCTGCACAG | AAAAGGCATT | TCTGACAGCC | GCATGCAGCG | GGGTGAGCCT | 2760 |
| GCCTCCAGCC | ATATGTAAGC | TACTACACGA | AATATACACT | GAAATGAAGG | CCAAATGCCT | 2820 |
| GGGGGCCTGG | AGGCGACTCG | TCTGCAATCG | GAGGCCCATT | ATGATATTAA | CCTCTTCCCT | 2880 |
| ACTGAAGCTC | TACAACACGT | ACGATACCGC | CGGGCTGCTC | TCTGAGCAGT | CCAGGGCCCT | 2940 |

```
CTGCCTTTTG  GTTTTCCAAC  CGGTCTACCT  TCCGAGGATT  ATGGCGCCGC  TGGAGATCAT  3000
GACCAAGGGT  CAGCTCGCCC  CTGAAAACTT  TTACAGCATC  ACCGGTTCTG  CTGAGAAACG  3060
CCGGCCAATT  ACCACCGGCA  AGGTCACTGG  ACTGTCCTAT  CCAGGAAGCG  GTCTCATGCC  3120
AGAATCTTTA  ATTTTGCCAA  TCCTGGAGCC  AGGACTGTTG  CCGGCTTCCA  TGGTAGACCT  3180
CAGCGATGTG  CTGGCAAAAC  CCGCCGTTAT  TCTGAGCGCC  CCTGCCCTGA  GCCAGTTTGT  3240
CATTAGCAAA  CCCCATCCCA  ACATGCCGCA  CACCGTCAGC  ATCATCCCCT  TTAACCCATC  3300
GGGTACAGAC  CCGGCGTTTA  TTAGTACGTG  GCAGGCCGCG  TCACAGAATA  TGGTGTACAA  3360
CACATCCACC  GCGCCCTTAA  AACCGGCCAC  CGGTAGTTCA  CAGACGGTGT  CAGTCAAGGC  3420
GGTTGCTCAA  GGGGCCGTGA  TTACTGCGAC  AACGGTGCCG  CAGGCAATGC  CAGCGCGGGG  3480
TACCGGAGGG  GAGTTGCCTG  TAATGTCAGC  GTCCACTCCT  GCAAGAGATC  AGGTCGCTGC  3540
ATGTTTTGTC  GCAGAGAACA  CCGGAGATTC  TCCCGACAAC  CCGAGCTCTT  TCCTGACGTC  3600
ATGTCACCCT  TGCGATCCGA  ACACGGTTAT  AGTGGCCCAG  CAATTTCAAC  CACCGCAATG  3660
CGTTACGTTG  TTGCAGGTTA  CCTGTGCCCC  CTCTTCGACA  CCACCCCCG   ATTCAACAGT  3720
CCGGGCCCCG  GTGGTGCAGT  TGCCAACAGT  AGTCCCTCTG  CCGGCCAGCG  CGTTCCTCCC  3780
GGCGCTCGCC  CAACCAGAAG  CCTCGGGCGA  AGAGCTTCCG  GGCGGTCATG  ACGGAGACCA  3840
AGGTGTGCCG  TGTAGAGATT  CAACGGCGGC  GGCTACGGCG  GCAGAGGCGA  CAACACCCAA  3900
ACGAAAGCAG  AGAAGCAAAG  AGAGGAGCTC  AAAGAAGCGT  AAGGCTTTGA  CCGTGCCAGA  3960
AGCCGACACC  ACGCCATCGA  CCACGACACC  TGGTACCTCT  TTGGGATCAA  TTACCACCCC  4020
CCAGGATGTG  CACGCCACGG  ATGTCGCCAC  GTCTGAGGGA  CCATCGGAGG  CACAACCCCC  4080
GCTACTGTCG  TTACCCCCGC  CACTGGACGT  AGATCAGAGT  CTATTCGCCC  TGTTAGACGA  4140
AGCGGGCCCT  GAAACATGGG  ATGTCGGGTC  GCCTCTCTCC  CCCACTGACG  ACGCGCTGTT  4200
GTCCAGTATT  CTGCAAGGAC  TGTACCAGCT  GGACACGCCA  CCGCCTCTGC  GGTCACCCTC  4260
CCCCGCTTCC  TTCGGCCCGG  AGTCTCCGGC  GGATATACCG  TCACCTTCTG  GTGGAGAGTA  4320
TACGCAACTG  CAACCGGTCA  GGGCGACCTC  GGCGACGCCC  GCTAACGAGG  TACAGGAGTC  4380
CGGCACACTG  TACCAGCTGC  ACCAATGGCG  TAATTACTTC  CGAGACTGAA  GTGTTCGCAA  4440
GGGCGTCTGT  GCCTGCGTTA  ACTTCCCAGG  CAGTTTATTT  TTAACAGTTT  GGTGCAAAGT  4500
GGAGTTAACC  TACAGATTCT  ACTTAAAATA  GCTCATTTTC  TCACGAATCT  GGTTGATTGT  4560
GACTATTTGT  GAAACAATAA  TGATTAAAGG  GGGTGGTATT  TCCTCCGTTG  TCGACTATAA  4620
CCTGGCGTGT  AAACGTGTAA  CCCTGCCAAA  TGCCCAGAAT  GAAGGACATA  CCTACTAAGA  4680
GTTCCCCGGG  AACGGACAAT  TCTGAGAAAG  ATGAAGCTGT  CATTGAGGAA  GATCTAAGCC  4740
TCAACGGGCA  ACCATTTTTT  ACGGACAATA  CTGACGGTGG  GGAAAACGAA  GTCTCTTGGA  4800
CAAGCTCGCT  GTTGTCAACC  TACGTAGGTT  GCCAGCCCCC  GGCCATACCG  GTCTGTGAAA  4860
CGGTCATTGA  CCTTACAGCG  CCTTCCCAAA  GTGGCGCGCC  CGGTGACGAA  CATCTGCCAT  4920
GCTCACTGAA  TGCAGAAACT  AAATTCCACA  TCCCCGATCC  TTCCTGGACG  CTCTCTCACA  4980
CACCACCAAG  AGGACCACAC  ATTTCGCAAC  AGCTTCCAAC  TCGCAGATCC  AAGAGGCGAC  5040
TACATAGAAA  GTTTGAAGAG  GAACGCTTAT  GCACTAAGGC  CAAACAGGGC  GCAGGTCGCC  5100
CCGTGCCTGC  GTCTGTAGTT  AAGGTAGGGA  ACATCACCCC  CCATTATGGG  GAAGAACTGA  5160
CAAGGGGTGA  CGCCGTCCCA  GCCGCCCCTA  TAACACCCCC  CTCCCCGCGC  GTTCAACGCC  5220
CAGCACAGCC  CACACATGTC  CTGTTTTCTC  CTGTTTTTGT  CTCTTTAAAG  GCCGAAGTAT  5280
GTGATCAGTC  ACATTCTCCC  ACGCGAAAGC  AAGGCAGATA  CGGCCGCGTG  TCATCGAAAG  5340
```

```
CATACACAAG ACAGCTGCAG CAGGTATAGA CGGGAAACAG GTGTCTATCT TGGCCGGCTG    5400
GTTACTCAAA TGGGAACAAT GGCGCCACCT TGCTGTCTTT GTAGGCATTA GAAGAAAAGG    5460
ATGCACAACT ATGTTTCCTA GCGGCGAGAT TGGAGGCACA TAAGGAACAG ATTATTTTCC    5520
TTCGCGACAT GCTGATGCGA ATGTGCCAGC AGCCAGCGTC GCCAACGGAC GCGCCACTCC    5580
CACCATGTTG AAGCTTGGTT GTGCCGTCGT CCGGGAGAAC CATGCCAGAC TTTGTGTGGT    5640
AAGAAGGAAT TGTTATCCGG CAGCAATATT AAAGGGACCC AAGTTAATCC CTTAATCCTC    5700
TGGGATTAAT AACCATGAGT TCCACACAGA TTCGCACAGA AATCCCTGTG GCGCTCCTAA    5760
TCCTATGCCT TTGTCTGGTG GCGTGCCATG CCAATTGTCC CACGTATCGT TCGCATTTGG    5820
GATTCTGGCA AGAGGGTTGG AGTGGACAGG TTTATCAGGA CTGGCTAGGC AGGATGAACT    5880
GTTCCTACGA GAATATGACG GCCCTAGAGG CCGTCTCCCT AAACGGGACC AGACTAGCAG    5940
CTGGATCTCC GTCGAGTGAG TATCCAAATG TCTCCGTATC TGTTGAAGAT ACGTCTGCCT    6000
CTGGGTCTGG AGAAGATGCA ATAGATGAAT CGGGGTCGGG GGAGGAAGAG CGTCCCGTGA    6060
CCTCCCACGT GACTTTTATG ACACAAAGCG TCCAGGCCAC CACAGAACTG ACCGATGCCT    6120
TAATATCAGC CTTTTCAGGT GTATTACACG TTTCAACTGT AATCCCTCGC AATTGGGTAA    6180
ACCGTCGGTG TGTAGGGATA AAGCGTAACC TTACGTTCTG TCTCATCTAC AGGATCATAT    6240
TCATCTGGGG AACCATCCAG GACCACGCGA ATTCGCGTAT CACCGGTCGC AGAAAACGGC    6300
AGAAATAGTG GTGCTAGTAA CCGTGTGCCA TTTTCTGCCA CCACTACAAC GACTAGAGGA    6360
AGAGACGCGC ACTACAATGC AGAAATACGG ACCCATCTTT ACATACTATG GGCTGTGGGT    6420
TTATTGCTGG GACTTGTCCT TATACTTTAC CTGTGCGTTC CACGATGCCG GCGTAAGAAA    6480
CCCTACATAG TGTAACACAA AACCATAAAA GTAAATAAAC GTGTTTATTG TTCACATGAT    6540
AAAGAGTGGT ACTCTTTACT GGTTTGGGGG TTGGGTTGTG GCGTGGTGGC TGGTCCGCGG    6600
TTCAGTCATC AACCCCCGCC CGTGTTGTCG AGGCTCCTCT TCGTCGCCTG TTATTGGCAC    6660
CAGGAGGCGG TTTAGCGGTG CCCCCGTCTG ACATGCAGAC GTCGATTCTA AGCGAAAGTC    6720
CCTTCAGGGC ATCGTCCACT TGCTTTTGTG TTACAACCTT GCTGAATATT GTCCTGACCC    6780
TGGCTTCGAT TTTCTTAGCG GCCGCCGCAC TCAGTGCACC CACAGTAGCG GTAAGCTGCG    6840
CTTCCTTCTC GGTGGCCGTC AGAGGCCGAT CTCTCGGATC GGCAGTGGAT CCCAGTGCTT    6900
TCCGAAGCTC CCGATTCTCC ACAGTCAATT GGCTTATCTT TGCGGTTAGG TCTTCCATCG    6960
TAAGGTCCTT TTTGGGTCTG CCCCTGGGCG CGGCCATGTC AGGTACGCGT AGATGTACGT    7020
GTTGGTGATG CTCACAACAA AAGCCCAAAT CCCTCCTTTA TACCCAGCTT TAAATACTTT    7080
ATTGAAAAAC CATAGCTTTC GTCAGCGCTT GTGCGAGTAA TCACATGCCA GTCTATGCAT    7140
GGACCACCTC GTCCACAAAC TTGAAAAAAC AAAGATATAC CAGATAGAAA AATGTGGCCA    7200
CGACGACTAG TAACGCGTTA ATCAAGGCCC AGACGCTAGA AAAGCTAGAA AGGGAGGGGC    7260
TAAAACTATC CGCGGAACAA GCAACGTCAT AGAATCCTGG GGTAGTGACT GATGTGGGAC    7320
CGGGCGAAGG CCTGGCGCTG AGCCCAGCCG TACTGGGACT AGAACGCTCT GTAGATGATG    7380
CGACACCTGT CGAGTTGGCC GTAACCCAGC AGTGACCTAG TATCGAGGCC ACAAATAAAG    7440
CCAGGGCCAC CGTGGACGCT GTCATTATGA ACAACGCCG AGGCTCAAG CCGTCTATCC    7500
AACGTTCCGC GTTCGCCTCT TATATACACT CTGCAATGCA GTCCGACTCT GCCCTCTAC    7560
CCAGGGTGGA ATATGTGTTC GAAACAAGCA AATTTAGAAT GACGTCGAGA GCAAATGAAG    7620
CCAGACTCAG ACTGACAAAT GAGTGTCCGA TACTGGTGAG ACCCCACGAG CCGTTCATCA    7680
TGCCCACCGG AATACACTTC ACGCGAACCC CTAGCTGCGC TTTCATCCTG ACCGGAGAGA    7740
```

```
CCGACAAGGA  TGTATTTTGC  CACACGGGCC  TAATCGACGG  AGGCTACCGC  GGGGAGATAC   7800
AGGTTATTTT  ACTCAACAAG  AGGAAGTACC  CTGTGACGCT  GTATCGCGGG  GAGCTCAACA   7860
TCTGCCTGTC  TGCTTTCAAT  TACGTGCTAC  CTCCGTTGAG  GGACGTATCA  TTCTTAACCC   7920
CCCCTATGTA  TGCAAACGAC  GCCGGATTTG  ACGTGATGGT  GATGCACTCT  ATGGTTATCC   7980
CTCCTACTAC  TGACCAACCG  TTCATGATAT  ATCTAGGAGT  GGAGACCCCA  GGCCCCCCTG   8040
AACCCCACGT  GGCTCTAGCA  TTGGGGCGAT  CCGGTCTAGC  ATCTAGGGGT  ATAGTTATAG   8100
ACGTTAGTGA  GTGGGGACCG  CGAGGATTGC  AGCTGAAGTT  TTATAACTAC  TCGGGGCAGC   8160
CGTGGCTGGC  GCAGCCCGGT  AGCCGCATAT  GCCAGATTGT  GTTTGTGGAA  CGCAGACACA   8220
TCCTCAAGGG  CTTCAAAAAG  TGCTTGCGCC  ATAGGAAGCT  AGCTCCTGGC  GTCCGTTTCC   8280
GGGAGGCTCG  AGTGCATTTT  CGCGAGGATA  CAAATAGCGT  CCGAAAACAT  ACCCACGAAG   8340
ACAACCCCGT  CCACGAACCC  AACGTAGCCA  CCGCTTCCGC  TGACATTCGT  GGAACCAAGG   8400
GGCTGGGGTC  GTCTGGGTTT  TAGAGCCGCC  GCCAAATGCG  GCCAGTTTAT  TAGGGCGATT   8460
CGATCCCGCA  ACCCACAGCA  TCCCCCAAAT  AAAAAAACGA  GTGTACACAG  CCAATGTTTT   8520
TATTATTGTT  CGATTCATTA  CTGGTACCAG  AGAATAAAGC  CAACCTATGT  CGAACCTATC   8580
GCGCTTTCTG  TCGTCTCTTC  CAGGGTTGAC  GAAGGCCGGG  GAGGGATTGA  CGAATGCATC   8640
GCGGAAACGG  ACGGGTCTTC  GGTGGGTGGC  TTGGGTAAAG  TTGCCTCCGG  CTGGCGCGTA   8700
ACGGCAGGCG  TGAGAGGCAA  TACAGAAGTG  GGTTCCGACA  AGGAGTGGCT  GATCTCAGAG   8760
GCCCATATTA  CCGAGTCGTC  TGACGCCATA  GCAGTCGCCA  GTTTTTCCAT  CTCCATGAGC   8820
GAAACGCATT  CCCCGGCCCT  TTTGTTTAAG  AGGGACTGGA  GCGCACTGTC  GTCCACGGTA   8880
ATCTCGCCGA  CCGCCAAGGC  CAGCATTGTG  TTCCACACGA  CGTTCTGAAT  AGACTGCAGT   8940
TTTTTCACCT  GGGTTTTCAC  GGTCTCCTGG  CAGCCCGCCG  GAATTTAGC   CACGTCAAAA   9000
CGCTTCAGGT  AGTCTGTGAT  CTTGTTTGAC  TGTACAGCCA  GAAGGTAGGT  CTGGTGCAGC   9060
GCCGTCGTGC  CAAGGTTCGA  CTGGACAACG  TCACCCAGAC  ACACTCCGGG  GGGGAGGCCC   9120
AAATCTATCT  CTTGCCGCCA  GCGCTCTGGA  CAGCCTTCCA  GAGGGTCACC  GAGGCGCTTG   9180
TAAGCGTGGT  TGCCGCGTCC  AAAAAGGTTT  ATACCGCAAC  ACGTCCAGGT  GTACCATGGA   9240
GACGACATAC  CGCCGCGAGG  CGCTGACAGT  AAGGGTTATT  TTTTGTACGA  GTGGCGACAG   9300
CGCCGAGACG  ATCGCCGACG  TCCTTACGGG  GGCCCCAACG  TCAGCGTCCT  TCTTTTCTGT   9360
ACTCCACGAC  CTTTTTTATT  CCCAGATACT  CGCCCCCAGG  GTAACCCTAA  AATTGTGCCT   9420
CCCCGCACGG  CGTCCTGGCA  ACGGCACAAG  GTGTTCGCCC  GTGTTGGTCC  TACGTACTGA   9480
CGCATCAGTG  GCCTCGGGGT  TCCTTGGCGG  CCGGCCACTG  GAGGCGTCCG  ACATTAAATA   9540
TATGCTGCTC  AGCGACCAGA  CCGCGGGGTT  GTTCAAGCCG  CTGTTGGAGA  TAATCGGTGG   9600
CGCGCGCGCA  CCACCAAATC  AGGACGCGTG  CACTTTCCAG  AGCCAGGTGG  CCTGGCTCAG   9660
AACGAAATTT  GTTACCGCAT  TGAGAAAACT  TTACAAGATG  ACTCCCTCAC  CCTACTGGAT   9720
GCTGTCTGCA  TTTGGCGCTC  AGGAAGCCCA  GTTCGTCCTG  ACCAGCTCAT  TCTATTTTTT   9780
TGAACACACT  GTGGTCTGTA  CCACAGAGAC  AGTTTCTCAC  CTGTCTAGAC  TGTTTTCGCC   9840
TCAACAGGGA  CAGACGCTGG  TTTCCGTTAC  CAGCCACGAG  GAGCTGGGGC  AGCTATACGG   9900
CACTTCCCCT  TTCAGGCGGC  GCGTCCCCGC  GTTCGTCGCT  TATGTAAAAG  AGAAATTAGC   9960
GAGAGACAGT  CTGGAGACGG  AGGCCATCGA  CCGCACCATA  GACCAGATCA  GGGGCAAACT  10020
CATGCTGTCT  AACCAGGACC  TGGTCCATTT  CATATATATC  TCCTTTTATC  AGTGCCTCAA  10080
CAAACGGGCG  TTCCTGCGCT  ACTCTAGACA  GACGTCCTCT  TCAAGTGCTC  TAAGGGAGCT  10140
```

```
GGGGGAAGAC  CCTCAATTGT  GTGGCGCCCT  ACACGGGGAG  TTTCGTGACC  ACGTCCAGTC  10200
CTACTACCAC  AAAAAAACCT  ACCTATCCAC  TTACATAGAC  ATTCGGTACG  TGGGTGGCGT  10260
ATTACCAGAC  GGCTATTTTG  GCGGGAGTCT  TGTAGGCGAG  CGGTGCGTTT  ATTGGTGCGG  10320
GCAGTCAAAG  GACACGGCCA  GCCTGTTGGC  CACCATTAGC  CAACAGGTGC  CGCACCTGAG  10380
GTTGCAAAAC  GAGTTCGCTG  GCATGCTAGA  CGTGGCCGCA  CTGCGAGGTT  CCGATGACGG  10440
TCAGTTTAAA  GAGGGCCTTT  TCTCCCACAG  TCAAGCCCTA  CCCCTGTACA  GGTGCGAGTT  10500
TCTGGGCAAG  CAGTTTTCA   CAATGCTTCA  GGAAGACGGC  CTAGAGCGAT  ACTGGGAGCA  10560
AAGTGTGATA  TTTCCAGGCG  ACCAGGACTG  GGATATGTTA  TCTGACAAAG  ACCTCACCTA  10620
CCGAATTTTT  TACCATGACC  TCAGCCTATC  GCTGCCAACA  CTGAAGGAAC  AGCTCCTTGT  10680
TTCAAGACAC  GAATACTTCA  ACCCTCGCTT  GCCAGTGTAT  AGATGGGTAT  TAGACTTTGA  10740
CCTGCCCGTC  TGCCGCGACA  TTGACAGGAC  ATTCGAGGAG  GTGCACTCTC  TCTGTTGTTC  10800
CCTGCGTGAG  GCCATACTCG  ACATCATTCA  ACTCCTTGGA  CCAGTGGATC  CTCGAACACA  10860
CCCAGTATAT  TTTTCAAAT   CAGCCTGTCC  ACCGGACGAG  TGGCGCGGCG  AAGACGTCGC  10920
CAGCACCAGC  TTCTGTCGGT  GTCATGACAA  ACTGGGTATG  CGTATTATCG  TCCCGTTCCC  10980
AGAAGGAGTA  TGCGTCGTTG  GGTCGGAGCC  CATGGTGGCA  CTCACTGGCA  TTCTAAACAG  11040
GACGATAAAG  CTTGATCCGG  AGCTGGTCCA  CAGATTCCCG  TCAATACAAA  AAAAGGGGGG  11100
CCCTTTCGAC  TGTGGCATAT  ACGGCCGAGG  ACGAAGCGTC  CGGCTTCCCC  ACTGTTACAA  11160
GGTGGGCTTA  GTGGGGGAAC  TCTGCCGCCT  ACTGAAGATA  CTAGTCTGTC  ACCCCGCCCC  11220
CAACGGCAAG  GCGCAGTACG  TGCGGCGCGC  CTTTACGCTT  CGCGAACTGC  TCCATCACTC  11280
CCCGGGCCAC  AGCGCCGGTC  ATGTCGGCCG  AATCATCTAT  AGCATCATGG  ATCGCAATGA  11340
GAATTTTTTA  GAAAACAAGA  CCATTAGCTA  TCTGCCGGCC  AAAATACCTC  ACATCTTTCA  11400
GCGGATAGAG  ACCCTATCCG  GTCGTTCAAT  AGAGGACTGG  CTACACTCGG  CCGTTTGGGA  11460
TAAAGCATAC  GACACTATAT  GTAAATTTTT  CCCAGATGAA  AAAGCACAAC  AGTTTTCTCA  11520
CGTTGCATTT  ACGCAACAAG  GGGAAAACAT  CATCCAGTTA  AGACCCCGTC  AGGGAAGACA  11580
CTTCCTCTGC  ATCAACCATA  ATCATAAAAA  CAAGTCAAAA  ACAGTCCGTG  TATTCCTTAC  11640
CCTTCATTCC  ATTAGGGTGA  GCGAAGTCAC  GGTAACACTT  ATGAGTCAGT  GTTTGCCAG   11700
CAAGTGTAAC  AATAATGTTC  CCACGGCCCA  TTTTTCGTTT  GTGGTACCAG  TGGGACTGGC  11760
CAGTTAATCC  CACTATATAA  CCTGGCTGCC  AGGTTCCCAA  AATAGCCCGC  GGCATACGGC  11820
TCACTTCCCC  CCACATTCCC  CCCGTGCACA  ATATAAGAAC  CAAAGGACAT  GGTACAAGCA  11880
ATGATAGACA  TGGACATTAT  GAAGGGCATC  CTAGAGGGTA  AGTCCTCGTC  TACAACAGAC  11940
TTTTCCCATT  TCTAACGTAT  CGTGCTATCT  TCGTCGCCCG  GCGGACCATC  CCCCCACCCC  12000
TCATTTATCG  CGTTTGATAT  TACAGACTCT  GTGTCCTCCT  CTGAGTTTGA  CGAATCGAGG  12060
GACGACGAGA  CGGACGCACC  GACACTGGAA  GACGAGCAAT  TGTCCGAACC  CGCCGAGCCT  12120
CCGGCAGACG  AGCGCATCCG  TGGTACCCAG  TCGGCCCAGG  GAATCCACC   CCCCCTGGGC  12180
CGCATCCCAA  AAAAATCTCA  AGGTCGTTCT  CAACTGCGCA  GTGAGATCCA  GTTTTGCTCC  12240
CCACTGTCTC  GACCCAGGTC  CCCCTCACCA  GTAAACAGGT  ACGGTAAAAA  AATCAAGTTT  12300
GGAACCGCCG  GTCAAAACAC  ACGTCCTCCC  CCTGAAAAGC  GTCCTCGGCG  CAGACCACGC  12360
GACCGCCTAC  AATACGGCAG  AACAACACGG  GGCGGACAGT  GTCGCGCTGC  ACCGAAGCGA  12420
GCGACCCGCC  GTCCGCAGGT  CAATTGCCAG  CGGCAGGATG  ACGACGTCAG  ACAGGGTGTG  12480
TCTGACGCCG  TAAAGAAACT  CAGACTCCCT  GCGAGCATGA  TAATTGACGG  TGAGAGCCCC  12540
```

```
CGCTTCGACG ACTCGATCAT CCCCCGCCAC CATGGCGCAT GTTTCAATGT CTTCATTCCC    12600
GCCCCACCAT CCCACGTCCC GGAGGTGTTT ACGGACAGGG ATATCACCGC TCTCATAAGA    12660
GCAGGGGGCA AAGACGACGA ACTCATAAAC AAAAAAATCA GCGCAAAAAA GATTGACCAC    12720
CTCCACAGAC AGATGCTGTC TTTTGTGACC AGCCGCCATA ATCAAGCGTA CTGGGTGAGT    12780
TGCCGTCGAG AAACCGCAGC CGCCGGAGGC CTGCAAACGC TTGGGGCTTT CGTGGAGGAA    12840
CAAATGACGT GGGCCCAGAC GGTTGTGCGC CACGGGGGT GGTTTGATGA GAAGGACATA    12900
GATATAATTT TGGACACCGC AATATTTGTC TGCAATGCGT TTGTTACCAG ATTTAGATTA    12960
CTTCATCTTT CCTGCGTTTT TGACAAGCAG AGCGAGCTAG CACTGATCAA ACAGGTGGCA    13020
TATTTGGTAG CGATGGGAAA CCGCTTAGTA GAGGCATGTA ACCTTCTTGG CGAGGTCAAG    13080
CTTAACTTCA GGGGAGGGCT GCTCTTGGCC TTTGTCCTAA CTATCCCAGG CATGCAGAGT    13140
CGCAGAAGTA TTTCTGCGCG CGGACAGGAG CTGTTTAGAA CACTTCTGGA ATACTACAGG    13200
CCAGGGGATG TGATGGGGCT ACTAAACGTG ATAGTAATGG AACATCACAG CTTGTGCAGA    13260
AACAGTGAAT GTGCAGCGGC AACCCGGGCC GCAATGGGGT CGGCCAAATT TAACAAGGGT    13320
TTATTCTTTT ATCCACTTTC TTAAGGATTG CCAAACCCCA TGGCAGAGTG TCTCCCGTAT    13380
TCCATGTAAC TCACGTAGCC TTTCTCTAAT AAACAAGCTA CCTGCAAACT ATACACAAAT    13440
GAAATGAGTC AGGCGTGGTC TCTTCTCTAC CGTGAATCGC ACCTTAAACA CAACACCAGA    13500
CCGCCACCAG GTGGCACCCA ACATCCATTA TGGAAAAACC CCGCGCCACC TTCCGCCACG    13560
TGGAGCCAAC AAACAAGACA CACCCGCCAA TGTTTTGGTC TCTTTATTGA TATGATATAC    13620
TCCCTCCCAT AACAATACGG TGTAGGCATT TTGTATTATT TATTGCATGG CATCCCATAA    13680
CGGCTTCGGC ATTATTTCGA GTACGACGCA GGCGTCTGAG AAATTACTGC ACCTCGCCGC    13740
AAAGTCTCGC GGGGACGGGG CGTGGGGCTC TAACTTGCCA ACCGCCACCG GTTTCCCCAG    13800
CCACAGCTTC ACCAAAGGAC ACGTCACGTG AGAGGGTGCT GGTAACGGTG AATTTGCCAA    13860
CCCCACCAGA AATGTATTCG GGTTAAATAT CCTCGTCGGT TTTCCCTGGG GCAGCAAGAG    13920
GGGGCCGGAG TCAGGCGGAA CGGTATTTCC AATAAAGTGC ACGGGCCCGT TATGATAACA    13980
TACGCAAAAT ATGCCATTAC AAGAGCTAGT CAGCAGAATG CCTTTTGCAC ATGCGTCCAG    14040
CGTATCGCAT AGCTCCGCT TGGCTATCTC GCAGGCCAGG TTTGGCACAT TGGGTAGCCA     14100
TACCTGGCCC GGAGACCCCA CTGCACAGTA ATGAACTGCG GGGTCCCTAC GCAAGGCCGA    14160
TGAGATTCGA CAGCCCGACT GGCTTGTCGT CAGTAACTCA TGAACCTGTT CGCCATTATA    14220
ATACATCCTG ATAAACAACC GACCCCAGTC AATGACGGCC TCCTGACCCT CTGCCGTCGT    14280
ACAAGATGGC ACGGGCGTTA CAATCTCGCC TGGCAAGCAC TGCCCCGGGG AAAAAAATCC    14340
CTCTTGCAAG AGACGTGCCA TATTGTTAAA ATCGTGGACG GCTCCGGCCA CGACTCCACA    14400
TTCCACGCAT TGTTCTTCCT CCGGTTTACG TACTCTAAAG ACCAGAAAAT GGTGTCCATC    14460
CTGAGAAATG CCTTTGCCAA TCTCTTGTAA ACCCCGCGTC CTGCGTAGCG CGGCAAGCAT    14520
TCGCCTGCGC CCCCTGGTGC CTTTAAACGA GGCGTCCACG GGCATGTTAC CCCTTTCGCG    14580
GATATACACA ACACCCAATT CCCCGTCTCT GCGCCATTCA AAACAGGGGT CCGCGAGGGG    14640
CGTAACTGGT ATACGGAAGC GGGTGCGCTC TTCGTCTTCC CACTCTACTC CGGGAAATTT    14700
TCCACTGTTG ACTTGACATA CTATCCAATC CTTGATTGAC GCTTTCCCCT CACTGGCACC    14760
GGTAGATATT CTTAGTTGTC GTGTCCGGCT CCACTCCGTT ATCGCAGCCA CCACAGCCTG    14820
CCGTGTAATA TCGCCTGCGG CTGCAGAACC CCCGGTCCCG GAGGGTCCTT CTCCCGGTGA    14880
CTCCGACCTG GATGGTTCAT CGCAAGGAGC CCCGGAGCCA GATGTTCCCG GTGACCCTTG    14940
```

```
TGACAAACAA  GGTTTTTTGG  GTATCGCCCC  AGGCGCCCCA  AAAGGGTTCG  GTCTTTGGCC   15000
TGGGTCCATT  GTCCCGCAAC  CAGACTAGCT  CGCGCCGCAA  TGTCCAGTGG  TAAGCACAGC   15060
TATGCCGGGG  AGCCACCGGC  CATCAGATAT  AGAGAGGCGA  CAGGCTCTCT  ATATATCACG   15120
GCTAGGTGGC  TGACATATTA  GTGGGCCTAG  CCGCAGAATT  GCCTGGGTAG  TCAAAAACCA   15180
GCGTTTCTCA  AATTAACCGA  AACTACATTT  TTCTATTTTA  AGTACGGGAT  ACAAAGCAGG   15240
GTCTGAGGCA  ATCTGCCGCC  CTCCACCCCC  ACCCACCATA  CCCAAAAAAG  ATATGTCAGA   15300
AAGAGCACTC  TACCTATTAA  CTCGTGGAGA  AACATCATAC  AAAATCTGTA  CATTATTTTT   15360
AATACTTTAA  TTTGTGCAGG  TTTCTTCACC  CCACACCTGC  TTTTTGTCTG  GTACAAAAAA   15420
CCACTGCAGG  GTCCGCCTA   TAGCCAACTC  CTAAGCGGGT  TTTTTGCTAA  AGCACTTTTT   15480
TAGACTGTCC  CAGAAACCAC  ATAGCTTCCT  TTTCACTCAT  TTGAAAAACA  GCCCCGCCCA   15540
ACTGCCTGGA  GAATTTTCCA  CCCCCTCTAC  CATTTCGCGC  CTTTACCGCT  GGTGCGAAAT   15600
CTAGCCATCC  TATCACCGCG  GATCCGCTGG  ACCAATATAC  CACGCCCACT  TTTCGTAATC   15660
AGCAACCCTC  TACGCCTACA  CCCCTATGAC  TGAATATAAC  CCCCAACAAG  GCTATGAAAT   15720
CATGAATGGT  AACTGTCTGG  ACACCAATCT  TCCGCGGGGT  GGCGGCAGTG  CGACGCAAGT   15780
ATCCACAATA  AATGGTGCAA  TAATTGGCGA  AATGTCGTGT  CTGGTTTATT  TGGACTACAA   15840
GATTACATCC  GGTTTTATAA  TTCACATATA  TGATCAATGT  AGACTATCCC  AAATGGAGCC   15900
TATAAAAATT  TTAACAGTCA  AGGGTACATT  TTGGAAATTT  TCTGTAGATG  CCGGGGATGC   15960
GCCGAAAAAT  ACCGTCCCGC  ACGTCACTGG  GTTGACGCTC  AGCGGTGTCT  GTGGGATTGC   16020
GGCTGTGGTT  GCCAGGTATC  GCGCGGTGTT  GAACAGCTGC  TGCGGAACTC  TGGGGCTAAA   16080
GCTTCGGAGG  ATGCGTTCAT  AGCGGGAATT  TGGATTACCA  AACCACCAGC  CTTCCACTTG   16140
AGTGGCGTTT  CTGGAGTATA  TTCCAGACAT  CGAGCAAAAT  ATTGGGAATC  CGTGGCCAAG   16200
GCCTTCAAAA  ACTCGGTTCA  AAATCTCCAT  TTGCTCGGGT  GAGGGACTG   TAAGACGCGG   16260
TATGCGAAGC  AGTTCTGGTA  CGAAACTCTG  ACATAGGTGC  CCCAACGTAT  CCCCAACAGG   16320
CCAGCTACAT  AACATTGCCT  CGCCCGCGTC  ACCTTCGCGT  CTCAGAGTTC  CACGAAGGTT   16380
CCCATACACA  AAGATTTCCA  CAACAAAAGA  CACCCGCTGA  CTATCAGGGG  GATCAAAAAA   16440
CATCTTTGAA  GGTGGCTTTT  CGGGACCGGA  GTGGCTAACG  GGCGTACGCC  GCCCGTGCGG   16500
GGACCTGGAC  CTCGGGCGCC  GCCTATCCGT  GGCCTGTCTG  GTTGAGGAGC  TCGGTTCCTC   16560
CTGCAGCTCA  GACAAAATGT  TACCCAACCC  TTCTTCCCAC  GTACATATAT  CCTCTCCTTG   16620
AAGGTTCGAG  AGCGTAAGAG  GGAGACCCAA  AGGCGGCGGC  ACTAAAGATT  GTTCTGGTCC   16680
ATAACCCCCC  ACTGCATATC  TATCTCCAGC  ATATGTACTA  ACAAGTGGAA  CTCTGGGCCT   16740
TTCGCCACTA  CCCGGGCACA  CACACTCCCG  CCGCTCCAGC  TCTGTCGGTA  AATGCGAAAC   16800
CTCGGGGTTC  ACAGCGGGCT  CCGGTGCAGA  ATAAAGCACC  GTAGGTTGGA  AAACGCGCGG   16860
CCCACTGACA  GGTAGGGGCG  TGGATGCTAC  AGTGGTAGAT  GGGGTATCGG  AATCCCCAGT   16920
GAGGTCAATA  ATCTCCACTT  CGAGGGCACC  AGAACTAGTT  GTCACGCGTC  TGTATCCAGT   16980
CGCCATGTTG  TCCCCCTGGC  AGACGTACGG  TATTCCAGAC  GAGGATGGCT  CCTGTCGCTC   17040
TGCCACCTCT  GGGGTGGGTG  GTGCGCCGGC  GGAGGGCGTG  GCCGACGCGC  CACCCTGCGT   17100
GTGGGAAAGA  CCCTGGTTTG  GAGCGCCTCC  ACTAGACCAC  GGAATCCAAA  GCGGTGTGCG   17160
AACTTCCGGC  ACCACGGCGT  GACCAACTGG  TGGGTGCCAA  ACAGGCGCGC  GTATGGGTCG   17220
CGTAGCTGGC  GGTTCTGCCA  ATGGACTCCA  ATTGTAACAT  GATGGTTTCG  CATACCCGGG   17280
CGCGGGGGCG  CTGGGCGGTT  GAGGTTCGAA  GGGATACACC  CGCTCACTCG  CAGCACCCTG   17340
```

```
AGGAGCCCGG CCTTCTGTAG ATGCCCCGCA AGCGCCTTCG GCACCGGTTT CCCGGCGGGG    17400
AAGCCACGCG CGAGCACATT GGCCGCTTTG GGGGAGCAAT CCCTGTGGCG CCAGAGGTGC    17460
ACCCTGGCTG AACTCACCGA CAAATGTTCC CGCTTGGGCG TGCGGCGGAA TCCAACTGGG    17520
GGCAGCAGGA TTCAGCTGGC TGCTAGGAAT CCCCGTATAT GTCCAACGGG GGGAAAGGGG    17580
ATCAAATTGG CCCGTGGTTG GCGGATGCAC TTTCTCCGGG AGACCAGACG CGCCCTGAGG    17640
CCACCATCCC GTGACAGGAA GATCTCCCCA TGGAAAACAC GCAGGTATCC ACGGGGACGT    17700
AGATGGCAGC CTAGACCCAT CGCGCATGGG AGGGGCTAGT TGCCCCGTAT CCCCGGCGT     17760
CTGTGCGACG CCGGAGACCC CTGACACAGT ACCGGCAAGC CGTGTTTCGT GCTGCGGCTT    17820
GGGCGGCGCC GTGCCCGGTA GGCCTGCACC AGATGAGTGA GGGTCTGAAG GCCGGTCAG     17880
CGTTGATGGA GCAGGCGGAT CTCCGGGAAC CGCCACGTA  AAGGACGAGG CCTGCGTAAC    17940
TTGTCGCGTC CAGAGGACC  CCATACCTGA GGTAGATGCG CCCTCATTCA CTGGTATCCA    18000
CACGGAGCAG GCAGCCTTCT GTTCAGTCGT TATATCGCCA ACATTGTAAT AGCGGTTCGA    18060
TTTCCGAGGG CGACCCCTCA GCCCCGATGG CGCCTTAGGG GGAGCAGGTG CTGCAGCCCC    18120
TGCCTCCTCG TAGCTTTGTT CTCTAAGTAA AAGGCACGAG AGTTAACGTG GTTAGGGTAC    18180
CTAAAGTATT TCCCGCCGAC ACCAACGCAT CAAACCTCAC ACCCCCTTCC CCGAGTTACA    18240
TACCTAGTGT CACTGCGTCG CGTAGCCGTG GTTTGCATTG GGGGGGACAA CAGACACTGA    18300
ATAAATCGCT GCAGTTTTC  AGGACCATAC GCGGCCCCAT AGCAATACGT ACAGTTTTA    18360
AACGGCGTTC GCACCAACTG CCATACTACG TAGCTACCAC CAAATGTGTC GCTGTACCGT    18420
AAATCGTTCC GCACGACGGC CCTCCTGGTT CCACGCAACA GTCTCCCAAA ACGTCCATAC    18480
ACCGTCTGTC CCACGACAGG CGATGGTCCG TAGACTCTAT CACACTCCTC ATCAAATGCA    18540
TGGTACACCG AATACCAGCC AGGCGGGATA TCGCTGCCGG CAGGCAGGGG CGCGGGGCT    18600
GCAAAAAGAA GGTTGTTCCT ATCAAACCAG GAAAATAGG  GAAACTTATT GTTTCAAGG    18660
GCATCAATAA TCCATAACGT GGCCCATTCT GAGCCACCGG CTTTAGGCAT GGTCCGACAC    18720
AGAAACCGAT CGGCGTTCGT CTTTGAGGCA CAGTCCCGAC TGAGCCTTAT AGTGCCCCC     18780
TTCTTGCTAT GAAAAAACC  CACGACCGTT ACGCAAATTT GAGGAGCTAC TCACCTAAAA    18840
GTAGCTCCTT TGACAAATGT CCTGGTTTTA TACCAATTGT TCACAATGAC ATATTGTGCT    18900
GGCGGAAACA GGTGTCCCGA TGTATCCTCG GCAAGTAAGC ACCATTACCA TGTGCCATCA    18960
TATTGTGTGG CACAAAAAAA GCAACTTTTC ACGCACGCAG CATAAGACCC GAGCCAGTCG    19020
CGCCCTCCAT CGCGCCTGCG AATTTCCCA  CCACCCAATA TTGTGGCAGA TCTTTCTTAT    19080
GTATATGTGG TTACAAACAC CACGCCCCTT AAGCTGTCCT CTCTCCCAAG GGGACTAGAT    19140
TATAACAGTG ACATACGAAA CCGAGACGCT CTCAAATGCT TTCTATTTTA TTTATCGATT    19200
CCGGGTTAAC ATAATCACAG GTAGCTATAA AATCCCCATC CTCTTGACCT GGTAACCCTG    19260
GCTTGAGGTT TCCTCTGTTA TCAAACAAAC CTGACCACAA CTGTACAGAG AAAAGTGGGT    19320
GAAATGTAGT GTTTATTTTA TCCTCACACT TTCACTTAAC CACAGCCCGT CAAACCACAG    19380
GGACCCTGTT GGCTGACTAT TAGTCATCAC ATGTAACTGA ACGCAATCTG AGCTTGATGA    19440
CGAGGGGAC  CATATCGAAC TGTTCTGCCG ACGTTGGGTC ACCTCCGATG AACACAGTTG    19500
TTTTTTTAAT GTGCTCATGT CCCTGTATGC GATATTGTGC CACATTAAAA ACATCCAGAA    19560
CAGCCCTAGA TGACAGTCCG CAGATCACAC CAAACTTCTT TGGAGGATTA TTTCCATGAT    19620
ATAATACGGT AGACTTGCAC AAATTCTTAA CATAAATGCC AGATCGGAGA GAAACTATCA    19680
CAAGACCCGA AGCAAACGAG CGCAGCACGG CCGCCAGCAG GTTAACGTCT CCTGGCCCTG    19740
```

```
TGTTATTGTC  GTCAGGTTTG  GGCAACAAAA  CTCTTAACCC  TTTGCGCGAA  TGCAAGCAAG   19800
AGTGGCTAAT  GTCTGCCAGT  GGGTTCTGGG  AACATAGAAT  AAACACCTTT  CGTTCCACTT   19860
CCAAAGACAT  TGCAGGGCGG  CCAAAATAAA  ACACTTCCAC  ACCAAGCCTA  TCGGTTATCA   19920
TTACTGGCGG  CCGTGCCACT  CTATAATATG  CGGATCTAAG  CTTCCTGTGG  CGAATGCGCC   19980
TCGTGGTAGG  CCTCTCGTGT  CTCCGTGGCC  CATCATCCCA  TAAAAATTCG  CCAACAACTG   20040
GCCGGCGTCT  GGACGCCGGC  GGCAGTCCAG  CACCATCATC  GACTTCTTCG  TCACTTATCT   20100
CCAACACATA  TTCCCCTGCT  ACATTCTGGG  CCTCGAGTGC  CCCAGCTAAG  TACACATCCT   20160
CTACACCCGC  CCCGACAGCC  GAGGCGGCGA  TTGAGCCCTC  TGTTACCACG  CCGCTTGCAT   20220
CCGTGTCGCC  TCCGGGCTGT  GATGTTGCGA  TAACATCCTC  TGGGATGCCA  AGCAGATCAA   20280
AGAGGTCTTC  ATCGCACATC  GCCCTCATTA  GCATGTCCAT  CTCCTGTCCC  ACGTGGTACA   20340
TCAATGCACA  TGCAGATTCT  TTATCAAGCA  GTGTGAGGTC  ATCTTCAACG  TTGTCTGTGT   20400
GCACCGTTGT  TTCATCGGCC  GGGGGGGGCT  GCGAGTCGCT  ATGACGCGTC  GAGGGTCCTT   20460
CGTCTCCAGA  GCCAGGAGAG  TCGGCATTGG  CATCATCAAC  TGGCTGAACC  CCAGACGCAC   20520
TATGGCGCGT  CGATGGTCCC  TCGTCTCCAG  AGTCCTCAGA  TTCCGCGCCC  GTCTGCGTGA   20580
CCGGCACATC  GCAAAAGGCT  GGGTGATCCT  CCTCACTGGA  ATCCGAGTTT  TCACCCACAA   20640
ATGGCCTACA  GAAAAAAAAA  CAAATATGTC  AACCGGACTA  GGGTGGCCAA  ACCATTTGCC   20700
CCACCCCTCC  CCACTCTTTC  CCCAGGGGAC  ACATCTTACC  TTGGTCTTCT  CCGATGCTTC   20760
TCGAGCCGTA  CACTGTGTTG  ATACAAAATT  TCCCATAGTG  ATGACCCACT  GTGTAGGTGA   20820
GTCCTGGCAT  GAACGCACCA  CCAGCATTCC  TTTACCTCGG  CACACAGGAG  GCGCCACCTT   20880
CTACAATTAA  TTCCCTGTAC  GACCTCGTAC  TCTTCACCTG  GCAAGCGTCT  AAGGCGCCGC   20940
GACGTGGTAC  ATATTTTCCC  AAAAGCCGTA  ATCGGCGAGC  CCAGTAAATC  TCTGGGATGC   21000
AGGCCCTTCG  ATAGGCATTC  CCTCTTAAAA  TCAATGAAAA  ACTGTAGGCT  ATCCAGAGGA   21060
ATTACGTCAT  TACGGGCAGC  CGGAGCAAGA  AATGTTCCAG  TAGATCTATC  TAGCCACTTG   21120
ACCAAAGGAT  ATTTATCAGA  GTCCAAAGCA  CCTACAATAA  ACTCAGAAAT  CCAGGTAAGC   21180
CTGCGTCCCG  CCATGTTGAC  CTGTCAGAAT  GGTCTGCCTC  CGAGCATTAC  CCCACCTCAA   21240
CAGAAGTAAT  CTACTACGCA  AACCACAACA  TGCTTCCTGC  AGCTTTAACC  TTCAGTCACG   21300
GGTCAAAAAG  CATTGCCTGT  ATTAGACACA  TGTGTTTCTC  ACTATGAATC  GTGCTCTCCA   21360
GCGCTGGCAA  GAACATCTGG  GGTGATGCTG  CCCCGGACCA  GCTTTGAAAC  AGGGTATTGC   21420
ATGCATAATG  AAGCCCACAT  GTTTGTCTTA  CTTTACTAAC  CTCATTACCT  TGCATTGCAG   21480
GGGACACCCC  CTTGCCTTGG  CAGCTGAGTG  AATCCCAACC  GCCTAGGAAA  AAAATAACCA   21540
CTCAGACTTT  ATTTTGCAGC  CACACGGTGG  CGCTAACCTT  TAATGATGTC  CCACTCAGTG   21600
AGTTTGGCCA  CTCCCAAGCC  CACATGGGCC  TACTATAACA  GGAAACATAG  AAGTTGCGGA   21660
TAGAGCCTGG  TTTCTAACGG  CAATGATATT  TATAGTGCAA  AACGGAGGGC  GGTAAGACAA   21720
AGGGAGGTAC  CCGGACAGAG  TGACAAGAAG  ACTTGTCAAA  ATTTAGTCT   CTGTGGTAAA   21780
ATGGGGCAAG  GTAAATGTGC  AAAATGACTG  GATAGTGATC  CGAGTCATAT  TCAGGCGACG   21840
GCCGGCGGCC  CAGAAACAGG  GACGCGTACC  GGGACCCTTC  AGGTTCTCGA  TTATGTCGCT   21900
CCACGTCAAA  AGCTTGTTGG  ATCTCGTGGC  GGTGGGACAG  GGGCCTACAT  TGCCTATTC   21960
TTCTTCGCGA  TGCATTTCCA  ACAAAGTATG  CTGGGTATTC  CAATAATCCC  TTCAGAAAAA   22020
TGCCCATGTT  TGTACCGATG  GCCACAACTC  CCATGGAAAA  CCTGTCCAGC  GTCTGTTCCA   22080
AAGTTCGGTT  TGCGTCCACA  CTACAGTGGG  CCGTTCTGGG  AAGTAAGCAT  TTATACGGGG   22140
```

-continued

| | | | | | |
|---|---|---|---|---|---|
| GTACCGTCTG | ACATATGTGT | TCAGGGGAGG | CCTCTGGGAC | TTGGGAGCAA | ATAACGATGC 22200 |
| CCCCCGTTAA | ATCAAAGTGG | GTCTTCACCT | TTTCTCCGAA | ATAATACACT | TCCACCACTA 22260 |
| GGGGCACAAG | CTTGTCACCC | ACTTTGTAAA | TAGCCTGTTT | CTTACTCAGG | TATGCTGCCA 22320 |
| CGGATTGGGT | GGCGGTTAAG | ACCTTGGGCC | TCATGTCGCT | TCCATACCAG | TAAAATGTCT 22380 |
| GGTCAGCTTT | CTCTTGGTCC | TCGACGTCCC | GGTCATCACG | ACACAACGGT | GGAATACAAT 22440 |
| CAATAAAATC | ATCCACATTG | TCGGAAGCTT | GGAAAGATGA | ACCCATGACA | GAGGCCCAG 22500 |
| GTGCCGAACT | CTCAAGGGGA | TGCGTGGCGG | GAAGTACTGA | GACACTCTCC | GTGGACCCT 22560 |
| CCTCACCTCC | CTCCGACTGC | ATCGGGCCCT | GAGGGCTCGC | AGTTTCACAC | AGAAGTTCAC 22620 |
| TCAGGTCGCC | TAAGTCAGGA | AGCTCCTGGC | CTGAACCCAT | GACAGAGGCC | CCAGGTGCCG 22680 |
| AACTCTCAAG | GGGATGCGTG | GCGGGAAGTA | CTGAGACACT | CTCCGTGGAC | CCCTCCTCAC 22740 |
| CTCCCTCCGA | CTGCATCGGG | CCCTGAGGGC | TCGCAGTTTC | ACACAGAAGT | TCACCCAGGT 22800 |
| CGCCTAAGTC | AGGAAGCTCC | TGGCCAACAT | CTGACAAGAG | ATCTAACAAA | CACCCCTCAA 22860 |
| TGTGATCCAC | CATCGGTAGG | CAATCATCCA | GCCCACTGAC | ATGACTGGGG | ACGGGGCCTT 22920 |
| CTGGGGAAAA | TGGGGTTTGC | GACTGTCCAG | CAGGCGGCGC | TAATAAGCCT | TGTGTCTCAT 22980 |
| GTGGAAAAAT | AACAGGAGAA | GGTAAACCCC | CCGTTGGCAA | ACATAGATCC | GTCGGGGTGT 23040 |
| GCACGTGTAA | TGGGCCCTGC | ACCTGGCTCG | TGGAGGGACG | CGGGGAATCC | GGAGCTAATA 23100 |
| AGCTCGATGA | CTGACCAGAT | GACCCAAACC | CCGACGGTTC | TGGCTCTTCA | AAAAACAAAC 23160 |
| TGTGCATATC | CCTCCCTACA | AAACCCTGAG | CCCCCACCCA | AAGTTCGTTT | TCGCTGTCAC 23220 |
| TCGATTCCGT | ATCTTCGCTC | TGTGACCGTG | ATGAAACTTC | AGCTGCGGAG | GATGTTGTGG 23280 |
| GCGTGGCGAC | TGCCGCCGCC | TGTTTCCTGG | CGGCCTCCCT | AAACAAAAGT | TAATTACACA 23340 |
| AAGGTAAGTC | TGAGTGACAT | CTCCAATTTC | CCGTGATGCC | CGCTGCACGT | ACATCCCGCC 23400 |
| GCCCACACAA | CCCACCGCCC | AGTACATCAA | CCATCCTACC | TCTGGGCTTT | TTTTCTAAGG 23460 |
| CTCCTTCTAA | GTGCCTTTTC | TCTGTGTTTG | TCATCATGGG | GATAGATCCC | AAACAATGCT 23520 |
| TTTAGCATGT | TTTTCATGGC | TGGTTCCTGC | GTCAAGTACA | CAAGACATCC | TTCACATCCC 23580 |
| TTGTATGGCC | TAGGTGTCAT | AATCCAGCGG | TTGAGTTTCA | TTTTTCCCTT | ATAGATGGTA 23640 |
| AAGGGCCTCT | CCTGTCTGGC | TCGATTGGCG | GTCCTTAATA | GCCGTCCAAA | GCAGCCCAGG 23700 |
| CCAGTCTCAG | TCTCCGGGAT | TTCTGGCAGC | CCGTGCCTAC | GTCGCTCCTC | CAAAAATGCC 23760 |
| TCATAGAAGT | CATCGAAGCC | TTCTGGCATT | CTCTCCCGCC | GGTTTCGACC | CGGCACGGTG 23820 |
| AATATTCTCT | TTTGTTCATC | CAACCACCCT | ACCCCCAGA | AGCGTCCACT | GTCTAAAGCA 23880 |
| TCTATAATAA | AGTCCGTGAG | CCATTCCGAC | TCCGTGTAGC | GAGGCATCTT | TTTAGGCAAA 23940 |
| AGCCACGACA | CAAAACACCT | TTTCCGTGGG | CGACTTTCTC | GCCACAACTA | GCTGGACCCC 24000 |
| AACCCCACTG | GCACGTAGAC | TCTGTGCCAT | CTAACAACAA | AACTCAATAT | ATGCAGCTCA 24060 |
| ACACCGCCCC | CCCCAGCCGG | TTGTCGGGCT | GCGGAAACTT | GTGGTTAGAA | CTCACTACGG 24120 |
| AAAAGGGAAC | CAATGCAGTT | GAACTACTGG | CACACACCCA | TAACCCGGGA | CAGCACCCAG 24180 |
| GCACTGTCCA | CCCTCTAATA | CAAGCGGCCT | TTGGACGCGA | GGGAGGGGTG | TCATGGTCAA 24240 |
| CAAACCAAGA | AAAACACATG | TATTATTCAA | TTAGCCAACA | ACTTTATTTA | TTACCGACAG 24300 |
| GAGACATGAG | ATACATAAAT | TTCCAACCGT | GCATAGGGCC | AATACCATCT | GTGGAGCGTT 24360 |
| AAGTGCCCTG | TGGAGTTTTC | GCCTAATTAG | CTGAATCTCG | ACCCCCATTG | CGGCCAGCAT 24420 |
| GCTCACGAGG | AATAGGCAGC | AGAGGCAGGA | CCTAACTAGG | AGCATATCCG | GACCTGATCC 24480 |
| AAGTATGTGC | ACCAAGGTGA | GCAACACTGC | CGCCAAAGGC | AGGAGAACAA | ATAGCGCTCG 24540 |

```
TCGGGAGGCG ACGGATACGC CCACGCATGA CAGTAACCCA ACATAAAATA GCGTCATATA    24600

CTTATCCAGG CCAATCAGGA CCGGAGTCAG CAGGCCGATC GAGGCCGTCG ATATCAGGGT    24660

GGCCAGCAGT AAGGTCACAA ACACGACAAC CTCGCGCCTA CAGTAGGCCC AGGCCTGGAA    24720

CACTGAATAG GTGATGTACT TCCCGGGCAT GATGAATATG GCCCTCCTCC TTTGCATTCC    24780

GGCCCTGATG TACACATGCT GTTCCAGGTG CCTAAATGCC AAAAGTCCCC CGACCAAGAA    24840

GACAATGAAG GGCAGCCAGA AAACGCCGGA CACAAAGACC TTCTTAAACA ACAGAAGGTA    24900

GTACACCATA AATGCTCCGC AGAAGCCCAG CTCATAGTAC CTGTGTACTA TTGGCGGCGC    24960

CTGATACACC GCCGTTGCGG TGGCTAGCGG ATAAGGTAAC AGCAGTAAAC AGTTAAGTAC    25020

GCACAGACCC GGTATGAAGG GCACACGAGA AAATGTAAAC CCAGAAAAGG CCGCGCAAAC    25080

TACAGCAGCA AACACTGCTG ACGCGCAGAT CCATTCCAGC CTCCGGTCCA GCTGTTTTTG    25140

CGCCGCAGGG CACAGACACA TGCATATCAG GGCCAAGTGC GTGACTGGCA GCGACCAGAA    25200

AAACACGGCC GTGATCTCTG TGGTAAAGAG TGTGAACGAG TACAGGGCCT TGAAGATAAA    25260

ACACCACAGA AAGGGGGTCG CCGCCAACGT CCCGCTCAGA TAACTGAAGA GCGACAGAGC    25320

GCGCTCACTG TCCAGGCGGC ACATGGTGTC AAATCAGGGG GTTAAATGTG GTTTTGGGCA    25380

CCTTCCCACG ATCCCTGGAC TGGCTCGAGT CTGAGCGCCT CTTGTGAGGC CTCTTTGTGC    25440

TGTCCTTAGT TGGCGCCGCT GGGGGGCAGC TGGTGACAGA GGCAGCGTCC TCAGAGGCGT    25500

CCTCCAGCGG CCCAAAGGGA CCAACTGGTG TGAGAGGGGG AGAATCCGGA GACTCCAATT    25560

CCGGCTGCCT CCTGGAGTCC GGTATAGAAT CGGGAACCTT TTGCGAAGAC TCGCCTCCCT    25620

CGGCAGACAC AGATCGGTTT ACCTCTAAAA GTAGGACACT TAACTTTACG TCACCTGATT    25680

GGCAGCCAGT GGGCACACCT TCCACTTCTA ATATTTCGTT GGAGTGCCAA ATCAGCCCGG    25740

GGGTAAACCA ACCCGGGACT TTACACAGTC TCAGGGCGGC GATTAAGGAC TCCAGGCTAA    25800

CCCGGCTCAG GGCGTCGGTG TGCACCACGC CCACATCCAC CGACTTCTTC CCCTTCAGAC    25860

CATCCCAGCC AGAAACGGGT TTGGTTTCTG GCTTGAAATC AATGATCTTG CTCACGCCAC    25920

CAAGAGAAAA TGTCACGATC GACAGCGTCT CGCTGACAGA CACAGTCACC GTTTGGTCCT    25980

CTTTTGTTTT TTGCTGCCTT AGCCACTTAA GTAGGAATGC ACCCGTTTTG CCACAGAGGA    26040

GAAGCCTGGT GGTCCTACCA CCCGGCTTCC ATCCGATCGTG GAAAGGTAGG ATACCCTTTT    26100
```

```
TCTGCGTGAC TGGGTTTTTC CTGTATCTCC ACCATAGTGT TGTACAACAT ACTGGCGGCC    27000
TTGGTGTGCA GCAGCTCGTC CCTGGAAATG TAATCGTTGG CAAGGCACAC CCCGGGCATG    27060
ATGCCTCGCA CCCTGCACAA ACTGATAGAG TAGAAGGAGC TAATAAAGTA TATCCCCTCC    27120
ACAATCAAAA ACATCAGAAT CTTCTGAGCT TTGGTGGTCG CCTTACGCAC CCTGGAGTGA    27180
AGCCACTCCA GCTTCTCGCA AAGGGCGGGG TCCAAAATGA TCTTGGCAGC ATATGCTAGA    27240
AGTTCGCCTC GACTGTTGTT GAAAAATATC TTCAAGATAT TGGCATACAC GACACCGTGG    27300
ATATTCTCCA TGGCAACCTG TTCGGCATAA TAGTGGGCCA CGTCGTGGCT GTTAAAATTT    27360
GTGACAAGGT CCTCAATGTT AAAGTTAACT AGGCGTTCGG CCATTCCCAA AAACGTAAAC    27420
AAAAATCTAT AAAAGTCCTT GTCGGCATCG CTGAGCTGGT GCACGTGGGA AACATCAAGG    27480
TGCAGGGGTA TCTGGCTAGG AAACCATCGG TTCTGCCAAG TCTCGCGCGT TAGCGCCAAA    27540
AATCCGTCGT GATCGCTTGT ATACAGAAAT CGATCAACTG AATCCATTGG CCTCACCCGG    27600
CTTGCAGAGA CCTACCTACT GACAGACCAG GCACTCGGGG TCTGCCGCGC AGGACTCCTC    27660
CTCCGGGTTT TTAGGTCCGG GTAACCACGC CCCATCTTGT TTCATCCCAG AGTGAGGCGG    27720
TGACCCTGGA TCTGCCAGGC ACTGAAGAGC CGTCAGACTA GATTGCTTCT GAACCCTACA    27780
GTAGTACATG AGGGTTTTTA GACCAAGCCT GTATCCATGT AGCAGCAGGT CCCTAAGATA    27840
GCTCGCATTC CTGACTCTGT CCTCCTTGAG GAAGAAGCTC ATGGACTGGC TCTGGTCTAC    27900
AAACGGCGCC CTGGCACGAG CCCTGTCCAG TAGCTTAAAT GGACAGTAAT CAAAGGCTGT    27960
TAGGAATACC CTATATCTTT CCCTGTGATG CTTGGGGAAC GTGGAAACGT CCCCACCATA    28020
CTGTCTAACC ACCCGAAGGT CGTCGGGGAG AACCTTCTTA AAAAAGTCA CATTGGGCCT     28080
CAACACCTCT TCTTTATTGG TGACCTTGGA AGATATATTA GCAAAAAGG GGTACACAGA     28140
CTCGGCATAG CCAGTTACTT GCGAGGTCCC AGCCGTCGGC ATCACCGCCA GAAACTGAGA    28200
ATTGAATATG CCATGCTCGG CAATGCTCTT TCCCAACGCG TCCCAGCGAT GGCGTGGTAC    28260
AAACGAAGCA TCCTCCCCCT CCCATGTTTG CCAATGAAAC CTGCCCTTGG CGAAGTTACT    28320
GACCTCCCAG CCATGAAATG GGACACCCTG TCCCTCCAAA ACAAGGTTGT GACTAGTCTC    28380
CACCGCGGTG TAGTACATAG ACTGGAATAT ATTCTTGTCT AACTCAGCGC TCTCAGCATC    28440
GAGGTACCCG TACCCCAATT CCGCAAACAC ATCCGCCAAC CCCTGAACAC CAATCCCCAT    28500
AGACCTCTCC TTTTGACCTC GCTCGACCCC CGGTGTTGGA TGGGAACCAC CCAGAATGCA    28560
GGCGTTGATG ACGAGGACTG CCACCCTTAC TGCGTCGCCC AAGGCCTCAA AACAAAAAAA    28620
CGGCCTGTTG GCGTCCGTGG TGCCAACCCT CGCGCTTTCA ACAGTTCTCA GACACTTTGG    28680
AAGGCAGATA TTTGCCAGGT TGCACACCGA AGTGTTTCTT CCTGGCAGTT GGACTATCTC    28740
TGCACACAAG TTTGAGCAGT TAATGGCCAT GCCCTGAGTG TCGGTCCAGT GGTGTTCATT    28800
GAGCGCTTCT TTTAAAAGCA CGTACGGTGA GCCTGTCTTT ATGATGGTGT GGATAAGAGT    28860
GAACATCATA GACTTCAACG GCATGCAACT AACGTACTTT CCAGCCCGCA CCAGGCGCTC    28920
GTATTCGTTA TCGAACGCAG CACCGTATAG CTTAATCAAA TTGGGGGCGG TGGCTGGATC    28980
GAACAAATAC CATAACTTGG ATGGGTCCTT TTCATACATC CTGAAAAACA ATGTTGGGAT    29040
GCACACGCCC TGAAAGAGAC TGTGACATCT GTCGGGATTC TCCGGTAGTT TGGCGTTCAA    29100
AAAATCACAG ATTTGACTGT GCCAGAGTTC CATGTATGCG CTCGCGCCAA CGGGCCTGAT    29160
GTTATTGTCA TTGAAATAAT GAACCTGGGC ATCACCAGT TTGAGGCAAC TGGCTATGTT     29220
CTTTTGGTGG GAGAATGACG TAACATCCAG ACCCACGCCT GACTTACTGG CCAGCAACGG    29280
ACTCATATCG TGGTACAGGG CGTCCAAAGT ACCCGACTCA TTCATCATGG AGGGCTGCAG    29340
```

```
AATAAAACAG CTGGCGAGTT GTCCGCCTTC GACTCCAGCT GAGCGCAGTA TTGGCGTGGC  29400
GCAGCACACG TGCTGCGCAG CGAGGTAGCC AAAAACGTAC TCCACTATAG CCATCTCAGA  29460
TACAGACTTA GCGTCCTCAA TAAGGTCCCG CGCCAACCAA TACAGGCATT CATGCTCTAA  29520
GCACTGACAG GCAACAAACA CGGAAACCCT CATAAACATT TGCGCCACGC TTTCATAGAC  29580
AGGCTCTGTC CCCATGGTCC TTAGGACGTA AGTATATAC AACCTCACGG CCGATAGGTA  29640
GCCACAGTTA AGTGTGTCCT CGTAAGCTTT GGACCGTCTG TAGGCGCACA ACATATCTTC  29700
CAAGGCATCA ATGTTCTTTT GAATAAACGA TTCCACCCGA TGTCCCAACA CGCCTCGAAA  29760
AATCCCAAGA TACTGCTTGA GAGTCGCTGG GCACCTAGCC TCCATAATTT GGTGCCACAG  29820
CCGCCCCGCC ATGGCATTGG CCCGCACGTC CCACCCGACC CTAACCTTTA GAAAGTCTAT  29880
GAGAGATTGG GCACACATAT CAAAATCCGA CAATTGTCCC GCAGACACCT GAGACCCGCG  29940
TCGCTCTGGT GGGACAGCTC CCAAGTGAAC CTGACAAAAT GTCCGGACAG ACATGACCTT  30000
ACAGAAACAC AGTCCAGGGG CCACACGCGG CCTCAAAGTT CGCAAACACC AGTACAGGCA  30060
AGGACGTGCC CTTCACGTTC AGACTTTGGT GCACCGGATG AGAATCAAAG GAACTGTGC   30120
CCAGCGTACA AACCGCCCCA AAAACAAGCC GATTTATATA CAGCTCGTGC CTCAGCTGAA  30180
TATACTTGGT CCGGATTACA TCCGTAAAGT GATCCTTTAT CATGGCCACA ACCTCCGCAA  30240
AGCCCTTCCC AGACTGGAAA AACGTCAGCG CCATAGATGG TCTCTGGTTC ACACGGAGAT  30300
AAACCAACGA GGCATAAATA GTAACGTTTA GGCCTGCCGG TTCCCGGCGC TGGACCATGG  30360
GACATGACTC ATCCAAATCA ACTAGCATAT CACAAGGGAG GGTCAAGCCT ACGTGTGCAC  30420
GGGGCTCGTC CCGGGCCAAC CCAACTCCCT TCATGGCGGA GGTGACCTTG GTCACGAAGG  30480
TACTGTGGAC ACTCTGGACC ATTGGACCTA CTGGGGTAAG GAGGGTATGA AACTCCCCAG  30540
TGTCCATGAG TTCACTCAAG TTAGGGATGA AATCCGCCAG GCCGGATCCA CTTCCGTACC  30600
ACACACCGGC CACTTTGTGA GTCTGTGGCG CTTTTGCCGC TTCCATTCCA GAGAGCATAA  30660
ACAGGGACGT GGGTGTTAGC AGCATATCCA TAGACGAGCC GTTGTCCTCC TGCTTGAATG  30720
AAAATAAAAA GGTTCCCAGA GGCTCCTGGG GACTAAAGGT CTGTGAATAC ACGAGGAAAT  30780
CTCCATAGGT CGGCTGCCTA AACGGCGCCT GCCGCAAGGC CTCATGCAGC GAGCCAACCG  30840
TGGGTCGTGT GGACGCCGCA TATTTAGAGA GTAAATCCCG CACCCCCTG GCAAACTCCG   30900
GTCCTCTAGT GAGGGATACC CGGTGAGTTG GTGGAGGTAA AAGACCCAAC ACTTGCCTAC  30960
CCAGGCGAGC CGCATTTTCA GCCTGCACCT TCATATCCAC GCCGGCAATG GACGGCACAG  31020
ACGCTCTTGA AAAGCTTACC AAAGGCCTGA GTGGGGAGG CGGGAGCCTT CACCAGACAA    31080
AGCTGTTGAT GGAATTTCAA CTCCGAGGAC TGCCGGTGCC TGCCCTCTTA AACAGCAGCA  31140
CAACAGAGCA GTTTTAAAT ACTGTTGCCC AACTGCCGAC GGACCTATCA AAATTTATAC   31200
GCGACTATCG CGTGTTCGCA CTGGTTCGCG CGGCGTATTT TTTAGAACCC CCTTCTAGCA  31260
TCGACCCCCT TGAGGCAGCG CGCGCTCTTG GACGCCTGGT TGATATATTA TCATCACAAC  31320
CACCGCAGAA CACCGCACCG GCGCAGCCAC CCACCTCCGA CGACACCCTG AATAACTGTA  31380
CATTGCTCAA ACTACTAGCC CACTACGCGG ATCAGATAGC AGGTTTCAAA ACCCCCGCTC  31440
TCCCTCCCGT GCCACCTGGA ATCATCGGCC TGTTCACATG CGTGGAACAG ATGTACCACG  31500
CATGTTTTCA GAAATACTGG GCAGCTGCAC TACCCCCAAT GTGGATACTG ACATACGACC  31560
CTCCCACTTC TCCGTTACAG GACTGGCTTA TAGTCGCCTA TGGTAACAAG GAAGGACTGC  31620
TACTCCCCTC TGGCATACCC TCGGAGGAGG TGTTAGCCAA AACATTAGTA ACAGAACACC  31680
ACGAGTTGTT CGTATCGCGG TCGAATTCGA CCGAGACCGC CGTCACCATG CCCGTATCCA  31740
```

```
AAGAACGCGC CCTCGCCATC TACCGGGTGT TCGCCAAGGG TGAGGTGGTG GCGGAAAATA   31800
CTCCCATTCT TGCCTTCACC GACGTGGAAC TATCCACACT CAAACCCCAC TATCTGTTCA   31860
TCTATGATTT TATCATAGAG GCATTATGCA AGAGCTACAC ATACTCATGC ACCCAGGCCC   31920
GCCTGGAATC CTTTTTGAGC CGAGGTATAG ACTTCATGAC TGACCTAGGT CAGTACCTAG   31980
ATACCGCTAC TAGCGGCAAG CAGCAGCTGA CGCACAGCCA AATAAAGGAA ATCAAATACA   32040
GGCTGCTAAG CTGCGGTCTC TCGGCTTCCG CGTGTGATGT TTTCAGAACT GTGATCATGA   32100
CCCTCCCATA TCGACCGACC CCCAACCTCG CTAACCTGTC CACGTTTATG GGATGGTTC    32160
ACCAACTGAC CATGTTCGGA CACTATTTCT ACCGGTGCCT GGGCAGCTAC AGTCCCACCG   32220
GCTTGGCCTT CACAGAATTG CAAAAGATAC TGACACGCGC CAGCGCGGAG CAAACGGAAC   32280
GTAACCCGTG GAGACATCCG GGTATCTCGG ACATTCCACT GCGTTGGAAA ATATCGCGTG   32340
CTCTAGCATT CTTCGTCCCT CCGGCCCCCA TAAACACTTT GCAGCGCGTG TACGCCGCGC   32400
TGCCCTCGCA ACTCATGCGG GCCATCTTCG AGATCTCGGT CAAGACCACA TGGGGAGGCG   32460
CCGTACCGGC AAACCTGGCG CGCGACATTG ACACAGGACC GAACACACAA CATATCTCCT   32520
CCACACCACC GCCCACCCTC AAGGATGTTG AGACATACTG TCAAGGTCTG CGGGTGGGAG   32580
ACACGGAGTA CGATGAGGAC ATTGTGAGAA GCCCGCTCTT TGCAGACGCG TTTACCAAGA   32640
GTCACTTGTT GCCTATACTG CGCGAGGTTC TGGAAAACCG CCTGCAGAAA AACAGAGCTC   32700
TGTTTCAGAT AAGATGGCTG ATAATATTTG CTGCCGAGGC GGCAACCGGG CTCATCCCTG   32760
CCAGGCGCCC GCTAGCCAGA GCCTACTTCC ACATCATGGA CATTCTGGAG GAGAGACATT   32820
CCCAAGACGC CCTATACAAC CTTTTGGACT GTATCCAGGA GCTCTTCACC CACATCAGGC   32880
AGGCTGTTCC AGACGCACAG TGTCCGCACG CCTTTCTACA GTCCCTGTTC GTCTTTCAAT   32940
TCCGCCCTTT CGTACTCAAA CACCAGCAGG GTGTAACCTT GTTTCTAGAT GGCTTGCAGA   33000
CATCCCTCCC CCCGGTGATA AGTCTGGCCA ACCTTGGAGA CAAGCTGTGT CGTCTCGAGT   33060
TCGAGTACGA CAGCGAGGGC GACTTCGTGC GCGTGCCAGT TGCACCGCCA GAACAACCAC   33120
CGCACGTACA TCTGTCGCAT TTCAAGAAGA CAATACAGAC CATCGAACAG GCCACCAGGG   33180
AGGCCACCGT AGCCATGACA ACAATCGCAA AGCCAATATA CCCCGCCTAC ATCCGGTTAC   33240
TGCAGCGGCT AGAATATCTT AACAGACTCA ACCACCACAT TCTCAGGATT CCCTTCCCAC   33300
AGGACGCCCT TTCTGAACTC CAGGAAACCT ACCTGGCGGC GTTTGCACGG TTGACAAAAT   33360
TGGCAGCGGA CGCAGCAAAC ACTTGTAGCT ACTCCCTCAC CAAGTACTTT GGAGTTTTAT   33420
TCCAACACCA GCTGGTCCCC ACGGCCATCG TTAAAAAACT GCTACATTTC GACGAGGCTA   33480
AAGATACCAC AGAAGCCTTT TTACAGAGCC TGGCACAACC CGTAGTGCAG GGACAACGGC   33540
AGGGGGCGGC TGGCGGGTCG GGTGTCCTGA CGCAGAAAGA ACTTGAGCTC TTGAACAAAA   33600
TAAACCCACA GTTTACAGAC GCTCAGGCTA ACATTCCTCC ATCTATTAAA CGTTCATATT   33660
CAAATAAATA TGACGTCCCT GAGGTCTCAG TCGACTGGGA AACGTACTCC CGGTCTGCCT   33720
TCGAGGCACC GGACGACGAA CTCCGTTTTG TCCCACTGAC GCTGGCAGGC CTCCGGAAAC   33780
TGTTTGTCGA ATAGAGGCCA TGGCAGCCCA GCCTCTGTAC ATGGAGGGAA TGGCCTCCAC   33840
CCACCAAGCT AACTGTATAT TCGGAGAACA TGCTGGATCC CAGTGCCTCA GCAACTGCGT   33900
CATGTACCTG GCGTCCAGCT ATTATAACAG CGAAACCCCC CTCGTCGACA GAGCCAGCCT   33960
GGACGATGTA CTTGAACAGG GCATGAGGCT GGACCTCCTC CTACGAAAAT CTGGCATGCT   34020
GGGATTTAGA CAATATGCCC AACTTCATCA CATCCCCGGA TTCCTCCGCA CAGACGACTG   34080
GGCCACCAAG ATCTTCCAGT CTCCAGAGTT TTATGGGCTC ATCGGACAGG ACGCGGCCAT   34140
```

| | | | | | | |
|---|---|---|---|---|---|---|
| CCGCGAGCCA | TTCATCGAGT | CCTTGAGGTC | GGTTTTGAGT | CGAAACTACG | CGGGCACGGT | 34200 |
| ACAGTACCTG | ATCATTATCT | GCCAGTCCAA | AGCCGGAGCA | ATCGTCGTCA | AGGACAAAAC | 34260 |
| GTATTACATG | TTTGACCCCC | ACTGCATACC | AAACATCCCC | AACAGTCCTG | CACACGTCAT | 34320 |
| AAAGACTAAC | GACGTTGGCG | TTTTATTACC | GTACATAGCC | ACACATGACA | CTGAATACAC | 34380 |
| CGGGTGCTTC | CTTTACTTTA | TCCCACATGA | CTACATCAGC | CCAGAGCACT | ACATCGCAAA | 34440 |
| CCACTACCGC | ACCATTGTGT | TCGAAGAACT | CCACGGGCCC | AGAATGGATA | TCTCCCGCGG | 34500 |
| GGTGGAATCA | TGCTCCATCA | CCGAAATCAC | GTCCCCTTCT | GTATCCCCCG | CGCCTAGTGA | 34560 |
| GGCACCATTG | CGCAGGGACT | CCACCCAATC | ACAAGACGAA | ACGCGCCCGC | GCAGACCTCG | 34620 |
| CGTCGTCATT | CCTCCTTACG | ATCCGACAGA | CCGCCCACGA | CCGCCTCACC | AAGACCGCCC | 34680 |
| GCCAGAGCAG | GCAGCGGGAT | ACGGTGGAAA | CAAAGGACGC | GGCGGTAACA | AAGGACGCGG | 34740 |
| CGGAAAGACG | GGACGTGGCG | GAAATGAAGG | ACGCGGTGGC | CACCAGCCAC | CAGACGAGCA | 34800 |
| CCAGCCCCCA | CACATCACCG | CGGAACACAT | GGACCAGTCC | GACGGACAAG | GCGCCGATGG | 34860 |
| AGACATGGAT | AGTACACCCG | CAAATGGTGA | GACATCCGTT | ACGGAAACCC | CGGGCCCCGA | 34920 |
| ACCCAATCCC | CCAGCACGGC | CTGACAGAGA | GCCACCGCCC | ACTCCCCGG | CGACCCCAGG | 34980 |
| CGCCACAGCG | CTGCTCTCTG | ACCTAACTGC | CACAAGAGGG | CAGAAACGCA | AATTTTCCTC | 35040 |
| GCTTAAAGAA | TCTTATCCCA | TCGACAGCCC | ACCCTCTGAC | GACGATGATG | TGTCCCAGCC | 35100 |

( 2 ) INFORMATION FOR SEQ ID NO:20:

( i ) SEQUENCE CHARACTERISTICS:
        ( A ) LENGTH: 32207 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:20:

| | | | | | | |
|---|---|---|---|---|---|---|
| CTCCCAACAA | ACGGCTCCGG | ATACTGAAGA | TATTTGGATT | GACGACCCAC | TCACACCCTT | 60 |
| GTACCCACTA | ACGGATACAC | CATCTTTCGA | CATAACGGCG | GACGTCACAC | CCGACAACAC | 120 |
| CCACCCCGAG | AAAGCAGCGG | ACGGGACTT | TACCAACAAG | ACCACAAGCA | CGGATGCGGA | 180 |
| CAGGTATGCC | AGCGCCAGTC | AGGAATCGCT | GGGCACCCTG | GTCTCGCCAT | ACGATTTTAC | 240 |
| AAACTTGGAT | ACACTGCTGG | CAGAGCTGGG | CCGGTTGGGA | ACGGCACAGC | CTATCCCTGT | 300 |
| AATCGTGGAC | AGACTAACAT | CGCGACCTTT | TCGAGAAGCC | AGCGCTCTAC | AGGCTATGGA | 360 |
| TAGGATACTA | ACACACGTGG | TCCTAGAATA | CGGTCTGGTT | TCGGGTTACA | GCACAGCTGC | 420 |
| CCCATCCAAA | TGCACCCACG | TCCTCCAGTT | TTTCATTTTG | TGGGGCGAAA | AACTCGGCAT | 480 |
| ACCAACGGAG | GACGCAAAGA | CGCTCCTGGA | AAGCGCACTG | GAGATCCCCG | CAATGTGCGA | 540 |
| GATCGTCCAA | CAGGGCCGGT | TGAAGGAGCC | CACGTTCTCC | CGCCACATTA | TAAGCAAGCT | 600 |
| AAACCCCTGC | TTGGAATCCC | TACACGCCAC | TAGTCGTCAG | GACTTCAAGT | CCCTGATACA | 660 |
| GGCATTCAAC | GCCGAAGGGA | TTAGGATCGC | CTCGCGTGAG | AGGGAGACGT | CCATGGCCGA | 720 |
| ACTGATAGAA | ACGATAACCG | CCCGCCTTAA | ACCAAATTTT | AACATTGTCT | GTGCCCGCCA | 780 |
| GGACGCACAA | ACCATTCAAG | ACGGCGTCGG | TCTCCTCAGG | GCCGAGGTTA | ACAAGAGAAA | 840 |
| CGCACAGATA | GCCCAGGAGG | CTGCGTATTT | TGAGAATATA | ATCACGGCCC | TCTCCACATT | 900 |
| CCAACCACCT | CCCCAATCGC | AACAGACGTT | CGAAGTGCTG | CCGGACCTCA | AACTGCGCAC | 960 |
| GCTCGTGGAG | CACCTGACCC | TGGTTGAGGC | GCAGGTGACA | ACGCAAACGG | TGGAAAGTCT | 1020 |

| | | | | | | |
|---|---|---|---|---|---|---|
| ACAGGCATAC | CTACAGAGCG | CTGCCACTGC | TGAGCATCAC | CTTACCAACG | TGCCCAACGT | 1080 |
| CCACAGTATA | CTGTCTAACA | TATCCAACAC | TCTAAAAGTT | ATAGATTATG | TAATTCCAAA | 1140 |
| ATTTATAATA | AACACCGATA | CACTGGCCCC | ATATAAACAG | CAGTTTTCAT | ATCTGGGGGG | 1200 |
| TGAACTGGCA | TCTATGTTCT | CCCTTGACTG | GCCTCACGCA | CCTGCAGAGG | CGGTAGAGCC | 1260 |
| ACTACCCGTG | CTGACTTCTC | TGCGAGGTAA | AATCGCAGAG | GCGCTGACGC | GTCAAGAAAA | 1320 |
| CAAAAACGCT | GTAGATCAAA | TTCTAACCGA | CGCCGAAGGC | CTCCTTAAGA | ACATTACCGA | 1380 |
| TCCAAACGGC | GCACACTTCC | ACGCCCAGGC | CGTATCAATT | CCAGTGTTAG | AAAACTACGT | 1440 |
| ACATAACGCG | GGGGTCCTTC | TCAAGGGCGA | AAAGAGCGAG | AGGTTCTCCC | GGCTGAAGAC | 1500 |
| CGCCATCCAA | AACCTGGTAT | CCTCCGAATC | ATTTATCACC | GTGACCCTAC | ACAGTACAAA | 1560 |
| CCTTGGAAAC | CTAGTTACCA | ACGTACCAAA | ACTTGGTGAG | GCGTTCACCG | GGGGCCCGCA | 1620 |
| CCTCCTGACA | AGCCCGTCCG | TGAGACAGTC | CCTTTCCACC | CTGTGCACAA | CCCTGCTGCG | 1680 |
| AGATGCCCTG | GACGCCCTGG | AAAAAAAGGA | TCCGGCCCTT | CTTGGTGAGG | GGACCACGTT | 1740 |
| GGCGCTGGAG | ACACTCCTAG | GATACGGGTC | GGTGCAGGAC | TACAAGGAGA | CGGTACAGAT | 1800 |
| AATATCCAGC | CTTGTGGGCA | TCCAAAAATT | AGTCAGGGAC | CAGGGCGCGG | ACAAGTGGGC | 1860 |
| CACTGCCGTG | ACAAGGCTAA | CTGACCTCAA | ATCAACTCTG | GCCACGACCG | CCATCGAGAC | 1920 |
| GGCTACGAAA | CGGAAACTAT | ACAGATTGAT | CCAAAGGGAC | CTCAAAGAGG | CTCAAAAACA | 1980 |
| CGAGACCAAT | CGGGCCATGG | AGGAATGGAA | GCAGAAAGTA | CTGGCTCTTG | ACAATGCGTC | 2040 |
| TCCGGAACGT | GTCGCCACCC | TCCTGCAACA | GGCTCCCACC | GCGAAGGCTA | GAGAGTTTGC | 2100 |
| AGAGAAGCAC | TTCAAAATAC | TACTCCCCGT | ACCCGCGGAC | GCCCCCGTCC | AAGCGTCTCC | 2160 |
| AACGCCGATG | GAATACAGCG | CCAGCCCCCT | CCCGGACCCA | AAGGATATAG | ACAGAGCTAC | 2220 |
| ATCCATCCAC | GGGGAACAGG | CGTGGAAGAA | GATACAGCAG | GCGTTCAAGG | ATTTCAACTT | 2280 |
| CGCCGTCCTG | CGGCCCGCTG | ACTGGGATGC | CCTGGCAGCG | GAGTACCAAC | GCCGTGGTTC | 2340 |
| GCCCCTTCCG | GCGGCCGTGG | GTCCAGCGCT | CTCAGGGTTC | CTGGAGACGA | TCCTAGGGAC | 2400 |
| GCTGAACGAC | ATCTACATGG | ATAAGCTCCG | CTCCTTTCTG | CCCGACGCGC | AGCCTTTTCA | 2460 |
| GGCGCCGCCC | TTCGACTGGC | TAACGCCGTA | TCAGGACCAA | GTCAGCTTTT | TCTTGCGCAC | 2520 |
| CATAGGGCTG | CCGCTGGTGC | GAGCGCTGGC | CGACAAGATC | AGCGTGCAGG | CACTGAGGCT | 2580 |
| TAGCCACGCG | CTCCAGTCCG | GCGATTTGCA | GCAGGCCACG | GTGGGCACGC | CCCTGGAGCT | 2640 |
| CCCTGCCACA | GAGTACGCGC | GCATCGCCTC | CAACATGAAG | TCCGTGTTCA | ACGACCACGG | 2700 |
| ACTTCAGGTG | CGATCAGAGG | TCGCGGATTA | TGTGGAGGCC | CAACGAGCCG | ACGCACACAC | 2760 |
| GCCACACGTC | CCACGTCCAA | AGATACAGGC | ACCAAAGACT | CTGATTCCAC | ATCCGGACGC | 2820 |
| AATCGTCGCG | GACGGACTAC | CCGCCTTTCT | TAAGACGTCC | CTACTGCAGC | AAGAGGCCAA | 2880 |
| ACTTCTGGCG | CTACAGCGGG | CGGACTTCGA | GTCGCTCGAG | AGCGACATGC | GCGCCGCAGA | 2940 |
| GGCCCAGAGA | AAAGCATCGC | GCGAGGAAAC | CCAGCGCAAA | ATGGCACACG | CCATCACTCA | 3000 |
| GCTCTTACAG | CAGGCACCCA | GTGCGATCTC | GGGGCGCCCG | CTATCCTTAC | AGGACCCGGT | 3060 |
| GGGCTTCCTC | GAGGGCATCA | TATACGACAA | GGTCCTGGAG | CGCGAATCCT | ACGAGACGGG | 3120 |
| TCTCGAGGGA | CTGTCCTGGC | TCGAGCAGAC | CATCAAGTCC | ATCACCGTAT | ACGCTCCCGT | 3180 |
| AGAGGAGAAG | CAAAGAATGC | ACGTGCTGCT | GGACGAGGTG | AAAAAGCAGC | GAGCAAACAC | 3240 |
| TGAGACCGCT | CTCGAGCTAG | AGGCCGCGGC | TACGCACGGC | GACGACGCTA | GACTCCTGCA | 3300 |
| GCGAGCGGTC | GATGAGCTGT | CACCGTTGCG | CGTTAAGGGG | GGGAAGGCCG | CGGTGGAATC | 3360 |
| CTGGCGGCAG | AAAATCCAAA | CCCTGAAATC | CCTGGTACAG | GAAGCGGAGC | AGGCCGGCCT | 3420 |

```
CCTGTTGGCC ACCATAGACA CGGTGGCCGG CCAGGCCCAG GAGACCATAT CACCATCCAC    3480
ACTCCAGGGA CTGTACCAAC AGGGACAGGA GGCCATGGCG GCCATTAAGC GGTTTAGGGA    3540
CTCGCCCCAG CTAGCTGGCC TGCAGGAAAA GCTGGCCGAG CTACAGCAGT ACGTCAAGTA    3600
CAAGAAGCAG TATCTGGAAC ACTTTGAGGC CACCCAAAGC GTAGTGTTTA CAGCCTTTCC    3660
GCTCACACAG GAGGTTACGA TCCCAGCCCT GCATTACGCG GGACCTTTCG ACAACTTGGA    3720
GCGGCTCTCA CGATACCTAC ACATCGGCCA GACGCAGCCG GCTCCGGGAC AGTGGCTCCT    3780
GACACTTCCC ACATTCGACC CCACGCGCCC GGCCTGCGTC CCAGCCGGCG GCCACGAACC    3840
CCCGTTGCAC AGACAGGTGG TGTTCTCCAG CTTTTTGGAG GCCCAGATCC GATTAGCGTT    3900
GTCCGTAGCG GGCCCCGTGC CTGGACGGGG TCTGCCCGGA ACACCGCAGA TCCGAAGGGG    3960
CGTGGAGGCT GCCGCTTGTT TCCTCCACCA GTGGGACGAG ATATCTCGCC TCCTTCCAGA    4020
GGTACTGGAC ACCTTTTTCC ACAACGCGCC CCTTCCCGCA GAGTCTTCCT CCAATGCTTT    4080
CCTGGCCATG TGCGTATTGA CGCACCTTGT CTACCTAGCT GGGCGCGCCG TCTTGGGCCC    4140
ACGGGAGCCG GAGCACGCCG CCCCGGACGC GTACCCAAGG GAGGTGGCGC TGGCCCCGCG    4200
CGACCTGACC TACCTTCTAC TGGCCATGTG GCCATCTTGG ATCTCGGCAA TTTTGAAACA    4260
GCCTTCGCAC GCGGAGGCGG CGCACGCATG TCTTGTCACG CTGCCAACAA TGCTCAAGGC    4320
TGTGCCGTAC CTCACGCTGG AAGCCTCAGC TGGACCACTG CCGGCGGACA TGCGCCACTT    4380
CGCCACGCCA GAAGCGCGTC TGTTTTTCCC CGCGCGATGG CACCACGTCA ACGTGCAGGA    4440
GAAACTGTGG CTGCGTAATG ATTTTATGTC GCTGTGTCAC CGTTCCCCGG GGCGCGCGCG    4500
CATAGCCGTC TTGGTGTGGG CCGTCACTTG CCTAGATCCT GAGGTAATAA GGCAGCTGTG    4560
GTCCACCTTG CGGCCCCTTA CTGCGGATGA ATCCGACACG GCTTCTGGAC TGCTGCGGGT    4620
GCTAGTAGAA ATGGAGTTTG GTCCGCCGCC CAAGACGCCG CGGCGGGAGG CGGTGGCGCC    4680
CGGCGCAACA CTGCCACCGT ACCCCTACGG CCTTGCCACC GGCGAGCGCC TGGTCGGCCA    4740
GGCGCAGGAA CGCTCTGGCG GCGCTGGCAA GATGCCGGTG TCCGGGTTTG AGATAGTTTT    4800
AGGCGCACTG CTGTTCCGCG CCCCCCTACG CATTTTCAGC ACCGCATCAA CCCACAGGAT    4860
CTCAGATTTC GAGGGCGGTT TCCAGATACT GACTCCTCTC CTGGACTGTT GCCCAGATCG    4920
CGAGCCATTC GCCTCCCTGG CCGCCGCACC ACGAAGGACG GTGCCACTGG GAGACCCGTG    4980
CGCCAACATT CACACCCCCG AAGAGATACA GATCTTTGCG CGTCAAGCCG CCTGGCTTCA    5040
ATATACCTTC GCAAATTACC AGATCCCAG CACCGACAAC CCGATACCGA TCGTTGTGCT    5100
AAACGCTAAC AATAACCTTG AAAACAGCTA CATCCCTCGC GATCGCAAAG CGGACCCGCT    5160
ACGACCATTC TATGTAGTCC CTCTGAAGCC GCAGGGTAGA TGGCCTGAAA TAATGACCAC    5220
AGCAACAACC CCCTGCCGCC TACCGACATC GCCAGAAGAG GCGGGATCAC AGTTCGCCAG    5280
ACTCCTTCAG AGCCAGGTGA GCGCCACATG GTCTGACATC TTCTCCAGGG TTCCCGAGCG    5340
CCTCGCTCCC AATGCGCCTC AGAAGAGTTC CCAGACAATG TCAGAAATCC ACGAGGTCGC    5400
CGCCACGCCG CCACTCACAA TCACCCCAAA TAAACCGACC GGAACCCCTC ACGTCTCCCC    5460
GGAGGCTGAT CCAATAACAG AACGCAAACG CGGACAGCAG CCGAAGATTG TCGCGGACAA    5520
CATGCCTAGT CGTATTCTCC CGTCGCTACC GACCCCGAAA CCCAGAGAGC CTAGAATCAC    5580
GCTACCCCAC GCACTGCCCG TTATATCACC CCCAGCACAT CGCCCGTCGC CTATACCGCA    5640
TCTGCCAGCA CCGCAGGTAA CGGAGCCCAA AGGGGTTCTC CAAAGCAAAC GTGGAACTCT    5700
CGTGCTGCGG CCCGCCGCGG TCATTGACCC ACGGAAGCCC GTCTCGGCAC CGATCACGCG    5760
ATATGAGAGG ACGGCGCTCC AGCCCCCCCG GACTGAGGGC GAAGGCCGGC GCCCTCCCGA    5820
```

| | | | | | | |
|---|---|---|---|---|---|---|
| CACGCAACCC | GTCACTTTAA | CCTTTCGTCT | CCCACCTACC | GCACCCACTC | CCGCAACTGC | 5880 |
| AGCCCTAGAA | ACCAAAACAA | CTCCCCCATC | CACGCCCCCA | CACGCCATAG | ACATTAGCCC | 5940 |
| ACCACAGACA | CCTCCCATGT | CCACCTCACC | TCACGCGAGA | GACACAAGCC | CCCCGCAGA | 6000 |
| AAAGCGGGCC | GCACCCGTCA | TTCGAGTAAT | GGCGCCCACG | CAACCGTCGG | GAGAGGCAAG | 6060 |
| AGTCAAGCGA | GTGGAGATCG | AACAGGGCCT | TTCCACACGC | AATGAAGCCC | CTCCCCTTGA | 6120 |
| ACGCTCGAAT | CACGCCGTGC | CCGCCGTTAC | CCCAAGGCGC | ACCGTAGCCC | GCGAAATCAG | 6180 |
| GATCCCGCCG | GAGATAAAGG | CGGGTTGGGA | CACTGCACCG | GACATTCCTC | TGCCCCACAG | 6240 |
| CTCCCCGGAG | TCATCCCCAC | CGACTTCCCC | CCAGCCTATC | CGCGTGGATG | ATAAATCGCC | 6300 |
| TCTTCCCAAC | CTCGTAGAGA | GATACGCGCG | GGGTTTCCTG | GACACGCCCT | CTGTAGAGGT | 6360 |
| GATGTCCCTG | GAAAATCAGG | ACATCGCCGT | GGACCCCGGA | CTGCTAACCC | GCCGGATTCC | 6420 |
| ATCCGTGGTG | CCCATGCCCC | ATCCAATTAT | GTGGTCACCC | ATAGTACCCA | TCAGTTTACA | 6480 |
| AAACACAGAC | ATAGACACTG | CAAAGATAAC | ACTGATTAGT | TTTATTAGAC | GCATCAAACA | 6540 |
| AAAGTGGCC | GCCCTATCGG | CGTCCCTGGC | GGAGACGGTT | GACAGAATAA | AGAAGTGGTA | 6600 |
| CTTGTGACTC | CACGGTTGTC | CAATCGTTGC | CTATTTCTTT | TTGCCAGAGG | GGGGTTTCCT | 6660 |
| CGCGTCGGCC | ACCGCGGGGG | CGGCCGTTTC | CGTCGTGGAT | GAGAGGGTTG | TGAGAATGTC | 6720 |
| TGACGCCGGC | GACAATGAAT | GGGGACCAGA | GGACAGGGTG | GTTATACTGC | TTCCCGAGAC | 6780 |
| CCCCAGTGAG | TCCTGGCCCC | CGGGCGTGGT | GCCGGATGCA | GGGCCTGGCC | TCGAAGGCAC | 6840 |
| GGTGAACGTC | CCCGCGTCGT | AAGCCGACGC | CGCGGAAACT | CGGTCAGCGC | GCTCGCGCGG | 6900 |
| TTTCTGATCC | CTAAGGGTCT | GCAGATGATC | CCGCCTTTGA | ATTCCACCCA | TCCTCCTCAG | 6960 |
| ATAGGCCTCA | TAATAATGAT | GGGCAATTAA | GAACACGAGA | TAGTGTCTCT | TTTGCACGAG | 7020 |
| GTATTCGGCC | TGCGACATAT | TTCCCTGATC | CAGGGTATTC | ATGCGAGCCA | CCAGGGGATG | 7080 |
| GTGAGCGTAG | TCATGATCCA | GTCGCTCCTG | GATCACGGGG | TCTCTCACCT | TAAAGTTGGA | 7140 |
| CATCTTCCAC | ACAGGCGGGC | GAAATAGCCT | CAGGAGGAAC | ACTTCCCGCA | ACAGAACTCC | 7200 |
| AGCAGCTGTG | AGGTGAGCTG | AAGCAGTCCG | CGCACGTCAC | GGTGCTTTAA | TAGGGCAGCC | 7260 |
| TCGCAGTCGG | GCGTCCCAAG | GCAAGGCACT | ACAAAACTGA | CAGTTTGATC | TAGGTCTCGA | 7320 |
| ATGGCAAGGG | CCGCGTTGTT | AGCTAGAACA | GCCCTGATTA | CGACGCGTGC | TAGGGTCCCG | 7380 |
| CGTCCGGTAA | TATCGCACAG | GGGATACACC | CTCATATGTT | CGCTGCCACA | GTAAGAACAG | 7440 |
| TAGATCCTCC | CCGTGGTCGC | ACAGATGGTG | AACTGCTTCT | CTTTCCTGTC | CCTGCTGAAA | 7500 |
| AACACGTTGG | TGGGAGGAAA | ATTGACAGTA | TGAAACTTGC | CCCTGCCAAA | GTTAAGACAG | 7560 |
| TGTCCACACT | CCATGCACAC | AACCGCCCGA | GCGCAACGCG | CCCGCTTGGC | AAGGGCCGCG | 7620 |
| CGGGCCACGC | GAGAACAGAT | GACGGGTATG | GACACGCAGG | GGGAGAGAAC | ATTGTATGCC | 7680 |
| AGAAGCCTCC | TGCCAAGGTT | CCGCACGAGA | CCAGGTCCCT | CCTGCTCGCA | GGCGGGCAGC | 7740 |
| ACTACGTGGC | GGGACTTAAT | AAGGCTCAAA | AAACACAGTG | ACCAAGCAT | GGCGTCGAAC | 7800 |
| GGGTTACCGC | AGGGAACCGT | AGGGGCGACG | CGCTCCAAGG | CCTCCCGGAG | GCCGGTATCT | 7860 |
| GCCGCCCCTA | TCCCGAGCCC | GTTACCGTCT | TCGGTCGCAG | CCACACCGCG | ACGGGTGTGC | 7920 |
| GAGGGCACCT | CCAGGAGGGG | ACGACGCGGC | AACGGCCCAT | GCCACTTCTT | CCTTAGCCAG | 7980 |
| GGTAGCGACG | GTGGGGCTT | CGAACAGCAG | GTCACTAACG | GAAAGCGAGA | GCAAAGCGCC | 8040 |
| AACAGCTTGC | AGAGTTGGGC | ACAGGCCTTG | GAAAATGGAA | GCGACAGGTA | TTTTGCCCAT | 8100 |
| ACGTGGCGCG | GTATCGCCCT | AGCATGGTCG | GCGGCCTGGG | CACGGGACAG | CGTCACCACA | 8160 |
| ACCCATACGT | GGGCGCCAAG | CAGCTGCTGC | GCCGCACAAA | TCTGCGCCTG | TTTGGCGACG | 8220 |

-continued

| | | | | | | |
|---|---|---|---|---|---|---|
| GTGTCTGAGC | CAGCGCGCAA | CACGGCGATC | GCCTGCGCCA | GCGACGGGCG | GTCCAACAGG | 8280 |
| TGCCTGGCCC | AGGAGGGCAT | GTTTCCCTGG | AAACCCCGCT | CCCCGAATAT | GACAAAAGCC | 8340 |
| ACATATTCCT | CCACTGGCAC | GCCATTCTCG | CCCTCGAACA | CGCGGTGGGC | CGTCAGCTGG | 8400 |
| GCCTCATCCA | AACCAAACCA | AGACACAAGA | AAGCGATCCC | AGCGCTGATC | CAGGGCCATG | 8460 |
| ACCTTCTCAC | CAGCGCGACC | GCACGGCCTA | AGCTCCACTG | AAAGGCGCCC | AGAATCCGCA | 8520 |
| CCGTCCTACC | CCCCTGGCCC | GCCCAATATA | CCGCTGTGAC | GTCTGATGTA | CAGGCCCGCG | 8580 |
| CGTCGCGGCC | GTTGGTGGGA | AAACCGGCAC | CACCCTGTGC | GGCCGAATCC | GCCACGGGGG | 8640 |
| CTGCCAGACA | GTACACTGTC | TCCAGCAGCG | ACTTCAGTCT | CTTGTGACTT | TTGGGCGTCA | 8700 |
| CCACCAAAAA | TTGCAAAACC | TGCCTGTAGT | CCGTGAAGTA | GGTACGGCAT | ATTACCATGG | 8760 |
| AGTTGTACAC | GCCCAGGTTC | TTTGAGAACA | CCAGGCTCGC | CTTGAACTTT | GTAAAGTCAT | 8820 |
| CCTGCCCCAG | CACGACAGAC | GTATTTTTGG | CAAGGTATAC | GTCCGACTCC | ACGGGAAGGA | 8880 |
| CGTGCCCAAA | CTGGGACACG | GCGTCGCTTG | GTCGGCACAG | AAAGCACTTC | AGGGTTGTGG | 8940 |
| AAAGGCCATT | ATTCGATATA | ACAAAGCAGG | GAGAGAACGG | GTAGTGCATC | TCCTCCAGGA | 9000 |
| GGTGCGCCCA | AAACTTATAC | ACAAACTCTA | AGTGGTACAC | GCAACCGTGC | TGCATTCTAA | 9060 |
| CCGTACATAT | GGCGGTAGCA | CCGCCCTTAG | CATAAACTGG | GGCCCCGTCG | ATGCACCGTT | 9120 |
| CCAAATCCAG | GGACTGACCA | GACTGTCCCA | AGTATGAGGA | TACCACCCGA | CACAGTTCGT | 9180 |
| CCACTACACG | CTTACCAACG | ACACTCATGG | CGACAGCGGG | GTGGGGCTGG | CAAGGCCCCC | 9240 |
| AAAGCGCGAC | ACCCGCAGTC | AATCAGGGCC | GTGCCCGCGC | CTCGGAGAAT | ACGGCGTCCG | 9300 |
| TGCTCACGAT | CTTGCGCAGG | ACCTGCCTTA | CCGTGTCCAC | CTTGCTCTCC | AACACCAGAG | 9360 |
| TATGATCGCA | GGCTGCAGGC | TGTGCCCGCT | GGACGAGAAA | GGTTTTTAAA | TACTGACAGT | 9420 |
| AGTTGATGGC | GTTCAATCTA | CAATAGATCG | TGGGAAATAA | AATTTGCATG | TCACGAGGCA | 9480 |
| GAAGCTGGTC | AGACGCGTAC | TCCATGTTGG | GTTCCACGGG | GAGGGGAACA | CACGCCCCAA | 9540 |
| GACACGACGG | CGCACATAGG | GAGCGGAGCA | AACAATTGAT | TCAAATATTT | GACTCCGCAG | 9600 |
| CGAGCCGGTT | TGCAGAGTGG | TCACCTGCCC | TGCTCCACAC | CCACCCCGC | GTCTCTTCCA | 9660 |
| ACTCTCAACT | CACGATCCAG | GGAAACCACC | GTCCAGTGGC | CATGTTTGTT | CCCTGGCAAC | 9720 |
| TCGGTACAAT | TACCCGTCAC | CGAGATGAGC | TCCAAAAACT | ACTGGCAGCC | TCCCTGCTCC | 9780 |
| CGGAGCACCC | GGAGGAGAGC | CTCGGTAACC | CCATAATGAC | ACAGATTCAC | CAGTCGCTCC | 9840 |
| AACCATCTTC | CCCCTGCAGG | GTCTGTCAGC | TCCTATTTTC | TCTGGTCCGC | GATTCGTCCA | 9900 |
| CCCCCATGGG | TTTCTTCGAG | GACTATGCCT | GCCTCTGCTT | CTTCTGTCTA | TACGCCCCAC | 9960 |
| ACTGCTGGAC | CTCGACCATG | GCGGCAGCGG | CAGACCTGTG | CGAGATCATG | CATCTGCACT | 10020 |
| TTCCAGAAGA | GGAGGCGACA | TACGGGCTAT | TCGGACCGGG | TCGCCTTATG | GGTATCGACT | 10080 |
| TGCAGCTGCA | CTTCTTTGTT | CAAAAGTGCT | TTAAGACCAC | CGCCGCCGAA | AAAATACTGG | 10140 |
| GAATATCCAA | CCTGCAATTT | TTAAAATCAG | AATTCATCCG | GGGCATGCTC | ACAGGCACCA | 10200 |
| TCACCTGCAA | CTTCTGCTTC | AAAACGTCCT | GGCCCAGGAC | AGACAAGGAG | GAGGCCACCG | 10260 |
| GCCCCACCCC | ATGCTGCCAG | ATTACAGACA | CCACCACCGC | ACCCGCGAGC | GGCATACCGG | 10320 |
| AACTAGCCCG | GGCCACATTC | TGCGGCGCAA | GTCGCCCCAC | AAAGCCCAGC | CTACTTCCCG | 10380 |
| CGCTAATAGA | TATCTGGTCC | ACGAGCTCAG | AGCTCCTTGA | CGAGCCGCGC | CCTCGACTGA | 10440 |
| TCGCAAGCGA | CATGAGTGAA | CTCAAATCCG | TGGTCGCATC | CCACGATCCG | TTCTTCTCTC | 10500 |
| CCCCGCTTCA | GGCAGACACC | TCACAGGGTC | CATGTCTGAT | GCACCCAACC | CTGGGGCTAC | 10560 |
| GATACAAAAA | CGGGACTGCA | TCCGTCTGCC | TCCTCTGCGA | GTGCCTTGCG | GCACACCCAG | 10620 |

| | | | | | | |
|---|---|---|---|---|---|---|
| AGGCACCCAA | GGCGCTGCAG | ACCCTTCAGT | GCGAGGTAAT | GGGCCATATA | GAAAACAACG | 10680 |
| TAAAGCTGGT | AGACAGAATT | GCCTTTGTGT | TGGACAACCC | ATTCGCCATG | CCATATGTAT | 10740 |
| CAGATCCGCT | ACTTAGAGAG | CTGATCCGGG | GCTGTACCCC | ACAGGAAATT | CACAAGCACC | 10800 |
| TGTTCTGCGA | CCCGCTGTGC | GCCCTCAATG | CTAAGGTGGT | GTCAGAGGAC | GTACTATTCC | 10860 |
| GCCTGCCCAG | GGAGCAGGAG | TATAAAAAGC | TCAGGGCATC | CGCGGCCGCC | GGACAGCTCC | 10920 |
| TCGATGCCAA | CACCCTGTTC | GACTGCGAGG | TCGTGCAGAC | TTTGGTCTTT | CTCTTTAAGG | 10980 |
| GTCTCCAAAA | CGCCAGGGTG | GGGAAAACCA | CCTCACTAGA | CATTATTCGG | GAGCTAACCG | 11040 |
| CACAACTAAA | AAGACACCGC | CTAGACCTGG | CCCACCCCTC | ACAGACGTCA | CACTTGTACG | 11100 |
| CTTGAGCTGG | TCCCGGGCCT | TCGCACCCCA | TCCACCGATG | CCGAAATCAG | TGTCCAGCCA | 11160 |
| CATCAGCTTG | GCGACCTCAA | CCGGTCGCAG | TGGACCGCGA | GACATCAGAA | GATGCTTGTC | 11220 |
| ATCCCGCCTG | CGGTCGGTCC | CGCCCGGGGC | GCGAAGCGCC | AGCGTCAGCA | GCAAGCACAG | 11280 |
| AAACGGCCTT | CGCAAGTTTA | TCTCAGACAA | GGTATTTTTT | AGCATCCTAT | CGCACAGACA | 11340 |
| CGAGCTAGGA | GTGGACTTTC | TCCGTGAGAT | GGAGACCCCG | ATATGCACCT | CCAAAACAGT | 11400 |
| AATGCTGCCC | CTAGACCTGT | CTACCGTCGC | ACCCGGCCGC | TGCGTCTCCC | TCTCTCCGTT | 11460 |
| TGGACACTCC | TCAAACATGG | GGTTCCAGTG | CGCTCTGTGC | CCATCCACAG | AAAATCCCAC | 11520 |
| CGTTGCCCAA | GGCTCCCGGC | CTCAGACAAT | GGTGGGCGAT | GCGCTCAAAA | AAAATAACGA | 11580 |
| GCTATGCTCG | GTAGCGCTGG | CCTTTTATCA | CCACGCAGAC | AAAGTGATCC | AACACAAGAC | 11640 |
| GTTTTACCTA | TCACTCCTCA | GTCACTCCAT | GGATGTGGTT | CGGCAGAGCT | TCCTGCAGCC | 11700 |
| TGGTCTACTG | TACGCTAACC | TGGTCCTAAA | AACCTTTGGG | CACGATCCCC | TACCCATCTT | 11760 |
| CACTACCAAC | AACGGCATGC | TAACAATGTG | CATCCTTTTT | AAAACCCGGG | CACTACATCT | 11820 |
| GGGAGAAACT | GCGCTTAGGC | TGCTTATGGA | TAACCTCCCC | AACTACAAGA | TATCGGCGGA | 11880 |
| CTGCTGCAGA | CAGTCCTACG | TGGTCAAGTT | TGTCCCAACG | CACCCGGACA | CCGCAAGCAT | 11940 |
| TGCAGTGCAG | GTACACACCA | TATGCGAAGC | GGTTGCGGCG | CTAGACTGCA | CCGACGAGAT | 12000 |
| GCGGGATGAC | ATTCAAAAGG | GAACCGCACT | TGTCAACGCC | CTATAACCTC | ACATGTAGCC | 12060 |
| TGTCACCCCA | GCTCCTATTG | CAACTGACCA | TGTTCAGGTG | GTAATAAAGT | CATTAAACGA | 12120 |
| CAAAGTGATT | CTTTTAATCT | GTTTATTGTT | TTTGAACATG | TGGCACACGC | TGCAATGTAC | 12180 |
| TGCCATGAAA | GGTGGTTCTA | TATCCACCAC | TTGGCGTCTG | CCGAAGTCAG | TGCCACAATT | 12240 |
| TCATTAACAA | ACAAGGTCAA | TACATTGTGA | GGGAGTGTTT | TTTGCCATGG | TACCATTCGT | 12300 |
| GTGGTTTGGG | AGAGCGGACG | CCATTTGCGT | GCAAAATGTG | CTTTGCTGGA | GGCCAACTTC | 12360 |
| CGTCGCGCTG | GTTGATGCGC | GGCACATTGT | GTCAACCAGG | GCACCCTCCC | CCACCGAGTG | 12420 |
| CTTTAATGCG | GAGAGGAATG | GTGGCCTGGT | TGACACCGCG | TGCCGGCCAT | CTGAACTGTG | 12480 |
| ACTGTGTTAT | GAGCCACGGG | TATGCCCTCG | ATACGCCTGC | TCTTCAGCAT | TGTATGTGTT | 12540 |
| TAATGTTGTG | CTTGGTGCAA | CCGTGATTGT | GTTTTTGTAT | TTTATTTTAC | TGACACTCTT | 12600 |
| TGGGAGGGCA | CGCTAGCTTC | AGTGCGCGCC | CGTTGCAACT | CGTGTCCTGA | ATGCTACGGG | 12660 |
| GCCACGCTGG | CCACTCGGGG | GGACAACACT | AATCGCCAAC | AGACAAACGA | GTGGTGGTAT | 12720 |
| CGCCCCAAGC | CTCCAGCGCC | ACCCATTTAG | TAACACATCC | GGGACATGAA | CTGCCACAAA | 12780 |
| CACCGTTAAG | CCTCTATCCA | TGCATTGGGA | TTGGAGTGAG | GAGGGAGGAG | GGCACCAGGT | 12840 |
| TCCCGGGGAG | GAGGGCACCA | GGTTCCCGGG | GAGGAGGGCA | CCAGGTTCCC | GGGAGGAGG | 12900 |
| GCACCAGGTT | CCCGGGGAGG | AGGGCACCAG | GTTCCCGGGG | AGGAGGGCAC | CAGGTTCCCG | 12960 |
| GGGAGGAGGG | CACCAGGTTC | CCGGGGAGGA | GGGCACCAGG | TTCCCGGGGA | GGAGGGCACC | 13020 |

| | | | | | | |
|---|---|---|---|---|---|---|
| AGGTTCCCGG | GGAGGAGGGC | ACCAGGTTCC | CGGGGAGGAG | GGCACCAGGT | TCCCGGGGAG | 13080 |
| GAGGGCACCA | GGTTCCCGGG | GAGGAGGGCA | CCAGGTTCCC | GGGGAGGAGG | CTGGGGTGCG | 13140 |
| CCGCGCCGGG | TTCCTGGGGT | GCGCCGCGCC | GGGTTCCTGG | GGTGCGCCGC | GCCGGGTTCC | 13200 |
| TGGGGTGCGC | CGCGCCGGGT | TCCTGGGGTG | CGCCGCGCCG | GGTTCCTGGG | GTGCGCCGCG | 13260 |
| CCGGGTTCCT | GGGGTGCGCC | GCGCCGGGTT | CCTGGGGTGC | GGGGTGCGGG | GGACCGCGCC | 13320 |
| GGGGTACTGC | AGGGTTCGCA | GGGTTCGGGG | GTACTACCTG | GTTTCCTGGG | GTGTGCCAGG | 13380 |
| ACGGGTTCCT | GGGGTGCCAC | CGCTCCTCGA | TACGTGTAAA | TCCAAGAGAT | CCGTCCTCCG | 13440 |
| TGCCGCCGCG | CGCGTAATGC | GCGAGGGGGG | TCGGTCTCCC | CTCTTCTTTA | TAGCGTTTCC | 13500 |
| TGCGAAGGGG | GCGTAACCGT | AGGACAAACT | GCTTATGTAG | GGGTTAGCCA | CCCATTTCCC | 13560 |
| GGGGCCGCGC | CAGAGGTGAG | CGTGGACCTA | GCATCCCGCT | CCCATTTACC | GAAACCACCC | 13620 |
| AGAGGCGAGA | TTCCAGGGCC | GTGACTCACT | AGCTCCCCTC | CCATCGAACA | ACCACGCTTG | 13680 |
| GCTAACACGG | CTGGAGTGGC | GGTGGGCGGG | GCCCCTATAA | TCCTGGCCCC | CATCTACTGA | 13740 |
| AACGACCCAG | TAGAAAAATC | CCAACCCCAT | GACTCATCAG | GCCCTATTAT | ATAGAATATC | 13800 |
| CCAGTAGAGT | GACCCAGCTG | GTTTCCATAA | ATGGATATAC | TTCCGGAAAA | CGAAGGAGGG | 13860 |
| TTGAATACAG | TTGGGGGTAG | TCCGCTGGTA | TTCCCAGCTG | AGGTTGCCTT | ATTTGGTAAT | 13920 |
| GCTTCCGGAA | ATACCACCTG | AGTACCCCAT | TGGTTTATAC | CTTGTTTAAT | TGTAGAATTA | 13980 |
| CAGCTGGATT | TACCCAGCCG | GGTTTACGCA | GCTGCGTATA | CCCAGCTGTG | TTTACGCAGC | 14040 |
| GGGGTTTACG | CAGCTGGGTA | GACCCAGCTG | GGTATACCTA | CTGGAATAGG | GGCTGCGATG | 14100 |
| ACTCAGCTGC | GCTAGGATTA | AAGGATTATA | TATATATATA | TAGGAAAAAT | CAAAACAAAA | 14160 |
| CTCTAATCGC | TGATTGGTTC | CCGCTCTGGG | CCAATCAGCT | TGGGAGTTCT | AGGGATAGGG | 14220 |
| GCCAATGGGA | GGCCTCCGAA | TTTGATTGAC | GGCTGGGGCG | TCCAATGGAA | TGGCGCGGTC | 14280 |
| GCCTAGCTCG | AACGGGATTG | GTCGGCCGGA | TGGGCCAATG | GCGGCTCGGA | AAACTTTGAT | 14340 |
| TGACGGGCCG | GCGGACCAAT | GGGAGCGGGG | CAGAGGATTA | TGGGGGATTA | GCAAATTCAA | 14400 |
| GATGGCGGCG | CCCATGAAAT | GGCCAAAAAT | TATAATTTTT | CGAGTCGCTC | ACGGTCCCAC | 14460 |
| CTAGCGGCGT | GACCTGGAGG | TGACCCCGTG | CACCCGGGCG | CTCTGAATTT | TTCTGCGCAT | 14520 |
| GCGCGACTCC | TCATCTACAT | AATTTATGCA | CATAAAAGGA | TTAGCGCATG | CAAATTAGTC | 14580 |
| AGATAGCAGG | GCCATCCACA | CTTTATGTTG | GCCGCGTGCC | AGGCGCCGGC | GTGGGCGCCG | 14640 |
| CGCGCGTGCT | CTCTCAGTCG | CGCCTAGCTG | CTTCCAACAG | ACAAAAGCGG | GGCGTTAGTG | 14700 |
| AGGGAGTGCG | CGCGCTGCGC | TGACTTGGCC | GATTTCCAGT | GCATGCTTTG | TCACCCCAGC | 14760 |
| GCGAGAATGG | AATTTTCATT | ATTGAGCAAT | TTGGGCACCC | TGGGCACGAT | AACCATACAT | 14820 |
| GGATACACGG | GTTCCAAATA | TGCAAAGTAG | ACACTAAGGT | ACCATTTGGC | ATATTTGGAC | 14880 |
| GTCCTGGGCA | GGTTAGCTAC | CCACCAGAAT | ATATGGGACT | CTGGGCAGGA | TAGCCACCCA | 14940 |
| CAATTGTTTT | GCGCCCCTCT | TTGGCCAGGG | GACCAAGGTC | GTATGGTTCG | CGCTACACTA | 15000 |
| AGCCCGAACG | TTCAGCTTTG | CGTGCTTTCG | ACGTCCAGGC | GGCTGGCACA | CGGGCCGTGA | 15060 |
| GCGCCAGCAA | CATGGGATCA | TGGTAGTAAG | ATACAGCATA | AATCCCCGTC | CGGTGGCGCT | 15120 |
| CAACGCCAAT | ATGCGCGGCT | GCGTGGTATC | TCATCGGTGG | GCACGCGTAC | GGTGGTCTCA | 15180 |
| TGGGTATTGG | ACTTGTAGGC | GAGGGAGGC | GCATACGACA | AAAATTGCCG | CCGTGAAGGT | 15240 |
| CGGGAACCCG | CCCGCGCTTC | CGCAAGGCAC | GGGGCCGCAT | CGGACACAGG | CTAAGCATTA | 15300 |
| AGGATCATAA | CACCGCCCTA | GAAATGTTTA | AGCTGTGACC | AAAGCGAACC | TCGCATGAGG | 15360 |
| CATACGCGAG | CGTGGAGGTA | GGATTCCCAA | GGCTATTGAG | AGACGGTGGG | TGAAATGATG | 15420 |

| | | | | | | |
|---|---|---|---|---|---|---|
| AAGAACACAC | AGAACAATAA | CGGGCGACTA | GATAAAAGA | CTCGCTCAAC | AGCCCGAAAA | 15480 |
| CCATCAGCCC | GACCGCCGAT | GGATTAGGTG | CTGCTGGACA | AGTCTTTCTA | AACCCGCGCA | 15540 |
| GGGTTTGTGT | CGATCCAGAC | GCTTACGAAC | GCCCGCTTTA | AAAACACTAT | TCATAATTAA | 15600 |
| CAGAAGTTGA | CACCAGCCCG | CAGTTACCCA | ACCTTCTATT | TTTTGGAGT | GTTGACAAGT | 15660 |
| TTCCATCGCC | CGTTTGGCGT | TTCCCGCATG | GTGTCAAATT | AGTGACGCAC | CCTCCCCCG | 15720 |
| TCACTATGGG | TTTACCCTGA | TTTAGTAAGT | AAAACTGCCG | CCCCCGCCCA | CTCATTTTT | 15780 |
| TACCCTGTTA | TTTGCTGTAT | TTACATCTAC | GGACCCCCTT | TTGGTGAGAT | TGCCGTGGTT | 15840 |
| CTAAATAACG | TTGTGGTTTT | CGGACCCTTT | CAGGGACCAA | ATCTTTTACG | TGTTGCCAAG | 15900 |
| GTAGCATTTG | CTGGACCCGC | ATAGGTTTTT | GTGGCACCAG | GTTATGGTCT | TATGAGCGGG | 15960 |
| CTTGACCGGC | AAGTTCCAGG | CATCCTAAGT | GCTTGATGTA | GACCCTTAGG | GCACCAGGGA | 16020 |
| CTACCTAGGT | CAAACTCCCC | CTTAGTCATG | ACGCCGTGCC | CACGAGGTTT | GAGAGGCGTA | 16080 |
| GACATCCGTG | TCGACTGCTG | GACGGAGGTA | GTATAATCAG | CTAGGCCTCA | GTATTCTATG | 16140 |
| TAACAAATGA | ATGCCCTAGA | GTACTGCGGT | TTAGCTAGTT | ATACTGCCCG | GTTCCACCAG | 16200 |
| GCGGCGTTGT | GGCCACGGGC | GGTTCGTCGC | TTGGACCTGG | AGGGGTGTCA | CATTCTGTGA | 16260 |
| CCGCGACGTT | GACGTTAGAC | ACACGTCGCT | GCCGTCCTCA | GAATGTGATA | GCCCATCACA | 16320 |
| GGCATTGTAG | CTGTTGCGTT | GGTTGGGAGT | TTGGGGACCA | AATTTCTATA | ATTGGTGTCA | 16380 |
| CCGCGGCAGC | TCTAGCCCTG | GAAGATCTGG | AAGCTTGCTT | CAATGGCTCA | GATCGACCCG | 16440 |
| GACTACAGTT | AGCGAAGTAG | ACCCATTATA | ATCTTAATCT | TAAATCTGGT | TGACGGACTT | 16500 |
| TCGCGCCGGG | AACACGCAGG | TGGCAGCGGA | TGTGTTTTGC | CCAAACACGA | GGGTTGCAGG | 16560 |
| AAACAGGTGC | TGCCGGGGAT | TATGTACAGC | TTACACCCAG | TTTCCTGTAA | TCGCCCGCAT | 16620 |
| CCGGCCGTCC | TGGGCAGCAC | CGCACCCTGC | GTAAACAACC | GCGTACTTTT | TCCTCCTCCC | 16680 |
| CCCACCCCCA | CATCCTTCCT | CCCACCCTGC | CAGTCCAACC | CGCTTCCTGT | TTTATTCGCC | 16740 |
| TTCAAACAGA | AGCACGCATT | CTAATGATTC | TTACAAAACT | TGTTAGTGTT | TATTAAATCA | 16800 |
| GATACATACA | TTCTACGGAC | CAAAAATTAG | CAACAGCTTG | TTATCTATGG | TGTATGGCGA | 16860 |
| TAGTGTTGGG | AGTGTGATGG | GCCGGAAAGG | TGAAGGCCCA | TTAGGGTTTG | CACTTGGCGC | 16920 |
| TGTAGGTCTA | CTCTTGACAA | AGATCTAAGC | ATTGACATTA | GGGCATCCAC | GTCAGTGGGA | 16980 |
| CCCAGTAGGT | CTAAGTTTTC | CATACAGTAC | ACCCAGTGTA | AGATGTCTGT | GGTGTGCTGC | 17040 |
| GAGACCCTAT | AGTGTCCTTG | CTTAAAAATA | TCAAAGACCT | AATATCCCTC | GCACACAGCT | 17100 |
| CCCCGTCTAC | GTGGAGAACA | GTGAGCTGAT | AAGGGCTGAA | ATAACTCATT | GTGCCCGCTA | 17160 |
| GGTGGCGCTC | TAAAAACGC | GGGTCTAAGT | GAAGCAGGTC | GCGCAAGAGG | TCTCTGCGAC | 17220 |
| CTGCACGAAA | CAGACATTCC | GCTAACAGGG | GAAACGTTAA | CCTGCCCTCC | TCCTTTAAAG | 17280 |
| CTCTAAGAGC | TCCAATTAAT | TGGGCCAGTG | TGGGTTGAGG | TATGAACACG | TTTAGGAGGA | 17340 |
| ACAATACCAC | TTCCCTGTCA | TCCGTGCCCA | GTTTCCGCGC | CACCTCACAG | AGAACCTCGT | 17400 |
| AAGTGGCCAT | GGTGCCGGCT | TGTATATGTG | AAGGCACCGA | TGTGGAAAAA | CAAAGGAAAA | 17460 |
| TTTATTTTC | CGCCCTAAAC | AAAATCACAA | GCTTAATAGC | TGTCCAGAAT | GCGCAGATCA | 17520 |
| AAGTCCGAAA | CAGATGTTAG | GATCTGTTCC | ACTGCCGCCT | GTAGAACGGA | AACATCGCAT | 17580 |
| CCCAATATGC | TTGCCAGCTG | AGGAACTACC | CCACCCGAGT | GGGTATCCTG | CGGAATGACG | 17640 |
| TTGGCAGGAA | CCAACAGCGC | ACAGCCTGCA | GCGCTGATAA | TAGAGGCGGG | CAATGAGCCA | 17700 |
| GTCTTTGGGT | CAACTAAGGC | TTTTGTAATC | AGGGTGTTGA | CCTCGTGGTG | CCAAAAGTCC | 17760 |
| AGGTGTTGGG | AGCCCCCCAG | CAATTTAAGT | AACAAGAAGG | AAGTGACGTC | CGTCGCTAAG | 17820 |

| | | | | | | |
|---|---|---|---|---|---|---|
| ACTGCCTCTG | TTCGCCACGC | CAACTTCTCA | AGGAGTTCTT | TCTCCTGGTC | TATAAGTTCT | 17880 |
| TGGCGGGAAA | AGGAGTCTGC | CGCGGCATAG | CAAAGTGAAC | TGGTAGAAAT | AGGCGTGAGG | 17940 |
| CTTCTGAGCT | TACTGGCCAC | TAACAGGCAG | GCGCTCCCTG | TCTTTTGAAA | GTGTTCTTTG | 18000 |
| GACACCTGCT | TTATAAGTAG | GAGTCTGTCC | AAAAGATTAA | GGGCCAACGC | GACCACGTTA | 18060 |
| GGTTCTAGGT | TGTATTCCTG | GCAAACTGAA | AACATCCATG | TGCCCAGTAA | CTTACGCATA | 18120 |
| TGCGAAGTAA | GAGATTGTTG | AAAGGTCCCA | AATACAGAGT | CAGAAGTTAA | AAAGCGCGGC | 18180 |
| TCAATTTCAA | GAATATTGTA | AAAGATCCGA | TCCTCACATA | GCGTGGGATC | CAGAAGTCCC | 18240 |
| GAGGGCGGGT | TATTGGCAGT | TGCCATATAG | AGTGGCGAGC | GTATGTGGCC | TACCTGTAGA | 18300 |
| GCCTGGAGTT | TCAGGGTGCT | CTGTCAGGTT | CTCCCATCGA | CGACGCTGGG | CCGCGAGAGT | 18360 |
| ACGCTAGCCG | TTGTCCGTGT | GTTCAGTTGA | GGTAGATGGG | TCGTGAGAAC | ACTGCCCCCC | 18420 |
| ACACACACCA | GCACCCATGG | CGCCAAATGC | AAGTGCGGAG | CGGCGACGGT | GGCTTCTAGG | 18480 |
| GAGGAAAAAG | GGGGAGAGGT | GTGGCTTTTA | TGTCATTTCC | TGTGGAGAGT | CCCCAGGACC | 18540 |
| TTGGTTTTCC | CCTGGCTGGG | TTAATGGCAG | GGGCTTTTTA | AACTTAACTA | TGGAAGATTG | 18600 |
| TAGGTTTCCT | GCCAGGGGGT | GACTAGCTTC | CCAGGCTAGG | CGGGCCATTT | GTACTTTCTT | 18660 |
| ACTTGTGTCT | TTGTTCTGAC | AATACACATA | TACACAATAA | GTTATGGGCG | ACTGGTCTGG | 18720 |
| TCCAGGGTGG | GGCAAGCAGG | ACACGGGGCC | TGCCTTTACT | CCTCCAAACT | GGAAGGCCTG | 18780 |
| AGATAATTTT | TTAAGTCCGT | ATGGGTCATT | GCCCCAAAAA | ATCACTGCAA | ACTTCCATTG | 18840 |
| ACACTTTGGA | TCTCGTCTTC | CATCCTTTCC | CAAAAAGCGT | CTATAAAAGA | TGTGTTGTGG | 18900 |
| CCTAGCTTTC | GCAGGACAAT | CATCTATCTG | TCTGTAAGGG | ACCGGTGGTT | GTTGGTATCT | 18960 |
| TGGATGGGC | TTTTTGGGT | GGGTAACTGG | AACGCGCCTC | ATACGAACTC | CAGGTCTGTG | 19020 |
| GGGTGGTGAT | GTTCTGAGTA | CATAGCGGTA | TTCGCGAGAT | GGGCCAGGTT | GTGGGTCATC | 19080 |
| GTCTGGTGTA | TTATCTCCTG | GTGGGCTACT | GGCAATTTGT | TCATGTGTGC | TAACAACAGG | 19140 |
| GTAATCCACT | TCCATTTCGT | CCTCGGATGA | CGACCCGTGC | AAGATTATGG | GCTCTTCCAC | 19200 |
| CGTCTCCTGC | TCCTGCTGTT | CCACCCCTG | CTGCTCCTGC | TCTTCCACCT | CCTCTAACTC | 19260 |
| CTGCTGCTCC | TGCTCTTCCA | CCTCCTCTAA | CTCCTGCTCT | TCCTGCTCTT | CCACCTCCTC | 19320 |
| TAACTCCTGC | TCTTCCTGCT | CTTCCACCTC | CTCTAACTCC | TGCTCCTCCT | GCTCCTCCTG | 19380 |
| CTCCTGCTCT | TGCTCCTCCA | CCTCCTCTAA | TTCCTGCTCT | TCCTGCTCCT | GCTCTTGCTC | 19440 |
| TTCCACCTCC | TGCTCTTGCT | CTTCCACCTC | CTGCTCCTCT | AACTCCTGCT | CCTGCTCCTC | 19500 |
| TAACTCCTGC | TCCTGCTCCT | CTAACTCCTG | CTCCTGCTCC | TCTAACTCCT | GCTCCTGCTC | 19560 |
| CTCTAACTCC | TGCTCCTGCT | CCTCTAACTC | CTGCTCCTGC | TCCTCTAACT | CCTGCTCCTG | 19620 |
| CTCCTCTAAC | TCCTGCTCCT | GCTCCTCTAA | CTCCTGCTCC | TGATCCTCTA | ACTCCTGCTC | 19680 |
| CTGCTCCTCT | AACTCCTGCT | CCTGCTCCTC | CTGCTGCTCC | TGCTCCTCCT | GCTGCTCCTG | 19740 |
| TTCATCCTGC | TGCTGCTGCT | CATCCTGCTG | CTGCTGCTCA | TCCTGCTGCT | GCTGCTCATC | 19800 |
| CTGCTGCTGC | TGCTCATCCT | GCTGCTGCTG | CTCATCCTGC | TGCTGCTCAT | CCTGCTGCTC | 19860 |
| CTGCTCATCC | TGCTGCTCCT | GCTCATCCTG | CTGCTCCTGC | TCATCCTGCT | GCTGCTCATC | 19920 |
| CTGCTGCTGC | TCATCCTGCT | GCTGCTCATC | CTGCTGCTGC | TCATCCTGCT | GCTGCTCATC | 19980 |
| CTGCTGCTGC | TCATCCTGCT | GCTGCTCATC | CTGCTGCTGC | TCATCCTGCT | GCTGCTCATC | 20040 |
| CTGCTGCTGC | TCATCCTGCT | GCTGCTCATC | CTGCTGCTGC | TCATCCTGCT | GCTGCTCATC | 20100 |
| CTGCTGCTGC | TCATCCTGCT | GCTGCTCATC | CTGCTGCTGC | TCATCCTGCT | GCTGCTCATC | 20160 |
| CTGCTGCTGC | TCATCCTGCT | GCTGCTCATC | CTGCTGCTGC | TCATCCTGCT | GCTGCTCATC | 20220 |

| | | | | | | |
|---|---|---|---|---|---|---|
| CCGCTGCTGT | GGCTCCCGCT | GCTGTGGCTC | CCGCTGCTGT | GGCTCCCGCT | GCTGTGGCTC | 20280 |
| CCGCTGCTGT | GGCTCCCGCT | GCTGTGGCTC | CCGCTGCTGG | GGCTCCCGCT | GCTGTGGCTC | 20340 |
| CCGCTGCTGT | GGCTCCTGCT | GCTGTGGCTC | CTGCTGCTGT | GGCTCCTGCT | GCTGTGGCTC | 20400 |
| CTGCTGCTGT | GGCTCCTGCT | GCTGTGGCTC | CTGCTGCTGT | GGCTCCTGCT | GCTGTGGCTC | 20460 |
| CTGCTGCTGT | GGCTCCTGCT | GTTGTGGCTC | CTGCTGTTGT | GGCTCCTGCA | GGGGCTCCTG | 20520 |
| CTGCTGTGGC | TCCTGCTGTT | GTGGCTCCTG | CAGGGGCTCC | TGCTGCTGTG | GCTCCTGCTG | 20580 |
| CTGTGGCTCC | TGCTGTTGTG | GCTCCTGCAG | GGGCTCCTGC | TGCTGTGGCT | CCTGCTGCTG | 20640 |
| TGGCTCCTGC | TGTTGTGGCT | CCTGCTGCTG | TTGTGAACTT | GGATGCTCA | ACGTTTTGTT | 20700 |
| TCCATCGCCC | CCGTCCTCCT | CGTCCTCCTT | CTTGTCCTCC | TCCTCGTCAT | CCTCCTCGTC | 20760 |
| CTCATTGTCC | TCATCATCGT | CATCCTCCTC | GTCCTCCTCC | TCCTCGTCCT | CCTCCTCGTC | 20820 |
| CTCCTCCTCG | TCCTCCTCCT | CGTCATCCTC | CTCGTCATCC | TCCTCGTCAT | CCTCCTCGTC | 20880 |
| ATCCTCCTCG | TCATCCTCCT | CGTCATCCTC | CTCGTCATCC | TCCTCGTCAT | CCTCCTCGTC | 20940 |
| ATCCTCCTCG | TCATCCTCCT | CGTCATCCTC | CTCGTCCTCC | TCATCTGTCT | CCTGCTCCTC | 21000 |
| CTCATCATCC | TTATTGTCAT | TGTCATCCTT | GTCAACCTGA | CTTTCCTTGC | TAATCTCGTT | 21060 |
| GTCCCCATTA | TCCTCGCCAG | CCTGATTATT | TTCGGAACAT | TCTTTTTCAT | TCTTGGATGC | 21120 |
| TTCTTCTGCA | ATCTCCGCAA | GGAGCACCAA | CATGGCTGTG | TCATCACCCC | AGGATCCCTC | 21180 |
| AGACGGGGAT | GATGATCCTA | TGGAGATGGG | AGATGTAGGC | GGTTGGCGTG | GCGGAGTATC | 21240 |
| GCCATGCTG | GATGATCCCA | CGTAGATCGG | GGACTCTGTG | GCCCATGGGG | GGTACACACT | 21300 |
| ACGGTTGGCG | AAGTCACATC | TAGGGGGAGA | GACTGGGGGC | GACTGACATA | TTGGGTTTAG | 21360 |
| TGTAGAGGGA | CCTTGGGGGG | ACGATAGCCT | TCTTTTTCTC | AGGCTACGCA | GGGTAGACGG | 21420 |
| AGCTAAAGAG | TCTGGTGACG | ACTTGGAGGG | AGGCTCGGGT | GGAGGAGTCG | TGGGTGAGTG | 21480 |
| TGGAGGTGTA | GTCTGCTGCG | AGGGTGGCGG | ACGCATAGGT | GTTGAAGAGT | CTGGCCTTCC | 21540 |
| TGTAGGACTT | GAAAGCGGTG | GCCTTTGAGA | AGACTCTGGA | GACTGCGTGG | GTGGCAATGC | 21600 |
| AGGAGATGGA | GAATGAGTAT | CCGTGGTCCC | CGGAGACACA | GGATGGGATG | GAGGGATTGG | 21660 |
| GGAGGAAGAC | GTGGTTACGG | GGGGTAAGAG | TGCCGGTGGA | GGTAAAGGTG | TTGCGGGAGC | 21720 |
| GGGTGAAGGA | ATGGGAGCCA | CCGGTAAAGT | AGGACTAGAC | ACAAATGCTG | GCAGCCCGGA | 21780 |
| TGTGAACACT | GTGGGACTTC | CAGGTATAGG | CAAGGTGTGG | GGTCCACATT | CCCGGCCGTC | 21840 |
| GATGGAGTCG | GCGACATGCT | TCCTTCGCGG | TTGTAGATGT | AGGTCATCGC | CAAGGTCACA | 21900 |
| TCTTTCCGGA | GACCTGTTTC | GTTTCCTACA | ACTTCCTCTC | GTTAAGGGCG | CGCCGGTGCT | 21960 |
| CCGTCCCGAC | CTCAGGCGCA | TTCCCGGGGG | CGCCATCCTC | GGGAAATCTG | GTCTGACAAC | 22020 |
| CAAAGTAAAA | TTATGGAGGC | GGTGGCAGTA | TATTCACATT | ATGCAATACC | CGTAGTGACC | 22080 |
| ACAAGGGGA | GCTCTCAGAC | AATTAAGCGG | TTACACACAG | TAGCAGGCTG | CAGTACCGCC | 22140 |
| CATGGCCACA | GGATGTAGAT | CGCAGACACT | GAAACGCTGA | AACACAGCAT | TAAGCTGCAA | 22200 |
| TACCGCCGAT | GGCCACCAGA | TGGCACGCGC | CGCCAGCAAA | TTTAAGTCCT | GGTGGCTCAC | 22260 |
| CTGCCAGGTA | AACAAGGTTA | AAGTGGGTTT | GCTGGCCTTG | CGTTGCCATG | GATGCTACCT | 22320 |
| AGGCAAGTCC | AGATATATAA | TCCGGGCGTG | AGAAACAGAA | ACGGCCAATA | ACCCATGTTT | 22380 |
| TTCGAAAACC | ACCACACACC | TTAACACAAA | TCATGTACAC | CTGGTATTAC | TATTTCCCAC | 22440 |
| ACATCTTATA | GCATTTCAAA | GATAAGGGTG | CCTTACGGGC | CGCCCGAAAC | AAGTGGGCGG | 22500 |
| GCGCTACTCA | CTGTTTATAA | GTCAGCCGGA | CCAAGCTGCT | GCTCTTGGGG | ACGTGACTGC | 22560 |
| TTCGTGGCGC | AGCTGCCTCC | AAATGATACA | CACATTTTTT | GATTGTCCCG | GGCGCCGCGT | 22620 |

| | | | | | | |
|---|---|---|---|---|---|---|
| AGTGGAGGGC | GGAGTTATAT | CAAGCTACTT | TCTGATTGGT | GCCCCAGGCA | GGACTGCCAT | 22680 |
| AAAAACTGAA | GAAGGCGTGT | CTGCTTTGCA | GAATTTACCC | CCCACTGTGC | TCCCGGTTGC | 22740 |
| TGGCACCGGT | TCAGTGGTCC | GACCTGTCGT | CTGTGCTCCC | CCGTGGACGA | CGCCGAGTGC | 22800 |
| CTCTCGGGGG | TCCATGTCTA | GCCTCTTCAT | TTCATTACCT | TGGGTGGCGT | TCATCTGGCT | 22860 |
| AGCCCTCCTT | GGCGCGGTTG | GGGGTGCCCG | CGTTCAGGGG | CCCATGCGGG | GCTCTGCTGC | 22920 |
| CCTCACCTGC | GCCATCACGC | CCCGTGCTGA | CATAGTTAGC | GTTACCTGGC | AAAAAAGGCA | 22980 |
| GCTCCCCGGT | CCCGTAAACG | TCGCCACGTA | CAGCCATTCA | TATGGGGTGG | TGGTTCAGAC | 23040 |
| CCAGTACCGC | CACAAGGCAA | ATATAACCTG | TCCTGGGCTT | TGGAACTCTA | CCCTTGTTAT | 23100 |
| CCATAACCTT | GCAGTGGATG | ATGAGGGCTG | TTACCTGTGT | ATCTTTAACT | CATTTGGTGG | 23160 |
| CCGGCAGGTG | TCATGCACAG | CCTGCCTGGA | AGTGACATCT | CCCCCTACTG | GACACGTGCA | 23220 |
| GGTAAATAGC | ACAGAAGACG | CAGACACCGT | CACCTGTTTG | GCAACTGGTC | GCCCACCCCC | 23280 |
| CAATGTCACC | TGGGCCGCAC | CCTGGAACAA | CGCCTCTTCT | ACCCAGGAGC | AGTTCACTGA | 23340 |
| CAGTGATGGT | CTTACAGTTG | CGTGGAGGAC | CGTGAGGCTG | CCGCGTGGGG | ATAATACCAC | 23400 |
| CCCAAGTGAG | GGAATATGTC | TCATCACCTG | GGGAAATGAG | AGCATATCAA | TCCCGGCTTC | 23460 |
| TATTCAAGGC | CCCTTGGCCC | ATGACCTTCC | CGCGGCCCAG | GGAACTCTTG | CCGGGGTTGC | 23520 |
| CATTACTCTG | GTGGGCCTAT | TTGGGATATT | CGCATTACAT | CATTGCCGCC | GCAAGCAGGG | 23580 |
| CGGTGCATCA | CCTACTTCAG | ATGACATGGA | CCCCCTATCC | ACCCAGTGAC | TAGATGGACA | 23640 |
| CCCCGTGAAC | CGTCGTGCTT | ACCCACCCCC | TTCTGATTCT | GACAGACAAC | ACTACTATGT | 23700 |
| CCCAAAGACT | GTTTTTTACA | GCCCGATGGC | CCTTCAGGCC | TCCTTGAGTG | TCTAGCTGGT | 23760 |
| CCCGTGGTCA | TTGTGTGGTT | TGGCAGTCAC | TTCCCCATTT | TGGTGTCGCG | TTTTGGGTTT | 23820 |
| TGCCCTGCCC | CCAGCCAACG | TGGATCATAT | TCTTTCCCGT | CAGGGGAGTG | ACAAGCTATA | 23880 |
| GGACAGAAAG | GTCACCTGGC | CCAAACGGAG | GATCCTAGGT | GGGTGTGCAT | TTATTAGACG | 23940 |
| TTGGTGTGTT | GAAGGACGGA | TCAGGCGGGG | AGGAGGGGGT | GGGGGAGACT | TACTGCAGCA | 24000 |
| CTAGGTTAGG | TTGAAAGCCG | GGGTAAAAGG | CGTGGCTAAA | CAACACCTAT | ACTACTTGTT | 24060 |
| ATTGTAGGCC | ATGGCGGCCG | AGGATTTCCT | AACCATCTTC | TTAGATGATG | ATGAATCCTG | 24120 |
| GAATGAAACT | CTAAATATGA | GCGGATATGA | CTACTCTGGA | AACTTCAGCC | TAGAAGTGAG | 24180 |
| CGTGTGTGAG | ATGACCACCG | TGGTGCCTTA | CACGTGGAAC | GTTGGAATAC | TCTCTCTGAT | 24240 |
| TTTCCTCATA | AATGTTCTTG | GAAATGGATT | GGTCACCTAC | ATTTTTTGCA | AGCACCGATC | 24300 |
| GCGGGCAGGA | GCGATAGATA | TACTGCTCCT | GGGTATCTGC | CTAAACTCGC | TGTGTCTTAG | 24360 |
| CATATCTCTA | TTGGCAGAAG | TGTTGATGTT | TTTGTTTCCC | AATATCATCT | CCACAGGCTT | 24420 |
| GTGCAGACTT | GAAATTTTTT | TTTACTATTT | ATATGTCTAC | TTGGATATCT | TCAGTGTTGT | 24480 |
| GTGCGTCAGT | CTAGTGAGGT | ACCTCCTGGT | GGCATATTCT | ACGCGTTCCT | GGCCCAAGAA | 24540 |
| GCAGTCCCTC | GGATGGGTAC | TGACATCCGC | TGCACTGTTA | ATTGCATTGG | TGCTGTCGGG | 24600 |
| GGATGCCTGT | CGACACAGGA | GCAGGGTGGT | CGACCCGGTC | AGCAAGCAGG | CCATGTGTTA | 24660 |
| TGAGAACGCG | GGAAACATGA | CTGCAGACTG | GCGACTGCAT | GTCAGAACCG | TGTCAGTTAC | 24720 |
| TGCAGGTTTC | CTGTTACCCC | TGGCCCTCCT | TATTCTGTTT | TATGCTCTCA | CCTGGTGTGT | 24780 |
| GGTGAGGAGG | ACAAAGCTGC | AAGCCAGGCG | GAAGGTAAGG | GGGTGATTG | TTGCTGTGGT | 24840 |
| GCTGCTGTTT | TTTGTGTTTT | GCTTCCCTTA | CCACGTACTA | AATCTACTGG | ACACTCTGCT | 24900 |
| AAGGCGACGC | TGGATCCGGG | ACAGCTGCTA | TACGCGGGGG | TTGATAAACG | TGGGTCTGGC | 24960 |
| AGTAACCTCG | TTACTGCAGG | CACTGTACAG | CGCCGTGGTT | CCCCTGATAT | ACTCCTGCCT | 25020 |

-continued

| | | | | | | |
|---|---|---|---|---|---|---|
| GGGATCCCTC | TTTAGGCAGA | GGATGTACGG | TCTCTTCCAA | AGCCTCAGGC | AGTCTTTCAT | 25080 |
| GTCCGGCGCC | ACCACGTAGC | CCGCGGATGT | CTACGTGCCC | TTCCCCCTTA | ATTTAATCTA | 25140 |
| GCCTCCCGTT | CCCATGATGC | AGAGAGGCGA | ATTTGGTTTG | TACACAGATG | TGACTATGTA | 25200 |
| TTTGTTTTAT | TATGCGATTA | AATGAGGGGT | CTGATCCCAA | AAGCAATGTT | TAGTGGTGGT | 25260 |
| CGTTGATCTT | CTTGACGCTC | CATAGGTAGA | TTGACTGGAA | CGCCATGGCC | CACGGGGACA | 25320 |
| TGGACAGGGG | TGTTAGGTCT | GGTGGAACAT | GCTGCCACTG | CCACGGATGG | AACATCAGAG | 25380 |
| ATGGGTCTAT | GATCAGGGCA | GCGTGTCGCC | CGTCACTGGA | TGTAAGTCCG | GCCACCGTGG | 25440 |
| AGTTGCCTGT | GGGGTTTCTG | GGATAGTGTC | TGGCTGGCAG | GGTCTCATCC | GCGGCATTTC | 25500 |
| CATGGTAGGT | GAGGGTTATC | TCGCCTCGCT | GTCTCAGTAT | GTACTCGAGG | GCGTCCTGCT | 25560 |
| CGTACCGGAC | CCCCAGGTAC | TCTCCCTGGG | CCCAGCTGGG | CAGCACCGTC | CCCCGCAACA | 25620 |
| CTCGGAGGAA | AACGCTCTTA | GTGTTCTGAG | GGATCTGTAT | GTTTAGCCAG | TGGCTGTCAT | 25680 |
| ACAGCTTGGA | CACGTTGGTC | TCCAGGTTTA | CCGCCCAGCG | CTGGGGTGGT | GTGGGTCCGT | 25740 |
| ACGTGTATGG | TGAGGATTCC | GACCGGCCCA | CTACACCCAG | GGCCACCAGC | AGCTGGAAGC | 25800 |
| CCACCTCGCC | ACAGCAGATG | GAGAATGTGT | CGGGTCTGTT | TAGAAACTCT | GTCAGGGTGG | 25860 |
| AGGCACAGGT | AGGGTCGTTA | CACAGCGCCA | GGACCCATCC | CCTGGCGCTG | GCGTAGCTGG | 25920 |
| CCTGGCAGCC | TGTTCTGAGA | CATGTAATCA | GACCAGAGAA | CCCCGACAAG | GACTGTCCTC | 25980 |
| GTTAAGCTC | TTCCACAGTC | ACCGTGGCCA | CCTCAAAGCC | CGTGTTCTGC | AACGCGGCCA | 26040 |
| TGAGCGCGTA | CGGGGCACTG | CTCCCAGGCA | GCACCAACGC | GGCCACACGG | CGCGGGGAGG | 26100 |
| TGGGGCACGA | AAACAGGCGC | AGCTGACTCC | CAAGGCACAT | GGCCCTTAGG | CTGCCCAGGT | 26160 |
| GATGCTCCAG | ACGACCCAGG | TCCTTCCTGT | GCATGTCCTC | CAGTGGGTGC | AGGGGAGGCG | 26220 |
| TCACCAGGTT | CCACATTTCG | TCAGAAAAGG | AGGTCCATGA | GACTTGCAAG | GAAGTCAGGG | 26280 |
| TCTCTTGAAA | CACAACTGTC | TCGTTCTGCA | AAACCGTGAC | GTTGTTGCCT | TGTCCCTCGG | 26340 |
| GGCCAACGGT | GCCCAGTGGG | TGTGCCACGC | AGCGGTAGTC | CCTGGCCGCC | CGCAGCACCT | 26400 |
| CTGACAAGTG | TACCTGGGGC | ACCTCAACCA | GTGCCCCAGG | GGTCTCTGAA | ACCATAAGTT | 26460 |
| CGAGCGGGTT | AGGGTGGGCG | GGTAGTGAGA | GCTGCAGTCC | CCTGCAGCCG | GCCAGGGCCA | 26520 |
| TCTCGATTGC | AGATGGGAGA | AGCCCTCCGT | CCCCTATGTC | GTGCCCAGAT | ACAATGAGCC | 26580 |
| TCTTGGACAT | CAGGTACTTA | ACAAGCATGA | ACAGGCTGGC | GACCGTGGAC | GGGTTCAGAG | 26640 |
| GGGGTATTGG | GTGCCTGGAT | GCCAGGAAGT | TGTGCTCGAA | GGTGGACCCG | CTATGAGAC | 26700 |
| AGCTCTGATT | CACGGCCAGG | TATACCAGGG | CGTTGCCTTC | GACCTTTACG | TCCGGGGTGA | 26760 |
| CCCTGTATCT | GGATCCCTTG | ACCTCGGCCC | AGCTGGTAAA | CACCACGAG | TTGAAGGGAA | 26820 |
| GGACCTCCAC | CGTTTCTTGC | TGTTGTGTGA | TGCGCACATG | GCGCTCCGAA | AGCGTCGGAG | 26880 |
| AGCTGGCAGC | CGAGGAGATG | GACAGTGCCA | CTCCCAGCTC | CCGGCAGAAT | TCCTTGCAGG | 26940 |
| CGAAGAGGCA | CTCCTGTAGG | AGGCCGGCTT | GGTGGTCCTC | TGGACTCCAC | GCCACGGCGC | 27000 |
| CAGTTAGCAC | TACGTCCTGG | AGCTTGGACA | CGGGACTGAA | CATGAGGTTG | GTGAGAGCCT | 27060 |
| CGGTGATGGC | ATAGGTGGCC | CCGGTGGATA | CATTAGTAGC | CATCTTGTAG | GCCTGCTCCC | 27120 |
| CCATGGCCAT | TGCCTGACCC | CTCCACGCTG | GCACTGGAAG | CAGCTCCTGG | GGCAGGGCCT | 27180 |
| TCACCCAGGT | CTCGAAGTCC | TTGTGTAGGA | GGTTGGCCAT | GGACGGAGTG | ATGGCCTCCA | 27240 |
| CCGTGTCGGG | CACTCTGGGC | GCCACCCTCT | CGGCCAGCAT | GGACGAGTGC | AGCACCAGGT | 27300 |
| GGTAGTCTGA | AACCGGTATG | TCCAGGGGTC | CCACGCCAGC | CTGTTGGGCG | ATGAGGCCGT | 27360 |
| TGGAGCATCG | GTCCATGTGT | CGCGTAAAGA | ACTCCTTGCT | GCCAACCGTC | GAGTGGCGAA | 27420 |

| | | | | | | |
|---|---|---|---|---|---|---|
| GTAACTGGTG | GATTGTGGAG | CCGGTGGCAA | AAAGGCCCCA | GTCAACATCC | TCGGGGTGCC | 27480 |
| CCGAGACGCG | GACACCATCG | GACAGCGCCA | GCCAGGGGGA | CGGGGGGGTG | GACGACGGCT | 27540 |
| GGTCTACAGA | GAAGACCCTC | GTGGTCTCCC | CGGTCAGGTC | GTCTACTATT | CTGATGCCTG | 27600 |
| GGTGCTCCGA | GGTCCTCCCG | AGGACCGTTA | CCTGGCACGC | GCACAGGCGC | GCGGCGCGCT | 27660 |
| GCAGTACCTC | CAACGGGGTC | TCGCCCAGAT | CCCCAGGCAC | CGCGCCCGAC | TCTGCCACCA | 27720 |
| CCGCAAACAC | CAGGGAGCAA | TACACGTTGA | GAAAGTGCTC | TGCCACCGCC | GCCTTCACGG | 27780 |
| CATCCGGACC | GGCCGCGGGA | TCCGCAGGCA | GGTGGGTGCG | CACCTCGTCG | GGTAGCTTGG | 27840 |
| AGACAAACAG | CTCCAGGCCG | GTCCGCGGCG | CCAGCGCCTG | CAGGTGCCTC | ACCACCGGGG | 27900 |
| CCGGGTCATG | CGATCTGTTT | AGTCCGGAGA | AGATAGGGCC | CTTGGCAAGC | CGCTGGACCA | 27960 |
| GCTTCAGGGT | CTCCAAGATG | CGCACCGCAT | TGTCGGAGCT | GTCGCGATAG | AGGTTAGGGT | 28020 |
| AGGTGTCCGG | TCCATCCGTG | GGCTCAAACC | TGCCCAGACA | CACCACTGTC | TGCTGGGGGA | 28080 |
| TCATCCTTCT | CAGGGAGATG | CATTCTTTGG | AAGTAGTGGT | AGAGATGGAG | CAGACTGCCA | 28140 |
| GGGCGTTGCC | AGGAGTGGTG | GCGATGGTGC | GCACCGTTTT | TAAGAAACCC | CCAGGGTGG | 28200 |
| GGACTCCCGC | TCCCTGCAGC | ATCTCGGCCT | GCTGTACGCC | CTTGGCGAAT | ATGCGACGGA | 28260 |
| ATCGGCTGTG | CGCACGGGGT | CCCAGGGCCG | GTTCGGTGGC | ATACAGGCCG | GTGAGGGCCC | 28320 |
| CCTGTGTCTG | TCCGCCTGGA | AACAGGGTGC | TGTGAAACAG | CAGGTTGCCA | AGGCCGCGAA | 28380 |
| TACCCCTCTG | CACGCTGCTG | TGGACGTGGG | TGTACGCTCC | GTGGATCCCG | AACGCCTGTC | 28440 |
| TGGCACAGTT | CCAGGGCCAC | CGTTCCATGG | TGCATCTTCC | CGGTATCACA | AAGTACCTGG | 28500 |
| CCACGTTATA | ATTGTCCCCG | GTTGAAGCCT | GCACCGCCAG | CGGTAGCAGG | TCTGCCCCCA | 28560 |
| GGGATATCAT | AACAGCCTGC | ATAATGACAT | CATCTTCAAT | GTGTGGCCTA | GCCACGGGCT | 28620 |
| GGGGACCCTC | GGGCACTTCC | AACCCCTCGT | ACGGTACCAG | GTCGGTATTT | TGTGTAAATG | 28680 |
| CCCTGATAAA | CTGAGGTGGG | TGTGGTTCTA | GCAGGGTCTG | TGTGATTTTG | GACACCAGGT | 28740 |
| GCCTGCCCAC | TTCCACTCTA | GCCCACTCCT | GCAATCCTAG | CTCTTGCAGC | AGAACTGCAA | 28800 |
| GCTCTGTTGA | CAATGTTGTG | GGCCGGTGGT | GCATGTTTGG | CCCGTAGCCA | AAGGATACAA | 28860 |
| CACGCTCGCT | CCCCCGTGGC | ACAGACCGCC | TGATGACATG | GGGATATCCA | AGGAGCGGTG | 28920 |
| ACAGCACAGC | GAGCACCGTC | TGTATTTCCA | CATCCCGTCT | CTCTCGCTCC | TCCCTCGAAG | 28980 |
| TGGGAGGTCT | TCGGAAAGTT | ATCCATAGCA | GATAGTAGCC | TCCGGTGCCA | CCGGGTACGA | 29040 |
| GAGTGAGTGT | GCCCGTACGG | CTTGTATAAA | AGTTCACAAA | AGCTTCCTCA | TCCGCGGTGA | 29100 |
| GATCACTCTC | CAACCACAGC | CCAGTGACGT | CGTAGGCCAT | GCCTAGAGGG | CGCACCGCCC | 29160 |
| CCGGGGACAC | CCTCTGTAGT | CAGGCTGCCG | AGAAACCCGC | GAGATCTCTG | GGGAGTAGGA | 29220 |
| AGAAACTTAG | AATCCCCAAA | TATGTCGCAG | TCACAGGTTG | TCGGGCAGAG | TCTGTTTCCG | 29280 |
| CTTTCATGGG | ATCCACAGTT | ACTTGTAGCC | ATGTCACTAA | CCTCAAATAC | TCAAAAAAG | 29340 |
| CTATCGATGG | AAAAATGCTG | TGGTCCTAGG | TTAGTCCGTG | GGAAACAAAA | CTTCCTCATA | 29400 |
| CACTTCATCT | GCAGGCTGAA | ATGGTGGCGG | ATCCAGACTC | CTTACACCAC | AGTTGCTCAC | 29460 |
| ATTAGAGATA | CCTGATTGGT | TAATACAAGC | GGACGCACGC | GTTGGTGGAG | GCGTGTTGTC | 29520 |
| GCCCAAGATA | CTAGCATAGG | TGACTGTGCG | TTCGCTATGT | AGTTGCTGCA | TTTCAAGTTG | 29580 |
| GGTCGTTACT | TCTGTGTTGC | AAACCCTTAC | TGGAGATAAT | GCCATGTCTG | TTGTGGAACT | 29640 |
| TAAAATACGC | GAGTGTATAA | CATTTCTAGA | TGGTAGAGGT | GGTAAACGGC | GAGCTAAATG | 29700 |
| ATTAACATCG | GGACATATCC | TGCCTGCATG | AGCATGTGGT | GTGTCGTGTG | GTGTATATAT | 29760 |
| TGGTAATCTT | GTTGTTACAT | TGTTGAACGA | CACAAGTCTG | CTCTCTCGGT | AGAGATAACC | 29820 |

| | | | | | | |
|---|---|---|---|---|---|---|
| CACCAGTACG | GCTTGGCCAG | TACCTAATAA | GAAAAAATAA | AATCGTTAAT | CTCTGTTTTT | 29880 |
| ATGTGGCGCT | GGTGTTCCAA | TTATAAATAA | AAACACAACT | CACTTAATAT | CACAATTACA | 29940 |
| CAAATCAGTC | CTGAAGTAAC | ACCTGTAGTC | CAACCGTCAG | TGTAGAGCAG | GACTAACTTA | 30000 |
| ACACAGCATC | CAGCACATGT | CCATGCTAAG | GAAATAAACC | AAAGTTATGT | TTCGGTTTGC | 30060 |
| TTTATGACCA | GGGAGCTGCT | ACCCAGGTAC | AAAAAATCCT | TACCCAAAAA | TAGAAACAGG | 30120 |
| AAGCCACCAG | AGAGTGAAGC | TTTGTGAAAG | CTTTGCCAGC | AGAAGAAACA | ATATAATAAA | 30180 |
| AAGCCACAGC | CTGCTAGTAA | TGTTATACTC | CCTGTAAATA | AAAAATATGG | ACAGTAATAA | 30240 |
| TTTATGACAC | CCAATAAGTA | TGTGGAAAAA | ATGTAATGTA | AACCACTATA | CTGGTAAAAA | 30300 |
| CATACCTTCG | TTATTGGTGT | CTTGTTCGCG | CTTTATAAAC | AGTATCCCTA | TTGTTGTGGT | 30360 |
| TAGTGTAACC | AACACTCCTC | CTTGTAAAAG | TAAAAATGAC | ATAAGCCCCT | TAGTTGATCC | 30420 |
| AATCCAATGT | CGTTTCATTG | TTATAAACAA | GCCGGTCATA | CCTGTAATAA | AGTTATTCAT | 30480 |
| TACAAAATGT | TATAATAGTA | TTGGTAATGT | TTAGTTAAGA | TAATGTAAAC | TTCACAGTAG | 30540 |
| TCATATACCA | ATATGTATGC | AGCTTATGCA | TCCTGCGATG | ATTACAGAAA | GGCATGAATG | 30600 |
| GGAAACGCAA | AAAAAGGCCG | GTGTTGCCTT | GAGTATACCT | GTAGTAAAAA | ATAAATAATA | 30660 |
| TTGTTGGTTG | CAATGCTTAG | GTGCAAGCAG | ACATAATTGC | ATAGCAGTAA | AAACCAGACT | 30720 |
| TACCACCACA | TATTGCAAAC | ACACATGCAG | CGAGCTTGAG | ACAAGGCCCA | TTATCTGTTG | 30780 |
| CAAAGATATG | TATAAAAAAA | ACAAGCAACA | ATGTCCATAA | TGGCAAAAAA | AACTGGCAAT | 30840 |
| GTGTCCAGTT | GTTGTAAATC | TGCAATCCCA | TTGAGAATAT | AAGTACCAAC | ACCATAACAA | 30900 |
| TGCACAGTAA | TCCGCTATCA | ATAGTGCATT | TAACGACTCT | TAATGTTCCA | CCAAGTGATA | 30960 |
| GAATGGCTGA | AAAACACATA | CAGGGGAATT | ACGTTTTTT | AAAAAATTGG | AAATATTAGA | 31020 |
| TACATAATTT | TTATTTAATA | AAAAACCTTT | AGTAAAACTT | ACCAGTAATT | ATAGACAATA | 31080 |
| AACTTATAAT | ACAAACACAA | ACAGTACTCA | AAGTACTTTG | AGTAGAGAAA | CTCCAACTGG | 31140 |
| CAAAGGCAAT | ACATCCTAAA | ACAAAAGACA | AATACACGAG | ACATTTAAAC | AATGTATACT | 31200 |
| TAGAAAGAAA | TAAGTTAAAC | ATTTAAAAAA | TGTAACTTAC | CAACAATTAT | AGATGGTCCA | 31260 |
| ATGGGAGGGG | AAGCTTGAAA | ACGTTGTTTT | TTTGACTGCA | CATATATGTT | GTTATTGTAC | 31320 |
| AAAAAAGTTG | GTAGTAAACA | CTTATGTTAC | TGAGCAAAAA | TATGGTGTTT | TGTAAATTTA | 31380 |
| TAGTTAAAAG | ACAAAACATA | ATAGACAAAC | ACCCACAACA | TGTTATAAGT | GCTGCAAACC | 31440 |
| AAGTACCCCA | CAGGTATTTT | TTGTAATTCA | TTGTAGACAA | AAAGCCCAAG | GCCCAAAAAT | 31500 |
| GAAGTGGACA | AAAGAAATAT | GTAATTAAGT | GTAGTTGGAC | AAGGAATTAT | ATAGCTGGAT | 31560 |
| GAGTTAGTTT | TGCACAGAAC | CAGACATCCT | ATTTTTGTTT | GGAAACCTAA | AATCCGGATG | 31620 |
| AAGGGCTTAT | AAAATGGCAC | AGCTGCAAAA | AGCTGATAAT | GTAACACTGC | ATCCTGGTGT | 31680 |
| TTTTGATTGT | AGCGGAAAAA | TGTAATAAAT | TTTACAGACA | GTTTGCCTA | CTGAGAACAT | 31740 |
| GTTGAAAAAA | AGGCACTAAG | GGCTTTTTTG | CCAAAGGAAA | AATGCCCCCG | TGGGGTTAGG | 31800 |
| GGAAAGGGGG | GATGGGGTGA | TGGGGAATG | GTGGGAAAGG | GGGGATGGGG | TGATGGGGGA | 31860 |
| ATGGTGGGAA | AGGGGTGATG | GGGTGATGGG | GGAATGGGGG | GAAAGGGGGA | ATGGGGGGAA | 31920 |
| AGGGGGAATG | GGGGGAAAGG | GGGAATGGGG | GGAAGGGGG | GATGGGGGGA | AAGGGGGAAT | 31980 |
| GGGGGGAAAG | GGGGAATGGG | GGGAAGGGGG | GGATGGGGGG | AAAGGGGAA | TGGGGGAAA | 32040 |
| GGGGGGATGG | GGGAAACGG | GGATGGGGGG | GAAAGGGGGG | ATGGGGGGA | AAGGGGGAT | 32100 |
| GGGGGGGAAA | GGGGGGATGG | GGGGGAAAGG | GGGGATGGGGG | GGGAAAGGGG | GGATGGGGAA | 32160 |
| GGGGGGGGGG | AGGGGGAAGG | GGGTGAAGGG | GGAAGGGGGG | AGGCGAA | | 32207 |

POLYPEPTIDES FROM KAPOSI'S SARCOMA-ASSOCIATED HERPESVIRUS, DNA ENCODING SAME AND USES THEREOF

The invention disclosed herein was made with Government support under a co-operative agreement CCU210852 from the Centers for Disease Control and Prevention, and under National Institutes of Health, National Cancer Institute award CA67391 of the Department of Health and Human Services. Accordingly, the U.S. Government has certain rights in this invention.

Throughout this application, various publications may be referenced by Arabic numerals in brackets. Full citations for these publications may be found at the end of the Detailed Description of the Invention. The disclosures of all publications cited herein are in their entirety hereby incorporated by reference into this application to more fully describe the state of the art to which this invention pertains.

BACKGROUND OF THE INVENTION

Kaposi's sarcoma-associated herpesvirus (KSHV) is a new human herpesvirus (HHV8) believed to cause Kaposi's sarcoma (KS) [1,2].

Kaposi's sarcoma is the most common neoplasm occurring in persons with acquired immunodeficiency syndrome (AIDS). Approximately 15–20% of AIDS patients develop this neoplasm which rarely occurs in immunocompetent individuals. Epidemiologic evidence suggests that AIDS-associated KS (AIDS-KS) has an infectious etiology. Gay and bisexual AIDS patients are approximately twenty times more likely than hemophiliac AIDS patients to develop KS, and KS may be associated with specific sexual practices among gay men with AIDS. KS is uncommon among adult AIDS patients infected through heterosexual or parenteral HIV transmission, or among pediatric AIDS patients infected through vertical HIV transmission. Agents previously suspected of causing KS include cytomegalovirus, hepatitis B virus, human papillomavirus, Epstein-Barr virus (EBV), human herpesvirus 6, human immunodeficiency virus (HIV), and Mycoplasma penetrans. Non-infectious environmental agents, such as nitrite inhalants, also have been proposed to play a role in KS tumorigenesis. Extensive investigations, however, have not demonstrated an etiologic association between any of these agents and AIDS-KS.

SUMMARY OF THE INVENTION

This invention provides an isolated nucleic acid molecule which encodes Kaposi's Sarcoma-Associated Herpesvirus (KSHV) polypeptides. This invention provides an isolated polypeptide molecule of KSHV. This invention provides an antibody specific to the polypeptide. Antisense and triplex oligonucleotide molecules are also provided. This invention provides a vaccine for Kaposi's Sarcoma (KS). This invention provides methods of vaccination, prophylaxis, diagnosis and treatment of a subject with KS and of detecting expression of a DNA virus associated with Kaposi's sarcoma in a cell.

BRIEF DESCRIPTION OF THE FIGURES

FIG. 2A–2D (FIG. 2A) Sequence of terminal repeat unit (TR) demonstrating its high G+C content (SEQ ID NO:16). Sequences highly similar to conserved herpesvirus pacd sites are underlined with less similar sites to specific pac1 and pac2 sequences italicized. (FIG. 2B) Southern blot of DNA from BC-1 (lane 1), BCP-1 (lane 2) and a KS lesion (lane 3) digested with NdeII which cuts once in the TR sequence and probed with a plasmid containing the TR sequence. The intense hybridization band at 0.8 kb represents multiple copies of the NdeII-digested single unit TR (FIG. 2C). A schematic representation (FIG. 2C) of genome structures of KSHV in BCP-1 and BC-1 cell lines consistent with the data presented in (FIG. 2B) and (FIG. 2D). TaqI (T) sites flank the TR regions and Nde II (N) sites are within the TRs. Lower case tr refers to the deleted truncated TR unit at the left end of the unique region. DR represents the duplicated region of the LUR buried within the TR. (FIG. 2D) Southern blot hybridization with TR probe of DNA from BC-1 (lane 1), BCP-1 (lane 2), a KS lesion (lane 3), and HBL-6 (lane 4) digested with Taq I, which does not cut in the TR. Taq I-digested DNA from both BC-1 (lane 1) and HBL-6 (lane 4) show similar TR hybridization patterns suggesting identical insertion of a unique sequence into the TR region, which sequencing studies demonstrate is a duplicated portion of the LUR (see Experimental Details Section). BCP-1 TR hybridization (lane 2) shows laddering consistent with a virus population having variable TR region lengths within this cell line due to lytic replication. The absence of TR laddering in KS lesion DNA (lane 3) suggests that a clonal virus population is present in the tumor.

FIGS. 3A–3C CLUSTAL W alignments of KSHV-encoded polypeptide sequences to corresponding human cell signaling pathway polypeptide sequences. FIG. 3A. Two KSHV MIP-like polypeptides (vMIP-I and vMIP-II) are compared to human MIP-1α, MIP-1β and RANTES (amino acid identity to vMIP-I indicated by black reverse shading, to vMIP-II alone by gray reverse shading, and the C—C dimer motif is italicized). Both KSHV MIP genes encode 19 residue N-terminus hydrophobic secretory leader sequences which are relatively poorly conserved (vMIP-I also has a second C—C dimer in the hydrophobic leader sequence without similarity to the chemokine dicysteine motif). Potential O-linked glycosylation sites for vMIP-I (gapped positions 22 and 27) are not present in vMIP-II, which has only one predicted potential serine glycosylation site (position 51) not found in vMIP-I. FIG. 3B. Alignment of the KSHV vIL-6 to human IL-6. FIGS. 3C-1 and 3C-2. Alignment of the KSHV vIRF polypeptide to human ICSBP and ISGF3 with the putative ICS-binding typtophans (W) for ICSBP and ISGF3 in italics.

FIGS. 4A–4F Northern hybridization of total RNA extracted from BCP-1 and BC-1 cells with or without 48 hour incubation with TPA and control P3HR1 cells after TPA incubation. All four genes (FIG. 4A, vMIP-I; FIG. 4B, vMIP-II; FIG. 4C, vIL-6; FIG. 4D, vIRF) are TPA inducible but constitutive, noninduced expression of vIL-6 (FIG. 4C) and vIRF (FIG. 4D) is also evident for BCP-1 and BC-1 and of vMIP-I for BCP-1 (FIG. 4A). Representative hybridizations to a human β-actin probe (FIGS. 4E–4F) demonstrate comparable loading of RNA for cell preparations.

FIG. 5B. Anti-huIL-6 monoclonal antibodies do not cross-react with cell-associated or recombinant vIL-6 preparations.

(FIG. 7C) Cytoplasmic localization of vIL-6 in spindle-shaped cells from an AIDS-KS lesion. Of eight KS lesions, only one had readily identifiable vIL-6 staining of a subpopulation of cells. In contrast, the majority of pelleted lymphoma cells from a nonAIDS, EBV-negative PEL have intense vIL-6 staining (FIG. 7E). No immunostaining is present in control angiosarcoma (FIG. 7D) or multiple myeloma tissues (FIG. 7F).

FIG. 8A. CD34 (red) and vIL-6 colocalize (blue) in a KS spindle cell (arrow). Purple coloration is due to overlapping chromagen staining (100×). FIG. 8B. CD45 common leukocyte antigen staining (blue, arrow) on vIL-6 (red) expressing Kaposi's sarcoma cells (100×). FIG. 8C. Low power magnification (20×) demonstrating numerous vIL-6 producing hematopoietic cells (red) in a lymph node from a patient with KS. Arrows only indicate the most prominently staining cells; nuclei counterstained with hematoxylin. FIG. 8D. Colocalization of CD20 (brown, arrows) with vIL-6 (red) in an AIDS-KS patient's lymph node (100×).

DETAILED DESCRIPTION OF THE INVENTION

DEFINITIONS

Figure 1:
FIG. 1 Annotated long unique region (LUR) and terminal repeat (TR) of the KSHV genome. The orientation of identified ORFs in the LUR are denoted by the direction of arrows, with ORFs similar to HVS in dark blue and dissimilar ORFs in light blue. Seven blocks (numbered) of conserved herpesvirus genes with nonconserved interblock regions (lettered) are shown under the kilobase marker; the block numbering scheme differs from the original description by Chee (Chee et al., 1990, Curr. Topics Microbiol. Immunol. 154, 125–169) The overlapping cosmid (Z prefix) and lambda (L prefix) clones used to map the KSHV genome are compared to the KS5 lambda phage clone from a KS lesion and shown below. Features and putative coding regions not specifically designated are shown above the ORF map. Repeat regions are shown as white lines (frnk, vnct, waka/jwka, zppa, moi, mdsk). Putative coding regions and other features (see Experimental Details Section I) not designated as ORFs are shown as solid lines.

The following standard abbreviations are used throughout the specification to indicate specific nucleotides:

C=cytosine

T=thymidine

A=adenosine

G=guanosine

The term "nucleic acid", as used herein, refers to either DNA or RNA, including complementary DNA (cDNA), genomic DNA and messenger RNA (mRNA). As used herein, "genomic" means both coding and non-coding regions of the isolated nucleic acid molecule. "Nucleic acid sequence" refers to a single- or double- stranded polymer of deoxyribonucleotide or ribonucleotide bases read from the 5' to the 3' end. It includes both self-replicating plasmids, infectious polymers of DNA or RNA and nonfunctional DNA or RNA.

The term "polypeptide", as used herein, refers to either the full length gene product encoded by the nucleic acid, or portions thereof. Thus, "polypeptide" includes not only the full-length protein, but also partial-length fragments, including peptides less than fifty amino acid residues in length.

The term "SSC" refers to a citrate-saline solution of 0.15M sodium chloride and 20 mM sodium citrate. Solutions are often expressed as multiples or fractions of this concentration. For example, 6× SSC refers to a solution having a sodium chloride and sodium citrate concentration of 6 times this amount or 0.9M sodium chloride and 120 mM sodium citrate. 0.2× SSC refers to a solution 0.2 times the SSC concentration or 0.03M sodium chloride and 4 mM sodium citrate.

The phrase "selectively hybridizing to" and the phrase "specific hybridization" describe a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization.

"Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al. (1989) *Molecular Cloning: A Laboratory Manual* (2nd ed.), Cold Spring Harbor Laboratory, Vols. 1–3 or Ausubel, F., et al. (1987) *Current Protocols in Molecular Biology*, New York.

The phrase "nucleic acid molecule encoding" refers to a nucleic acid molecule which directs the expression of a specific polypeptide. The nucleic acid sequences include both the DNA strand sequence that is transcribed into RNA, the complementary DNA strand, and the RNA sequence that is translated into protein. The nucleic acid molecule includes both the full length nucleic acid sequence as well as non-full length sequences. It being further understood that the sequence includes the degenerate codons of the native sequence or sequences which may be introduced to provide codon preference in a specific host cell.

A nucleic acid probe is "specific" for a target organism of interest if it includes a nucleotide sequence which when detected is determinative of the presence of the organism in the presence of a heterogeneous population of proteins and other biologics. A specific nucleic acid probe is targeted to that portion of the sequence which is determinative of the organism and will not hybridize to other sequences, especially those of the host, where a pathogen is being detected.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a polypeptide produced using non-native cells. The cells produce the protein because they have been genetically altered by the introduction of the appropriate nucleic acid sequence.

The following terms are used to describe the sequence relationships between two or more nucleic acid molecules: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences in a comparison window may be conducted by the algorithm of Smith and Waterman (1981) *Adv. Appl. Math.* 2:482, by the algorithm of Needleman and Wunsch (1970) *J. Mol. Biol.* 48:443, by the search-for-similarity method of Pearson and Lipman (1988) *Proc. Natl. Acad. Sci.* 85:2444, or by computerized implementations of these algorithms (GAP, BESTFIT, FASTA, and TFASTA in GCG, the Wisconsin Genetics Software Package Release 8.0, Genetics Computer Group, 575 Science Dr., Madison, Wis.).

As applied to polypeptides, the terms "substantial identity" or "substantial sequence identity" mean that two peptide sequences, when optimally aligned, such as by the programs GAP or BESTFIT using default gap which share at least 90 percent sequence identity, preferably at least 95 percent sequence identity, more preferably at least 99 percent sequence identity or more.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties, such as charge or polarity, are not likely to effect the properties of a protein. Examples include glutamine for asparagine or glutamic acid for aspartic acid.

The phrase "substantially purified" or "isolated" when referring to a herpesvirus polypeptide, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a polypeptide, refers to a binding reaction which is determinative of the presence of the KSHV polypeptide of the invention in the presence of a heterogeneous population of polypeptides and other biologics including viruses other than KSHV. Thus, under designated immunoassay conditions, the specified antibodies bind to the KSHV antigen and do not bind in a significant amount to other antigens present in the sample.

"Specific binding" to an antibody under such conditions may require an antibody that is selected for its specificity for a particular antigen. For example, antibodies raised to KSHV antigens described herein can be selected to obtain antibodies specifically immunoreactive with KSHV polypeptides and not with other polypeptides.

"Biological sample" as used herein refers to any sample obtained from a living organism or from an organism that has died. Examples of biological samples include body fluids and tissue specimens.

It will be readily understood by those skilled in the art and it is intended here, that when reference is made to particular sequence listings, such reference includes sequences which substantially correspond to the listing and it's complement, including allowances for minor sequencing errors, single base changes, deletions, substitutions and the like, such that any such sequence variation corresponds to the nucleic acid sequence of the pathogenic organism or disease marker to which the relevant sequence listing relates.

I. Nucleic Acid Molecule from KSHV

This invention provides an isolated nucleic acid molecule which encodes a Kaposi's sarcoma-associated herpesvirus (KSHV) polypeptide.

In one embodiment, the isolated nucleic acid molecule which encodes a KSHV polypeptide has the nucleotide sequence as set forth in GenBank Accession Number U75698 and the start and stop codons set forth in Table 1. In another embodiment, the isolated nucleic acid molecule which encodes a KSHV polypeptide has the amino acid sequence defined by the translation of the nucleotide sequence set forth in GenBank Accession Number U75698 and the start and stop codons set forth in Table 1.

In one embodiment, the isolated nucleic acid molecule for a KSHV polypeptide has the 5' untranslated sequence as set forth in GenBank Accession Number U75698 upstream of the ATG start codon. In another embodiment, the isolated nucleic acid molecule for a KSHV polypeptide has the 3' untranslated sequence as set forth in GenBank Accession Number U75698 downstream of the stop codon.

In one embodiment the isolated nucleic acid molecule is genomic DNA. In another embodiment the isolated nucleic acid molecule is cDNA. In another embodiment RNA is derived from the isolated nucleic acid molecule or is capable of hybridizing with the isolated nucleic acid molecule.

Further, the nucleic acid molecule above may be associated with lymphoproliferative diseases including, but not limited to: Hodgkin's disease, non-Hodgkin's lymphoma, lymphatic leukemia, lymphosarcoma, splenomegaly, reticular cell sarcoma, Sezary's syndrome, mycosis fungoides, central nervous system lymphoma, AIDS related central nervous system lymphoma, post- transplant lymphoproliferative disorders, and Burkitt's lymphoma. A lymphoproliferative disorder is characterized as being the uncontrolled clonal or polyclonal expansion of lymphocytes involving lymph nodes, lymphoid tissue and other organs.

A. Isolation and Propagation of KSHV

KSHV can be propagated in vitro. For example, techniques for growing herpesviruses have been described by Ablashi et al. in *Virology* 184, 545–552. Briefly, PHA stimulated cord blood mononuclear cells, macrophage, neuronal, or glial cell lines are cocultivated with cerebrospinal fluid, plasma, peripheral blood leukocytes, or tissue extracts containing viral infected cells or purified virus. The recipient cells are treated with 5 µg/ml polybrene for 2 hours at 37° C. prior to infection. Infected cells are observed by demonstrating morphological changes, as well as being viral antigen positive.

For KSHV isolation, the virus is either harvested directly from cell culture fluid by centrifugation, or the infected cells are harvested, homogenized or lysed and the virus is separated from cellular debris and purified by standard methods of isopycnic sucrose density gradient centrifugation.

One skilled in the art may isolate and propagate KSHV employing the following protocol. Long- term establishment of a B lymphoid cell line infected with KSHV (e.g., RCC-1, HBL-6 or BCBL-1) is accomplished using body-cavity based lymphomas and standard techniques (Glick, 1980, *Fundamentals of Human Lymphoid Culture*, Marcel Dekker, New York; Knowles et al., 1989, *Blood* 73, 792–798; Metcalf, 1984, *Clonal Culture of Hematopoeitic Cells: Techniques and Applications, Elsevier*, New York).

Fresh lymphoma tissue containing viable infected cells is filtered to form a single cell suspension. The cells are separated by Ficoll-Plaque centrifugation and lymphocyte layer is removed. The lymphocytes are then placed at >1×10$^6$ cells/ml into standard lymphocyte tissue culture medium, such as RPMI 1640 supplemented with 10% fetal calf serum. Immortalized lymphocytes containing KSHV are indefinitely grown in the culture media while non-immortalized cells die during course of prolonged cultivation.

Further, KSHV may be propagated in a new cell line by removing media supernatant containing the virus from a continuously-infected cell line at a concentration of >1×10$^6$ cells/ml. The media is centrifuged at 2000×g for 10 minutes and filtered through a 0.45µ filter to remove cells. The media is applied in a 1:1 volume with cells growing at >1×10$^6$ cells/ml for 48 hours. The cells are washed, pelleted and placed in fresh culture medium, then tested for KSHV after 14 days.

KSHV may be isolated from a cell line in the following manner. An infected cell line is lysed using standard methods, such as hyposmotic shock or Dounce homogenization or using repeated cycles of freezing and thawing in a small volume (<3 ml), and pelleted at 2000×g for 10 minutes. The supernatant is removed and centrifuged again at 10,000×g for 15 minutes to remove nuclei and organelles. The resulting low-speed, cell-free supernatant is filtered through a 0.45µ filter and centrifuged at 100,000×g for 1 hour to pellet the virus. The virus can then be washed and re-pelleted. The DNA is extracted from the viral pellet by standard techniques (e.g., phenol/chloroform) and tested for the presence of KSHV by Southern blotting and/or PCR using the specific probes described above.

For banding whole virion, the low-speed cell-free supernatant is adjusted to contain 7% PEG-8000. The PEG-supernatant is spun at 10,000×g for 30 min. The supernatant is poured off and the pellet collected and resuspended in a small volume (1–2 ml) of virus buffer (VB, 0.1M NaCl, 0.01M Tris, pH 7.5). The virion are isolated by centrifugation at 25,000 rpm in a 10–50% sucrose gradient made with VB. One ml fractions of the gradient are obtained by standard techniques (e.g., using a fractionator) and each fraction is tested by dot blotting using specific hybridizing probes to determine the gradient fraction containing the purified virus (preparation of the fraction is needed in order to detect the presence of the virus, i.e., standard DNA extraction).

The method for isolating the KSHV genome is based on Pellicer et al.,1978, *Cell* 14, 133–141 and Gibson and Roizmann, 1972, *J. Virol.* 10, 1044–52.

A final method for isolating the KSHV genome is clamped homogeneous electric field (CHEF) gel electrophoresis. Agarose plugs are prepared by resuspending cells infected with KSHV in 1% LMP agarose (Biorad) and 0.9% NaCl at 42° C. to a final concentration of 2.5×10$^7$ cells/ml. Solidified agarose plugs are transferred into lysis buffer (0.5M EDTA pH 8.0, 1% sarcosyl, proteinase K at 1 mg/ml final concentration) and incubated for 24 hours. Approximately 10$^7$ cells are loaded in each lane. Gels are run at a gradient of 6.0 V/cm with a run time of 28 h on a CHEF Mapper XA pulsed field gel electrophoresis apparatus (Biorad), Southern blotted and hybridized to KS631Bam, KS330Bam and an EBV terminal repeat sequence.

To make a new cell line infected with KSHV, already-infected cells are co-cultivated with a Raji cell line separated by a 0.45µ filter. Approximately, 1–2×10$^6$ already-infected BCBL-1 and 2×10$^6$ Raji cells are co-cultivated for 2–20 days in supplemented RPMI alone or with 20 ng/ml 12-O-tetradecanoyl phorbol-13-acetate (TPA). After 2–20 days co-cultivation, Raji cells are removed, washed and placed in supplemented RPMI 1640 media. A Raji culture co-cultivated with BCBL-1 in 20 ng/ml TPA for 2 days survived and has been kept in continuous suspension culture for >10 weeks. This cell line, designated RCC-1 (Raji Co-Culture, No.1) remains PCR positive for the KSHV sequence after multiple passages. RCC-1 cells periodically undergo rapid cytolysis suggestive of lytic reproduction of KSHV. Thus, RCC-1 is a Raji cell line newly-infected with KSHV. RCC-1 and RCC-$1_{2F5}$ were deposited on Oct. 19, 1994 under ATCC Accession No. CRL 11734 and CRL 11735, respectively, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. HBL-6 was deposited (as BHL-6) on Nov. 18, 1994 under ATCC Accession No. CRL 11762 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

B. Hybridization Probes of KSHV

This invention provides a nucleic acid molecule of at least 14 nucleotides capable of specifically hybridizing with the isolated nucleic acid molecule as set forth in GenBank Accession Numbers U75698, U75699, U75700.

In one embodiment the nucleic acid molecule set forth in GenBank Accession Number U75698 comprises the long unique region (LUR) encoding KSHV polypeptides. In another embodiment the nucleic acid molecule set forth in GenBank Accession Number U75699 comprises the prototypical terminal repeat (TR). In another embodiment the nucleic acid molecule set forth in GenBank Accession Number U75700 comprises the incomplete terminal repeat (ITR).

In one embodiment the molecule is 8 to 36 nucleotides. In another embodiment the molecule is 12 to 25 nucleotides. In another embodiment the molecule is 14 nucleotides.

In one embodiment the molecule is DNA. In another embodiment the molecule is RNA.

In one embodiment the TR molecule contains cis-active elements required for DNA replication and packaging. In another embodiment the TR molecule is contained in a gene-cloning vector. In another embodiment the TR molecule is contained in a gene-therapy vector. In another embodiment the gene-therapy vector is expressed in lymphoid cells. In another embodiment, the TR comprises a molecular marker for determining the clonality of a tumor. In another embodiment, the marker provides a defining feature of the natural history of a tumor in a diagnostic assay.

This invention provides a B-lymphotrophic DNA vector comprising a plasmid or other self-replicable DNA molecule containing the 801 bp KSHV TR or a portion thereof.

High stringency hybridization conditions are selected at about 5° C. lower than the thermal melting point ($T_m$) for the specific sequence at a defined ionic strength and pH. The $T_m$ is the temperature (under defined ionic strength and pH) at which 50% of the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. For example, high stringency may be attained by overnight hybridization at about 68° C. in a 6× SSC solution, washing at room temperature with 6× SSC solution, followed by washing at about 68° C. in a 0.6× SSC solution. Hybridization with moderate stringency may be attained for example by: 1) filter pre-hybridizing and hybridizing with a solution of 3× SSC, 50% formamide, 0.1M Tris buffer at pH 7.5, 5× Denhardt's solution; 2) pre-hybridization at 37° C. for 4 hours; 3) hybridization at 37° C. with amount of labeled probe equal to 3,000,000 cpm total for 16 hours; 4) wash in × SSC and 0.1% SDS solution; 5) wash 4× for 1 minute each at room temperature in 4× SSC at 60° C. for 30 minutes each; and 6) dry and expose to film.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, 1981, Tetrahedron Lett. 22, 1859–1862 or by the triester method according to Matteucci et al., 1981, Am. Chem. Soc. 103:3185. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 base pairs (bp) or more in length is also encompassed for use as a probe.

The nucleic acid molecules of the subject invention also include molecules coding for polypeptide analogs, fragments or derivatives of antigenic polypeptides which differ from naturally-occurring forms in terms of the identity or location of one or more amino acid residues (deletion analogs containing less than all of the residues specified for the polypeptide, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

C. Polypeptides of KSHV and Antibodies (Ab's) Thereto

This invention provides an isolated KSHV polypeptide, one from the list as set forth in Table 1 and below.

This invention provides the isolated KSHV polypeptide comprising viral macrophage inflammatory protein III (vMIP-III). In one embodiment, vMIP-III comprises an orphan cytokine. In another embodiment, vMIP-III is encoded by nucleotides 22,529–22,185. In another embodiment, vMIP-III comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising dihydrofolate reductase (DHFR) encoded by ORF 2. In one embodiment, DHFR participates in KSHV nucleotide synthesis. In another embodiment, DHFR comprises an enzyme essential for viral replication, inhibition of which prevents virus production. In another embodiment, DHFR comprises a subunit vaccine. In another embodiment, DHFR comprises an antigen for immunologic assays.

In another embodiment, DHFR has the amino acid sequence as set forth in SEQ ID NO:1.

In another embodiment, KSHV DHFR is inhibited by a sulfa drug known to inhibit bacterial DHFR. In a preferred embodiment, KSHV DHFR is inhibited by methotrexate or a derivative thereof known to inhibit mammalian DHFR. In another embodiment, the sulfa drug, methotrexate or a derivative thereof is selective among the human herpesviruses for inhibition of KSHV.

This invention provides the isolated KSHV polypeptide comprising thymidylate synthase (TS) encoded by ORF 70. In one embodiment, TS participates in KSHV nucleotide metabolism. In another embodiment, TS comprises an enzyme essential for viral replication, inhibition of which prevents virus production. In another embodiment, TS comprises a subunit vaccine. In another embodiment, TS comprises an antigen for immunologic assays.

This invention provides the isolated KSHV polypeptide comprising DNA polymerase encoded by ORF 9. In one embodiment, DNA polymerase comprises an enzyme essential for viral replication, inhibition of which prevents virus production. In another embodiment, DNA polymerase comprises a subunit vaccine. In another embodiment, DNA polymerase comprises an antigen for immunologic assays.

This invention provides the isolated KSHV polypeptide comprising alkaline exonuclease encoded by ORF 37. In one embodiment, alkaline exonuclease packages KSHV DNA into the virus particle. In another embodiment, alkaline exonuclease comprises an enzyme essential for viral replication, inhibition of which prevents virus production. In another embodiment, alkaline exonuclease comprises a subunit vaccine. In another embodiment, alkaline exonuclease comprises an antigen for immunologic assays.

This invention provides the isolated KSHV polypeptide comprising helicase-primase, subunits 1, 2 and 3 encoded by ORFs 40, 41 and 44, respectively. In one embodiment, helicase-primase comprises an enzyme activity essential for viral DNA replication. In another embodiment, helicase-primase is inhibited by nucleotide analogs. In another embodiment, helicase-primase is inhibited by known antiviral drugs. In another embodiment, inhibition of helicase-primase prevents KSHV replication.

This invention provides the isolated KSHV polypeptide comprising uracil DNA glycosylase (UDG) encoded by ORF 46. In one embodiment, uracil DNA glycosylase comprises an enzyme essential for KSHV DNA repair during DNA replication. In another embodiment, uracil DNA glycosylase is inhibited by known antiviral drugs. In another embodiment, uracil DNA glycosylase comprises a subunit vaccine. In another embodiment, uracil DNA glycosylase comprises an antigen for immunologic assays.

This invention provides the isolated KSHV polypeptide comprising single-stranded DNA binding protein (SSBP) encoded by ORF 06. In one embodiment, SSBP comprises an enzyme essential for KSHV DNA replication. In another embodiment, SSBP is inhibited by known antiviral drugs. In another embodiment, SSBP increases the processivity of polymerase reactions such as in the conventional PCR method for DNA amplification.

This invention provides the isolated KSHV polypeptide comprising viral protein kinase encoded by ORF 36. In another embodiment, viral protein kinase comprises an antigen for immunologic assays. In another embodiment, viral protein kinase comprises a subunit vaccine.

This invention provides the isolated KSHV polypeptide comprising lytic cycle transactivator protein (LCTP) encoded by ORF 50. In one embodiment, LCTP is required for activation of productive infection from the latent state. In another embodiment, LCTP is inhibited by known antiviral drugs. In another embodiment, prevention of LCTP expression maintains is the virus in a latent state unable to replicate.

This invention provides the isolated KSHV polypeptide comprising ribonucleotide reductase, a two-subunit enzyme in which the small and large subunits are encoded by ORF 60 and ORF 61, respectively. In another embodiment, ribonucleotide reductase catalyzes conversion of ribonucleotides into deoxyribonucleotides for DNA replication. In another embodiment, ribonucleotide reductase is inhibited by known antiviral drugs in terminally differentiated cells not expressing cellular ribonucleotide reductase. In another embodiment, ribonucleotide reductase comprises an antigen for immunologic assays. In another embodiment, ribonucleotide reductase comprises a subunit vaccine. In another embodiment, ribonucleotide reductase comprises a transforming agent for establishment of immortalized cell lines.

This invention provides the isolated KSHV polypeptide comprising the protein encoded by ORF K1.

This invention provides the isolated KSHV polypeptide comprising complement-binding protein (v-CBP; CCP) encoded by ORF 4.

This invention provides the isolated KSHV polypeptide comprising transport protein encoded by ORF 7.

This invention provides the isolated KSHV polypeptide comprising glycoprotein B encoded by ORF 8.

This invention provides the isolated KSHV polypeptide comprising the protein encoded by ORF 10.

This invention provides the isolated KSHV polypeptide comprising the protein encoded by ORF 11.

This invention provides the isolated KSHV polypeptide comprising viral interleukin 6 (vIL-6) encoded by ORF K2. In one embodiment, antibodies selectively recognizing vIL-6 allow differentiation among lymphomas.

This invention provides the isolated KSHV polypeptide comprising BHV4-IE1 I encoded by ORF K3.

This invention provides the isolated KSHV polypeptide comprising vMIP-II encoded by ORF K4. In one embodiment, vMIP-II comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising BHV4-IE1 II encoded by ORF K5.

This invention provides the isolated KSHV polypeptide comprising vMIP-I encoded by ORF K6. In one embodiment, vMIP-I comprises an anti-inflammatory drug. In a preferred embodiment, the drug is useful in treatment of an autoimmune disorder. In the most preferred embodiment, the drug is useful in treatment of rheumatoid arthritis.

This invention provides the isolated KSHV polypeptide comprising the protein encoded by ORF K7.

This invention provides the isolated KSHV polypeptide comprising Bcl-2 encoded by ORF 16.

This invention provides the isolated KSHV polypeptide comprising capsid protein I encoded by ORF 17.

This invention provides the isolated KSHV polypeptide comprising the protein encoded by ORF 18.

This invention provides the isolated KSHV polypeptide comprising tegument protein I encoded by ORF 19.

This invention provides the isolated KSHV polypeptide comprising the protein encoded by ORF 20.

This invention provides the isolated KSHV polypeptide comprising thymidine kinase encoded by ORF 21.

This invention provides the isolated KSHV polypeptide comprising glycoprotein H encoded by ORF 22.

In one embodiment, the isolated KSHV polypeptide comprises the protein encoded by ORF 23.

This invention provides the isolated KSHV polypeptide comprising the protein encoded by ORF 24.

This invention provides the isolated KSHV polypeptide comprising major capsid protein encoded by ORF 25.

This invention provides the isolated KSHV polypeptide comprising capsid protein II encoded by ORF 26.

This invention provides the isolated KSHV polypeptide comprising the protein encoded by ORF 27.

This invention provides the isolated KSHV polypeptide comprising the protein encoded by ORF 28.

This invention provides the isolated KSHV polypeptide comprising packaging protein II encoded by ORF 29b.

This invention provides the isolated KSHV polypeptide comprising the protein encoded by ORF 30.

This invention provides the isolated KSHV polypeptide comprising the protein encoded by ORF 31.

This invention provides the isolated KSHV polypeptide comprising the protein encoded by ORF 32.

This invention provides the isolated KSHV polypeptide comprising the protein encoded by ORF 33.

This invention provides the isolated KSHV polypeptide comprising packaging protein I encoded by ORF 29a.

This invention provides the isolated KSHV polypeptide comprising the protein encoded by ORF 34.

This invention provides the isolated KSHV polypeptide comprising the protein encoded by ORF 35.

This invention provides the isolated KSHV polypeptide comprising the protein encoded by ORF 38.

This invention provides the isolated KSHV polypeptide comprising glycoprotein M encoded by ORF 39.

This invention provides the isolated KSHV polypeptide comprising the protein encoded by ORF 42.

This invention provides the isolated KSHV polypeptide comprising capsid protein III encoded by ORF 43.

This invention provides the isolated KSHV polypeptide comprising virion assembly protein encoded by ORF 45.

This invention provides the isolated KSHV polypeptide comprising glycoprotein L encoded by ORF 47.

This invention provides the isolated KSHV polypeptide comprising the protein encoded by ORF 48.

This invention provides the isolated KSHV polypeptide comprising the protein encoded by ORF 49.

This invention provides the isolated KSHV polypeptide comprising the protein encoded by ORF K8.

This invention provides the isolated KSHV polypeptide comprising the protein encoded by ORF 52.

This invention provides the isolated KSHV polypeptide comprising the protein encoded by ORF 53.

This invention provides the isolated KSHV polypeptide comprising dUTPase encoded by ORF 54.

This invention provides the isolated KSHV polypeptide comprising the protein encoded by ORF 55.

This invention provides the isolated KSHV polypeptide comprising DNA replication protein I encoded by ORF 56.

This invention provides the isolated KSHV polypeptide comprising immediate early protein II (IEP-II) encoded by ORF 57.

This invention provides the isolated KSHV polypeptide comprising viral interferon regulatory factor 1 (vIRF1; ICSBP) encoded by ORF K9. In one embodiment, vIRF1 is a transforming polypeptide.

This invention provides the isolated KSHV polypeptide comprising the protein encoded by ORF K10.

This invention provides the isolated KSHV polypeptide comprising the protein encoded by ORF K11.

This invention provides the isolated KSHV polypeptide comprising phosphoprotein encoded by ORF 58.

This invention provides the isolated KSHV polypeptide comprising DNA replication protein II encoded by ORF 59.

This invention provides the isolated KSHV polypeptide comprising assembly/DNA maturation protein encoded by ORF 62.

This invention provides the isolated KSHV polypeptide comprising tegument protein II encoded by ORF 63.

This invention provides the isolated KSHV polypeptide comprising tegument protein III encoded by ORF 64.

This invention provides the isolated KSHV polypeptide comprising capsid protein IV encoded by ORF 65.

This invention provides the isolated KSHV polypeptide comprising the protein encoded by ORRF 66.

This invention provides the isolated KSHV polypeptide comprising tegument protein IV encoded by QRF 67.

This invention provides the isolated KSHV polypeptide comprising glycoprotein encoded by ORF 68.

This invention provides the isolated KSHV polypeptide comprising the protein encoded by ORF 69.

This invention provides the isolated KSHV polypeptide comprising Kaposin encoded by ORF K12.

This invention provides the isolated KSHV polypeptide comprising the protein encoded by ORF K13.

This invention provides the isolated KSHV polypeptide comprising cyclin D encoded by ORF 72.

This invention provides the isolated KSHV polypeptide comprising immediate-early protein VEP) encoded by ORF 73.

This invention provides the isolated KSHV polypeptide comprising OX-2 encoded by ORF K14.

This invention provides the isolated KSHV polypeptide comprising G-protein coupled receptor encoded by ORF 74.

This invention provides the isolated KSHV polypeptide comprising tegument protein/FGARAT encoded by ORF 75.

This invention provides the isolated KSHV polypeptide comprising the protein encoded by ORF K15.

This invention provides the isolated KSHV polypeptide comprising viral interferon regulatory factor 2 (vIRF2) encoded by nucleotides 88,910–88,410.

This invention provides the isolated KSHV polypeptide comprising viral interferon regulatory factor 3 (vIRF3) encoded by nucleotides 90,541–89,600.

This invention provides the isolated KSHV polypeptide comprising viral interferon regulatory factor 4 (vIRF4) encoded by nucleotides 94,127–93,636.

This invention provides the isolated KSHV polypeptide comprising a precursor of secreted glycoprotein X (gX) encoded by nucleotides 90,173–90,643.

This invention provides the isolated KSHV polypeptide comprising protein T1.1 (nut-1) encoded by nucleotides 28,661–29,741.

Further, the isolated polypeptide may be linked to a second polypeptide to form a fusion protein by linking the isolated nucleic acid molecule to a second nucleic acid molecule and expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the polypeptide encoded by the isolated nucleic acid molecule. In one embodiment the antibody is a monoclonal antibody. In another embodiment the antibody recognizes an epitope of the KSHV polypeptide. In another embodiment the antibody is a polyclonal antibody. In another embodiment the antibody recognizes more than one epitope of the KSHV polypeptide. In another embodiment the antibody is an anti-idiotypic antibody.

An antibody, polypeptide or isolated nucleic acid molecule may be labeled with a detectable marker including, but not limited to: a radioactive label, or a colorimetric, a luminescent, or a fluorescent marker, or gold. Radioactive labels include, but are not limited to: $^{3}H$, $^{14}C$, $^{32}P$, $^{33}P$, $^{35}S$, $^{36}Cl$, $^{51}Cr$, $^{57}Co$, $^{59}Co$, $^{59}Fe$, $^{90}Y$, $^{125}I$, $^{131}I$, and $^{186}Re$. Fluorescent markers include, but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody, polypeptide or nucleic acid molecule may be detected by a second antibody which may be linked to an enzyme, such as alkaline phosphatase or horseradish peroxidase. Other enzymes which may be employed are well known to one of ordinary skill in the art.

This invention provides a method of producing a polypeptide encoded by the isolated nucleic acid molecule, which comprises growing a host-vector system under suitable conditions permitting production of the polypeptide and recovering the polypeptide so produced. Suitable host cells include bacteria, yeast, filamentous fungal, plant, insect and mammalian cells. Host-vector systems for producing and recovering a polypeptide are well known to those skilled in the art and include, but are not limited to, E. coli and pMAL (New England Biolabs), the Sf9 insect cell-baculovirus expression system, and mammalian cells (such as HeLa, COS, NIH 3T3 and HEK293) transfected with a mammalian expression vector by Lipofectin (Gibco-BRL) or calcium phosphate precipitation or other methods to achieve vector entry into the cell. Those of skill in the art are knowledgeable in the numerous expression systems available for expression of KSHV polypeptide.

This invention provides a method to select specific regions on the polypeptide encoded by the isolated nucleic acid molecule of the DNA virus to generate antibodies. Amino acid sequences may be analyzed by methods well known to those skilled in the art to determine whether they produce hydrophobic or hydrophilic regions in the polypeptides which they build. In the case of a cell membrane polypeptide, hydrophobic regions are well known to form the part of the polypeptide that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, nucleic acid may be cloned and expressed and the resulting polypeptide recovered and used as an immunogen.

Polyclonal antibodies against the polypeptide may be produced by immunizing animals using a selected KSHV polypeptide. Monoclonal antibodies are prepared using hybridoma technology by fusing antibody producing B cells from immunized animals with myeloma cells and selecting the resulting hybridoma cell line producing the desired antibody, as described further below.

II. Immunoassays

The antibodies raised against KSHV polypeptide antigens may be detectably labeled, utilizing conventional labelling techniques well-known to the art, as described above.

In addition, enzymes may be used as labels. Suitable enzymes include alkaline phosphatase, beta-galactosidase, glucose-6-phosphate dehydrogenase, maleate dehydrogenase and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; activity is thus measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

A description of a radioimmunoassay (RIA) may be found in: *Laboratory Techniques in Biochemistry and Molecular Biology* (1978) North Holland Publishing Company, New York, with particular reference to the chapter entitled "An Introduction to Radioimmune Assay and Related Techniques" by T. Chard. A description of general immunometric assays of various types can be found in the following U.S. Pat. Nos. 4,376,110 (David et al.) or 4,098,876 (Piasio).

A. Assays for KSHV Polypeptide Antigens

One can use immunoassays to detect the virus, its components, or antibodies thereto. A general overview of the applicable technology is in Harlow and Lane (1988) *Antibodies, A Laboratory Manual*, Cold Spring Harbor Publication, New York.

In one embodiment, antibodies to KSHV polypeptide antigens can be used. In brief, to produce antibodies, the polypeptide being targeted is expressed and purified. The product is injected into a mammal capable of producing antibodies. Either polyclonal or monoclonal antibodies (including recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane at pages 567–573 and 584–589.

Monoclonal antibodies or recombinant antibodies may be obtained by techniques familiar to those skilled in the art. Briefly, spleen cells or other lymphocytes from an animal immunized with a desired antigen are immortalized, commonly by fusion with a myeloma cell (see, Kohler and Milstein, 1976, *Eur. J. Immunol.* 6, 511–519). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Newer techniques using recombinant phage antibody expression systems can also be used to generate monoclonal antibodies. See, for example: McCafferty et al. (1990) *Nature* 348, 552; Hoogenboom et al. (1991) *Nuc. Acids Res.* 19, 4133; and Marks et al. (1991) *J. Mol Biol.* 222, 581–597.

Methods for characterizing naturally processed peptides bound to MHC (major histocompatibility complex) I molecules can be used. See Falk et al., 1991, *Nature* 351, 290 and PCT publication No. WO 92/21033 published Nov. 26, 1992. Typically, these methods involve isolation of MHC class I molecules by immunoprecipitation or affinity chromatography from an appropriate cell or cell line. Other methods involve direct amino acid sequencing of the more abundant peptides in various HPLC fractions by known automatic sequencing of peptides eluted from Class I molecules of the B cell type (Jardetzkey et al., 1991, *Nature* 353, 326), and of the human MHC class I molecule, HLA-A2.1 type by mass spectrometry (Hunt et al., 1991, *Eur. J. Immunol.* 21, 2963–2970). See also, Rötzschke and Falk, 1991, *Immunol. Today* 12, 447, for a general review of the characterization of naturally processed peptides in MHC class I. Further, Marloes et al., 1991, *Eur. J. Immunol.* 21, 2963–2970, describe how class I binding motifs can be applied to the identification of potential viral immunogenic peptides in vitro.

The polypeptides described herein produced by recombinant technology may be purified by standard techniques well known to those of skill in the art. Recombinantly produced viral polypeptides can be directly expressed or expressed as a fusion protein.

The protein is then purified by a combination of cell lysis (e.g., sonication) and affinity chromatography. For fusion products, subsequent digestion of the fusion protein with an appropriate proteolytic enzyme releases the desired peptide.

The polypeptides may be purified to substantial purity by standard techniques well known in the art, including selective precipitation with such substances as ammonium sulfate, column chromatography, immunopurification methods, and others. See, for instance, Scopes, 1982, *Protein Purification: Principles and Practice*, Springer-Verlag, New York.

B. Assays for Antibodies Specifically Binding To KSHV Polypeptides

Antibodies reactive with polypeptide antigens of KSHV can also be measured by a variety of immunoassay methods that are similar to the procedures described above for measurement of antigens. For a review of immunological and immunoassay procedures applicable to the measurement of antibodies by immunoassay techniques, see *Basic and Clinical Immunology,*. 7th Edition, Stites and Terr, Eds., and Harlow and Lane, 1988, *Antibodies, A Laboratory Manual*, Cold Spring Harbor, New York.

In brief, immunoassays to measure antibodies reactive with polypeptide antigens of KSHV can be either competitive or noncompetitive binding assays. In competitive binding assays, the sample analyte competes with a labeled analyte for specific binding sites on a capture agent bound to a solid surface. Preferably the capture agent is a purified recombinant human herpesvirus polypeptide produced as described above. Other sources of human herpesvirus polypeptides, including isolated or partially purified naturally occurring polypeptide, may also be used.

Noncompetitive assays are typically sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labeled binding agent can be used. A variety of different immunoassay formats, separation techniques and labels can also be used similar to those described above for the measurement of KSHV polypeptide antigens.

Hemagglutination Inhibition (HI) and Complement Fixation (CF) are two laboratory tests that can be used to detect infection with human herpesvirus by testing for the presence of antibodies against the virus or antigens of the virus.

Serological methods can also be useful when one wishes to detect antibody to a specific viral variant. For example, one may wish to see how well a vaccine recipient has responded to a new preparation by assay of patient sera.

IIA. Vector, Cell Line and Transgenic Mammal

This invention provides a replicable vector containing the isolated nucleic acid molecule encoding a KSHV polypeptide. The vector includes, but is not limited to: a plasmid, cosmid, λ phage or yeast artificial chromosome (YAC) which contains the isolated nucleic acid molecule.

To obtain the vector, for example, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are available and well-known to those skilled in the art.

This invention provides a host cell containing the vector. Suitable host cells include, but are not limited to, bacteria (such as *E. coli*), yeast, fungi, plant, insect and mammalian cells. Suitable animal cells include, but are not limited to Vero cells, HeLa cells, Cos cells, CV1 cells and various primary mammalian cells.

This invention provides a transgenic nonhuman mammal which comprises the isolated nucleic acid molecule introduced into the mammal at an embryonic stage. Methods of producing a transgenic nonhuman mammal are known to those skilled in the art.

III. Diagnostic Assays for KS

This invention embraces diagnostic test kits for detecting the presence of KSHV in biological samples, such as skin samples or samples of other affected tissue, comprising a container containing a nucleic acid sequence specific for a KSHV polypeptide and instructional material for performing the test. A container containing nucleic acid primers to any one of such sequences is optionally included.

This invention further embraces diagnostic test kits for detecting the presence of KSHV in biological samples, such as serum or solid tissue samples, comprising a container containing antibodies to a KSHV polypeptide, and instructional material for performing the test. Alternatively, inactivated viral particles or polypeptides derived from the human herpesvirus may be used in a diagnostic test kit to detect antibodies specific for a KSHV polypeptide.

A. Nucleic Acid Assays

This invention provides a method of diagnosing Kaposi's sarcoma in a subject which comprises: (a) obtaining a nucleic acid molecule from a tumor lesion or a suitable bodily fluid of the subject; (b) contacting the nucleic acid molecule with a labeled nucleic acid molecule of at least 15 nucleotides capable of specifically hybridizing with the isolated nucleic acid molecule of KSHV under hybridizing conditions; and (c) determining the presence of the nucleic acid molecule hybridized, the presence of which is indicative of Kaposi's sarcoma in the subject, thereby diagnosing Kaposi's sarcoma in the subject.

In one embodiment the nucleic acid molecule from the tumor lesion is amplified before step (b). In another embodiment the polymerase chain reaction (PCR) is employed to amplify the nucleic acid molecule. Methods of amplifying nucleic acid molecules are known to those skilled in the art.

A person of ordinary skill in the art will be able to obtain appropriate nucleic acid sample for diagnosing Kaposi's sarcoma in the subject. The DNA sample obtained by the above described method may be cleaved by restriction enzyme before analysis, a technique well-known in the art.

In the above described methods, a size fractionation may be employed which is effected by a polyacrylamide gel. In one embodiment, the size fractionation is effected by an agarose gel. Further, transferring the nucleic acid fragments into a solid matrix may be employed before a hybridization step. One example of such solid matrix is nitrocellulose paper.

This invention provides a method of detecting expression of a KSHV gene in a cell which comprises obtaining mRNA from the cell, contacting the mRNA with a labeled nucleic acid molecule of KSHV under hybridizing conditions, determining the presence of mRNA hybridized to the molecule, thereby detecting expression of the KSHV gene. In one embodiment cDNA is prepared from the mRNA obtained from the cell and used to detect KSHV expression.

Accepted means for conducting hybridization assays are known and general overviews of the technology can be had from a review of: *Nucleic Acid Hybridization: A Practical Approach* (1985) Hames and Higgins, Eds., IRL Press; *Hybridization of Nucleic Acids Immobilized on Solid Supports*, Meinkoth and Wahl; *Analytical Biochemistry* (1984) 238, 267–284 and Innis et al., *PCR Protocols* (1990) Academic Press, San Diego.

Target-specific probes may be used in the nucleic acid hybridization diagnostic assays for KS. The probes are specific for or complementary to the target of interest. For precise allelic differentiations, the probes should be about 14 nucleotides long and preferably about 20–30 nucleotides. For more general detection of KSHV, nucleic acid probes are about 50 to 1000 nucleotides, most preferably about 200 to 400 nucleotides.

A specific nucleic acid probe can be RNA, DNA, oligonucleotide, or their analogs. The probes may be single or double stranded nucleic acid molecules. The probes of the invention may be synthesized enzymatically, using methods well known in the art (e.g., nick translation, primer extension, reverse transcription, the polymerase chain reaction, and others) or chemically (e.g., by methods described by Beaucage and Carruthers or Matteucci et al., supra).

The probe must be of sufficient length to be able to form a stable duplex with its target nucleic acid in the sample, i.e., at least about 14 nucleotides, and may be longer (e.g., at least about 50 or 100 bases in length). Often the probe will be more than about 100 bases in length. For example, when probe is prepared by nick-translation of DNA in the presence of labeled nucleotides the average probe length may be about 100–600 bases.

For discussions of nucleic acid probe design and annealing conditions see, for example, Ausubel et al., supra; Berger and Kimmel, Eds., *Methods in Enzymology* Vol. 152, (1987) Academic Press, New York; or *Hybridization with Nucleic Acid Probes*, pp. 495–524, (1993) Elsevier, Amsterdam.

Usually, at least a part of the probe will have considerable sequence identity with the target nucleic acid. Although the extent of the sequence identity required for specific hybridization will depend on the length of the probe and the hybridization conditions, the probe will usually have at least 70% identity to the target nucleic acid, more usually at least 80% identity, still more usually at least 90% identity and most usually at least 95% or 100% identity.

The following stringent hybridization and washing conditions will be adequate to distinguish a specific probe (e.g., a fluorescently labeled nucleic acid probe) from a probe that is not specific: incubation of the probe with the sample for 12 hours at 37° C. in a solution containing denatured probe, 50% formamide, 2× SSC, and 0.1% (w/v) dextran sulfate, followed by washing in 1× SSC at 70° C. for 5 minutes; 2× SSC at 37° C. for 5 minutes; 0.2× SSC at room temperature for 5 minutes, and $H_2O$ at room temperature for 5 minutes. Those of skill are aware that it will often be advantageous in nucleic acid hybridizations (i.e., in situ, Southern, or Northern) to include detergents (e.g., sodium dodecyl sulfate), chelating agents (e.g., EDTA) or other reagents (e.g., buffers, Denhardt's solution, dextran sulfate) in the hybridization or wash solutions. To evaluate specificity, probes can be tested on host cells containing KSHV and compared with the results from cells containing non-KSHV virus.

It will be apparent to those of ordinary skill in the art that a convenient method for determining whether a probe is specific for a KSHV nucleic acid molecule utilizes a Southern blot (or Dot blot) using DNA prepared from the virus. Briefly, to identify a target-specific probe, DNA is isolated from the virus. Test DNA, either viral or cellular, is transferred to a solid (e.g., charged nylon) matrix. The probes are labeled by conventional methods. Following denaturation and/or prehybridization steps known in the art, the probe is hybridized to the immobilized DNAs under stringent conditions, such as defined above.

It is further appreciated that in determining probe specificity and in utilizing the method of this invention to detect KSHV, a certain amount of background signal is typical and can easily be distinguished by one of skill from a specific signal. Two-fold signal over background is acceptable.

A preferred method for detecting the KSHV polypeptide is the use of PCR and/or dot blot hybridization. Other methods to test for the presence or absence of KSHV for detection or prognosis, or risk assessment for KS includes Southern transfers, solution hybridization or non-radioactive detection systems, all of which are well known to those of skill in the art. Hybridization is carried out using probes. Visualization of the hybridized portions allows the qualitative determination of the presence or absence of the causal agent.

Similarly, a Northern transfer or reverse transcriptase PCR may be used for the detection of KSHV messenger RNA in a sample. These procedures are also well known in the art. See Sambrook et al. (1989) *Molecular Cloning: A Laboratory Manual* (2nd ed.), Cold Spring Harbor Laboratory, Vols. 1–3.

An alternative means for determining the presence of the human herpesvirus is in situ hybridization, or more recently, in situ polymerase chain reaction. In situ PCR is described in Neuvo et al. (1993) Intracellular localization of PCR-amplified hepatitis C DNA, in *American Journal of Surgical Pathology* 17(7), 683–690; Bagasra et al. (1992) Detection of HIV-1 provirus in mononuclear cells by in situ PCR, in *New England Journal of Medicine* 326(21),1385–1391; and Heniford et al.(1993) Variation in cellular EGF receptor mRNA expression demonstrated by in situ reverse transcriptase polymerase chain reaction, in *Nucleic Acids Research* 21, 3159–3166. In situ hybridization assays are well known and are generally described in *Methods Enzymol.* Vol. 152, (1987) Berger and Kimmel, Eds., Academic Press, New York. In an in situ hybridization, cells are fixed to a solid support, typically a glass slide. The cells are then contacted with a hybridization solution at a moderate temperature to permit annealing of target-specific probes that are labeled. The probes are preferably labeled with radioisotopes or fluorescent reporters.

The above-described probes are also useful for in situ hybridization or in order to locate tissues which express the gene, or for other hybridization assays for the presence of the gene or its mRNA in various biological tissues. In situ hybridization is a sensitive localization method which is not dependent on expression of polypeptide antigens or native versus denatured conditions.

Synthetic oligonucleotide (oligo) probes and riboprobes made from KSHV phagemids or plasmids are also provided. Successful hybridization conditions in tissue sections is readily transferrable from one probe to another. Commercially-synthesized oligonucleotide probes are prepared using the nucleotide sequence of the identified gene. These probes are chosen for length (45–65 mers), high G-C content (50–70%) and are screened for uniqueness against other viral sequences in GenBank.

Oligos are 3'end-labeled with $[\alpha-^{35}S]dATP$ to specific activities in the range of $1\times10^{10}$ dpm/$\mu$g using terminal deoxynucleotidyl transferase. Unincorporated labeled nucleotides are removed from the oligo probe by centrifugation through a Sephadex G-25 column or by elution from a Waters Sep Pak C-18 column.

KS tissue embedded in OCT compound and snap frozen in freezing isopentane cooled with dry ice is cut at 6 $\mu$m intervals and thawed onto 3-aminopropyltriethoxysilane treated slides and allowed to air dry. The slides are then fixed in 4% freshly prepared paraformaldehyde and rinsed in water. Formalin-fixed, paraffin embedded KS tissues cut at 6 $\mu$m and baked onto glass slides can also be used. These sections are then deparaffinized in xylenes and rehydrated through graded alcohols. Prehybridization in 20 mM Tris pH 7.5, 0.02% Denhardt's solution, 10% dextran sulfate for 30 min at 37° C. is followed by hybridization overnight in a solution of 50% formamide (v/v), 10% dextran sulfate (w/v), 20 mM sodium phosphate (pH 7.4), 3× SSC, 1× Denhardt's solution, 100 $\mu$g/ml salmon sperm DNA, 125 $\mu$g/ml yeast tRNA and the oligo probe ($10^6$ cpm/ml) at 42° C. overnight. The slides are washed twice with 3× SSC and twice with 1× SSC for 15 minutes each at room temperature and visualized by autoradiography. Briefly, sections are dehydrated through graded alcohols containing 0.3M ammonium acetate, and air dried. The slides are dipped in Kodak NTB2 emulsion, exposed for days to weeks, developed, and counterstained with hematoxylin and eosin (H&E).

Alternative immunohistochemical protocols may be employed which are well known to those skilled in the art.

B. Immunologic Assays

This invention provides a method of diagnosing Kaposi's sarcoma in a subject, which comprises (a) obtaining a suitable bodily fluid sample from the subject, (b) contacting the suitable bodily fluid of the subject to a support having already bound thereto an antibody recognizing the KSHV polypeptide, so as to bind the antibody to a specific KSHV polypeptide antigen, (c) removing unbound bodily fluid from the support, and (d) determining the level of the antibody bound by the antigen, thereby diagnosing Kaposi's sarcoma.

This invention provides a method of diagnosing Kaposi's sarcoma in a subject, which comprises (a) obtaining a suitable bodily fluid sample from the subject, (b) contacting the suitable bodily fluid of the subject to a support having already bound thereto the KSHV polypeptide antigen, so as to bind the antigen to a specific Kaposi's sarcoma antibody, (c) removing unbound bodily fluid from the support, and (d) determining the level of the antigen bound by the Kaposi's sarcoma antibody, thereby diagnosing Kaposi's sarcoma.

The suitable bodily fluid sample is any bodily fluid sample which would contain Kaposi's sarcoma antibody, antigen or fragments thereof. A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting. Other methods are known to those skilled in the art. Further, a subject infected with KSHV may be diagnosed as infected with the above-described methods.

The detection of KSHV and the detection of virus-associated KS are essentially identical processes. The basic principle is to detect the virus using specific ligands that bind to the virus but not to other polypeptides or nucleic acids in a normal human cell or its environs. The ligands can be nucleic acid molecules, polypeptides or antibodies. The ligands can be naturally-occurring or genetically or physically modified, such as nucleic acids with non-natural nucleotide bases or antibody derivatives, i.e., Fab or chimeric antibodies. Serological tests for detection of antibodies to the virus present in subject sera may also be performed by using the KSHV polypeptide as an antigen, as described herein.

Samples can be taken from patients with KS or from patients at risk for KS, such as AIDS patients. Typically the samples are taken from blood (cells, serum and/or plasma) or from solid tissue samples such as skin lesions. The most accurate diagnosis for KS will occur if elevated titers of the virus are detected in the blood or in involved lesions. KS may also be indicated if antibodies to the virus are detected and if other diagnostic factors for KS are present.

See Immunoassays above for more details on the immunoreagents of the invention for use in diagnostic assays for KS.

IV. Treatment of Human Herpesvirus-Induced KS

This invention provides a method for treating a subject with Kaposi's sarcoma (KS) comprising administering to the subject having KS a pharmaceutically effective amount of an antiviral agent in a pharmaceutically acceptable carrier, wherein the agent is effective to treat the subject with KSHV.

Further, this invention provides a method of prophylaxis or treatment for Kaposi's sarcoma (KS) by administering to a patient at risk for KS, an antibody that binds to KSHV in a pharmaceutically acceptable carrier.

This invention provides a method of treating a subject with Kaposi's sarcoma comprising administering to the subject an effective amount of an antisense molecule capable of hybridizing to the isolated DNA molecule of KSHV under conditions such that the antisense molecule selectively enters a KS tumor cell of the subject, so as to treat the subject.

A. Nucleic Acid Therapeutics

This invention provides an antisense molecule capable of hybridizing to the isolated nucleic acid molecule of KSHV. In one embodiment the antisense molecule is DNA. In another embodiment the antisense molecule is RNA. In another embodiment, the antisense molecule is a nucleic acid derivative (e.g., DNA or RNA with a protein backbone).

The present invention extends to the preparation of antisense nucleic acids and ribozymes that may be used to interfere with the expression of a polypeptide either by masking the mRNA with an antisense nucleic acid or cleaving it with a ribozyme, respectively.

This invention provides inhibitory nucleic acid therapeutics which can inhibit the activity of herpesviruses in patients with KS by binding to the isolated nucleic acid molecule of KSHV. Inhibitory nucleic acids may be single-stranded nucleic acids, which can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of herpesvirus genes. These different types of inhibitory nucleic acid technology are described in Helene and Toulme (1990) *Biochim. Biophys. Acta.* 1049, 99–125, which is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom et al. (1988) *PNAS* 85, 1028–1032 and Harel-Bellan et al. (1988) *Exp. Med.* 168, 2309–2318. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation, as described in Helene and Toulme.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

An example of an antiherpes virus inhibitory nucleic acid is ISIS 2922 (ISIS Pharmaceuticals) which has activity against CMV (see *Biotechnology News* 14:5).

A problem associated with inhibitory nucleic acid therapy is the effective delivery of the inhibitory nucleic acid to the target cell in vivo and the subsequent internalization of the inhibitory nucleic acid by that cell. This can be accomplished by linking the inhibitory nucleic acid to a targeting moiety to form a conjugate that binds to a specific receptor on the surface of the target infected cell, and which is internalized after binding.

B. Antiviral Agents

The use of combinations of antiviral drugs and sequential treatments are useful for treatment of herpesvirus infections and will also be useful for the treatment of herpesvirus-induced KS. For example, Snoeck et al. (1992) *Eur. J. Clin. Micro. Infect. Dis.* 11, 1144–1155, found additive or synergistic effects against CMV when combining antiherpes drugs (e.g., combinations of zidovudine [3'-azido-3'-deoxythymidine, AZT] with HPMPC, ganciclovir, foscarnet or acyclovir or of HPMPC with other antivirals). Similarly, in treatment of cytomegalovirus retinitis, induction with ganciclovir followed by maintenance with foscarnet has been suggested as a way to maximize efficacy while minimizing the adverse side effects of either treatment alone. An anti-herpetic composition that contains acyclovir and, e.g., 2-acetylpyridine-5-((2-pyridylamino)thiocarbonyl)-thiocarbonohydrazone is described in U.S. Pat. No. 5,175,165 (assigned to Burroughs Wellcome Co.). Combinations of TS-inhibitors and viral TK-inhibitors in antiherpetic medicines are disclosed in U.S. Pat. No. 5,137,724, assigned to Stichting Rega VZW. A synergistic inhibitory effect on EBV replication using certain ratios of combinations of HPMPC with AZT was reported by Lin et al. (1991) *Antimicrob Agents Chemother* 35:2440–3.

U.S. Pat. Nos. 5,164,395 and 5,021,437 (Blumenkopf; Burroughs Wellcome) describe the use of a ribonucleotide reductase inhibitor (an acetylpyridine derivative) for treatment of herpes infections, including the use of the acetylpyridine derivative in combination with acyclovir. U.S. Pat. No. 5,137,724 (Balzari et al. (1990) *Mol. Pharm.* 37,402–7) describes the use of thymidylate synthase inhibitors (e.g., 5-fluoro-uracil and 5-fluro-2'-deoxyuridine) in combination with compounds having viral thymidine kinase inhibiting activity.

With the discovery of a disease causal agent for KS now identified, effective therapeutic or prophylactic protocols to alleviate or prevent the symptoms of herpes virus-associated KS can be formulated. Due to the viral nature of the disease, antiviral agents have application here for treatment, such as interferons, nucleoside analogues, ribavirin, amantadine, and pyrophosphate analogues of phosphonoacetic acid (foscarnet) (reviewed in Gorbach et al., 1992, *Infectious Disease* Ch.35, 289, W. B. Saunders, Philadelphia, Pa.) and the like. Immunological therapy will also be effective in many cases to manage and alleviate symptoms caused by the disease agents described here. Antiviral agents include agents or compositions that directly bind to viral products and interfere with disease progress; and, excludes agents that do not impact directly on viral multiplication or viral titer. Antiviral agents do not include immunoregulatory agents that do not directly affect viral titer or bind to viral products. Antiviral agents are effective if they inactivate the virus, otherwise inhibit its infectivity or multiplication, or alleviate the symptoms of KS.

The antiherpesvirus agents that will be useful for treating virus-induced KS can be grouped into broad classes based on their presumed modes of action. These classes include agents that act (1) by inhibition of viral DNA polymerase, (2) by targeting other viral enzymes and proteins, (3) by miscellaneous or incompletely understood mechanisms, or (4) by binding a target nucleic acid (i.e., inhibitory nucleic acid therapeutics, supra). Antiviral agents may also be used in combination (i.e., together or sequentially) to achieve synergistic or additive effects or other benefits.

Although it is convenient to group antiviral agents by their supposed mechanism of action, the applicants do not intend to be bound by any particular mechanism of antiviral action. Moreover, it will be understood by those of skill that an agent may act on more than one target in a virus or virus-infected cell or through more than one mechanism.

i) Inhibitors of DNA Polymerase

Many antiherpesvirus agents in clinical use or in development today are nucleoside analogs believed to act through inhibition of viral DNA replication, especially through inhibition of viral DNA polymerase. These nucleoside analogs act as alternative substrates for the viral DNA polymerase or as competitive inhibitors of DNA polymerase substrates. Usually these agents are preferentially phosphorylated by viral thymidine kinase (TK), if one is present, and/or have higher affinity for viral DNA polymerase than for the cellular DNA polymerases, resulting in selective antiviral activity. Where a nucleoside analogue is incorporated into the viral DNA, viral activity or reproduction may be affected in a variety of ways. For example, the analogue may act as a chain terminator, cause increased lability (e.g., susceptibility to breakage) of analogue-containing DNA, and/or impair the ability of the substituted DNA to act as template for transcription or replication (see, e.g., Balzarini et al., supra).

It will be known to one of skill that, like many drugs, many of the agents useful for treatment of herpes virus infections are modified (i.e., "activated") by the host, host cell, or virus-infected host cell metabolic enzymes. For example, acyclovir is triphosphorylated to its active form, with the first phosphorylation being carried out by the herpes virus thymidine kinase, when present. Other examples are the reported conversion of the compound HOE 602 to ganciclovir in a three-step metabolic pathway (Winkler et al., 1990, *Antiviral Research* 14, 61–74) and the phosphorylation of ganciclovir to its active form by, e.g., a CMV nucleotide kinase. It will be apparent to one of skill that the specific metabolic capabilities of a virus can affect the sensitivity of that virus to specific drugs, and is one factor in the choice of an antiviral drug. The mechanism of action of certain anti-herpesvirus agents is discussed in De Clercq (1993, *Antimicrobial Chemotherapy* 32, Suppl. A, 121–132) and in other references cited supra and infra.

Anti-herpesvirus medications suitable for treating viral induced KS include, but are not limited to, nucleoside analogs including acyclic nucleoside phosphonate analogs (e.g., phosphonylmethoxyalkylpurines and -pyrimidines), and cyclic nucleoside analogs. These include drugs such as: vidarabine (9-β-D-arabinofuranosyladenine; adenine arabinoside, ara-A, Vira-A, Parke-Davis); 1-β-D-arabinofuranosyluracil (ara-U); 1-β-D-arabinofuranosylcytosine (ara-C); HPMPC [(S)-1-[3-hydroxy-2-(phosphonylmethoxy)propyl]cytosine (e.g., GS 504, Gilead Science)] and its cyclic form (cHPMPC); HPMPA [(S)-9-(3-hydroxy-2-phosphonylmethoxypropyl) adenine] and its cyclic form (cHPMPA); (S)-HPMPDAP [(S)-9-(3-hydroxy-2-phosphonylmethoxypropyl)-2,6-diaminopurine]; PMEDAP [9-(2-phosphonyl-methoxyethyl)-2,6-diaminopurine]; HOE 602 [2-amino-9-(1,3-bis (isopropoxy)-2-propoxymethyl)purine]; PMEA [9-(2-phosphonylmethoxyethyl)adenine]; bromovinyldeoxyuridine (Burns and Sandford, 1990, *J. Infect. Dis.* 162:634–7); 1-β-D-arabinofuranosyl-E-5-(2-bromovinyl)-uridine or -2'-deoxyuridine; BVaraU (1-β-D-arabinofuranosyl-E-5-(2-bromovinyl)-uracil, brovavir, Bristol-Myers Squibb, Yamsa Shoyu); BVDU [(E)-5-(2-bromovinyl)-2'-deoxyuridine, brivudin, e.g., Helpin] and its carbocyclic analogue (in which the sugar moiety is replaced by a cyclopentane ring); IVDU [(E)-5-(2-iodovinyl)-2'-deoxyuridine] and its carbocyclic analogue, C-IVDU (Balzarini et al., supra); and 5-mercutithio analogs of 2'-deoxyuridine (Holliday and Williams, 1992, *Antimicrob. Agents Chemother.* 36, 1935); acyclovir [9-([2-hydroxyethoxy]methyl)guanine; e.g., Zovirax (Burroughs Wellcome)]; penciclovir (9-[4-hydroxy-2-(hydroxymethyl) butyl]-guanine); ganciclovir [(9-[1,3-dihydroxy-2 propoxymethyl]-guanine) e.g., Cymevene, Cytovene (Syntex), DHPG (Stals et al., 1993, *Antimicrobial Agents Chemother.* 37, 218–223; isopropylether derivatives of ganciclovir (see, e.g., Winkelmann et al., 1988, *Drug Res.* 38, 1545–1548); cygalovir; famciclovir [2-amino-9-(4-acetoxy-3-(acetoxymethyl)but-1-yl)purine (Smithkline Beecham)]; valacyclovir (Burroughs Wellcome); desciclovir [(2-amino-9-(2-ethoxymethyl)purine)] and 2-amino-9-(2-hydroxyethoxymethyl)-9H-purine, prodrugs of acyclovir]; CDG (carbocyclic 2'-deoxyguanosine); and purine nucleosides with the pentafuranosyl ring replaced by a cyclo butane ring (e.g., cyclobut-A [(+–)-9- [1β, 2α, 3β)-2,3-bis (hydroxymethyl)-1-cyclobutyl]adenine], cyclobut-G [(+–)-9-[1β,2α, 3β)-2,3-bis(hydroxymethyl)-1-cyclobutyl]

guanine], BHCG [(R)-(1α, 2β, 1α)-9-(2 , 3-bis (hydroxymethyl) cyclobutyl]guanine], and an active isomer of racemic BHCG, SQ 34,514 [1R-1α, 2β, 3α)-2-amino-9-[2,3-bis(hydroxymethyl)cyclobutyl]-6H-purin-6-one (see, Braitman et al., 1991, *Antimicrob. Agents and Chemotherapy* 35, 1464–1468). Certain of these antiherpesviral agents are discussed in Gorach et al., 1992, *Infectious Disease Ch.*35, 289, W. B. Saunders, Philadelphia; Saunders et al., 1990, *J. Acquir. Immune Defic. Syndr.* 3, 571; Yamanaka et al., 1991, *Mol. Pharmacol.* 40, 446; and Greenspan et al., 1990, *J. Acquir. Immune Defic. Syndr.* 3, 571.

Triciribine and triciribine monophosphate are potent inhibitors against herpes viruses. (Ickes et al., 1994, *Antiviral Research* 23, Seventh International Conf. on Antiviral Research, Abstract No. 122, Supp. 1.), HIV-1 and HIV-2 (Kucera et al., 1993, *AIDS Res. Human Retroviruses* 9, 307–314) and are additional nucleoside analogs that may be used to treat KS. An exemplary protocol for these agents is an intravenous injection of about 0.35 mg/meter$^2$ (0.7 mg/kg) once weekly or every other week for at least two doses, preferably up to about four to eight weeks.

Acyclovir and ganciclovir are of interest because of their accepted use in clinical settings. Acyclovir, an acyclic analogue of guanine, is phosphorylated by a herpesvirus thymidine kinase and undergoes further phosphorylation to be incorporated as a chain terminator by the viral DNA polymerase during viral replication. It has therapeutic activity against a broad range of herpesviruses, Herpes simplex Types 1 and 2, Varicella- Zoster, Cytomegalovirus, and Epstein-Barr Virus, and is used to treat disease such as herpes encephalitis, neonatal herpesvirus infections, chickenpox in immunocompromised hosts, herpes zoster recurrences, CMV retinitis, EBV infections, chronic fatigue syndrome, and hairy leukoplakia in AIDS patients. Exemplary intravenous dosages or oral dosages are 250 mg/kg/m$^2$ body surface area, every 8 hours for 7 days, or maintenance doses of 200–400 mg IV or orally twice a day to suppress recurrence. Ganciclovir has been shown to be more active than acyclovir against some herpesviruses. See, e.g., Oren and Soble, 1991, *Clinical Infectious Diseases* 14, 741–6. Treatment protocols for ganciclovir are 5 mg/kg twice a day IV or 2.5 mg/kg three times a day for 10–14 days. Maintenance doses are 5–6 mg/kg for 5–7 days.

Also of interest is HPMPC. HPMPC is reported to be more active than either acyclovir or ganciclovir in the chemotherapy and prophylaxis of various HSV-1, HSV-2, TK- HSV, VZV or CMV infections in animal models (De Clercq, supra).

Nucleoside analogs such as BVaraU are potent inhibitors of HSV-1, EBV, and VZV that have greater activity than acyclovir in animal models of encephalitis. FIAC (fluroidoarbinosyl cytosine) and its related fluroethyl and iodo compounds (e.g. , FEAU, FIAU) have potent selective activity against herpesviruses, and HPMPA ((S)-1-([3-hydroxy-2-phosphorylmethoxy]propyl)adenine) has been demonstrated to be more potent against HSV and CMV than acyclovir or ganciclovir and are of choice in advanced cases of KS. Cladribine (2-chlorodeoxyadenosine) is another nucleoside analogue known as a highly specific antilymphocyte agent (i.e., a immunosuppressive drug).

Other useful antiviral agents include: 5-thien-2-yl-2'-deoxyuridine derivatives, e.g., BTDU [5–5(5-bromothien-2-yl)-2'-deoxyuridine] and CTDU [b-(5-chlorothien-2-yl)-2'-deoxyuridine]; and OXT-A [9-(2-deoxy-2-hydroxymethyl-β-D-erythro-oxetanosyl)adenine] and OXT-G [9-(2-deoxy-2-hydroxymethyl-β-D-erythrooxetanosyl)guanine]. Although OXT-G is believed to act by inhibiting viral DNA synthesis its mechanism of action has not yet been elucidated. These and other compounds are described in Andrei et al., 1992, *Eur. J. Clin. Microbiol. Infect. Dis.* 11, 143–51. Additional antiviral purine derivatives useful in treating herpesvirus infections are disclosed in U.S. Pat. No. 5,108,994 (assigned to Beecham Group P.L.C.). 6-Methoxypurine arabinoside (ara-M; Burroughs Wellcome) is a potent inhibitor of varicella-zoster virus, and will be useful for treatment of KS.

Certain thymidine analogs [e.g., idoxuridine (5-ido-2'-deoxyuridine)] and triflurothymidine) have antiherpes viral activity, but due to their systemic toxicity, are largely used for topical herpesviral infections, including HSV stromal keratitis and uveitis, and are not preferred here unless other options are ruled out.

Other useful antiviral agents that have demonstrated antiherpes viral activity include foscarnet sodium (trisodium phosphonoformate, PFA, Foscavir (Astra)) and phosphonoacetic acid (PAA). Foscarnet is an inorganic pyrophosphate analogue that acts by competitively blocking the pyrophosphate-binding site of DNA polymerase. These agents which block DNA polymerase directly without processing by viral thymidine kinase. Foscarnet is reported to be less toxic than PAA.

ii) Other Antivirals

Although applicants do not intend to be bound by a particular mechanism of antiviral action, the antiherpesvirus agents described above are believed to act through inhibition of viral DNA polymerase. However, viral replication requires not only the replication of the viral nucleic acid but also the production of viral proteins and other essential components. Accordingly, the present invention contemplates treatment of KS by the inhibition of viral proliferation by targeting viral proteins other than DNA polymerase (e.g., by inhibition of their synthesis or activity, or destruction of viral proteins after their synthesis). For example, administration of agents that inhibit a viral serine protease, e.g., such as one important in development of the viral capsid will be useful in treatment of viral induced KS.

Other viral enzyme targets include: OMP decarboxylase inhibitors (a target of, e.g., parazofurin), CTP synthetase inhibitors (targets of, e.g., cyclopentenylcytosine), IMP dehydrogenase, ribonucleotide reductase (a target of, e.g., carboxyl-containing N-alkyldipeptides as described in U.S. Pat. No. 5,110,799 (Tolman et al., Merck)), thymidine kinase (a target of, e.g., 1-[2-(hydroxymethyl) cycloalkylmethyl]-5-substituted-uracils and -guanines as described in, e.g., U.S. Pat. Nos. 4,863,927 and 4,782,062 (Tolman et al., Merck) as well as other enzymes. It will be apparent to one of ordinary skill in the art that there are additional viral proteins, both characterized and as yet to be discovered, that can serve as target for antiviral agents.

Kutapressin is a liver derivative available from Schwarz Parma of Milwaukee, Wis. in an injectable form of 25 mg/ml. The recommended dosage for herpesviruses is from 200 to 25 mg/ml per day for an average adult of 150 pounds.

Poly(I) Poly($C_{12}U$), an accepted antiviral drug known as Ampligen from HEM Pharmaceuticals of Rockville, Md. has been shown to inhibit herpesviruses and is another antiviral agent suitable for treating KS. Intravenous injection is the preferred route of administration. Dosages from about 100 to 600 mg/m$^2$ are administered two to three times weekly to adults averaging 150 pounds. It is best to administer at least 200 mg/m$^2$ per week.

Other antiviral agents reported to show activity against herpes viruses (e.g., varicella zoster and herpes simplex) and will be useful for the treatment of herpesvirus-induced KS include mappicine ketone (SmithKline Beecham); Compounds A,79296 and A,73209 (Abbott) for varicella zoster, and Compound 882C87 (Burroughs Wellcome) (see, *The Pink Sheet* 55(20) May 17, 1993).

Interferon is known inhibit replication of herpes viruses. See Oren and Soble, supra. Interferon has known toxicity problems and it is expected that second generation derivatives will soon be available that will retain interferon's antiviral properties but have reduced side affects.

It is also contemplated that herpes virus-induced KS may be treated by administering a herpesvirus reactivating agent to induce reactivation of the latent virus. Preferably the reactivation is combined with simultaneous or sequential administration of an anti-herpesvirus agent. Controlled reactivation over a short period of time or reactivation in the presence of an antiviral agent is believed to minimize the adverse effects of certain herpesvirus infections (e.g., as discussed in PCT Application WO 93/04683). Reactivating agents include agents such as estrogen, phorbol esters, forskolin and β-adrenergic blocking agents.

Agents useful for treatment of herpesvirus infections and for treatment of herpesvirus-induced KS are described in numerous U.S. Patents. For example, ganciclovir is an example of a antiviral guanine acyclic nucleotide of the type described in U.S. Pat. Nos. 4,355,032 and 4,603,219.

Acyclovir is an example of a class of antiviral purine derivatives, including 9 -(2-hydroxyethylmethyl)adenine, of the type described in U.S. Pat. Nos. 4,287,188, 4,294,831 and 4,199,574.

Brivudin is an example of an antiviral deoxyuridine derivative of the type described in U.S. Pat. No. 4,424,211.

Vidarabine is an example of an antiviral purine nucleoside of the type described in British Pat. 1,159,290.

Brovavir is an example of an antiviral deoxyuridine derivative of the type described in U.S. Pat. Nos. 4,542,210 and 4,386,076.

BHCG is an example of an antiviral carbocyclic nucleoside analogue of the type described in U.S. Pat. Nos. 5,153,352, 5,034,394 and 5,126,345.

HPMPC is an example of an antiviral phosphonyl methoxyalkyl derivative with of the type described in U.S. Pat. No. 5,142,051.

CDG (Carbocyclic 2'-deoxyguanosine) is an example of an antiviral carbocyclic nucleoside analogue of the type described in U.S. Pat. Nos. 4,543,255, 4,855,466, and 4,894,458.

Foscarnet is described in U.S. Pat. No. 4,339,445.

Trifluridine and its corresponding ribonucleoside is described in U.S. Pat. No. 3,201,387.

U.S. Pat. No. 5,321,030 (Kaddurah-Daouk et al.; Amira) describes the use of creatine analogs as antiherpes viral agents. U.S. Pat. No. 5,306,722 (Kim et al.; Bristol-Meyers Squibb) describes thymidine kinase inhibitors useful for treating HSV infections and for inhibiting herpes thymidine kinase. Other antiherpesvirus compositions are described in U.S. Pat. Nos. 5,286,649 and 5,098,708 (Konishi et al., Bristol-Meyers Squibb) and 5,175,165 (Blumenkopf et al.; Burroughs Wellcome). U.S. Pat. No. 4,880,820 (Ashton et al., Merck) describes the antiherpes virus agent (S)-9-(2,3-dihydroxy-1-propoxymethyl)guanine.

U.S. Pat. No. 4,708,935 (Suhadolnik et al., Research Corporation) describes a 3'-deoxyadenosine compound effective in inhibiting HSV and EBV. U.S. Pat. No. 4,386,076 (Machida et al., Yamasa Shoyu Kabushiki Kaisha) describes use of (E)-5-(2-halogenovinyl)-arabinofuranosyluracil as an antiherpesvirus agent. U.S. Pat. No. 4,340,599 (Lieb et al., Bayer Aktiengesellschaft) describes phosphonohydroxyacetic acid derivatives useful as antiherpes agents. U.S. Pat. Nos. 4,093,715 and 4,093,716 (Lin et al., Research Corporation) describe 5'-amino-5'-deoxythymidine and 5-iodo-5'-amino-2', 5'-dideoxycytidine as potent inhibitors of herpes simplex virus. U.S. Pat. No. 4,069,382 (Baker et al., Parke, Davis & Company) describes 9-(5-O-Acyl-beta-D-arabinofuranosyl)adenine compounds useful as antiviral agents. U.S. Pat. No. 3,927,216 (Witkowski et al.) describes the use of 1,2,4- triazole-3-carboxamide and 1,2,4-triazole-3-thiocarboxamide for inhibiting herpes virus infections. U.S. Pat. No. 5,179,093 (Afonso et al., Schering) describes quinoline-2,4-dione derivatives active against herpes simplex virus 1 and 2, cytomegalovirus and Epstein Barr virus.

iii) Administration

The subjects to be treated or whose tissue may be used herein may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with Kaposi's sarcoma or a subject infected with a DNA virus associated with Kaposi's sarcoma.

The antiviral compositions for treating herpesvirus-induced KS are preferably administered to human patients via oral, intravenous or parenteral administrations and other systemic forms. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

V. Immunological Approaches to Therapy

Having identified a primary causal agent of KS in humans as a novel human herpesvirus, there are immunosuppressive therapies that can modulate the immunologic dysfunction that arises from the presence of viral-infected tissue. In particular, agents that block the immunological attack of the viral-infected cells will ameliorate the symptoms of KS and/or reduce disease progression. Such therapies include antibodies that prevent immune system targeting of viral-infected cells. Such agents include antibodies which bind to cytokines that otherwise upregulate the immune system in response to viral infection.

The antibody may be administered to a patient either singly or in a cocktail containing two or more antibodies, other therapeutic agents, compositions, or the like, including, but not limited to, immunosuppressive agents, potentiators and side-effect relieving agents. Of particular interest are immunosuppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the *Physician Desk Reference*, 41st Ed. (1987), Publisher Edward R. Barnhart, New Jersey.

Immune globulin from persons previously infected with human herpesviruses or related viruses can be obtained using standard techniques. Appropriate titers of antibodies are known for this therapy and are readily applied to the treatment of KS. Immune globulin can be administered via parenteral injection or by intrathecal shunt. In brief, immune globulin preparations may be obtained from individual donors who are screened for antibodies to the KS-associated human herpesvirus, and plasmas from high-titered donors are pooled. Alternatively, plasmas from donors are pooled and then tested for antibodies to the human herpesvirus of the invention; high-titered pools are then selected for use in KS patients.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously or intraperitoneally or directly into KS lesions. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared.

Systemic administration of antibody is made daily, generally by intramuscular injection, although intravascular infusion is acceptable. Administration may also be intranasal or by other nonparenteral routes. Antibody or immunotoxin may also be administered via microspheres, liposomes or other microparticulate delivery systems placed in certain tissues including blood.

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of KS without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

VI. Vaccines and Prophylaxis for KS

This invention provides substances suitable for use as vaccines for the prevention of KS and methods for administering them. The vaccines are directed against KSHV and most preferably comprise antigens obtained from KSHV. In one embodiment, the vaccine contains attenuated KSHV. In another embodiment, the vaccine contains killed KSHV. In another embodiment, the vaccine contains a nucleic acid vector encoding a KSHV polypeptide. In another embodiment, the vaccine is a subunit vaccine containing a KSHV polypeptide.

This invention provides a recombinant KSHV virus with a gene encoding a KSHV polypeptide deleted from the genome. The recombinant virus is useful as an attenuated vaccine to prevent KSHV infection.

This invention provides a method of vaccinating a subject against Kaposi's sarcoma, comprising administering to the subject an effective amount of the peptide or polypeptide encoded by the isolated DNA molecule, and a suitable acceptable carrier, thereby vaccinating the subject. In one embodiment naked DNA is administered to the subject in an effective amount to vaccinate the subject against Kaposi's sarcoma.

This invention provides a method of immunizing a subject against disease caused by KSHV which comprises administering to the subject an effective immunizing dose of an isolated herpesvirus subunit vaccine.

A. Vaccines

The vaccine can be made using synthetic peptide or recombinantly-produced polypeptide described above as antigen. Typically, a vaccine will include from about 1 to 50 micrograms of antigen. More preferably, the amount of polypeptide is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049. More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques," *Bioconjugate Chem.* 1, 2–12 (1990).

Vaccines against a number of the Herpesviruses have been successfully developed. Vaccines against Varicella-Zoster Virus using a live attenuated Oka strain is effective in preventing herpes zoster in the elderly, and in preventing chickenpox in both immunocompromised and normal children (Hardy, I., et al., 1990, *Inf. Dis. Clin. N. Amer.* 4, 159; Hardy, I. et al., 1991, *New Engl. J. Med.* 325, 1545; Levin, M. J. et al., 1992, *J. Inf. Dis.* 166, 253; Gershon, A. A., 1992, *J. Inf. Des.* 166(Suppl), 563. Vaccines against Herpes simplex Types 1 and 2 are also commercially available with some success in protection against primary disease, but have been less successful in preventing the establishment of latent infection in sensory ganglia (Roizman, B., 1991, *Rev. Inf. Disease* 13(Suppl. 11), S892; Skinner, G. R. et al., 1992, *Med. Microbiol. Immunol.* 180, 305).

Vaccines against KSHV can be made from the KSHV envelope glycoproteins. These polypeptides can be purified and used for vaccination (Lasky, L. A., 1990, *J. Med. Virol.* 31, 59). MHC-binding peptides from cells infected with the human herpesvirus can be identified for vaccine candidates per the methodology of Marloes, et al., 1991, *Eur J. Immunol.* 21, 2963–2970.

The KSHV antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionibacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 $\mu$g to about 100 $\mu$g protein per patient. A preferable range is from about 1 $\mu$g to about 50 $\mu$g per dose. A more preferred range is about 15 $\mu$g to about 45 $\mu$g. A suitable dose size is about 0.5 ml. Accordingly, a dose for intramuscular injection, for example, would comprise 0.5 ml containing 45 $\mu$g of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral polypeptides from the human herpesvirus. For example, it is known in the protein art that certain amino acid residues can be substituted with amino acids of similar size and polarity without an undue effect upon the biological activity of the protein. The human herpesvirus polypeptides have significant tertiary structure and the epitopes are usually conformational. Thus, modifications should generally preserve conformation to produce a protective immune response.

B. Antibody Prophylaxis

Therapeutic, intravenous, polyclonal or monoclonal antibodies can been used as a mode of passive immunotherapy of herpesviral diseases including perinatal varicella and CMV. Immune globulin from persons previously infected with the human herpesvirus and bearing a suitably high titer of antibodies against the virus can be given in combination with antiviral agents (e.g. ganciclovir), or in combination with other modes of immunotherapy that are currently being evaluated for the treatment of KS, which are targeted to modulating the immune response (i.e. treatment with copolymer-1, antiidiotypic monoclonal antibodies, T cell "vaccination"). Antibodies to human herpesvirus can be administered to the patient as described herein. Antibodies specific for an epitope expressed on cells infected with the human herpesvirus are preferred and can be obtained as described above.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

C. Monitoring Therapeutic Efficacy

This invention provides a method for monitoring the therapeutic efficacy of treatment for Kaposi's sarcoma which comprises: (a) determining in a first sample from a subject with Kaposi's sarcoma the presence of the isolated nucleic acid molecule; (b) administering to the subject a therapeutic amount of an agent such that the agent is contacted to the cell in a sample; (c) determining after a suitable period of time the amount of the isolated nucleic acid molecule in the second sample from the treated subject; and (d) comparing the amount of isolated nucleic acid molecule determined in the first sample with the amount determined in the second sample, a difference indicating the effectiveness of the agent, thereby monitoring the therapeutic efficacy of treatment for Kaposi's sarcoma. As defined herein "amount" is viral load or copy number. Methods of determining viral load or copy number are known to those skilled in the art.

VII. Screening Assays For Pharmaceuticals for Alleviating the Symptoms of KS

Since an agent involved in the causation or progression of KS has been identified and described, assays directed to identifying potential pharmaceutical agents that inhibit the biological activity of the agent are possible. KS drug screening assays which determine whether or not a drug has activity against the virus described herein are contemplated in this invention. Such assays comprise incubating a compound to be evaluated for use in KS treatment with cells which express the KS associated human herpesvirus polypeptides or peptides and determining therefrom the effect of the compound on the activity of such agent. In vitro assays in which the virus is maintained in suitable cell culture are preferred, though in vivo animal models would also be effective.

Compounds with activity against the agent of interest or peptides from such agent can be screened in in vitro as well as in vivo assay systems. In vitro assays include infecting peripheral blood leukocytes or susceptible T cell lines such as MT-4 with the agent of interest in the presence of varying concentrations of compounds targeted against viral replication, including nucleoside analogs, chain terminators, antisense oligonucleotides and random polypeptides (Asada et al., 1989, *J. Clin. Microbiol.* 27, 2204; Kikuta et al., 1989, *Lancet Oct.* 7, 861). Infected cultures and their supernatants can be assayed for the total amount of virus including the presence of the viral genome by quantitative PCR, by dot blot assays or by using immunologic methods. For example, a culture of susceptible cells could be infected with KSHV in the presence of various concentrations of drug, fixed on slides after a period of days, and examined for viral antigen by indirect immunofluorescence with monoclonal antibodies to viral polypeptides (Kikuta et al., supra). Alternatively, chemically adhered MT-4 cell monolayers can be used for an infectious agent as say using indirect immunofluorescent antibody staining to search for focus reduction (Higashi et al., 1989, *J. Clin. Micro.* 27, 2204).

As an alternative to whole cell in virro assays, purified KSHV enzymes isolated from a host cell or produced by recombinant techniques can be used as targets for rational drug design to determine the effect of the potential drug on enzyme activity. KSHV enzymes amenable to this approach include, but are not limited to, dihydrofolate reductase (DHFR), thymidylate synthase (TS), thymidine kinase or DNA polymerase. A measure of enzyme activity indicates effect on the agent itself.

Drug screens using herpes viral products are known and have been previously described in EP 0514830 (herpes proteases) and WO 94/04920 ($U_L13$ gene product)

This invention provides an assay for screening anti-KS chemotherapeutics. Infected cells can be incubated in the presence of a chemical agent that is a potential chemotherapeutic against KS (e.g., acyclo-guanosine) The level of virus in the cells is then determined after several days by immunofluorescence assay for antigens, Southern blotting for viral genome DNA or Northern blotting for mRNA and compared to control cells. This assay can quickly screen large numbers of chemical compounds that may be useful against KS.

Further, this invention provides an assay system that is employed to identify drugs or other molecules capable of binding to the nucleic acid molecule or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

This invention provides a method of screening for a KSHV-selective antiviral drug in vivo comprising: (a) expression of KSHV DHFR or KSHV TS in a bacterial auxotroph (nutritional mutant); (b) measuring bacterial growth rate in the absence and presence of the drug; and (c) comparing the rates so measured so as to identify the drug that inhibits KSHV DHFR or KSHV TS in vivo.

Methods well known to those skilled in the art allow selection or production of a suitable bacterial auxotroph and measurement of bacterial growth.

The following reviews of antifolate compounds are provided to more fully describe the state of the art, particularly as it pertains to inhibitors of dihydrofolate reductase and thymidylate synthase: (a) Unger, 1996, Current concepts of treatment in medical oncology: new anticancer drugs, *Journal of Cancer Research & Clinical Oncology* 122, 189–198; (b) Jackson, 1995, Toxicity prediction from metabolic pathway modelling, *Toxicology* 102, 197–205; (c) Schultz, 1995, Newer antifolates in cancer therapy, *Progress in Drug Research* 44, 129–157; (d) van der Wilt and Peters, 1994, New targets for pyrimidine antimetabolites in the treatment of solid tumours 1: Thymidylate synthase, *Pharm World Sci* 16, 167; (e) Fleisher, 1993, Antifolate analogs: mechanism of action, analytical methodology, and clinical efficacy, *Therapeutic Drug Monitoring* 15, 521–526; (f) Eggott et al., 1993, Antifolates in rheumatoid arthritis: a hypothetical mechanism of action, *Clinical & Experimental Rheumatology* 11 Suppl 8, S101–S105; (g) Huennekens et al., 1992, Membrane transport of folate compounds, *Journal of Nutritional Science & Vitaminology* Spec No, 52–57; (h) Fleming and Schilsky, 1992, Antifolates: the next generation, *Seminars in Oncology* 19, 707–719; and (i) Bertino et al., 1992, Enzymes of the thymidylate cycle as targets for chemotherapeutic agents: mechanisms of resistance, *Mount Sinai Journal of Medicine* 59, 391–395.

This invention provides a method of determining the health of a subject with AIDS comprising: (a) measuring the plasma concentration of vMIP-I, vMIP-II or vMIP-III; and (b) comparing the measured value to a standard curve relating AIDS clinical course to the measured value so as to determine the health of the subject.

VIII. Treatment of HIV

This invention provides a method of inhibiting HIV replication, comprising administering to the subject or treating cells of a subject with an effective amount of a polypeptide which is encoded by a nucleic acid molecule, so as to inhibit replication of HIV. In one embodiment, the polypeptide is one from the list provided in Table 1.

This invention is further illustrated in the Experimental Details Sections which follow. These sections are set forth to aid in understanding the invention but is not intended to, and should not be construed to, limit in any way the invention as set forth in the claims which follow thereafter.

EXPERIMENTAL DETAILS SECTION I

NUCLEOTIDE SEQUENCE OF THE KAPOSI'S SARCOMA-ASSOCIATED HERPESVIRUS

The genome of the Kaposi's sarcoma-associated herpesvirus (KSHV or HHV8) was mapped with cosmid and phage genomic libraries from the BC-1 cell line. Its nucleotide sequence was determined except for a 3 kb region at the right end of the genome that was refractory to cloning. The BC-1 KSHV genome consists of a 140.5 kb long unique coding region (LUR) flanked by multiple G+C rich 801 bp terminal repeat sequences. A genomic duplication that apparently arose in the parental tumor is present in this cell culture-derived strain. At least 81 open reading frames (ORFs), including 66 with similarity to herpesvirus saimiri ORFs, and 5 internal repeat regions are present in the LUR. The virus encodes genes similar to complement-binding proteins, three cytokines (two macrophage inflammatory proteins and interleukin-6), dihydrofolate reductase, bcl-2, interferon regulatory factor, IL-8 receptor, NCAM-like adhesin, and a D-type cyclin, as well as viral structural and metabolic proteins. Terminal repeat analysis of virus DNA from a KS lesion suggests a monoclonal expansion of KSHV in the KS tumor. The complete genome sequence is set forth in Genbank Accession Numbers U75698 (LUR), U75699 (TR) and U75700 (ITR).

Kaposi's sarcoma is a vascular tumor of mixed cellular composition (Tappero et al., 1993, *J. Am. Acad. Dermatol.* 28, 371–395). The histology and relatively benign course in persons without severe immunosuppression has led to suggestions that KS tumor cell proliferation is cytokine induced (Ensoli et al., 1992, *Immunol. Rev.* 127, 147–155). Epidemiologic studies indicate the tumor is under strict immunologic control and is likely to be caused by a sexually transmitted infectious agent other than HIV (Peterman et al., 1993, *AIDS* 7, 605–611). KS-associated herpesvirus (KSHV) was discovered in an AIDS-KS lesion by representational difference analysis (RDA) and shown to be present in almost all AIDS-KS lesions (Chang et al., 1994, *Science* 265, 1865–1869). These findings have been confirmed and extended to nearly all KS lesions examined from the various epidemiologic classes of KS (Boshoff et al., 1995, *Lancet* 345, 1043–1044; Dupin et al., 1995, *Lancet* 345, 761–762; Moore and Chang, 1995, *New Eng. J. Med.* 332, 1181–1185; Schalling et al., 1995, *Nature Med.* 1, 707–708; Chang et al., 1996, *Arch. Int. Med.* 156, 202–204). KSHV is the eighth presumed human herpesvirus (HHV8) identified to date.

The virus was initially identifed from two herpesvirus DNA fragments, KS330Bam and KS631Bam (Chang et al., 1994, *Science* 265, 1865–1869). Subsequent sequencing of a 21 kb AIDS-KS genomic library fragment (KS5) hybridizing to KS330Bam demonstrated that KSHV is a gammaherpesvirus related to herpesvirus saimiri (HVS) belonging to the genus Rhadinovirus (Moore et al., 1996, *J. Virol.* 70, 549–558). Colinear similarity (synteny) of genes in this region is maintained between KSHV and HVS, as well as Epstein-Barr virus (EBV) and equine herpesvirus 2 (EHV2). A 12 kb region (L54 and SGL-1) containing the KS631Bam sequence includes cyclin D and IL-8Ra genes unique to rhadinoviruses.

KSHV is not readily transmitted to uninfected cell lines (Moore et al., 1996, *J. Virol.* 70, 549–558), but it is present in a rare B cell primary effusion (body cavity-based) lymphoma (PEL) frequently associated with KS (Cesarman et al., 1995, *New Eng. J. Med.* 332, 1186–1191). BC-1 is a PEL cell line containing a high KSHV genome copy number and is coinfected with EBV (Cesarman et al., 1995, *Blood* 86, 2708–2714). The KSHV genome form in BC-1 and its parental tumor comigrates with 270 kb linear markers on pulsed field gel electrophoresis (PFGE) (Moore et al., 1996, *J. Virol.* 70, 549–558). However, the genome size based on encapsidated DNA from an EBV-negative cell line (Renne et al., 1996, *Nature Med.* 2, 342–346) is estimated to be 165 kb (Moore et al., 1996, *J. Virol.* 70, 549–558). Estimates from KS lesions indicate a genome size larger than that of EBV (172 kb) (Decker et al., 1996, *J. Exp. Med.* 184, 283–288).

To determine the genomic sequence of KSHV and identify novel virus genes, contiguous overlapping virus DNA inserts from BC-1 genomic libraries were mapped. With the exception of a small, unclonable repeat region at its right end, the genome was sequenced to high redundancy allowing definition of the viral genome structure and identification of genes that may play a role in KSHV-related pathogenesis.

MATERIALS AND METHODS

Library generation and screening. BC-1, HBL-6 and BCP-1 cells were maintained in RPMI 1640 with 20% fetal calf serum (Moore et al., 1996, *J. Virol.* 70, 549–558; Cesarman et al., 1995, *Blood* 86, 2708–2714; Gao et al., 1996, *Nature Med.* 2, 925–928). DNA from BC-1 cells was commercially cloned (Sambrook et al., 1989, *Molecular*

*Cloning: A laboratory manual*, Cold Spring Harbor Press, Salem, Mass.) into either Lambda FIX II or S-Cosl vectors (Stratagene, La Jolla, Calif.). Phage and cosmid libraries were screened by standard methods (Benton et al., 1977, *Science* 196, 180–182; Hanahan and Meselson, 1983, *Methods Enzymol*. 100, 333–342).

Initial library screening was performed using the KS330Bam and KS631Bam RDA fragments (Chang et al., 1994, *Science* 265; 1865–1869). Overlapping clones were sequentially identified using probes synthesized from the ends of previously identified clones (FIG. 1) (Feinberg and vogelstein, 1983, *Anal. Biochem*. 132, 6; Melton et al., 1984, *Nucl. Acids Res*. 12, 7035–7056). The map was considered circularly permuted by the presence of multiple, identical TR units in cosmids Z2 and Z6. Each candidate phage or cosmid was confirmed by tertiary screening.

Shotgun sequencing and sequence verification

Lambda and cosmid DNA was purified by standard methods (Sambrook et al., 1989, *Molecular Cloning: A laboratory manual*, Cold Spring Harbor Press, Salem, Mass.). Shotgun sequencing (Deininger, 1983, *Anal. Biochem*. 129, 216–223; Bankier et al., 1987, *Meth. Enzymol*. 155, 51–93) was performed on sonicated DNA. A 1–4 kb fraction was subcloned into M13mpl9 (New England Biolabs, Inc., Beverly, Mass.) and propagated in XL1-Blue cells (Stratagene, La Jolla, Calif.) (Sambrook et al., 1989, *Molecular Cloning: A laboratory manual*, Cold Spring Harbor Press, Salem, Mass.) M13 phages were positively screened using insert DNA from the phage or cosmid, and negatively screened with vector arm DNA or adjacent genome inserts.

Automated dideoxy cycle sequencing was performed with M13 (-21) CS+ or FS dye primer kits (Perkin-Elmer, Branchburg N.J.) on ABI 373A or 377 sequenators (ABI, Foster City, Calif.). Approximately 300 M13 sequences were typically required to achieve initial coverage for each 10 kb of insert sequence. Minimum sequence fidelity standards were defined as complete bidirectional coverage with at least 4 overlapping sequences at any given site. For regions with sequence gaps, ambiguities or frameshifts that did not meet these criteria, primer walking was done with custom primers (Perkin-Elmer) and dye terminator chemistry (FS or Ready Reaction kits, Perkin-Elmer). An unsequenced 3 kb region adjacent to the right end TR sequence in the Z2 cosmid insert could not be cloned into M13 or Bluescript despite repeated efforts.

Sequence assembly and open reading frame analysis

Sequence data were edited using Factura (ABI, Foster City, Calif.) and assembled into contiguous sequences using electropherograms with AutoAssembler (ABI, Foster City, Calif.) and into larger assemblies with AssemblyLIGN (IBI-Kodak, Rochester N.Y.). Base positions not clearly resolved by multiple sequencing attempts (less than 10 bases in total) were assigned the majority base pair designation. The entire sequence (in 1–5 kb fragments) and all predicted open reading frames (ORFs) were analyzed using BLASTX, BLASTP and BLASTN (Altschul et al., 1990, *J. Mol. Biol*. 215, 403–410). The sequence was further analyzed using MOTIFS (Moore et al., 1996, *J. Virol*. 70, 549–558), REPEAT and BESTFIT (GCG), and MacVector (IBI, New Haven, Conn.).

ORF assignment and nomenclature

All ORFs with similarities to HVS were identified. These and other potential ORFs having >100 amino acids were found using MacVector. ORFs not similar to HVS ORFs were included in the map (FIG. 1) based on similarity to other known genes, optimum initiation codon context (Kozak, 1987, *Nucl. Acids Res*. 15, 8125–8148), size and position. Conservative selections were made to minimize spurious assignments; this underestimates the number of true reading frames. KSHV ORF nomenclature is based on HVS similarities; KSHV ORFs not similar to HVS genes are numbered in consecutive order with a K prefix. ORFs with sequence but not positional similarity to HVS ORFs were assigned the HVS ORF number (e.g., ORF 2). As new ORFs are identified, it is suggested that they be designated by decimal notation. The standard map orientation (FIG. 1) of the KSHV genome is the same as for HVS (Albrecht et al., 1992, *J. Virol*. 66, 5047–5058) and EHV2 (Telford et al., 1995, *J. Mol. Biol*. 249, 520–528), and reversed relative to the EBV standard map (Baer et al., 1984, *Nature* 310, 207–211).

RESULTS

Genomic mapping and sequence characteristics

Complete genome mapping was achieved with 7 lambda and 3 cosmid clones (FIG. 1). The structure of the BC-1 KSHV genome is similar to HVS in having a long unique region (LUR) flanked by TR units. The ~140.5 kb LUR sequence has 53.5% G+C content and includes all identified KSHV ORFs. TR regions consist of multiple 801 bp direct repeat units having 84.5% G+C content (FIG. 2A) with potential packaging and cleavage sites. Minor sequence variations are present among repeat units. The first TR unit at the left (Z6) TR junction (205bp) is deleted and truncated in BC-1 compared to the prototypical TR unit.

The genome sequence abutting the right terminal repeat region is incomplete due to a 3 kb region in the Z2 cosmid insert that could not be cloned into sequencing vectors. Partial sequence information from primer walking indicates that this region contains stretches of 16 bp A+G rich imperfect direct repeats interspersed with at least one stretch of 16 bp C+T rich imperfect direct repeats. These may form a larger inverted repeat that could have contributed to our difficulty in subcloning this region. Greater than 12-fold average sequence redundancy was achieved for the entire LUR with complete bidirectional coverage by at least 4 overlapping reads except in the unclonable region.

The BC-1 TR region was examined by Southern blotting since sequencing of the entire region is not possible due to its repeat structure. BC-1, BCP-1 (an EBV-negative, KSHV infected cell line) and KS lesion DNAs have an intense ~800 bp signal consistent with the unit length repeat sequence when digested with enzymes that cut once in the TR and hybridized to a TR probe (FIGS. 2B and 2C). Digestion with enzymes that do not cut in the TR indicates that the BC-1 strain contains a unique region buried in the TR, flanked by ~7 kb and ~35 kb TR sequences (FIGS. 2C and 2D). An identical pattern occurs in HBL-6, a cell line independently derived from the same tumor as BC-1, suggesting that this duplication was present in the parental tumor (FIGS. 2C and 2D). The restriction pattern with Not I, which also cuts only once within the TR but rarely within the LUR, suggests that the buried region is at least 33 kb. Partial sequencing of this region demonstrates that it is a precise genomic duplication of the region beginning at ORF K8. The LUR is 140 kb including the right end unsequenced gap (<3kb). The estimated KSHV genomic size in BC-1 and HBL-6 (including the duplicated region) is approximately 210 kb.

Based on the EBV replication model used in clonality studies (Raab-Traub and Flynn, 1986, *Cell* 47, 883–889), the polymorphic BCP-1 laddering pattern may reflect lytic virus replication and superinfection (FIG. 2C). The EBV laddering pattern occurs when TR units are deleted or duplicated during lytic replication and is a stochastic process for each infected cell (Raab-Traub and Flynn, 1986, *Cell* 47, 883–889). No laddering is present for BC-1 which is under tight latent KSHV replication control (Moore et al., 1996, *J. Virol.* 70, 549–558). KS lesion DNA also shows a single hybridizing band suggesting that virus in KS tumor cells may be of monoclonal origin.

Features and coding regions of the KSHV LUR

The KSHV genome shares the 7 block (B) organization (B1-B7, FIG. 1) of other herpesviruses (Chee et al., 1990, *Curr. Topics Microbiol. Immunol.* 154, 125–169), with subfamily specific or unique ORFs present between blocks (interblock regions (IB) a–h, FIG. 1). ORF analysis indicates that only 79% of the sequenced 137.5 kb LUR encodes 81 identifiable ORFs which is likely to be due to a conservative assignment of ORF positions. The overall LUR CpG dinucleotide observed/expected (O/E) ratio is 0.75 consistent with a moderate loss of methylated cytosines, but there is marked regional variation. The lowest CpG O/E ratios (<0.67) occur in IBa (bp 1–3200), in B5 (68,602–69,405) and IBh (117,352–137,507). The highest O/E ratios (>0.88) extend from B2 to B3 (30,701–47,849), in IBe (67,301–68,600), and in B6 (77,251–83,600). Comparison to the KS5 sequence (Moore et al., 1996, *J. Virol.* 70, 549–558) shows a high sequence conservation between these two strains with only 21 point mutations over the comparable 20.7 kb region (0.1%). A frameshift within BC-1 ORF 28 (position 49,004) compared to KS5 ORF 28 was not resolvable despite repeated sequencing of KS5 and PCR products amplified from BC-1. Two additional frameshifts in noncoding regions (bp 47,862 and 49,338) are also present compared to the KS5 sequence.

Several repeat regions are present in the LUR (FIG. 1). A 143 bp sequence is repeated within ORF K11 at positions 92,678–92,820 and 92,852–92,994 (waka/jwka). Complex repeats are present in other regions of the genome: 20 and 30 bp repeats in the region from 24,285–24,902 (frnk), a 13 bp repeat between bases 29,775 and 29,942 (vnct), two separate 23 bp repeat stretches between bases 118,123 and 118,697 (zppa), and 15 different 11–16 bp repeats throughout the region from 124,527 to 126,276 (moi). A complex A-G rich repeat region (mdsk) begins at 137,099 and extends into the unsequenced gap.

Conserved ORFs with similar genes found in other herpesviruses are listed in Table 1, along with their polarity, map positions, sizes, relatedness to HVS and EBV ORFs, and putative functions. Conserved ORFs coding for viral structural proteins and enzymes include genes involved in viral DNA replication (e.g., DNA polymerase (ORF 9)), nucleotide synthesis (e.g., dihydrofolate reductase (DHFR, ORF 2), thymidylate synthase (TS, ORF 70)), regulators of gene expression (R transactivator (LCTP, ORF50)) and 5 conserved herpesvirus structural capsid and 5 glycoprotein genes.

Several genes that are similar to HVS ORFs also have unique features. ORF 45 has sequence similarity to nuclear and transcription factors (chick nucleolin and yeast SIR3) and has an extended acidic domain typical for transactivator proteins between amino acids 90 and 115. ORF73 also has an extended acidic domain separated into two regions by a glutamine-rich sequence encoded by the moi repeat. The first region consists almost exclusively of aspartic and glutamic acid residue repeats while the second glutamic acid rich region has a repeated leucine heptad motif suggestive of a leucine zipper structure. ORF 75, a putative tegument protein, has a high level of similarity to the purine biosynthetic enzyme of *E. coli* and *D. melanogaster* N-formylglycinamide ribotide amidotransferase (FGARAT).

ORFs K3 and K5 are not similar to HVS genes but are similar to the major immediate early bovine herpesvirus type 4 (BHV4) gene IE1 (12 and 13% identity respectively) (van Santen, 1991, *J. Virol.* 65, 5211–5224). These genes have no significant similarity to the herpes simplex virus I (HSV1) a0 (which is similar to BHV4 IE1), but encode proteins sharing with the HSV1 ICP0 protein a cysteine-rich region which may form a zinc finger motif (van Santen, 1991, *J. Virol.* 65, 5211–5224). The protein encoded by ORF K5 has a region similar to the nuclear localization site present in the late form of the BHV4 protein. ORF K8 has a purine binding motif (GLLVTGKS) in the C-terminus of the protein which is similar to a motif present in the KSHV TK (ORF21) (Moore et al., 1996, *J. Virol.* 70, 549–558).

No KSHV genes with similarity to HVS ORFs 1, 3, 5, 12, 13, 14, 15, 51 and 71 were identified in the KSHV LUR sequence. HVS ORF 1 codes for a transforming protein, responsible for HVS-induced in vitro lymphocyte transformation (Akari et al., 1996, *Virology* 218, 382–388) and has poor sequence conservation among HVS strains (Jung and Desrosiers, 1991, *J. Virol.* 65, 6953–6960; Jung and Desrosiers, 1995, *Molec. Cellular Biol.* 15, 6506–6512). Functional KSHV genes similar to this gene may be present but were not identifiable by sequence comparison. Likewise, no KSHV genes similar to EBV latency and transformation-associated proteins (EBNA-1, EBNA-2, EBNA-LP, LMP-1, LMP-2 or gp350/220) were found despite some similarity to repeat sequences present in these genes. KSHV also does not have a gene similar to the BZLF1 EBV transactivator gene.

Several sequences were not given ORF assignments although they have characteristics of expressed genes. The sequence between bp 90,173 and 90,643 is similar to the precursor of secreted glycoprotein X (gX) encoded by a number of alphaherpesviruses (pseudorabies, EHV1), and which does not form part of the virion structure. Like the cognate gene in EHV1, the KSHV form lacks the highly-acidic carboxy terminus of the pseudorabies gene.

Two polyadenylated transcripts expressed at high copy number in BCBL-1 are present at positions 28,661–29,741 (T1.1) in IBb and 118,130–117,436 (T0.7) in IBh. T0.7 encodes a 60 residue polypeptide (ORF K12, also called Kaposin) and T1.1 (also referred to as nut-1) has been speculated to be a U RNA-like transcript.

Cell cycle regulation and cell signaling proteins

A number of ORFs which are either unique to KSHV or shared only with other gammaherpesviruses encode genes similar to oncoproteins and cell signaling proteins. ORF 16, similar to EBV BHRF1 and HVS ORF16, encodes a functional Bcl-2-like protein which can inhibit Bax-mediated apoptosis. ORF 72 encodes a functional cyclin D gene, also found in HVS (Nicholas et al., 1992, *Nature* 355, 362–365), that can substitute for human cyclin D in phosphorylating the retinoblastoma tumor suppressor protein.

KSHV encodes a functionally-active IL-6 (ORF K2) and two macrophage inflammatory proteins (MIPs) (ORFs K4 and K6) which are not found in other human herpesviruses. The vIL-6 has 62% amino acid similarity to the human IL-6 and can substitute for human IL-6 in preventing mouse myeloma cell apoptosis. Both MIP-like proteins have conserved C—C dimer signatures characteristic of β-chemokines and near sequence identity to human MIP-1α in their N-terminus regions. vMIP-I (ORF K6) can inhibit CCR-5 dependent HIV-1 replication. An open reading frame spanning nucleotide numbers (bp) 22,529–22,185 (vMIP-III) has low conservation with MIP 1β (BLASTX poisson p=0.0015) but retains the C—C dimer motif. ORF K9 (vIRF1) encodes a 449 residue protein with similarity to the family of interferon regulatory factors (IRF) (David, 1995, Pharmac. Ther. 65, 149–161). It has 13.4% amino acid identity to human interferon consensus sequence binding protein and partial conservation of the IRF DNA-binding domain. Three additional open reading frames at bp 88,910–88,410 (vIRF2), bp 90,541–89,600 (vIRF3) and bp 94,127–93,636 (vIRF4) also have low similarity to IRF-like proteins (p>0.35). No conserved interferon consensus sequences were found in this region of the genome.

Other genes encoding signal transduction polypeptides, which are also found in other herpesviruses, include a complement-binding protein (v-CBP, ORF 4), a neural cell adhesion molecule (NCAM)-like protein (v-adh, ORF K14) and an IL8 receptor (ORF 74). Genes similar to ORFs 4 and 74 are present in other rhadinoviruses and ORF 4 is similar to variola B19L and D12L proteins. ORF K14 (v-adh) is similar to the rat and human OX-2 membrane antigens, various NCAMs and the poliovirus receptor-related protein PRR1. OX-2 is in turn similar to ORF U85 of human herpesviruses 6 and 7 but there is no significant similarity between the KSHV and betaherpesvirus OX-2/NCAM ORFs. Like other immunoglobulin family adhesion proteins, v-adh has V-like, C-like, transmembrane and cytoplasmic domains, and an RGD binding site for fibronectin at residues 268–270. The vIL-8R has a seven transmembrane spanning domain structure characteristic of G-protein coupled chemoattractant receptors which includes the EBV-induced EBIL protein (Birkenbach et al., 1993, J. Virol. 67, 2209–2220).

DISCUSSION

The full-length sequence of the KSHV genome in BC-1 cells provides the opportunity to investigate molecular mechanisms of KSHV-associated pathogenesis. The KSHV genome has standard features of rhadinovirus genomes including a single unique coding region flanked by high G+C terminal repeat regions which are the presumed sites for genome circularization. In addition to having 66 conserved herpesvirus genes involved in herpesvirus replication and structure, KSHV is unique in encoding a number of proteins mimicking cell cycle regulatory and signaling proteins.

Our estimated size of the BC-1 derived genome (210 kb including the duplicated portion) is consistent with that found using encapsidated virion DNA (Zhong et al., 1996, Proc. Natl. Acad. Sci. USA 93, 6641–6646). Genomic rearrangements are common in cultured herpesviruses (Baer et al., 1984, Nature 310, 207–211; Cha et al., 1996, J. Virol. 70, 78–83). However, the genomic duplication present in the BC-1 KSHV probably did not arise during tissue culture passage. TR hybridization studies indicate that this insertion of a duplicated LUR fragment into the BC-1 TR is also present in KSHV from the independently derived HBL-6 cell line (Gaidano et al., 1996, Leukemia 10, 1237–40).

Despite this genomic rearrangement, the KSHV genome is well conserved within coding regions. There is less than 0.1% base pair variation between the BC-1 and the 21 kb KS5 fragment isolated from a KS lesion. Higher levels of variation may be present in strains from other geographic regions or other disease conditions. Within the LUR, synteny to HVS is lost at ORFs 2 and 70 but there is concordance in all other regions conserved with HVS. Several conserved genes, such as thymidine kinase (TK) (Cesarman et al., 1995, Blood 86, 2708–2714), TS and DHFR (which is present in HVS, see Albrecht et al., 1992, J. Virol. 66, 5047–5058, but not human herpesviruses), encode proteins that are appropriate targets for existing drugs.

Molecular mimicry by KSHV of cell cycle regulatory and signaling proteins is a prominent feature of the virus. The KSHV genome has genes similar to cellular complement-binding proteins (ORF 4), cytokines (ORFs K2, K4 and K6), a bcl-2 protein (ORF 16), a cytokine transduction pathway protein (K9), an IL-8R-like protein (ORF74) and a D-type cyclin (ORF72). Additional regions coding for proteins with some similarity to MIP and IRF-like proteins are also present in the KSHV genome. There is a striking parallel between the KSHV genes that are similar to cellular genes and the cellular genes known to be induced by EBV infection. Cellular cyclin D, CD21/CR2, bcl-2, an IL-8R-like protein (EBI1), IL-6 and adhesion molecules are upregulated by EBV infection (Birkenbach et al., 1993, J. Virol. 67, 2209–2220; Palmero et al., 1993, Oncogene 8, 1049–1054; Finke et al., 1992, Blood 80, 459–469; Finke et al., 1994, Leukemia & Lymphoma 12, 413–419; Jones et al., 1995, J. Exper. Med. 182, 1213–1221). This suggests that KSHV modifies the same signaling and regulation pathways that EBV modifies after infection, but does so by introducing exogenous genes from its own genome.

Cellular defense against virus infection commonly involves cell cycle shutdown, apoptosis (for review, see Shen and Shenk, 1995, Curr. Opin. Genet. Devel. 5, 105–111) and elaboration of cell-mediated immunity (CMI). The KSHV-encoded v-bcl-2, v-cyclin and v-IL-6 are active in preventing either apoptosis or cell cycle shutdown (Chang et al., 1996, Nature 382, 410). At least one of the β-chemokine KSHV gene products, v-MIP-I, prevents CCR5-mediated HIV infection of transfected cells. β-chemokines are not known to be required for successful EBV infection of cells although EBV-infected B cells express higher levels of MIP-1α than normal Lonsillar lymphocytes (Harris et al., 1993, 151, 5975–5983). The autocrine dependence of EBV-infected B cells on small and uncharacterized protein factors in addition to IL-6 (Tosato et al., 1990, J. Virol. 64, 3033–3041) leads to speculation that β-chemokines may also play a role in the EBV life cycle.

KSHV has not formally been shown to be a transforming virus and genes similar to the major transforming genes of HVS and EBV are not present in the BC-1 strain KSHV. Nonetheless, dysregulation of cell proliferation control caused by the identified KSHV-encoded proto-oncogenes and cytokines may contribute to neoplastic expansion of virus-infected cells. Preliminary studies suggest that subgenomic KSHV fragments can transform NIH 3T3 cells. If KSHV replication, like that of EBV, involves recombination of TR units (Raab-Traub and Flynn, 1986, Cell 47, 883–889), a monomorphic TR hybridization pattern present in a KS lesion would indicate a clonal virus population in the tumor. This is consistent with KS being a true neoplastic proliferation arising from single transformed, KS-infected cell rather than KSHV being a "passenger virus". Identification of KSHV genes similar to known oncoproteins and cell proliferation factors in the current study provides evidence that KSHV is likely to be a transforming virus.

EXPERIMENTAL DETAILS SECTION II:

MOLECULAR MIMICRY OF HUMAN CYTOKINE AND CYTOKINE RESPONSE PATHWAY GENES BY KSHV

Four virus genes encoding proteins similar to two human macrophage inflammatory protein (MIP) chemokines, an IL-6 and an interferon regulatory factor (IRF or ICSBP) polypeptide are present in the genome of Kaposi's sarcoma-associated herpesvirus (KSHV). Expression of these genes is inducible in infected cell lines by phorbol esters. vIL-6 is functionally active in B9 cell proliferation assays. It is primarily expressed in KSHV-infected hematopoietic cells rather than KS lesions. vMIP-I inhibits replication of CCR5-dependent HIV-1 strains in vitro indicating that it is functional and could contribute to interactions between these two viruses. Mimicry of cell signaling proteins by KSHV may abrogate host cell defenses and contribute to KSHV-associated neoplasia.

Kaposi's sarcoma-associated herpesvirus (KSHV) is a gammaherpesvirus related to Epstein-Barr virus (EBV) and herpesvirus saimiri (HVS). It is present in nearly all KS lesions including the various types of HIV-related and HIV-unrelated KS (Chang et al., 1994, Science 265, 1865–1869; Boshoff et al., 1995, Lancet 345, 1043–1044; Dupin et al., 1995, Lancet 345, 761–762; Schalling et al., 1995, Nature Med. 1, 707–708). Viral DNA preferentially localizes to KS tumors (Boshoff et al., 1995, Nature Med. 1, 1274–1278) and serologic studies show that KSHV is specifically associated with KS. Related lymphoproliferative disorders frequently occurring in patients with KS, such as primary effusion lymphomas (PEL), a rare B cell lymphoma, and some forms of Castleman's disease are also associated with KSHV infection (Cesarman et al., 1995, New Eng. J. Med. 332, 1186–1191; Soulier et al., 1995, Blood 86, 1276–1280). Three KSHV-encoded cytokine-like polypeptides and a polypeptide similar to interferon regulatory factor genes have now been identified. Paradoxically, while cytokine dysregulation has been proposed to cause Kaposi's sarcoma (Ensoli et al., 1994, Nature 371, 674–680; Miles, 1992, Cancer Treatment & Research 63, 129–140), in vitro spindle cell lines used for these studies over the past decade are uniformly uninfected with KSHV (Ambroziak et al., Science 268, 582–583; Lebbé et al., 1995, Lancet 345, 1180).

Figure 3A:
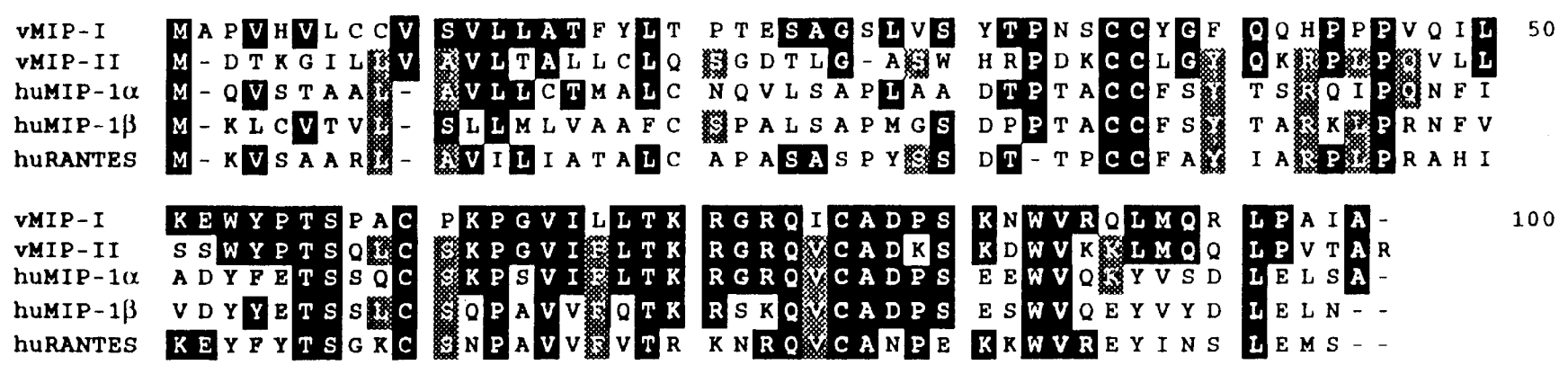
Figure 3B:
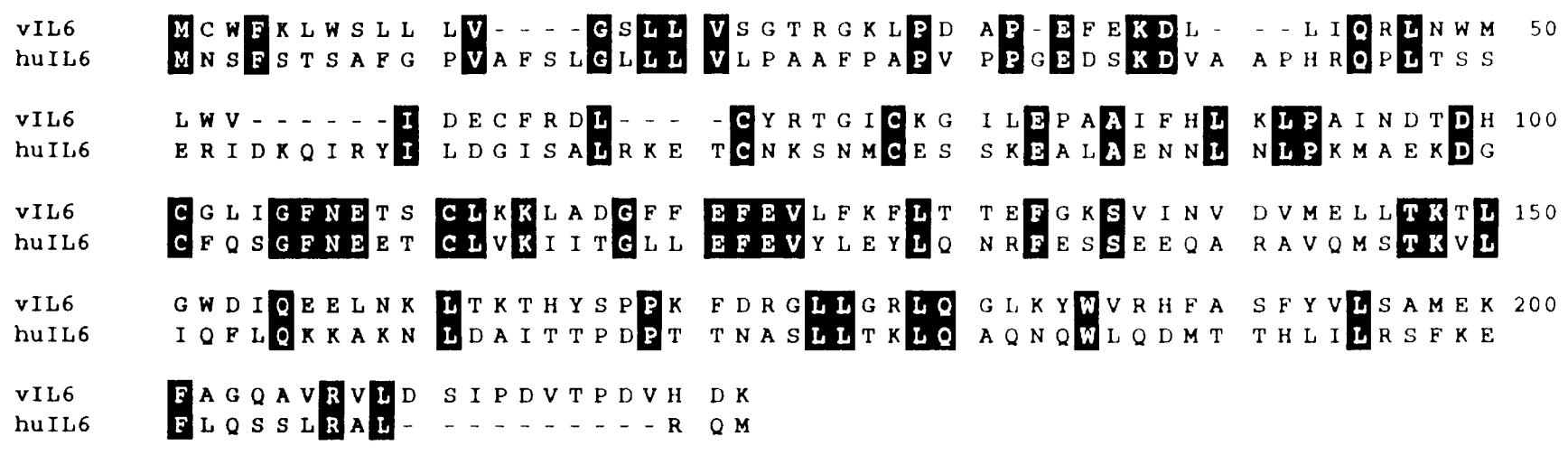

To identify unique genes in the KSHV genome, genomic sequencing (see METHODS) was performed using Supercos-1 and Lambda FIX II genomic libraries from BC-1, a nonHodgkin's lymphoma cell line stably infected with both KSHV and EBV (Cesarman et al., 1995, Blood 86, 2708–2714). The KSHV DNA fragments KS330Bam and KS631Bam (Chang et al., 1994, Science 265, 1865–1869) were used as hybridization starting points for mapping and bi-directional sequencing. Open reading frame (ORF) analysis (see METHODS) of the Z6 cosmid sequence identified two separate coding regions (ORFs K4 and K6) with sequence similarity to β-chemokines and a third coding region (ORF K2) similar to human interleukin-6 (huIL-6); a fourth coding region (ORF K9) is present in the Z8 cosmid insert sequence with sequence similarity to interferon regulatory factor (IRF) polypeptides (FIGS. 3A–3C). None of these KSHV genes are similar to other known viral genes. Parenthetically, a protein with conserved cysteine motifs similar to β-chemokine motif signatures has recently been reported in the molluscum contagiosum virus (MCV) genome. Neither vMIP-I nor VMIP-II has significant similarity to the MCV protein.

The cellular counterparts to these four viral genes encode polypeptides involved in cell responses to infection. For example, the MIP/RANTES (macrophage inflammatory protein/regulated on activation, normal T cell expressed and secreted) family of 8–10 kDa β-chemoattractant cytokines (chemokines) play an important role in virus infection-mediated inflammation (Cook et al., 1995, Science 269, 1583–1585). β-chemokines are the natural ligand for CCR5 and can block entry of non-syncytium inducing (NSI), primary lymphocyte and macrophage-tropic HIV-1 strains in vitro by binding to this HIV co-receptor (Cocchi et al., 1995, Science 270, 1811–1815). IL-6, initially described by its effect on B cell differentiation (Hirano et al., 1985, Proc Natl Acad Sci, USA 85, 5490; Kishimoto et al., 1995, Blood 86, 1243–1254), has pleiotropic effects on a wide variety of cells and may play a pathogenic role in multiple myeloma, multicentric Castleman's disease (a KSHV-related disorder), AIDS-KS and EBV-related postransplant lymphoproliferative disease (Klein et al., 1995, Blood 85, 863–872; Hilbert et al., 1995, J Exp Med 182, 243–248; Brandt et al., 1990, Curr Topic Microbiol Immunol 166, 37–41; Leger et al., 1991, Blood 78, 2923–2930; Burger et al., 1994, Annal Hematol 69, 25–31; Tosato et al., 1993, J Clin Invest 91, 2806–2814). IL-6 production is induced by either EBV or CMV infection and is an autocrine factor for EBV-infected lymphoblastoid cells that enhances their tumorigenicity in nude mice (Tosato et al., 1990, J Virol 64, 3033–3041; Scala et al., 1990, J Exp Med 172, 61–68; Almeida et al., 1994, Blood 83, 370–376). Cell lines derived from KS lesions, although not infected with KSHV, also produce and respond to IL-6 (Miles et al., 1990, Proc Natl Acad Sci USA 87, 4068–4072; Yang et al., 1994, J Immunol 152, 943–955). While MIP and IL-6 are secreted cytokines, the IRF family of polypeptides regulate interferon-inducible genes in response to γ- or α-/β-interferon cytokines by binding to specific interferon consensus sequences (ICS) within interferon-inducible promoter regions. A broad array of cellular responses to interferons is modulated by the repressor or transactivator functions of IRF polypeptides and several members (IRF-1 and IRF-2) have opposing anti-oncogenic and oncogenic activities (Sharf et al., 1995, J Biol Chem 270, 13063–13069; Harada et al., 1993, Science 259, 971–974; Weisz et al., 1994, Internat Immunol 6, 1125–1131; Weisz et al., 1992, J Biol Chem 267, 25589–25596).

The 289 bp ORF K6 (ORF MIP1) gene encodes a 10.5 kDa polypeptide (vMIP-I; MIP1) having 37.9% amino acid identity (71% similarity) to huMIP-1α and slightly lower similarity to other β-chemokines (FIG. 3A) ORF K4 also encodes a predicted 10.5 kDa polypeptide (vMIP-II; vMIP1α-II) with close similarity and amino acid hydrophobicity profile to vMIP-I. The two KSHV-encoded MIP β-chemokines are separated from each other on the KSHV genome by 5.5 kb of intervening sequence containing at least 4 ORFs (see METHODS). Both polypeptides have conserved β-chemokine motifs (FIG. 3A, residues 17–55) which include a characteristic C—C dicysteine dimer (FIG. 3A, residues 36–37), and have near sequence identity to human MIP-1α at residues 56–84. However, the two polypeptides show only 49.0% amino acid identity to each other and are markedly divergent at the nucleotide level indicating that this duplication is not a cloning artifact. The two viral polypeptides are more closely related to each other phylogenetically than to huMIP-1α, huMIP-1β or huRANTES suggesting that they arose by gene duplic atio n rather than independent acquisition from the host genome (see Sequence alignment in METHODS).

The reason for this double gene dosage in the viral genome is unknown.

The KSHV ORF K2 (FIG. 3B) encodes a hypothetical 204 residue, 23.4 kDa IL-6-like polypeptide with a hydrophobic 19 amino acid secretory signaling peptide having 24.8% amino acid identity and 62.2% similarity to the human polypeptide. vIL-6 also has a conserved sequence characteristic for IL-6-like interleukins (amino acids 101–125 of the gapped polypeptide) as well as conserved four cysteines which are present in IL-6 polypeptides (gapped alignment residue positions 72, 78, 101 and 111 in FIG. 3B). IL-6 is a glycosylated cytokine and potential N-linked glycosylation sites in the vIL-6 sequence are present at gapped positions 96 and 107 in FIG. 3C. The 449 residue KSHV vIRF polypeptide encoded by ORF K9 has lower overall amino acid identity (approximately 13%) to its human cellular counterparts than either of the vMIPs or the vIL-6, but has a conserved region derived from the IRF family of polypeptides (FIG. 3C, gapped residues 88–121). This region includes the tryptophan-rich IRF ICS DNA binding domain although only two of four tryptophans thought to be involved in DNA binding are positionally conserved. It is preceded by an 87-residue hydrophilic N-terminus with little apparent IRF similarity. A low degree of amino acid similarity is present at the C-terminus corresponding to the IRF family transactivator/repressor region.

Figure 5A:
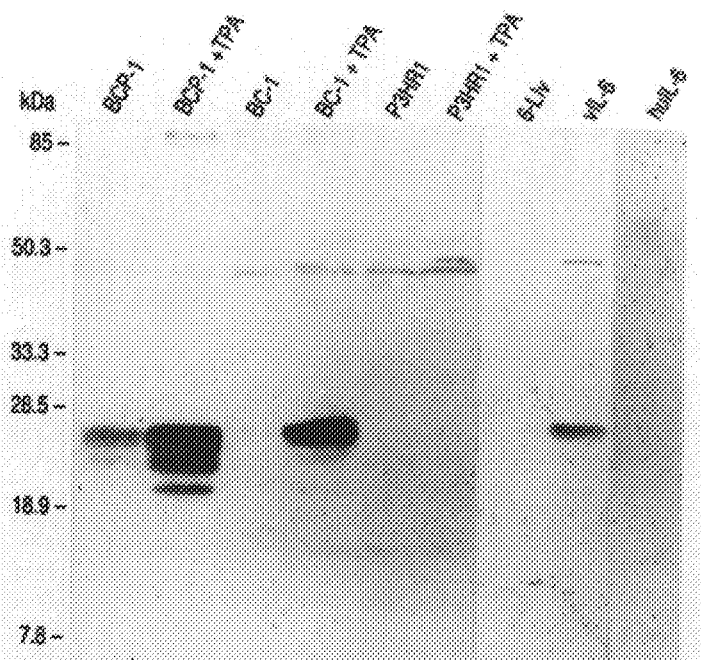
FIGS. 5A–5B FIG. 5A. Immunoblot of rabbit antipeptide antibodies generated from amino acid sequences of vIL-6, THYSPPKFDR (SEQ ID NO:2) and PDVTPDVHDR (SEQ ID NO:3), against cell lysates of BCP-1, BC-1, P3HR1 cell lines with and without TPA induction (lanes 1–6), 1 μg human rIL-6 (lane 7), and concentrated COS7 rvIL-6 and 6-LIv supernatants (lanes 8–9). Anti-vIL-6 antibodies specifically recognize the viral IL-6 polypeptide in both recombinant supernatants and cell lines but not human IL-6. The BCP-1 cell line constitutively expresses low levels of vIL-6 whereas polypeptide expression increases on TPA treatment for both BC-1 (KSHV and EBV coinfected) and BCP-1 (KSHV infection alone) indicating lytic phase expression. Preimmune sera from immunized rabbits did not react on immunoblotting to any of the preparations.
Figure 5B:
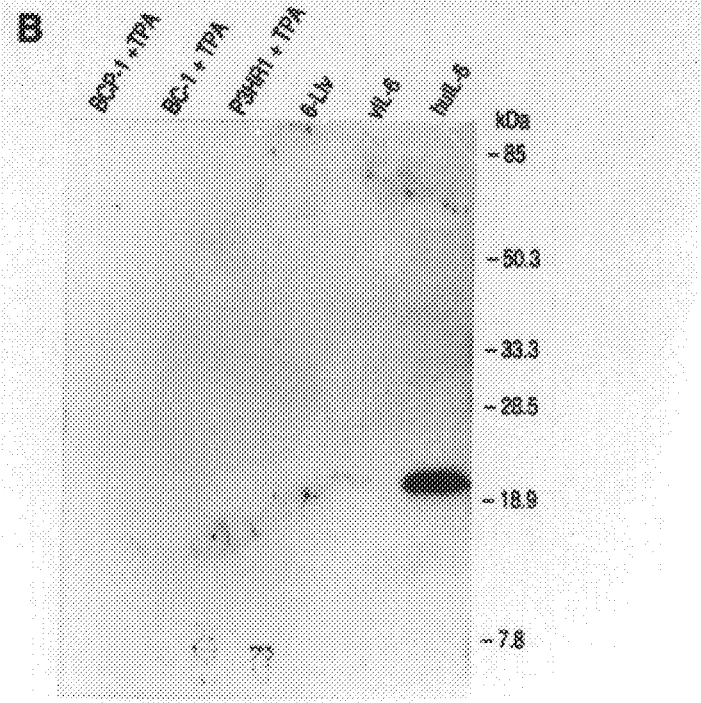
Figure 6:
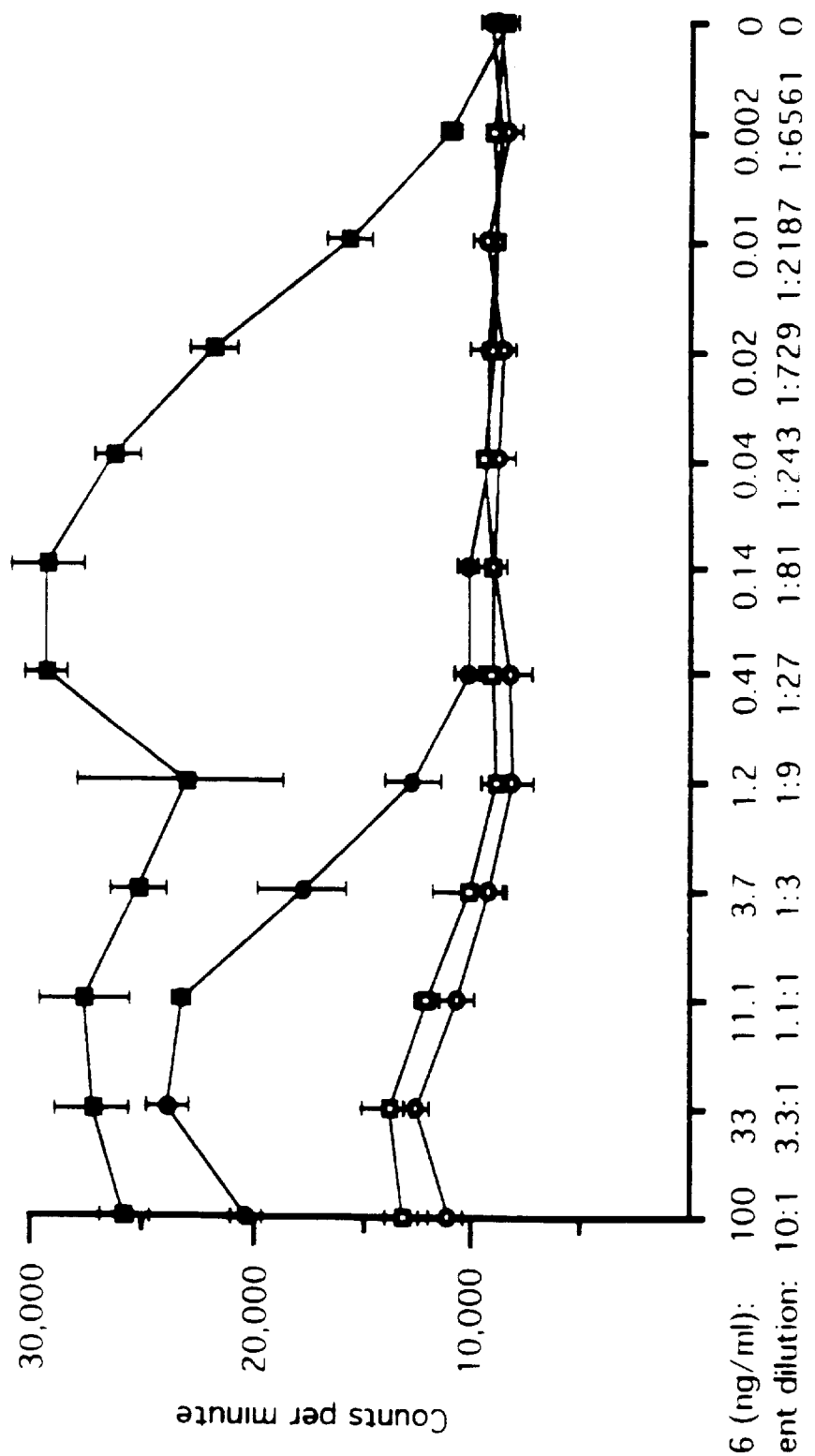
FIG. 6 Dose-response curves for $^3$H-thymidine uptake in IL-6-dependent B9 mouse plasmacytoma cells with serial dilutions of rhuIL-6 (filled squares) and COS7 supernatants of rvIL-6 (filled circles) r6-LIv (open squares) or control LacZ (open circles) pMET7 transfections. Undiluted rvIL-6 supernatants from this transfection lot show similar B9 proliferation activity to huIL-6 >0.02 ng/ml whereas the reverse construct (r6-LIv) and the LacZ control show no increased ability to induce B9 proliferation. Concentrated supernatants at greater than 1:1 dilution may have increased activity due to concentration of COS7 conditioning factors.

The four KSHV cell signaling pathway genes show similar patterns of expression in virus-infected lymphocyte cell lines by Northern blotting (see METHODS). Whole RNA was extracted from BCP-1 (a cell line infected with KSHV alone) and BC-1 (EBV and KSHV coinfected, see Cesarman et al., 1995, Blood 86, 2708–2714) with or without pretreatment with 20 ng/ml 12-O-tetradecanoylphorbol-13-acetate (TPA, Sigma, St. Louis Mo.) for 48 hours. While constitutive expression of these genes was variable between the two cell lines, expression of all four gene transcripts increased in BCP-1 and BC-1 cells after TPA induction (FIGS. 4A–4D). This pattern is consistent with expression occurring primarily during lytic phase virus replication. Examination of viral terminal repeat sequences of BCP-1 and BC-1 demonstrates that low level of virus lytic replication occurs in BCP-1 but not BC-1 without TPA induction (see METHODS), and both cell lines can be induced to express lytic phase genes by TPA treatment despite repression of DNA replication in BC-1. Lower level latent expression is also likely, particularly for vIL-6 (FIG. 4C) and vIRF (FIG. 4D), since these transcripts are detectable without TPA induction in BC-1 cells which are under tight latency control. To determine if in vitro KS spindle cell cultures retain defective or partial virus sequences that include these genes, DNA was extracted from four KS spindle cell lines (KS-2, KS-10, KS-13 and KS-22) and PCR amplified for vMIP-I, vMIP-II, vIL-6 and vIRF sequences (see METHODS). None of the spindle cell DNA samples were positive for any of the four genes.

vIL-6 was examined in more detail using bioassays and antibody localization studies to determine whether it is functionally conserved. Recombinant vIL-6 (rvIL-6) is specifically recognized by antipeptide antibodies which do not cross-react with huIL-6 (FIGS. 5A–5B) (see METHODS). vIL-6 is produced constitutively in BCP-1 cells and increases markedly after 48 hour TPA induction, consistent with Northern hybridization experiments. The BC-1 cell line coinfected with both KSHV and EBV only shows vIL-6 polypeptide expression after TPA induction (FIG. 5A, lanes 3–4) and control EBV-infected P3HR1 cells are negative for vIL-6 expression (FIG. 5A, lanes 5–6). Multiple high molecular weight bands present after TPA induction (21–25 kDa) may represent precursor forms of the polypeptide. Despite regions of sequence dissimilarity between huIL-6 and vIL-6, the virus interleukin 6 has biologic activity in functional bioassays using the IL-6-dependent mouse plasmacytoma cell line B9 (see METHODS). COS7 supernatants from the forward construct (rvIL-6) support B9 cell proliferation measured by $^3$H-thymidine uptake indicating that vIL-6 can substitute for cellular IL-6 in preventing B9 apoptosis (FIG. 6). vIL-6 supported B9 proliferation is dose dependent with the unconcentrated supernatant from the experiment shown in FIG. 6 having biologic activity equivalent to approximately 20 pg per ml huIL-6.

Figure 7A:
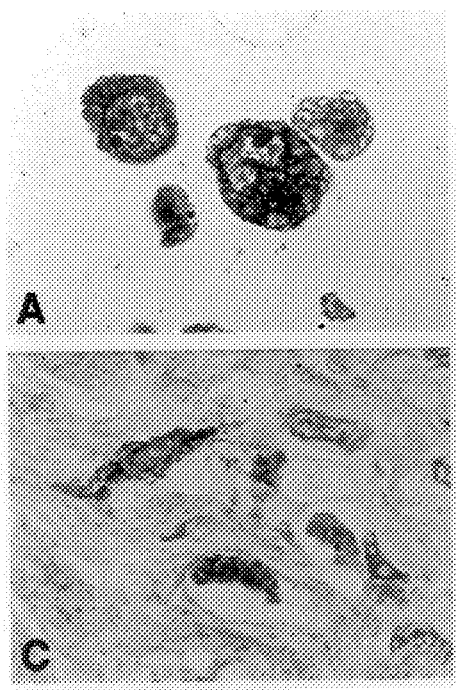
FIGS. 7A–7F Rabbit anti-vIL-6 peptide antibody reactivity localized using goat-antirabbit immunoglobulin-peroxidase conjugate (brown) with hematoxylin counterstaining (blue) at ×100 magnification demonstrates vIL-6 production in both KSHV-infected cell lines and tissues. The KSHV-infected cell line BCP-1 (FIG. 7A), but not the control EBV-infected cell line P3HR1 (FIG. 7B), shows prominent cytoplasmic vIL-6 localization.
Figure 7B:
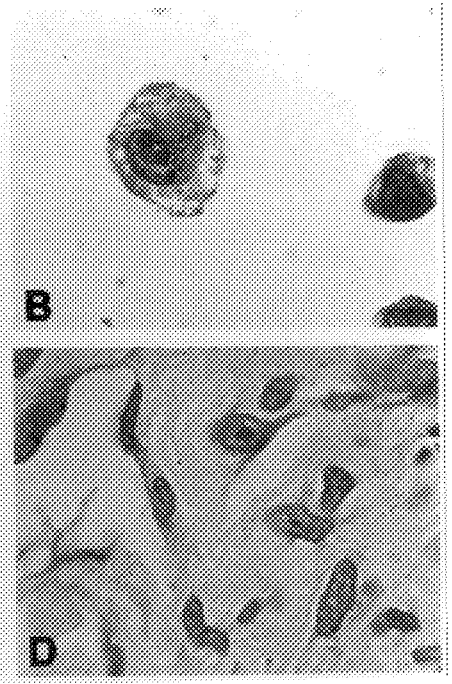
Figure 7C:
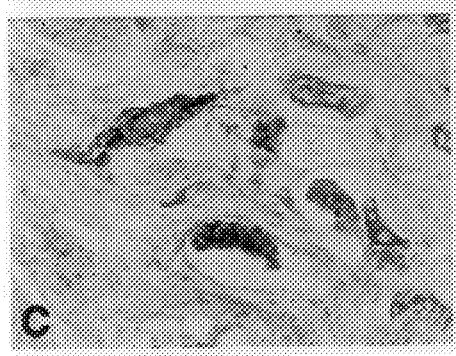
Figure 7D:
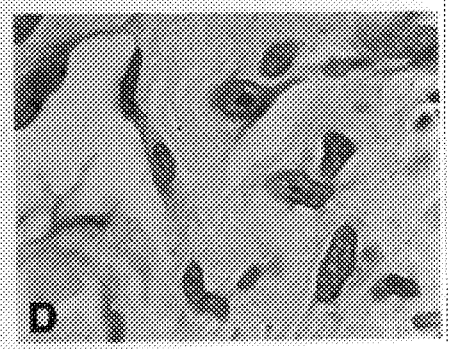
Figure 7E:
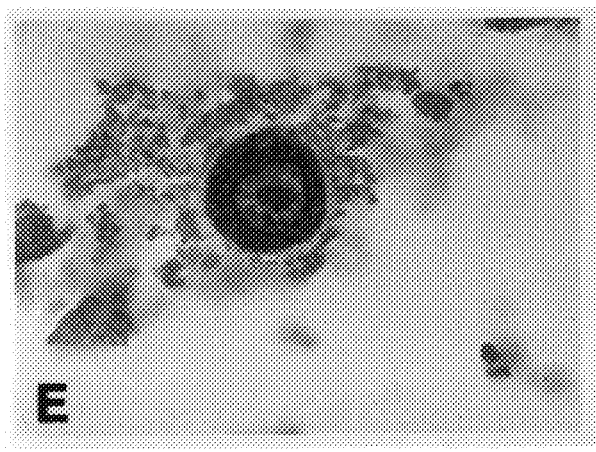
Figure 7F:
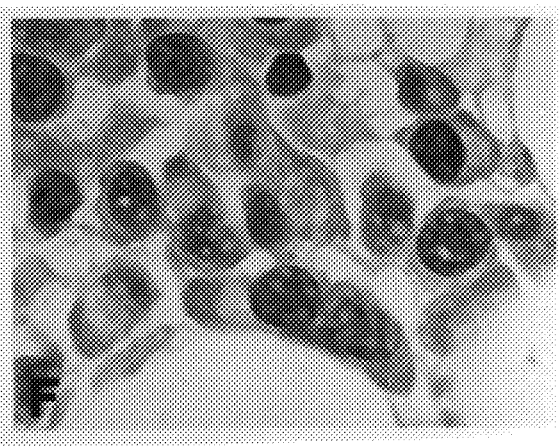
Figures 8A, 8B, 8C, 8D:
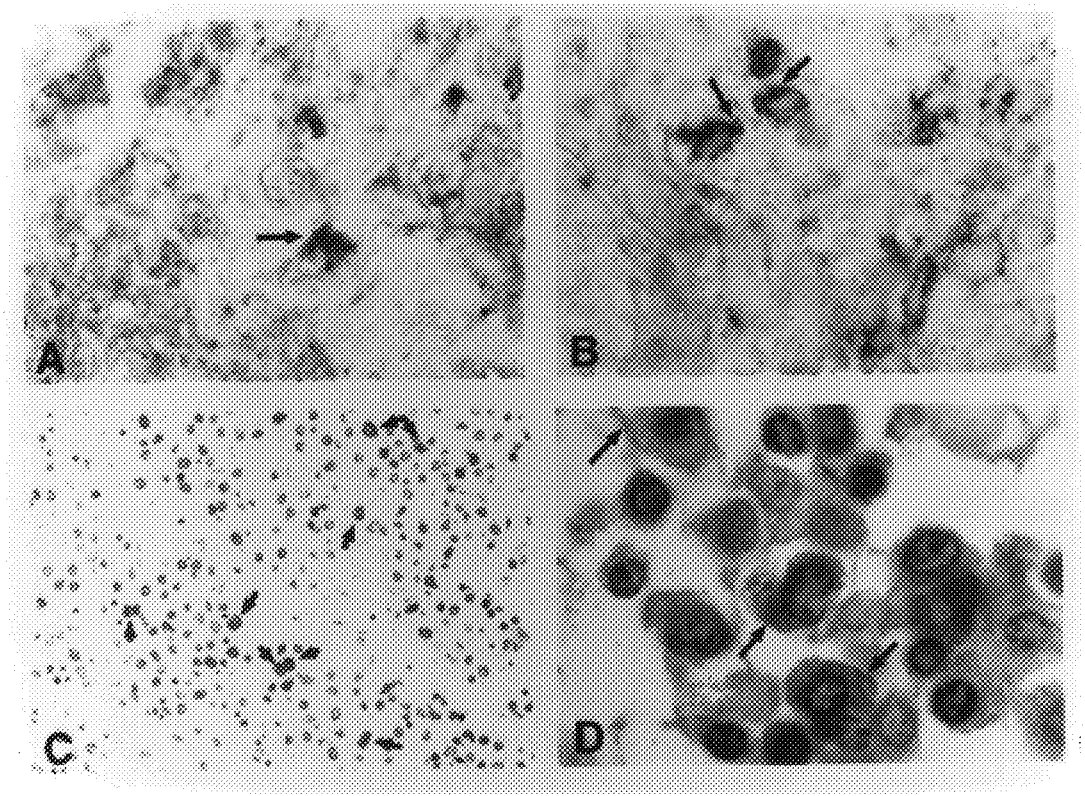
FIGS. 8A–8D Double antibody labeling of anti-vIL-6 and cell surface antigens. Examples of both CD34 and CD20 colocalization with vIL-6 were found in a KS lesion.

Forty-three percent of noninduced BCP-1 cells (FIG. 7A) have intracellular cytoplasmic vIL-6 immunostaining (see METHODS) suggestive of constitutive virus polypeptide expression in cultured infected cells, whereas no specific immunoreactive staining is present in uninfected control P3HR1 cells (FIG. 7B). vIL-6 production was rarely detected in KS tissues and only one of eight KS lesions examined showed clear, specific vIL-6 immunostaining in less than 2% of cells (FIG. 7C). The specificity of this low positivity rate was confirmed using preimmune sera and neutralization with excess vIL-6 peptides. Rare vIL-6-producing cells in the KS lesion are positive for either CD34, an endothelial cell marker (FIG. 8A), or CD45, a pan-hematopoietic cell marker (FIG. 8B), demonstrating that both endothelial and hematopoietic cells in KS lesions produce vIL6. It is possible that these rare vIL-6 positive cells are entering lytic phase replication which has been shown to occur using the KSHV T1.1 lytic phase RNA probe. In contrast, well over half (65%) of ascitic lymphoma cells pelleted from an HIV-negative PEL are strongly positive for vIL-6 (FIG. 7E) and express the plasma cell marker EMA (Cesarman et al., 1995, Blood 86, 2708–2714) indicating that either most PEL cells in vivo are replicating a lytic form of KSHV or that latently infected PEL cells can express high levels of vIL-6. No specific staining occurred with any control tissues examined including normal skin, tonsillar tissue, multiple myeloma or angiosarcoma using either preimmune or post-immune rabbit anti-vIL-6 antibody (FIG. 7E and 7F).

Virus dissemination to nonKS tissues was found by examining a lymph node from a patient with AIDS-KS who did not develop PEL. Numerous vIL-6-staining hematopoietic cells were present in this lymph node (FIG. 8C) which was free of KS microscopically. vIL-6 positive lymph node cells were present in relatively B-cell rich areas and some express CD20 B cell surface antigen (FIG. 8D), but not EMA surface antigen (unlike PEL cells) (Cesarman et al., 1995, Blood 86, 2708–2714). No colocalization of vIL-6 positivity with the T cell surface antigen CD3 or the macrophage antigen CD68 was detected, although phagocytosis of vIL-6 immunopositive cells by macrophages was frequently observed.

To investigate whether the vMIP-I can inhibit NSI HIV-1 virus entry, human CD4+ cat kidney cells (CCC/CD4) were transiently transfected with plasmids expressing human CCR5 and VMIP-I or its reverse construct I-PIMV (see CCR5 and vMIP-I cloning in METHODS). These cells were infected with either M23 or SF162 primary NSI HIV-1 isolates which are known to use CCR5 as a co-receptor (Clapham et al., 1992, J Virol 66, 3531–3537) or with the HIV-2 variant ROD/B which can infect CD4+ CCC cells without human CCRS. Virus entry and replication was assayed by immunostaining for retroviral antigen production (FIG. 9). vMIP-I cotransfection reduced NSI HIV-1 foci generation to less than half that of the reverse-construct negative control but had no effect on ROD/B HIV-2 replication.

Molecular piracy of host cell genes is a newly recognized feature of some DNA viruses, particularly herpesviruses and poxviruses (Murphy, 1994, Infect Agents Dis 3, 137–154; Albrecht et al., 1992, J Virol 66, 5047–5058; Gao and Murphy, 1994, J Biol Chem 269, 28539–28542; Chee et al., 1990, Curr Top Microbiol Immunol 154, 125–169; Massung et al., 1994, Virol 201, 215–240). The degree to which KSHV has incorporated cellular genes into its genome is exceptional. In addition to vMIP-I and vMIP-II, vIL-6 and vIRF, KSHV also encodes polypeptides similar to bcl-2 (ORF 16), cyclin D (ORF 72), complement-binding proteins similiar to CD21/CR2 (ORF 4), an NCAM-like adhesion protein (ORF K14), and an IL-8 receptor (ORF 74). EBV also either encodes (BHRF1/bcl-2) or induces (CR-2; cyclin D; IL-6; bcl-2; adhesion molecules and an IL-8R-like EBI1 protein) these same cellular polypeptides (Cleary et al., 1986, *Cell* 47, 19–28; Tosato et al., 1990, *J Virol* 64, 3033–3041; Palmero et al., 1993, *Oncogene* 8, 1049; Larcher et al., 1995, *Eur J Immunol* 25, 1713–1719; Birkenbach et al., 1993, *J Virol* 67, 2209–2220). Thus, both viruses may modify similar host cell signaling and regulatory pathways.

EBV appears to effect these changes through induction of cellular gene expression whereas KSHV introduces the polypeptides exogenously from its own genome.

Identification of these virus-encoded cellular-like polypeptides leads to speculation about their potential roles in protecting against cellular antiviral responses. huIL-6 inhibits γ-interferon-induced, Bax-mediated apoptosis in myeloma cell lines (Lichtenstein et al., 1995, *Cellular Immunology* 162, 248–255) and vIL-6 may play a similar role in infected B cells. KSHV-encoded vIRF, vbcl-2 and v-cyclin may also interfere with host-cell mediated apoptosis induced by virus infection and v-cyclin may prevent G1 cell cycle arrest of infected cells. Interference with interferon-induced MHC antigen presentation and cell-mediated immune response (Holzinger et al., 1993, *Immunol Let* 35, 109–117) by vIRF is also possible. The β-chemokine polypeptides vMIP-I and vMIP-II may have agonist or antagonist signal transduction roles. Their sequence conservation and duplicate gene dosage are indicative of a key role in KSHV replication and survival.

Uncontrolled cell growth from cell-signaling pathway dysregulation is an obvious potential by-product of this virus strategy. Given the paucity of vIL-6 expressing cells in KS lesions, it is unlikely that vIL-6 significantly contributes to KS cell neoplasia. KSHV induction of hu-IL6, however, with subsequent induction of vascular endothelial growth factor-mediated angiogenesis (Holzinger et al., 1993, *Immunol Let* 35, 109–117), is a possibility. vIL-6 could also potentially contribute to the pathogenesis of KSHV-related lymphoproliferative disorders such as PEL or the plasma cell variant of Castleman's disease.

The oncogenic potential of cellular cyclin and bcl-2 overexpression is well-established and these virus-encoded polypeptides may also contribute to KSHV-related neoplasia.

Figure 9:
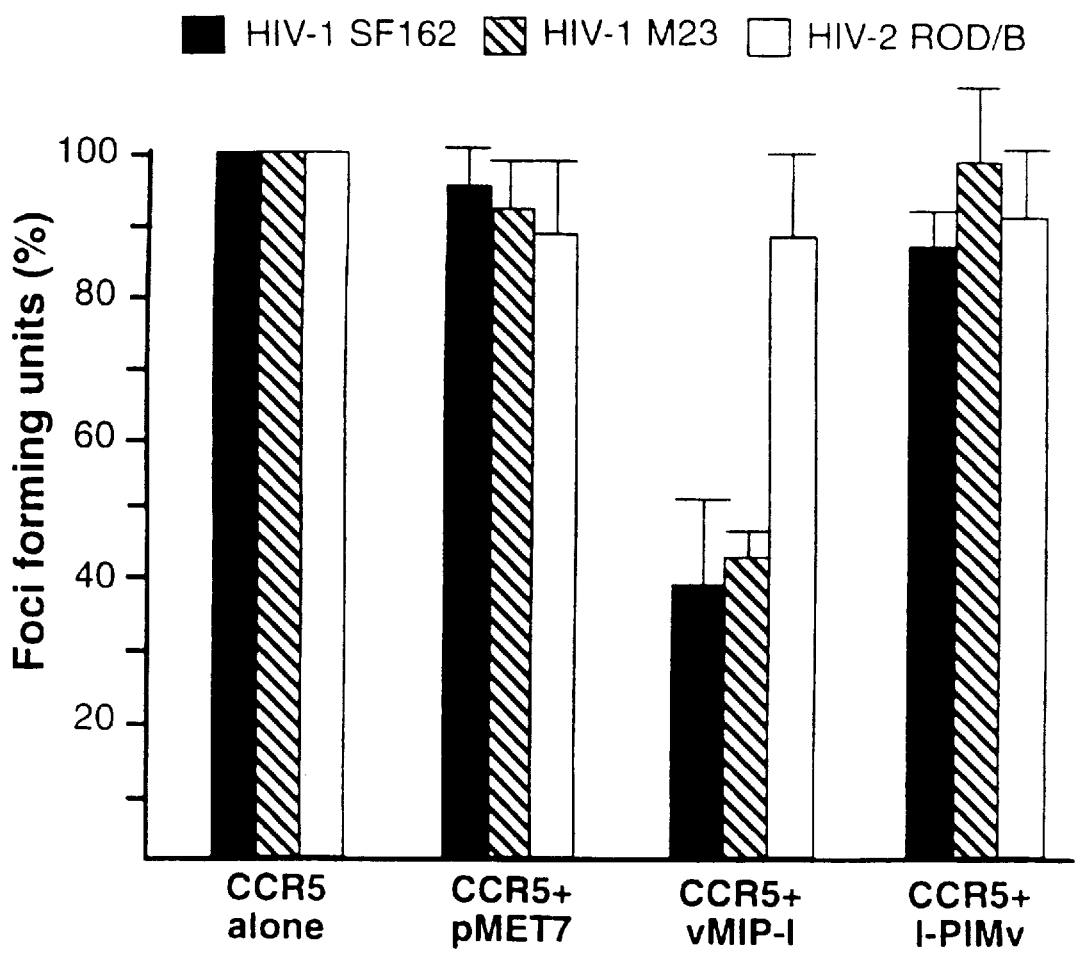
FIG. 9 Quantification of CCC/CD4 cell infection by primary NSI SF162 and M23 HIV-1 strains and HIV-2 strain ROD/B in the presence or absence of vMIP-I. CCC/CD4 cells were transiently cotransfected with CCR5 alone, CCR5 plus empty pMET7 vector, CCR5 plus vMIP-I in pMET7 vector, or CCR5 plus the reverse orientation I-PIMv. The results after 72 hours of incubation with each retrovirus are expressed as a percentage of the foci forming units for cells transfected with CCR5 alone. The forward vMIP-I construct inhibited NSI HIV-1 replication but not HIV-2 replication while the reverse I-PIMv construct had no effect on replication of any of the retroviruses.

KSHV VMIP-I inhibits NSI HIV-1 replication in vitro (FIG. 9). Studies from early in the AIDS epidemic indicate that survival is longer for AIDS-KS patients than for other AIDS patients, and that 93% of US AIDS patients surviving >3 years had KS compared to only 28% of remaining AIDS patients dying within 3 years of diagnosis (Hardy, 1991, *J AIDS* 4, 386–391; Lemp et al., 1990, *J Am Med Assoc* 263, 402–406; Rothenberg et al., 1987, *New Eng J Med* 317, 1297–1302; Jacobson et al., 1993, *Am J Epidemiol* 138, 953–964; Lundgren et al., 1995, *Am J Epidemiol* 141, 652–658). This may be due to KS occuring at relatively high CD4+ counts and high mortality for other AIDS-defining conditions. Recent surveillance data also indicates that the epidemiology of AIDS-KS is changing as the AIDS epidemic progresses (ibid).

METHODS

Genomic Sequencing. Genomic inserts were randomly sheared, cloned into M13mp18, and sequenced to an average of 12-fold redundancy with complete bidirectional sequencing. The descriptive nomenclature of KSHV polypeptides is based on the naming system derived for herpesvirus saimiri (Albrecht et al., 1992, *J Virol* 66, 5047–5058).

Open reading frame (ORF) analysis. Assembled sequence contigs were analyzed using MacVector (IBI-Kodak, Rochester, N.Y.) for potential open reading frames greater than 25 amino acid residues and analyzed using BLASTX and BEAUTY-BLASTX (Altschul et al., 1990, *J Mol Biol* 215, 403–410; Worley et al., 1995, *Genome Res* 5, 173–184; http://dot.imgen.bcm.tmc.edu:9331/seq-search/nucleic_acid-search.html). Similar proteins aligned to the four KSHV polypeptides (in italics:) included (name (species, sequence bank accession number, smallest sum Poisson distribution probability score)): (1) vMIP-I: LD78 (MIP-1α) (human, gi 127077, p=9.8xe-22), MIP-1α (Rattus, gi 790633, p=3.3xe-20), MIP-1α (Mus, gi 127079, p=1.7xe-19), MIP-1β (Mus, gi 1346534, p=7.8xe-18); (2) vMIP-II: LD78 (MIP-1a) (human, gi 127077, p=7.1xe-23), MIP1α (Mus, gi 127079, p=8.9xe-21), MIP-1α (Rattus, gi 790633, p=1.2xe-20), MIP-1β (Mus, gi 1346534, p=3.8xe-20) ; (3) vIL-6: 26 kDa polypeptide (IL-6) (human, gi 23835, p=7.2xe-17), IL-6 (Macaca, gi 514386, p=1.6xe-16) ; and (4) VIRF: ICSBP (Gallus, gi662355, p=1.1xe-11), ICSBP (Mus, sp p23611, p=1.0xe-10), lymphoid specific interferon regulatory factor (Mus, gi 972949, p=2.0xe-10), ISGF3 (Mus, gi 1263310, p=8.1xe-10), IRF4 (human, gi 1272477, p=1.0xe-9), ISGF3 (human, sp Q00978, 3.9xe-9), ICSBP (human, sp Q02556, p=2.3xe-8)

Sequence alignment. Amino acid sequences were aligned using CLUSTAL W (Thompson et al., 1994, *Nuc Acids Res* 22, 4673–4680) and compared using PAUP 3.1.1. Both rooted and unrooted bootstrap comparisons produced phylogenetic trees having all 100 bootstrap replicates with viral polypeptides being less divergent from each other than from the human polypepides.

Northern blotting. Northern blotting was performed using standard conditions with random-labeled probes (Chang et al., 1994, *Science* 265, 1865–1869) derived from PCR products for the following primer sets: vMIP-I: 5'-AGC ATA TAA GGA ACT CCC CGT TAC-3' (SEQ ID NO:4), 5'-GGT AGA TAA ATC CCC CCC CTT TG-3' (SEQ ID NO:5); vMIP-II: 5'-TGC ATC AGC TTC TTC ACC CAG-3' (SEQ ID NO:6), 5'-TGC TGT CTC GGT TAC CAG AAA AG-3' (SEQ ID NO:7); vIL-6: 5'-TCA CGT CGC TCT TTA CTT ATC GTG-3' (SEQ ID NO:8), 5'-CGC CCT TCA GTG AGA CTT CGT AAC-3' (SEQ ID NO:9); VIRF: 5° C.TT GCG ATG AAC CAT CCA GG-3' (SEQ ID NO:10), 5'-ACA ACA CCC AAT TCC CCG TC-3' (SEQ ID NO:11) on total cell RNA extracted with RNAzol according to manufacturer's instructions (TelTest Inc, Friendswood Tex.) and 10 μg of total RNA was loaded in each lane. BCP-1, BC-1 and P3HR1 were maintained in culture conditions and induced with TPA as previously described (Gao et al., 1996, *New Eng J Med* 335, 233–241). PCR amplification for these viral genes was performed using the vMIP-I, vMIP-II, vIL-6, and vIRF primer sets with 35 amplification cycles and compared to dilutions of whole BC-1 DNA as a positive control using PCR conditions previously described (Moore and Chang, 1995, *New Eng J Med* 332, 1181–1185). KS spindle cell line DNA used for these experiments was described in Dictor et al., 1996, *Am J Pathol* 148, 2009–2016. Amplifiability of DNA samples was confirmed using human HLA-DQ alpha and pyruvate dehydrogenase primers.

vIL-6 cloning. vIL-6 was cloned from a 695 bp polymerase chain reaction (PCR) product using the following primer set: 5'-TCA CGT CGC TCT TTA CTT ATC GTG-3'

(SEQ ID NO:12) and 5'-CGC CCT TCA GTG AGA CTT CGT AAC-3' (SEQ ID NO:13), amplified for 35 cycles using the 0.1 μg of BC-1 DNA as a template. PCR product was intially cloned into pCR 2.1 (Invitrogen, San Diego Calif.) and an EcoRV insert was then cloned into the pMET7 expression vector (Takebe et al., 1988, *Mol Cell Biol* 8, 466–472) and transfected using DEAE-dextran with chloroquine into COS7 cells (CRL-1651, American Type Culture Collection, Rockville, Md.). The sequence was also cloned into the pMET7 vector in the reverse orientation (6-LIv) relative to the SRa promoter as a negative control, with orientation and sequence fidelity of both constructs confirmed by bidirectional sequencing using dye-primer chemistry on an ABI 377 sequenator (Applied Biosystems Inc, Foster City Calif.).

15 ml of serum-free COS7 supernatants were concentrated to 1.5 ml by ultrafiltration with a Centriplus 10 filter (Amicon, Beverly Mass.) and 100 μl of supernatant concentrate or 1 μg of rhuIL-6 (R&D Systems, Minneapolis Minn.) was loaded per each lane in Laemmli buffer. For cell lysate immunoblotting, exponential phase cells with and without 20 ng/ml TPA induction for 48 hours were pelleted and 100 μg of whole cell protein solubilized in Laemmli buffer was loaded per lane, electrophoresed on a 15% SDS-polyacrylamide gel and immunoblotted and developed using standard conditions (Gao et al., 1996, *New Eng J Med* 335, 233–241) with either rabbit antipeptide antibody (1:100–1:1000 dilution) or anti-huIL-6 (1 μg per ml, R&D Systems, Minneapolis Minn.).

Cell line B9. B9 mouse plasmacytoma cell line were maintained in Iscove's Modified Dulbecco's Medium (IMDM) (Gibco, Gaithersburg, Md), 10% fetal calf serum, 1% penicillin/streptomycin, 1% glutamine, 50 μM β-mercaptoethanol, and 10 ng per ml rhuIL-6 (R&D Systems, Minneapolis, Minn.). $^3$H-thymidine uptake was used to measure B9 proliferation in response to huIL-6 or recombinant supernatants according to standard protocols (R&D Systems, Minneapolis, Minn.). Briefly, serial 1:3 dilutions of huIL-6 or Centriplus 10 concentrated recombinant supernatants were incubated with $2\times10^4$ cells per well in a 96 well plate for 24 hours at 37° C. with 10 μl of thymidine stock solution (50 μl of 1mCi/ml $^3$H-thymidine in 1 ml IMDM) added to each well during the final four hours of incubation.

Cells were harvested and incorporated $^3$H-thymidine determined using a liquid scintillation counter. Each data point is the average of six determinations with standard deviations shown.

vIL-6 immunostaining. Immunostaining was performed using avidin-biotin complex (ABC) method after deparaffinization of tissues and quenching for 30 minutes with 0.03% $H_2O_2$ in PBS. The primary antibody was applied at a dilution of 1:1250 after blocking with 10% normal goat serum, 1% BSA, 0.5% Tween 20. The secondary biotinylated goat anti-rabbit antibody (1:200 in PBS) was applied for 30 minutes at room temperature followed by three 5 minute washes in PBS. Peroxidase-linked ABC (1:100 in PBS) was applied for 30 minutes followed by three 5 minute washes in PBS. A diamino-benzidine (DAB) chromogen detection solution (0.25% DAB, 0.01% $H_2O_2$ in PBS) was applied for 5 minutes. Slides are then washed, counter-stained with hematoxylin and coverslipped. Amino ethyl carbazole (AEC) or Vector Red staining was also used allowing better discrimination of double-labeled cells with Fast Blue counterstaining for some surface antigens. For CD68, in which staining might be obscured by vIL-6 cytoplasmic staining, double label immunofluorescence was used. Microwaved tissue sections were blocked with 2% human serum, 1% bovine serum albumin (BSA) in PBS for 30 minutes, incubated overnight with primary antibodies and developed with fluorescein-conjugated goat anti-rabbit IgG (1:100, Sigma) for vIL-6 localization and rhodamine-conjugated horse anti-mouse IgG (1:100, Sigma) for CD68 localization for 30 minutes. After washing, secondary antibody incubation was repeated twice with washing for 15 minutes each to amplify staining. For the remaining membrane antigens, slides were developed first for vIL-6 and then then secondly with the cellular antigen, as well as the reverse localization (cellular antigen antibody first, anti-vIL-6 second) to achieve optimal visualization and discrimination of both antigens. In each case, the first antibody was developed using AEC (Sigma) with blocking solution pre-incubation (1% BSA, 10% normal horse serum, 0.5% Tween 20 for 30 minutes) and development per manufacturer's instructions. The second antibody was developed using the ABC-alkaline phosphatase technique with Fast Blue chromagen. Both microwaving and trypsinization resulted in poorer localization and specificity of vIL-6 immunolocalization. In cases where this was required for optimal localization of membrane antigen, these techniques were applied after vIL-6 AEC localization. Vector-Red (Vector, Burlingame, Calif.) staining was used as an alternative stain to AEC to achieve optimal discrimination and was performed per manufacturer's protocol using the ABC-alkaline phosphatase technique. Cell antigen antibodies examined included CD68 (1:800, from clone Kim 6), epithelial membrane antigen (EMA, 1:500, Dako, Carpinteria, Calif.), CD3 (1:200, Dako), CD20, (1:200, Dako), OPD4 (1:100, Dako), CD34 (1:15, Dako), CD45 (1:400, from clone 9.4), L26 (1:100, Immunotech, Westbrook, Me.) and Leu22 (1:100, Becton-Dickinson, San Jose, Calif.) on tissues prepared according to manufacturer's instructions. Specific vIL-6 colocalization was only found with CD34 and CD45 in KS lesions, EMA in PEL, and CD20 and CD45 in lymph node tissues.

Immunohistochemical vIL-6 localization was performed on exponential phase BCP-1 cells with or without 48 hour TPA incubation after embedding in 1% agar in saline. The percentages of positive cells were determined from cell counts of three random high power microscopic fields per slide. Lower percentages of BCP-1 cells stain positively for vIL-6 after TPA treatment possibly reflecting cell lysis and death from lytic virus replication induction by TPA. Immunostaining of cells and tissues was demonstrated to be specific by neutralization using overnight incubation of antisera with 0.1 μg/ml vIL-6 synthetic peptides at 4° C. and by use of preimmune rabbit antisera run in parallel with the postimmune sera for the tissues or cell preparations. No specific staining was seen after either peptide neutralization or use of preimmune sera.

CCR5 and vMIP-I cloning. CCR5 was cloned into pRc-CMV vector (Invitrogen) and both forward and reverse orientations of the vMIP-I gene were cloned into pMET7 after PCR amplification using the following primer pairs: 5'-AGC ATA TAA GGA ACT CGG CGT TAC-3' (SEQ ID NO:14), 5'-GGT AGA TAA ACT CCC CCC CTT TG-3' (SEQ ID NO:15). CCR5 alone and with the forward construct (vMIP-I), the reverse construct (I-PIMv) and empty pMET7 vector were transfected into CCC/CD4 cells (CCC cat cells stably expressing human CD4, see McKnight et al., 1994, *Virol* 201, 8–18) using Lipofectamine (Gibco). After 48 hours, media was removed from the transfected cells and 1000 TCID$_{50}$ of SF162, M23 or ROD/B virus culture stock was added. Cells were washed four times after 4 hours of virus incubation and grown in DMEM with 5% FCS for 72 hours before immunostaining for HIV-1 p24 or HIV-2 gp105 as previously described. Each condition was replicated 3–4 times (FIG. 9) with medians and error bars representing the standard deviations expressed as percentages of the CCR5 alone foci.

EXPERIMENTAL DETAILS SECTION III:

The following patents are hereby incorporated by reference to more fully describe the invention described herein:

1. Fowlkes, CARBOXY TERMINAL IL-6 MUTEINS, U.S. Pat. No. 5,565,336, ISSUED Oct. 15, 1996;
2. Skelly et al., METHOD OF MAKING CYSTEINE DEPLETED IL-6 MUTEINS, U.S. Pat. No. 5,545,537, ISSUED Aug. 13, 1996;
3. Ulrich, COMPOSITION AND METHOD FOR TREATING INFLAMMATION, U.S. Pat. No. 5,376,368, ISSUED Dec. 27, 1994;
4. Skelly et al., CYSTEINE DEPLETED IL-6 MUTEINS, U.S. Pat. No. 5,359,034, ISSUED Oct. 25, 1994;
5. Williams, ULTRAPURE HUMAN INTERLEUKIN 6, U.S. Pat. No. 5,338,834, ISSUED Aug. 16, 1994;
6. Fowlkes, CARBOXY TERMINAL IL-6 MUTEINS, U.S. Pat. No. 5,338,833, ISSUED Aug. 16, 1994;
7. Ulrich, COMPOSITION AND METHOD FOR TREATING INFLAMMATION, U.S. Pat. No. 5,300,292, ISSUED Apr. 5, 1994;
8. Mikayama et al., MODIFIED HIL-6, U.S. Pat. No. 5,264,209, ISSUED Nov. 23, 1993;
9. Park, HYPERGLYCOSYLATED CYTOKINE CONJUGATES, U.S. Pat. No. 5,217,881, ISSUED Jun. 8, 1993;
10. Goldberg and Faquin, INTERLEUKIN 6 TO STIMULATE ERYTHROPOIETIN PRODUCTION, U.S. Pat. No. 5,188,828, ISSUED Feb. 23, 1993;
11. Miles et al., METHOD TO TREAT KAPOSI'S SARCOMA, U.S. Pat. No. 5,470,824, ISSUED Nov. 28, 1995;
12. Li and Ruben, MACROPHAGE INFLAMMATORY PROTEIN –3 AND –4 [Isolated polynucleotide encoding said polypeptide], U.S. Pat. No. 5,504,003, ISSUED Apr. 2, 1996;
13. Gewirtz, SUPPRESSION OF MEGAKARYOCYTOPOIESIS BY MACROPHAGE INFLAMMATORY PROTEINS [Reducing number of circulating platelets in bloodstream], U.S. Pat. No. 5,306,709, ISSUED Apr. 26, 1994;
14. Fahey et al., METHOD AND AGENTS FOR PROMOTING WOUND HEALING, U.S. Pat. No. 5,145,676, ISSUED Sep. 8, 1992;
15. Rosen et al., POLYNUCLEOTIDE ENCODING MACROPHAGE INFLAMMATORY PROTEIN GAMMA, U.S. Pat. No. 5,556,767, ISSUED Sep. 17, 1996;
16. Chuntharapai et al., ANTIBODIES TO HUMAN IL-8 TYPE A RECEPTOR, U.S. Pat. No. 5,543,503, ISSUED Aug. 6, 1996;
17. Chuntharapai et al., ANTIBODIES TO HUMAN IL-8 TYPE B RECEPTOR [A monoclonal antibody as anti-inflammatory agent treating an inflammatory disorder], U.S. Pat. No. 5,440,021, ISSUED Aug. 8, 1995;
18. Kunkel et al., LABELLED MONOCYTE CHEMOATTRACTANT PROTEIN MATERIAL AND MEDICAL USES THEREOF, U.S. Pat. No. 5,413,778, ISSUED May 9, 1995;
19. Lyle and Kunkel, LABELLED INTERLEUKIN-8 AND MEDICAL USES THEREOF [Radionuclide labeled chemokines, imaging agents], U.S. Pat. No. 5,346,686, ISSUED Sep. 13, 1994;
20. Jones et al., ANTI-CANCER QUINAZOLINE DERIVATIVES, U.S. Pat. No. 4,564,616, ISSUED Jan. 14, 1986;
21. DeGraw et al., ANTIINFLAMMATORY AND ANTI-NEOPLASTIC 5-DEAZAAMINOPTERINS AND 5,10-DIDEAZAAMINOPTERINS, U.S. Pat. No. 5,536,724, ISSUED Jul. 16, 1996;
22. Mahan et al., IN VIVO SELECTION OF MICROBIAL VIRULENCE GENES [Genetic engineering and expression using auxotrophic or antibiotic sensitive microorganism's chromosome], U.S. Pat. No. 5,434,065, ISSUED Jul. 18, 1995;
23. DeGraw et al., 8,10-DIDEAZATETRAHYDROFOLIC ACID DERIVATIVES [Antitumor agents], U.S. Pat. No. 5,167,963, ISSUED Dec. 1, 1992; and
24. Watanabe, 6,7-DIHYDROPYRROL[3,4-C]PYRIDO[2,3-D] PYRIMIDINE DERIVATIVES [STRUCTURALLY SIMILAR TO THYMIDYLIC ACID], U.S. Pat. No. 4,925,939, ISSUED May 15, 1990.

REFERENCES

1. Chang, Yuan, E Cesarman, M S Pessin, F Lee, J Culpepper, D M Knowles and Patrick S Moore (1994) Identification of herpesvirus-like DNA sequences in AIDS-associated Kaposi's sarcoma. *Science* 265, 1865–1869.
2. Moore, Patrick S and Yuan Chang (1995) Detection of herpesvirus-like DNA sequences in Kaposi's sarcoma in patients with and those without HIV infection. *New Eng J Med* 332, 1181–1185.
3. Cesarman, E, Yuan Chang, Patrick S Moore, J W Said and D M Knowles (1995) Kaposi's sarcoma-associated herpesvirus-like DNA sequences are present in AIDS-related body cavity based lymphomas. *New Eng J Med* 332, 1186–1191.
4. Cesarman, E, Patrick S Moore, P H Rao, G Inghirami, D M Knowles and Yuan Chang (1995) In vitro establishment and characterization of two AIDS-related lymphoma cell lines containing Kaposi's-sarcoma associated herpesvirus-like (KSHV) DNA sequences. *Blood* 86, 2708–2714.

TABLE 1

KSHV Genome ORFs and their similarity to genes in other herpesviruses.

| Name | Pol | Start | Stop | Size | HVS % Sim | HVS % Id | EBV Name | EBV % Sim | EBV % Id | Function |
|---|---|---|---|---|---|---|---|---|---|---|
| K1 | + | 105 | 974 | 289 | | | | | | |
| ORF4* | + | 1142 | 2794 | 550 | 45.3 | 31.2 | | | | Complement binding protein (v-CBP) |
| ** | | | | | 46.4 | 34.0 | | | | |
| ORF6 | + | 3210 | 6611 | 1133 | 74.1 | 55.2 | BALF2 | 65.6 | 42.1 | ssDNA binding protein (SSBP) |
| ORF7 | + | 6628 | 8715 | 695 | 65.0 | 44.7 | BALF3 | 59.9 | 41.3 | Transport protein |
| ORF8 | + | 8699 | 11,236 | 845 | 72.5 | 54.9 | BALF4 | 62.1 | 42.6 | Glycoprotein B (gB) |
| ORF9 | + | 31,363 | 14,401 | 1012 | 77.6 | 62.1 | BALF5 | 70.9 | 55.6 | DNA polymerase (pol) |
| ORF10 | + | 14,519 | 15,775 | 418 | 50.4 | 26.2 | | | | |
| ORF11 | + | 15,790 | 17,013 | 407 | 49.4 | 28.9 | Raji LF2 | 44.4 | 27.9 | |
| K2 | − | 17,875 | 17,261 | 204 | | | | | | vIL-6 |
| ORF02 | − | 18,553 | 17,921 | 210 | 65.8 | 48.4 | | | | DHFR |
| K3 | − | 19,609 | 18,608 | 333 | | | | | | BHV4-IE1 I |
| ORF70 | − | 21,104 | 20,091 | 337 | 79.5 | 66.4 | | | | Thymidylate synthase (TS) |
| K4 | − | 21,832 | 21,548 | 94 | | | | | | vMIP-II |
| K5 | − | 26,483 | 25,713 | 257 | | | | | | BHV4-IE1 II |
| K6 | − | 27,424 | 27,137 | 95 | | | | | | vMIP-I |
| K7 | + | 28,622 | 29,002 | 126 | | | | | | |
| ORF16 | + | 30,145 | 30,672 | 175 | 50.0 | 26.7 | BHRF1 | 46.3 | 22.8 | Bcl-2 |
| ORF17 | − | 32,482 | 30,821 | 553 | 60.3 | 42.9 | BVRF2 | 58.8 | 34.3 | Capsid protein I |
| ORF18 | + | 32,424 | 33,197 | 257 | 70.6 | 48.4 | | | | |
| ORF19 | − | 34,843 | 33,194 | 549 | 62.8 | 43.8 | BVRF1 | 62.5 | 42.0 | Tegument protein I |
| ORF20 | − | 35,573 | 34,611 | 320 | 59.6 | 42.7 | BXRF1 | 54.7 | 34.6 | |
| ORF21 | + | 35,383 | 37,125 | 580 | 50.9 | 32.5 | BXLF1 | 50.7 | 28.2 | Thymidine kinase (TK) |
| ORF22 | + | 37,113 | 39,305 | 730 | 53.9 | 35.1 | BXLF2 | 48.3 | 26.5 | Glycoprotein H (gH) |
| ORF23 | − | 45,516 | 39,302 | 404 | 57.4 | 33.7 | BTRF1 | 51.0 | 31.0 | |
| ORF24 | − | 42,778 | 40,520 | 752 | 65.8 | 45.6 | BcRF1 | 56.4 | 37.7 | |
| ORF25 | + | 42,777 | 46,907 | 1376 | 80.9 | 65.8 | BcLF1 | 74.8 | 56.8 | Major capsid protein (MCP) |
| ORF26 | + | 46,933 | 47,850 | 305 | 76.8 | 58.3 | BDLF1 | 73.4 | 48.8 | Capsid protein II |
| ORF27 | + | 47,873 | 48,745 | 290 | 49.6 | 29.6 | BDLF2 | 43.3 | 19.6 | |
| ORF28 | + | 48,991 | 49,299 | 102 | 42.2 | 21.7 | BDLF3 | | | |
| ORF29b | − | 50,417 | 49,362 | 351 | 41.8 | 17.0 | BDRF1 | 43.3 | 16.3 | Packaging protein II |
| ORF30 | + | 50,623 | 50,856 | 77 | 52.1 | 31.0 | BDLF3.5 | | | |
| ORF31 | + | 50,763 | 51,437 | 224 | 63.0 | 43.5 | BDLF4 | 58.9 | 36.4 | |
| ORF32 | + | 51,404 | 52,768 | 454 | 51.7 | 30.1 | BGLF1 | 47.0 | 26.6 | |
| ORF33 | + | 52,761 | 53,699 | 312 | 58.6 | 36.4 | BGLF2 | 52.8 | 32.2 | |
| ORF29a | − | 54,676 | 53,738 | 312 | 41.9 | 15.8 | BGRF1 | 57.1 | 40.6 | Packaging protein I |
| ORF34 | + | 54,675 | 55,658 | 327 | 58.9 | 42.7 | BGLF3 | 54.8 | 33.0 | |
| ORF35 | + | 55,639 | 56,091 | 151 | 60.0 | 31.7 | BGLF3.5 | | | |
| ORF36 | + | 55,976 | 57,310 | 444 | 49.4 | 31.1 | BGLF4 | 50.0 | 30.2 | Viral protein kinase |
| ORF37 | + | 57,273 | 58,733 | 486 | 65.9 | 50.4 | BGLF5 | 60.1 | 42.7 | Alkaline exonuclease (AE) |
| ORF38 | + | 58,688 | 58,873 | 61 | 58.6 | 39.7 | BBLF1 | 52.5 | 23.0 | |
| ORF39 | − | 60,175 | 58,976 | 399 | 73.2 | 52.1 | BBRF3 | 65.2 | 43.6 | Glycoprotein M (gM) |
| ORF40 | + | 60,308 | 61,681 | 457 | 51.9 | 28.1 | BBLF2 | 47.1 | 23.3 | Helicase-primase, subunit 1 |
| ORF41 | + | 61,827 | 62,444 | 205 | 53.4 | 29.2 | BBLF3 | | | Helicase-primase, subunit 2 |
| ORF42 | − | 63,272 | 62,436 | 278 | 55.8 | 38.9 | BBRF2 | 52.9 | 33.0 | |
| ORF43 | − | 64,953 | 83,136 | 605 | 74.9 | 60.5 | RBRF1 | 67.6 | 50.1 | Capsid protein III |
| ORF44 | + | 64,892 | 67,258 | 788 | 75.5 | 61.4 | BBLF4 | 67.8 | 51.1 | Helicase-primase, subunit 3 |
| ORF45 | − | 68,576 | 67,353 | 407 | 50.2 | 30.7 | BKRF4 | 48.9 | 26.2 | Virion assembly protein |
| ORF46 | − | 69,404 | 68,637 | 255 | 73.0 | 59.5 | BKRF3 | 69.2 | 54.8 | Uracil DNA glycosylase (UDG) |
| ORF47 | − | 69,915 | 69,412 | 167 | 53.0 | 29.9 | BKRF4 | 53.8 | 24.2 | Glycoprotein L (gL) |
| ORF48 | − | 71,381 | 70,173 | 402 | 47.3 | 24.4 | BRRF2 | 46.1 | 18.8 | |
| ORF49 | − | 72,538 | 71,630 | 302 | 45.4 | 21.2 | BRRF1 | 49.8 | 28.0 | |
| ORF50 | + | 72,734 | 74,629 | 631 | 46.5 | 24.9 | BRLF1 | 41.4 | 19.0 | Transactivator (LCTP) |
| K8 | + | 74,850 | 75,569 | 239 | | | | | | |
| ORF52 | − | 77,197 | 76,802 | 131 | 50.0 | 33.3 | BLRF2 | 54.6 | 36.9 | |
| ORF53 | − | 77,665 | 77,333 | 110 | 59.6 | 36.0 | BLRF1 | 58.1 | 40.9 | |
| ORF54 | + | 77,667 | 78,623 | 318 | 55.0 | 35.5 | BLLF3 | 53.7 | 32.4 | dUTPase |
| ORF55 | − | 79,448 | 78,765 | 227 | 64.4 | 46.4 | BSRF1 | 61.6 | 44.0 | |
| ORF56 | + | 79,436 | 81,967 | 843 | 62.5 | 44.3 | BSLF1 | 56.6 | 35.4 | DNA replication protein I |
| ORF57 | + | 82,717 | 83,544 | 275 | 56.9 | 31.5 | BMLF1 | 45.1 | 22.0 | Immediate-early protein II (IEP-II) |
| K9 | − | 85,209 | 83,860 | 449 | | | | | | vIRF1 (ICSBP) |
| K10 | − | 88,164 | 86,074 | 696 | | | | | | |
| K11 | − | 93,367 | 91,964 | 467 | | | | | | |
| ORF58 | − | 95,544 | 94,471 | 357 | 55.9 | 28.7 | BMRF2 | 50.6 | 25.3 | Phosphoprotein |
| ORF59 | − | 96,739 | 95,549 | 396 | 54.1 | 32.3 | BMRF1 | 50.7 | 28.3 | DNA replication protein II |
| ORF60 | − | 97,787 | 96,870 | 305 | 79.3 | 64.6 | BaRF1 | 74.8 | 57.3 | Ribonucleotide reductase, small |
| ORF61 | − | 100,194 | 97,816 | 792 | 69.4 | 52.4 | BORF2 | 64.1 | 43.6 | Ribonucleotide reductase, large |
| ORF62 | − | 102,194 | 100,199 | 331 | 64.6 | 40.2 | BORF1 | 57.7 | 34.7 | Assembly/DNA maturation |
| ORF63 | + | 101,208 | 103,994 | 927 | 53.1 | 32.1 | BDLF1 | 47.0 | 24.5 | Tegument protein II |
| ORF64 | + | 104,000 | 111,957 | 2635 | 50.1 | 29.7 | BPLF1 | 46.6 | 26.1 | Tegument protein III |
| ORF65 | − | 112,443 | 111,931 | 170 | 60.4 | 40.3 | BFRF3 | 49.4 | 27.8 | Capsid protein IV |
| ORF66 | − | 113,759 | 112,470 | 429 | 58.7 | 34.7 | BFRF2 | 50.0 | 28.0 | |
| O5F67 | − | 114,508 | 113,693 | 271 | 71.8 | 53.0 | BFRF1 | 62.8 | 39.5 | Tegument protein IV |

TABLE 1-continued

KSHV Genome ORFs and their similarity to genes in other herpesviruses.

| Name | Pol | Start | Stop | Size | HVS % Sim | HVS % Id | EBV Name | EBV % Sim | EBV % Id | Function |
|---|---|---|---|---|---|---|---|---|---|---|
| ORF68 | + | 114,768 | 116,405 | 545 | 64.7 | 45.4 | BFLF1 | 58.3 | 36.2 | Glycoprotein |
| ORF69 | + | 116,669 | 117,346 | 225 | 71.1 | 53.6 | BFLF2 | 60.7 | 41.7 | |
| K12 | − | 118,101 | 117,919 | 60 | | | | | | Kaposin |
| K13 | − | 122,710 | 122,291 | 139 | | | | | | |
| ORF72 | − | 123,566 | 122,793 | 257 | 53.0 | 32.5 | | | | Cyclin D |
| ORF73 | − | 127,296 | 123,808 | 1162 | 51.2 | 31.8 | | | | Immediate-early protein (IEP) |
| K14 | + | 127,883 | 128,929 | 348 | | | | | | OX-2 (v-adh) |
| ORF74 | + | 129,371 | 130,399 | 342 | 57.8 | 34.1 | | | | G-protein coupled receptor |
| ORF75 | − | 134,440 | 130,550 | 1296 | 54.8 | 36.3 | BNRF1 | | | Tegument protein/FGARAT |
| K15 | − | 136,279 | 135,977 | 100 | | | | | | |

Legend to Table 1. Name (e.g. K1 or ORF4) refers to the KSHV ORF designation; Pol signifies polarity of the ORF within the KSHV genome; Start refers to the position of the first LUR nucleotide in the start codon; Stop refers to the position of the last LUR nucleotide in the stop codon; Size indicates the number of amino acid residues encoded by the KSHV ORF; HVS%Sim indicates the percent similarity of the indicated KSHV ORF to the corresponding ORF of herpesvirus saimiri; HVS%Id indicates the percent identity of the indicated KSHV ORF to the corresponding ORF of herpesvirus saimiri; EBV Name indicates the EBV ORF designation; EBV%Sim indicates the percent similarity of the indicated KSHV ORF to the named Epstein-Barr virus ORF; EBV%Id indicates the percent identity of the indicated KSHV ORF to the named Epstein-Barr virus ORF. The asterisks in the KSHV Name column indicate comparison of KSHV ORF4 to HVS ORF4a (*) and HVS ORF4b (**) The entire unannotated genomic sequence is deposited in GenBank. under the accession numbers: U75698 (LUR), U75699 (terminal repeat), and U75700 (incomplete terminal repeat). The sequence of the LUR (U75698) is also set forth in its entirety in the Sequence Listing below. Specifically, the sequence of the LUR is set forth in 5' to 3' order in SEQ ID Nos:17–20. More specifically, nucleotides 1–35,100 of the LUR are set forth in SEQ ID NO:17 numbered nucleotides 1–35,100, respectively; nucleotides 35,101–70,200 of the LUR are set forth in SEQ ID NO:18 numbered nucleotides 1–35,100, respectively; nucleotides 70,201–105,300 of the LUR are set forth in SEQ ID NO:19 numbered nucleotides 1–35,100, respectively; and nucleotides 105,301–137,507 of the LUR are set forth in SEQ ID NO:20 numbered nucleotides 1–32,207, respectively.

What is claimed is:

1. An isolated nucleic acid consisting of the nucleotide sequence encoding Kaposi's sarcoma-associated herpesvirus dihydrofolate reductase having an amino acid sequence as set forth in SEQ ID NO:1.

2. The isolated nucleic acid of claim 1 which is cDNA.

3. The isolated nucleic acid of claim 1 which is RNA.

4. The isolated nucleic acid of claim 1 which is labeled with a detectable marker.

5. The isolated nucleic acid of claim 4, wherein the marker is a radioactive, a colorimetric, a luminescent, or a fluorescent label.

6. A recombinant vector containing the isolated nucleic acid of claim 1.

7. A host cell comprising the vector of claim 6.

8. The cell of claim 7 which is a eukaryotic cell.

9. The bacterial cell of claim 7 which is a bacterial cell.

10. A plasmid, cosmid, λ phage or YAC comprising the isolated nucleic acid of claim 1.

11. A nucleic acid of at least 14 nucleotides which specifically hybridized with the isolated nucleic acid of claim 1.

12. The isolated nucleic acid of claim 1 which is a genomic DNA.

* * * * *